US012805190B2

(12) United States Patent
Iwawaki et al.

(10) Patent No.: US 12,805,190 B2
(45) Date of Patent: Nov. 17, 2026

(54) ORGANIC COMPOUND AND ORGANIC LIGHT-EMITTING ELEMENT

(71) Applicant: CANON KABUSHIKI KAISHA, Tokyo (JP)

(72) Inventors: Hironobu Iwawaki, Kanagawa (JP); Naoki Yamada, Tokyo (JP); Jun Kamatani, Tokyo (JP); Hiroki Ohrui, Tokyo (JP); Yosuke Nishide, Kanagawa (JP); Hirokazu Miyashita, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 1039 days.

(21) Appl. No.: 18/055,195

(22) Filed: Nov. 14, 2022

(65) Prior Publication Data

US 2023/0157166 A1 May 18, 2023

(30) Foreign Application Priority Data

Nov. 17, 2021 (JP) ................................ 2021-187046

(51) Int. Cl.
*H10K 85/60* (2023.01)
*C07D 405/14* (2006.01)
(Continued)

(52) U.S. Cl.
CPC ....... *H10K 85/6572* (2023.02); *C07D 405/14* (2013.01); *H10K 85/6574* (2023.02);
(Continued)

(58) Field of Classification Search
CPC ................................................ H10K 85/6572
See application file for complete search history.

(56) References Cited

U.S. PATENT DOCUMENTS

2013/0048971 A1* 2/2013 Kitano ................. C07D 403/14 257/E51.026
2014/0034925 A1 2/2014 Osaka et al.
2020/0255358 A1* 8/2020 Nishide ................... C07C 25/18

FOREIGN PATENT DOCUMENTS

JP 2013063963 A 4/2013
KR 20110042004 A * 4/2011 ............. H05B 33/20

OTHER PUBLICATIONS

Machine Translation of KR20110042004A (Year: 2011).*

* cited by examiner

*Primary Examiner* — Jenna N Chandhok
(74) *Attorney, Agent, or Firm* — Canon U.S.A., Inc. IP Division

(57) ABSTRACT

An organic compound denoted by formula (1) below.

[1]

A:

(Continued)

-continued

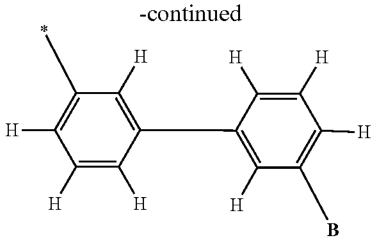

B:

[B-1]

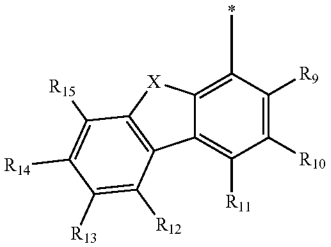

In formula (1), each of $R_1$ to $R_8$ is selected from the group consisting of a hydrogen atom, an alkyl group, and the like. A represents a structure denoted by A above, * represents a position where bonding is performed. In A, B is selected from structures denoted by (B-1) and the like above, * represents a position where bonding is performed. In (B-1) and the like, each of $R_9$ to $R_{17}$ is selected from a hydrogen atom, an alkyl group, and the like. X represents an oxygen atom or a sulfur atom.

14 Claims, 8 Drawing Sheets

(51) Int. Cl.
*H10K 50/11* (2023.01)
*H10K 59/12* (2023.01)
*H10K 101/10* (2023.01)

(52) U.S. Cl.
CPC .............. *H10K 50/11* (2023.02); *H10K 59/12* (2023.02); *H10K 2101/10* (2023.02)

ORGANIC COMPOUND AND ORGANIC LIGHT-EMITTING ELEMENT

BACKGROUND OF THE INVENTION

Field of the Invention

The present disclosure relates to an organic compound and an organic light-emitting element including the same.

Description of the Related Art

The organic light-emitting element (hereafter also referred to as "organic electroluminescence element" or "organic EL element") is an electronic element including a pair of electrodes and an organic compound layer disposed between the electrodes. An electron and a hole being injected from the pair of electrodes generates an exciton of a light-emitting organic compound in the organic compound layer, and the organic light-emitting element emits light when the exciton returns to a ground state. Recently, the organic light-emitting element has significantly progressed so as to enable a low driving voltage, diverse emission wavelengths, high speed responsiveness, and thickness reduction and weight reduction of a light-emitting apparatus to be realized.

In this regard, to date, creation of compounds suitable for the organic light-emitting element have been intensively performed. The reason for this is that creation of a compound having excellent element life characteristics is important for providing a high-performance organic light-emitting element. Regarding the compounds created until now, examples of the compound in which an end of a phenylene group in diphenyldiazatriphenylene is substituted with a condensed polycyclic group include Compound 1-A below which is described in US 2014/0034925.

1-A

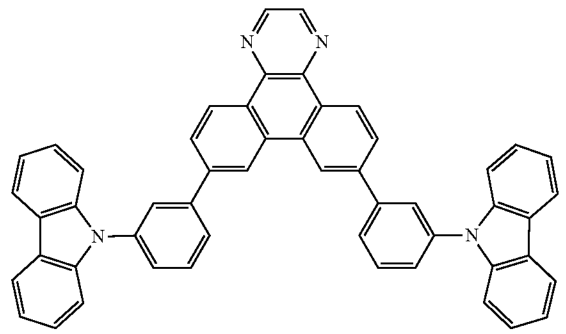

According to examination of the present inventors, since Compound 1-A has small $S_1$ (singlet energy) and has room for improvement in thermal properties, when Compound 1-A is used for the organic light-emitting element, an element life is short, and an organic light-emitting element having excellent durability characteristics is not obtained.

SUMMARY OF THE INVENTION

The present disclosure provides an organic compound having excellent element life characteristics when used for an organic light-emitting element. In addition, the present disclosure provides an organic light-emitting element having excellent life characteristics.

The organic compound according to the present disclosure is denoted by formula (1) below.

(1)

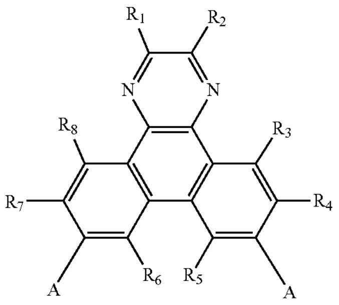

In formula (1), each of $R_1$ to $R_8$ is selected from the group consisting of a hydrogen atom, a deuterium atom, a halogen atom, a substituted or unsubstituted alkyl group, a substituted or unsubstituted alkoxy group, a substituted or unsubstituted amino group, a substituted or unsubstituted aryloxy group, a substituted or unsubstituted heteroaryloxy group, a substituted or unsubstituted silyl group, a substituted or unsubstituted aromatic hydrocarbon group, a substituted or unsubstituted heterocyclic group, and a cyano group.

A is a structure denoted by A below, * represents a position where bonding is performed.

A:

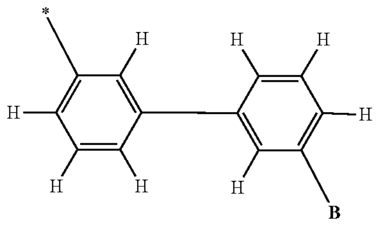

In A above, B is selected from the group consisting of structures denoted by (B-1) to (B-15) below, * represents a position where bonding is performed.

B:

(B-1)

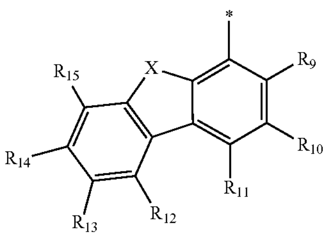

-continued
(B-2)
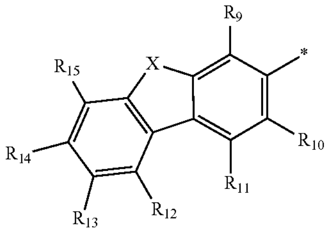
(B-3)
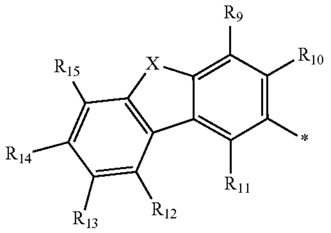
(B-3)
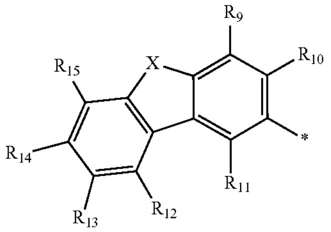
(B-4)
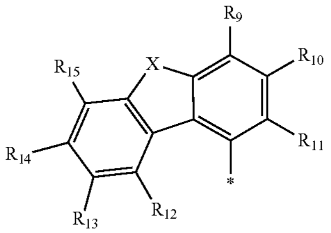
(B-5)
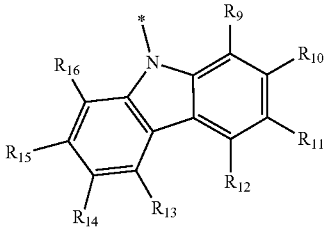
(B-6)
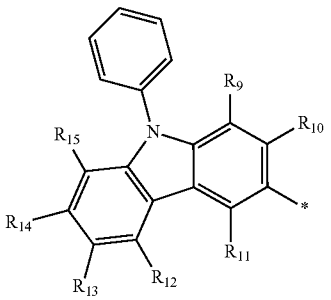
-continued
(B-7)
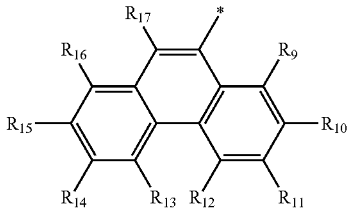
(B-8)
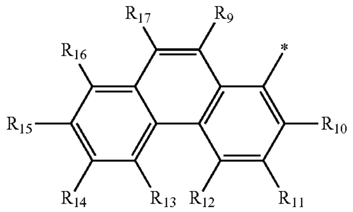
(B-9)
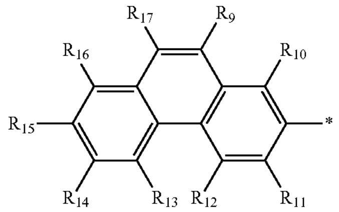
(B-10)
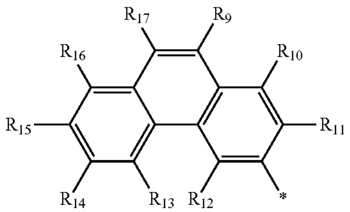
(B-11)
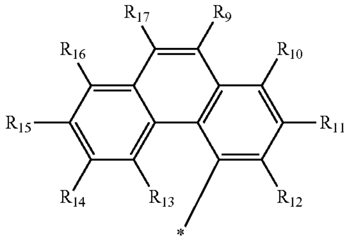
(B-12)
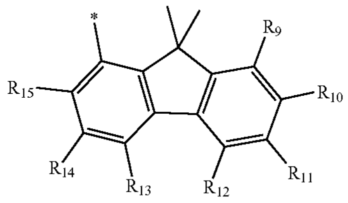
(B-13)
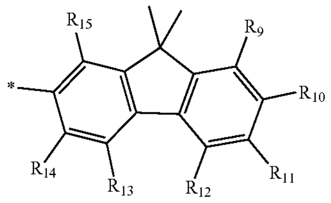

-continued (B-14)

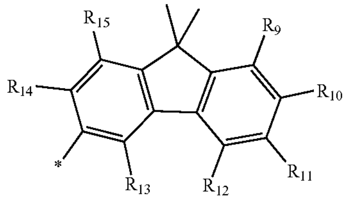

(B-15)

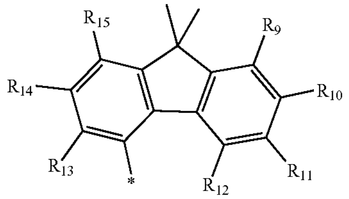

In (B-1) to (B-15) above, each of $R_9$ to $R_{17}$ is selected from the group consisting of a hydrogen atom, a deuterium atom, a halogen atom, a substituted or unsubstituted alkyl group, a substituted or unsubstituted alkoxy group, a substituted or unsubstituted amino group, a substituted or unsubstituted aryloxy group, a substituted or unsubstituted heteroaryloxy group, a substituted or unsubstituted silyl group, a substituted or unsubstituted aromatic hydrocarbon group, a substituted or unsubstituted heterocyclic group, and a cyano group.

X represents an oxygen atom or a sulfur atom.

Further features of the present disclosure will become apparent from the following description of exemplary embodiments with reference to the attached drawings.

BRIEF DESCRIPTION OF THE DRAWINGS

Each of FIG. 8B

DESCRIPTION OF THE EMBODIMENTS

Organic Compound

Figure 1A:
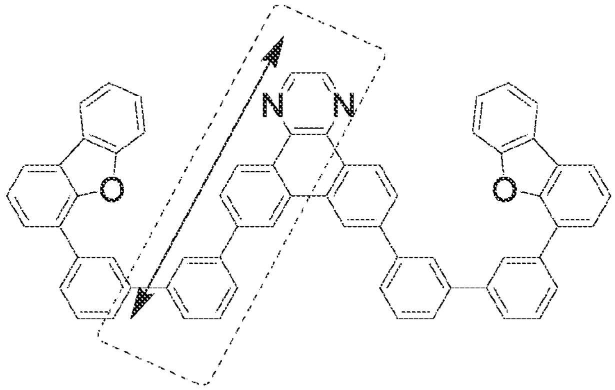
FIGS. 1A and 1B are diagrams illustrating a feature of the compound according to the present disclosure.

An organic compound according to the present embodiment is denoted by formula (1) below.

(1)

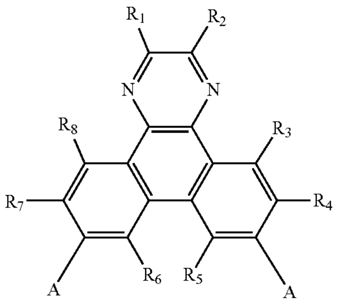

$R_1$ to $R_8$

In formula (1), each of $R_1$ to $R_8$ is selected from the group consisting of a hydrogen atom, a deuterium atom, a halogen atom, a substituted or unsubstituted alkyl group, a substituted or unsubstituted alkoxy group, a substituted or unsubstituted amino group, a substituted or unsubstituted aryloxy group, a substituted or unsubstituted heteroaryloxy group, a substituted or unsubstituted silyl group, a substituted or unsubstituted aromatic hydrocarbon group, a substituted or unsubstituted heterocyclic group, and a cyano group.

Examples of the halogen atom include fluorine, chlorine, bromine, and iodine, but the halogen atom is not limited to these.

Examples of the alkyl group include a methyl group, an ethyl group, a n-propyl group, an isopropyl group, a n-butyl group, a tert-butyl group, a sec-butyl group, an octyl group, a cyclohexyl group, a 1-adamantyl group, and 2-adamantyl group, but the alkyl group is not limited to these. The carbon number of the alkyl group can be 1 or more and 10 or less.

Examples of the alkoxy group include a methoxy group, an ethoxy group, a propoxy group, a 2-ethyl-octyloxy group, and a benzyloxy group, but the alkoxy group is not limited to these. The carbon number of the alkoxy group can be 1 or more and 10 or less.

Examples of the amino group include an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tert-butylphenyl)

amino group, an N-phenyl-N-(4-trifluoromethylphenyl) amino group, and an N-piperidyl group, but the amino group is not limited to these.

Examples of the aryloxy group or the heteroaryloxy group include a phenoxy group and a thienyloxy group, but the aryloxy group or the heteroaryloxy group is not limited to these.

Examples of the silyl group include a trimethylsilyl group and a triphenylsilyl group, but the silyl group is not limited to these.

Examples of the aromatic hydrocarbon group include a phenyl group, a naphthyl group, an indenyl group, a biphenyl group, a terphenyl group, a fluorenyl group, a phenanthryl group, a fluoranthenyl group, and triphenylenyl group, but the aromatic hydrocarbon group is not limited to these.

Examples of the heterocyclic group include a pyridyl group, an oxazolyl group, an oxadiazolyl group, a thiazolyl group, a thiadiazolyl group, a carbazolyl group, an acridinyl group, a phenanthrolyl group, a dibenzofuranyl group, and a dibenzothiophenyl group, but the heterocyclic group is not limited to these.

Examples of the substituent that may be further included in the above-described alkyl group, alkoxy group, amino group, aryloxy group, heteroaryloxy group, silyl group, aromatic hydrocarbon group, or heterocyclic group include a deuterium atom; halogen atoms such as fluorine, chlorine, bromine, and iodine; alkyl groups such as a methyl group, an ethyl group, a n-propyl group, an isopropyl group, a n-butyl group, and a tert-butyl group; alkoxy groups such as a methoxy group, an ethoxy group, and a propoxy group; amino groups, such as a dimethylamino group, a diethylamino group, a dibenzylamino group, a diphenylamino group, and a ditolylamino group; aryloxy groups such as a phenoxy group; aromatic hydrocarbon groups such as a phenyl group and a biphenyl group; heterocyclic groups such as a pyridyl group and a pyrrolyl group; and cyano groups, but the substituent is not limited to these.

A

In formula (1), A is a structure denoted by A below, * represents a position where bonding is performed.

A:

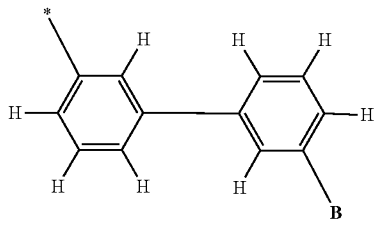

B

In A above, B is selected from the group consisting of structures denoted by (B-1) to (B-15) below, * represents a position where bonding is performed. The two Bs may be the same or differ from each other but can be the same.

B:

(B-1)

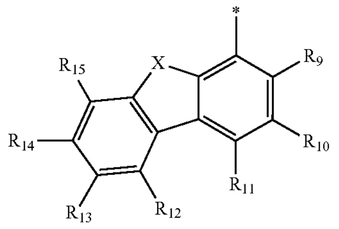

(B-2)

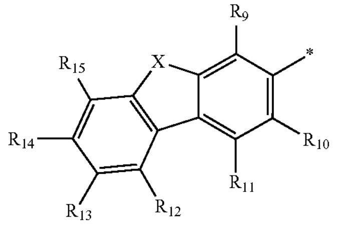

(B-3)

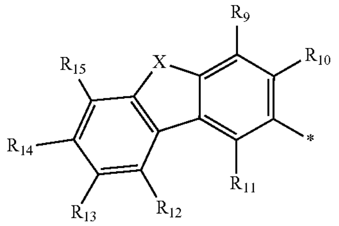

(B-3)

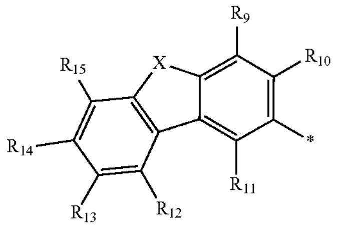

(B-4)

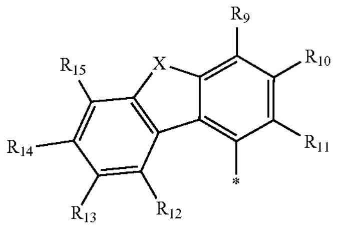

(B-5)

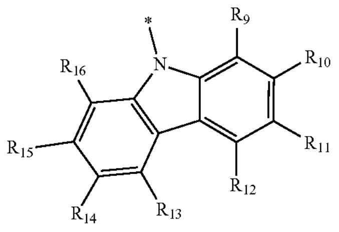

-continued (B-6)

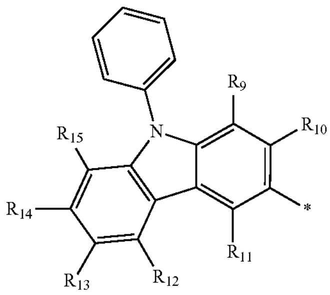

(B-7)

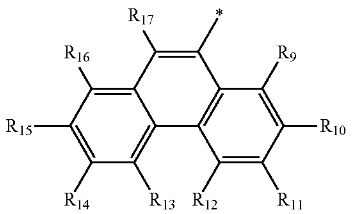

(B-8)

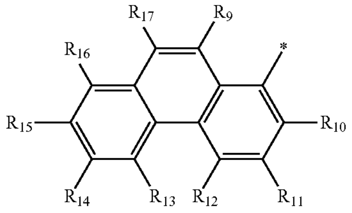

(B-9)

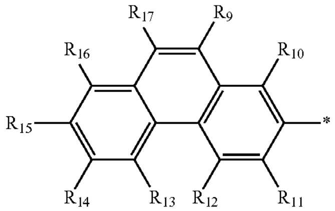

(B-10)

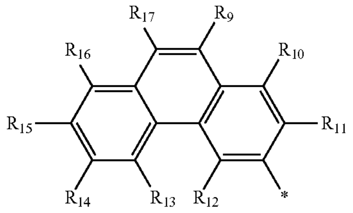

(B-11)

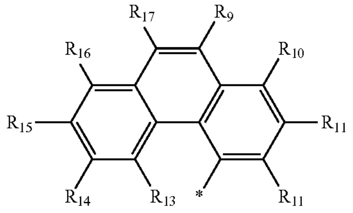

(B-12)

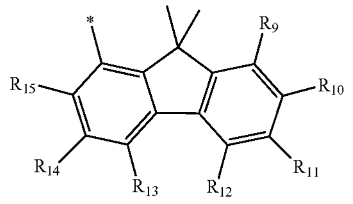

-continued (B-13)

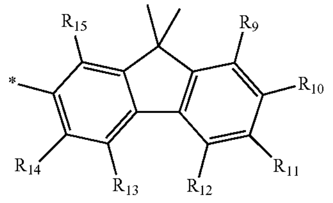

(B-14)

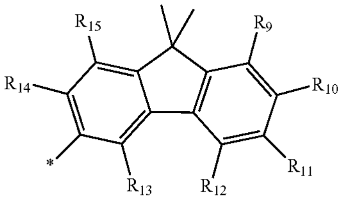

(B-15)

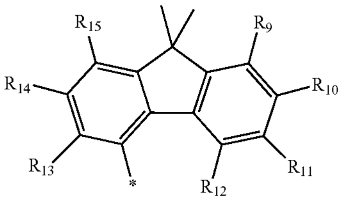

$R_9$ to $R_{17}$

In (B-1] to (B-15), each of $R_9$ to $R_{17}$ is selected from the group consisting of a hydrogen atom, a deuterium atom, a halogen atom, a substituted or unsubstituted alkyl group, a substituted or unsubstituted alkoxy group, a substituted or unsubstituted amino group, a substituted or unsubstituted aryloxy group, a substituted or unsubstituted heteroaryloxy group, a substituted or unsubstituted silyl group, a substituted or unsubstituted aromatic hydrocarbon group, a substituted or unsubstituted heterocyclic group, and a cyano group.

Specific examples of the halogen atom, the alkyl group, the alkoxy group, the amino group, the aryloxy group, the heteroaryloxy group, the silyl group, the aromatic hydrocarbon group, or the heterocyclic group include the groups akin to that described with respect to $R_1$ to $R_8$, but the group is not limited to these. The carbon number of the alkyl group can be 1 or more and 10 or less. The carbon number of the alkoxy group can be 1 or more and 10 or less. In this regard, specific examples of the substituent that may be further included in the alkyl group, the alkoxy group, the amino group, the aryloxy group, the heteroaryloxy group, the silyl group, the aromatic hydrocarbon group, or the heterocyclic group include the substituents akin to that described with respect to $R_1$ to $R_8$, but the substituent is not limited to these.

X

X represents an oxygen atom or a sulfur atom.

B can be selected from the group consisting of structures denoted by (C-1) to (C-3) below.

C:

(C-1)

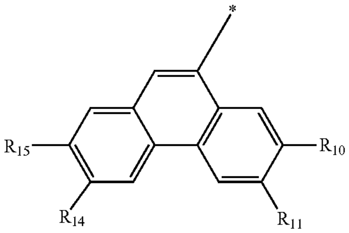

(C-2)

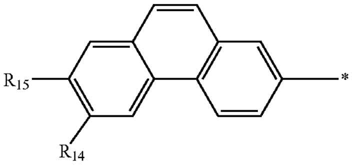

(C-3)

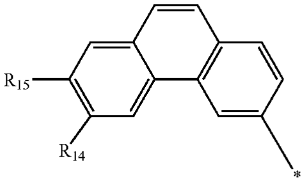

B can be selected from the group consisting of structures denoted by (D-1) to (D-6) below.

D:

(D-1)

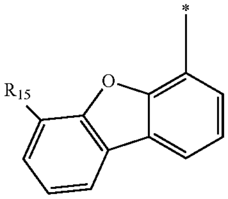

(D-2)

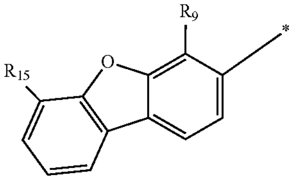

-continued (D-3)

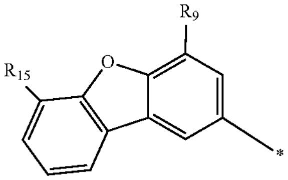

(D-4)

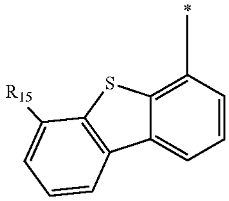

(D-5)

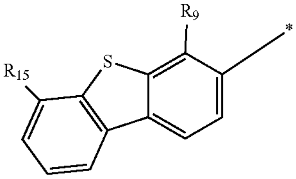

(D-6)

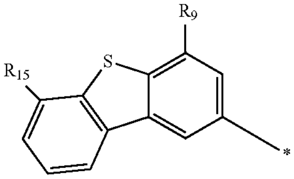

Synthesis Method

Next, a method for synthesizing the organic compound according to the present embodiment will be described. The organic compound according to the present embodiment is synthesized in accordance with, for example, a reaction scheme described below.

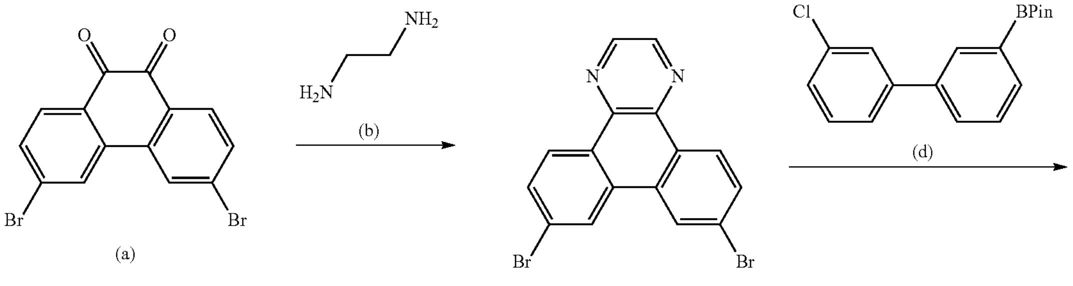

(a)

(c)

-continued

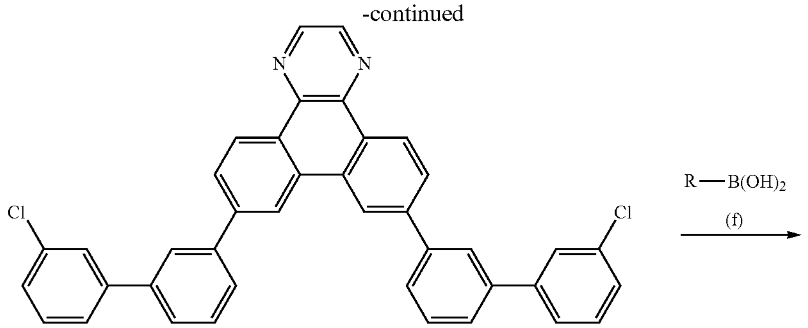

(e)

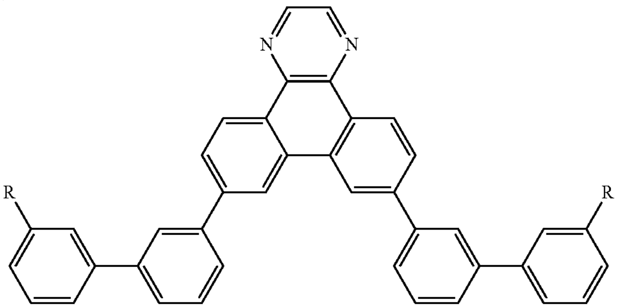

(g)

Herein, various compounds are obtained by appropriately changing the compounds denoted by (b), (f), and the like above. The method for synthesizing the organic compound according to the present embodiment is not limited to the above-described synthesis scheme, and various synthesis schemes and reagents are usable. In this regard, the synthesis method will be described in detail in the examples.

Specific Examples of Organic Compound

Specific examples of the organic compound according to the present embodiment will be described below, but the organic compound is not limited to these, as a matter of course.

A1

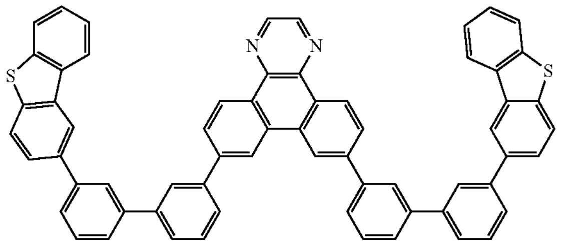

A2

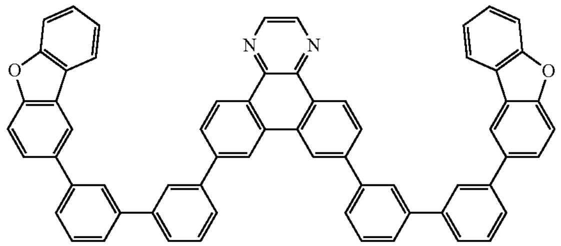

A3

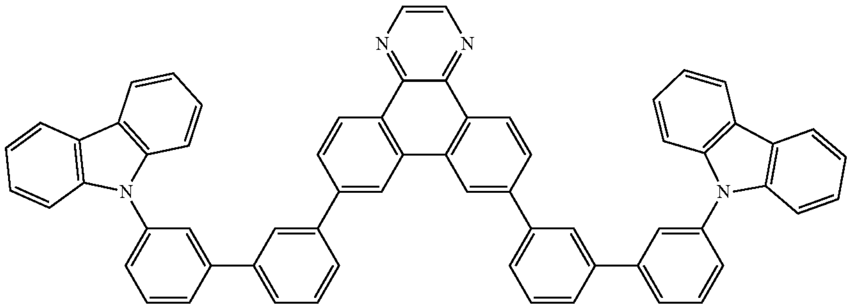

-continued
A4
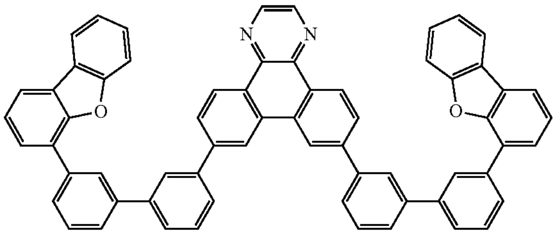
A5
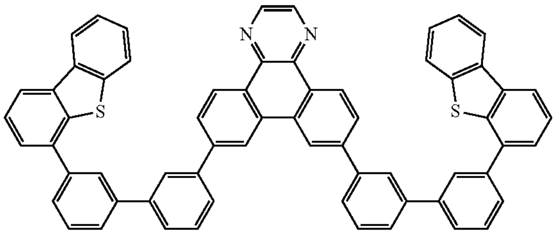
A6
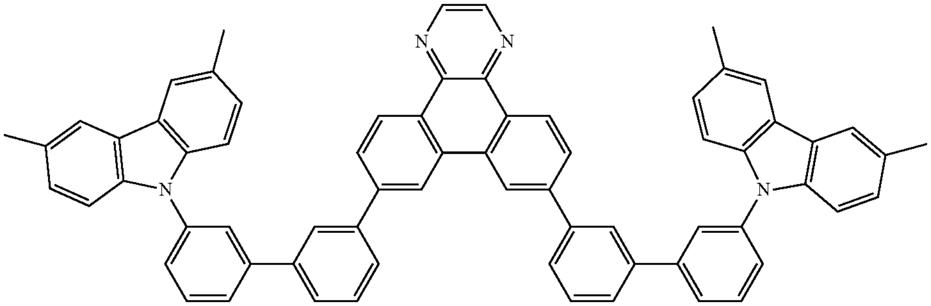
A7
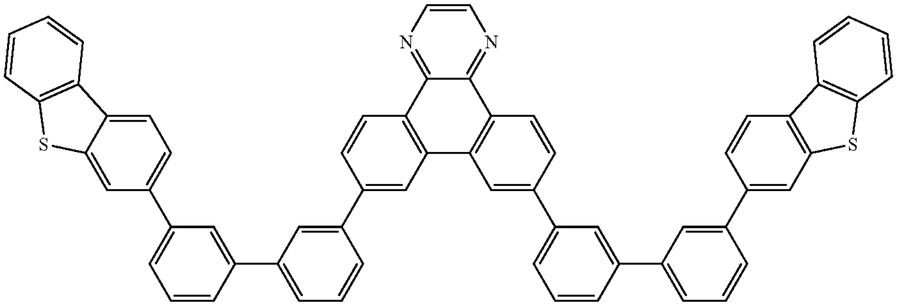
A8
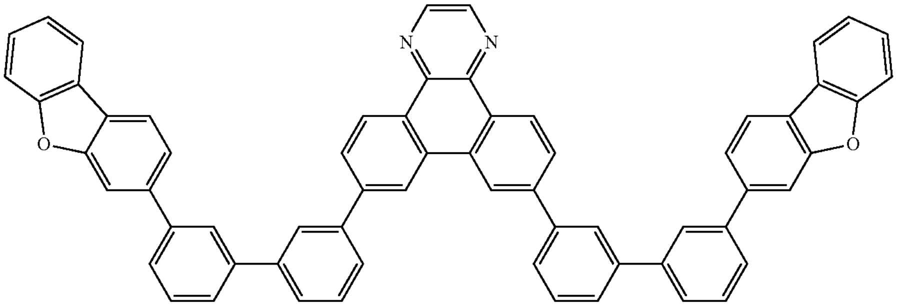
A9
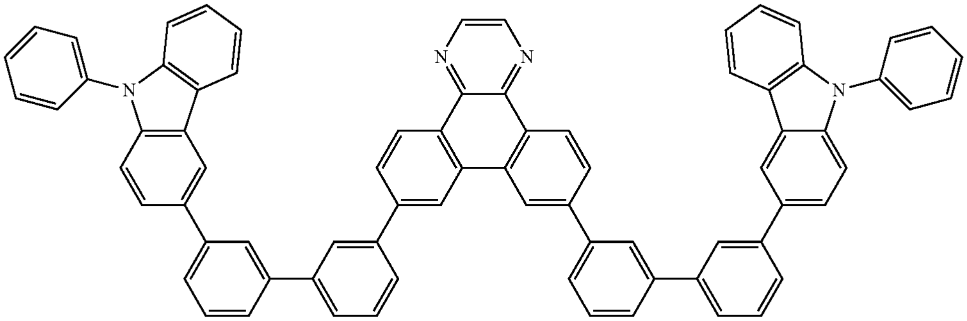

-continued
A10
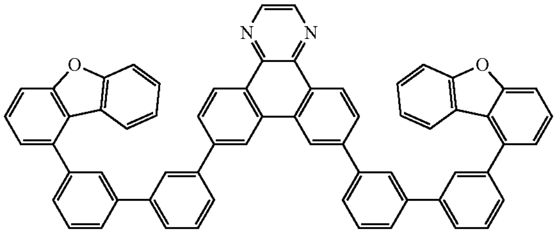
A11
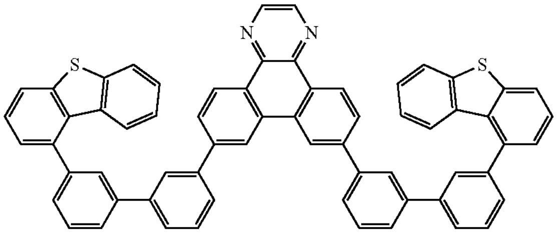
A12
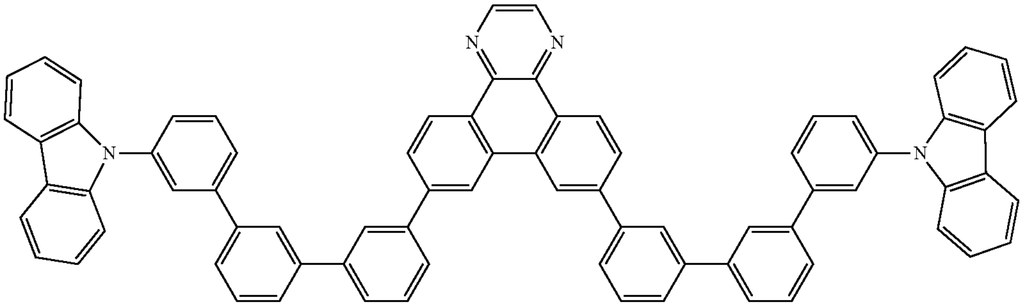
A13
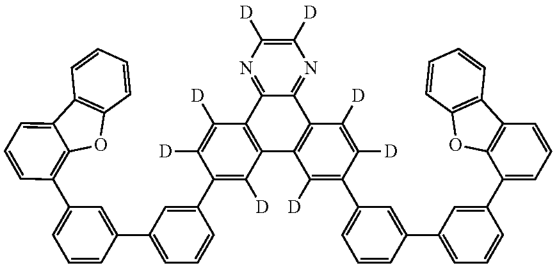
A14
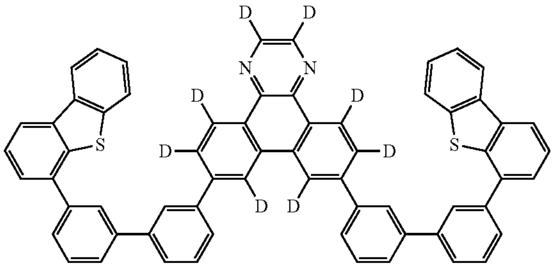
A15
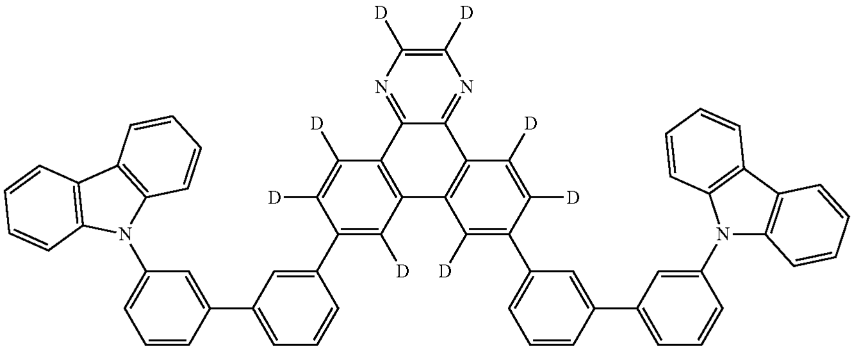
A16
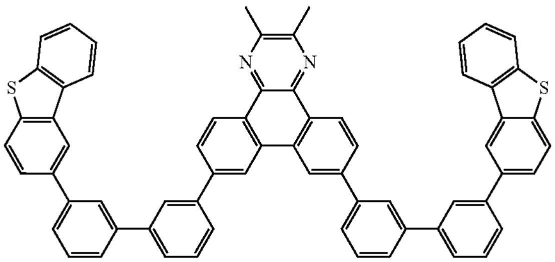
A17
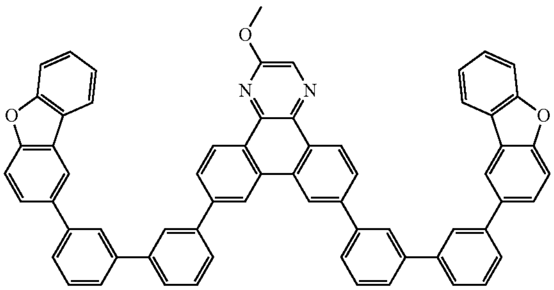

-continued
A18
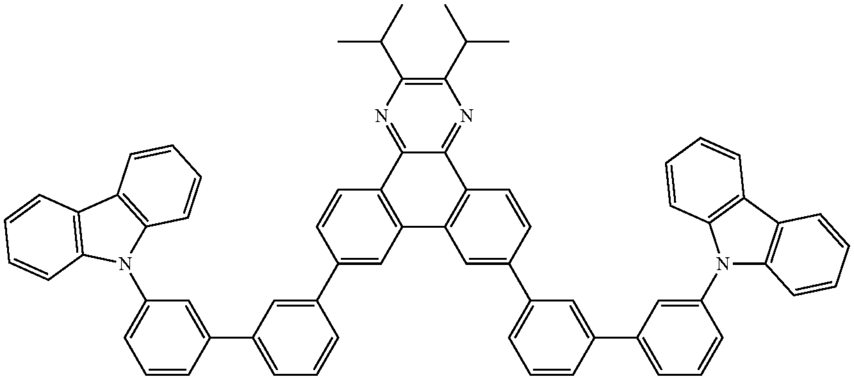
A20
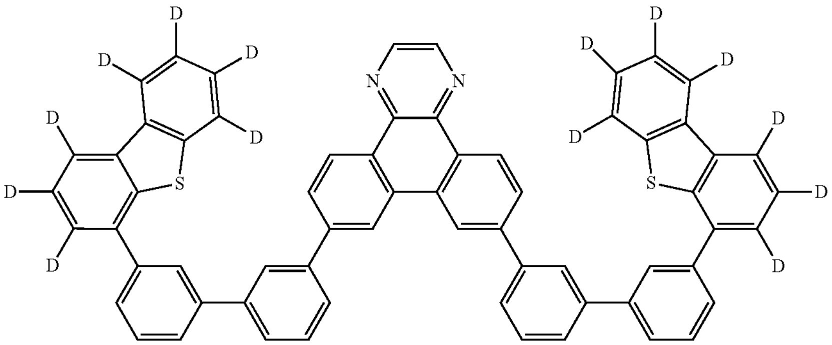
A21
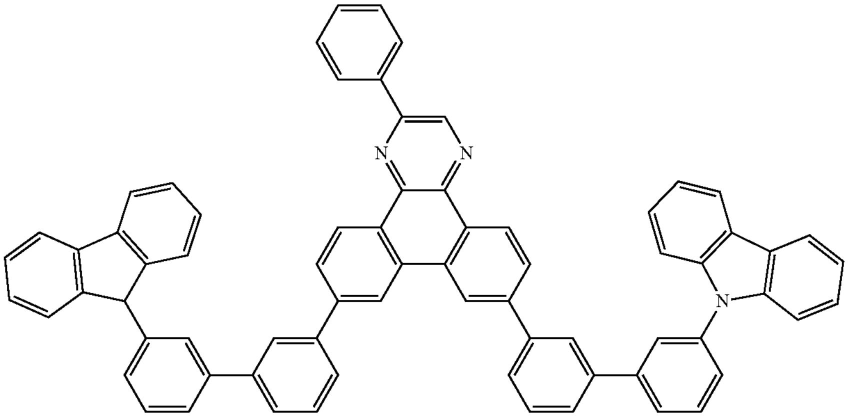
A22
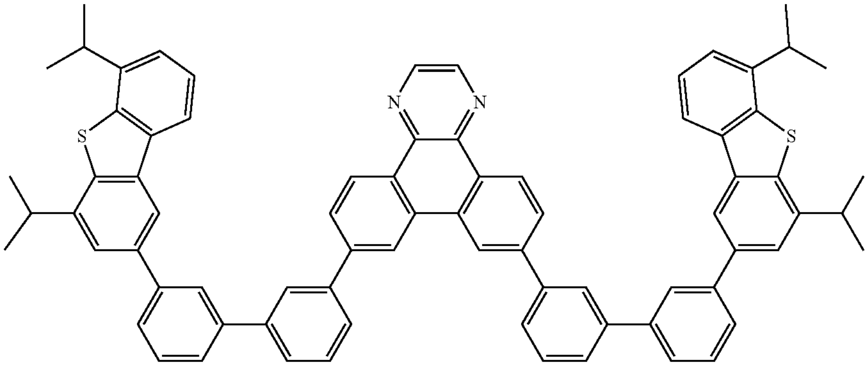

-continued
A23
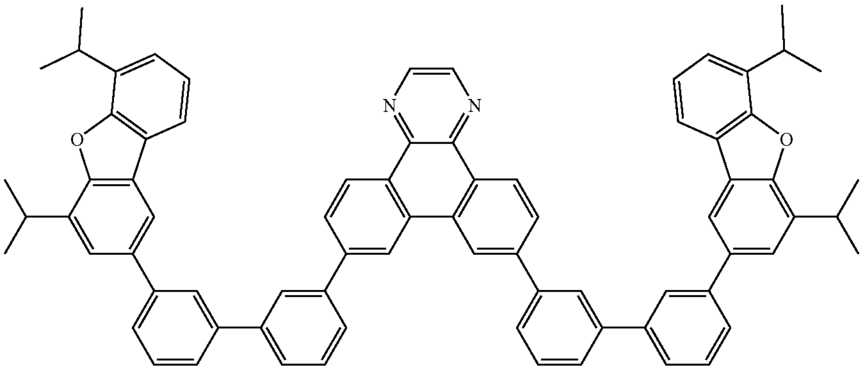
A24
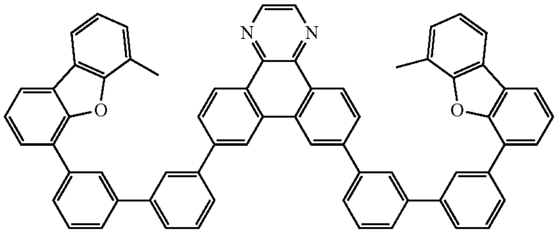
A25
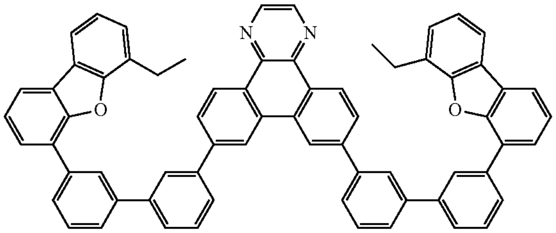
A26
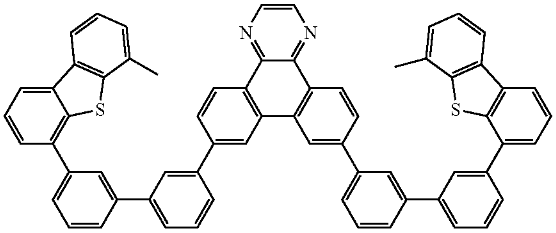
A27
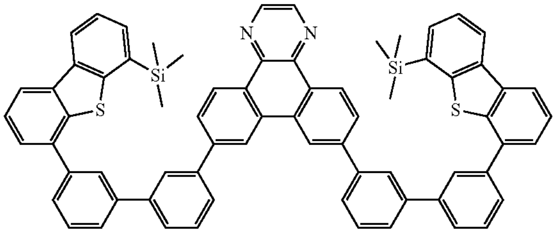
A28
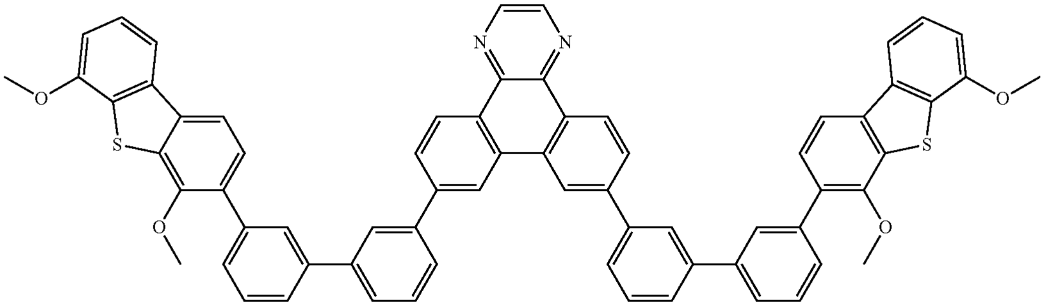
A29
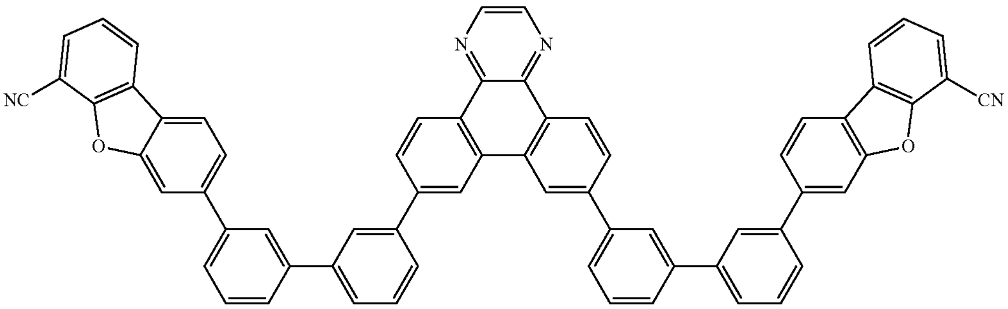

-continued
A30
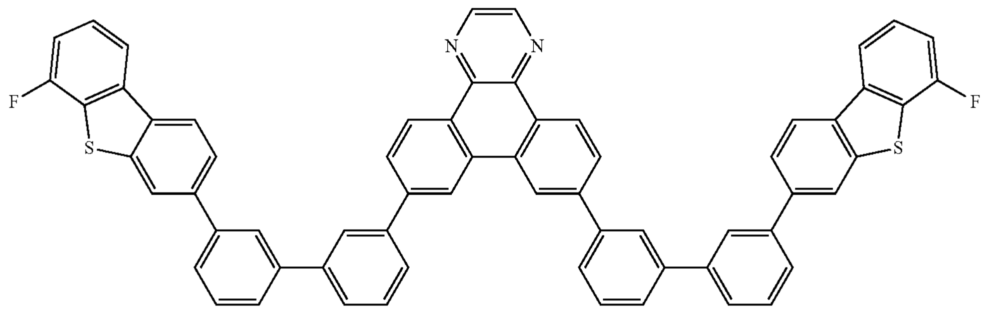
A31
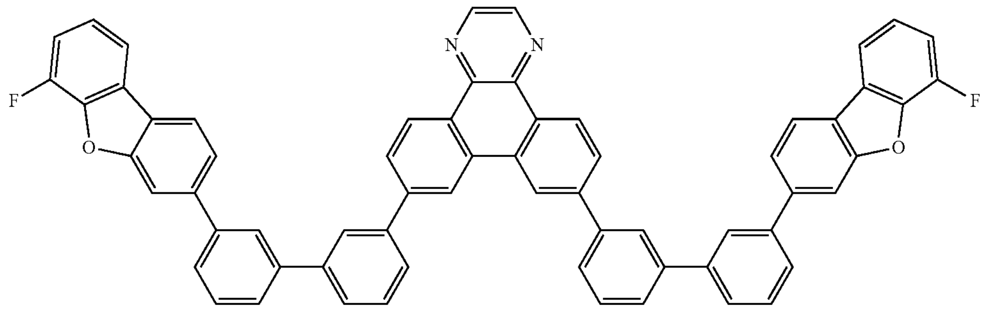
B1
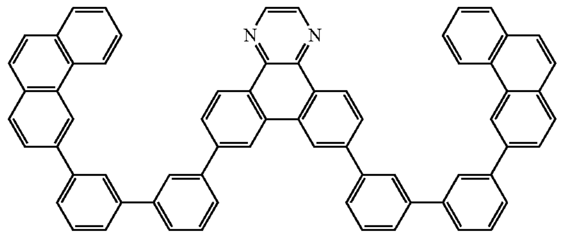
B2
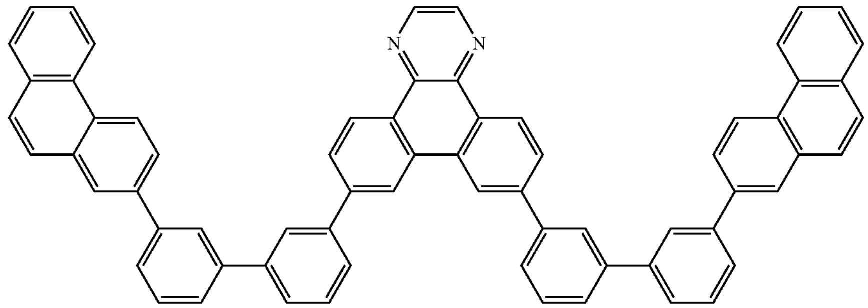
B3
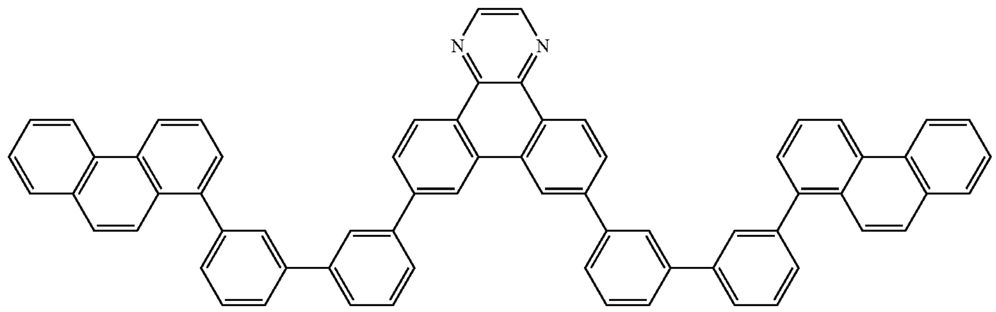

-continued
B4
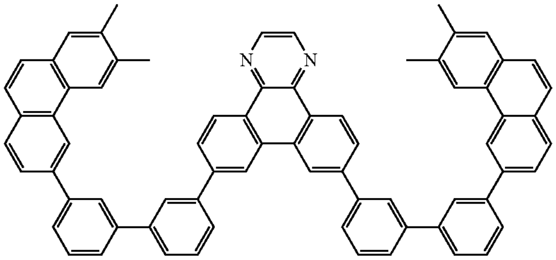
B5
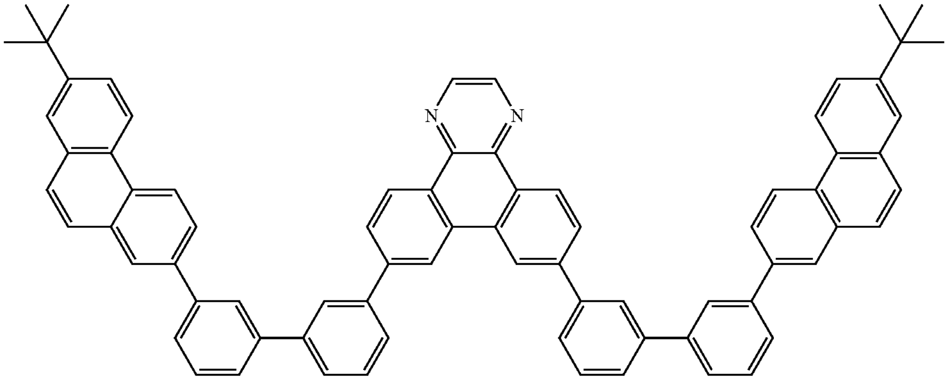
B6
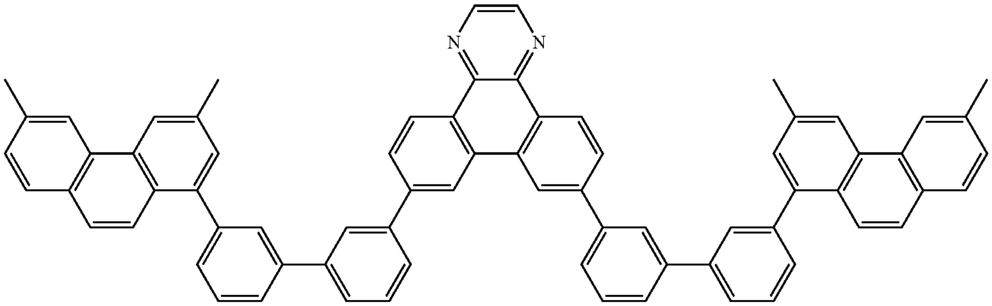
B7
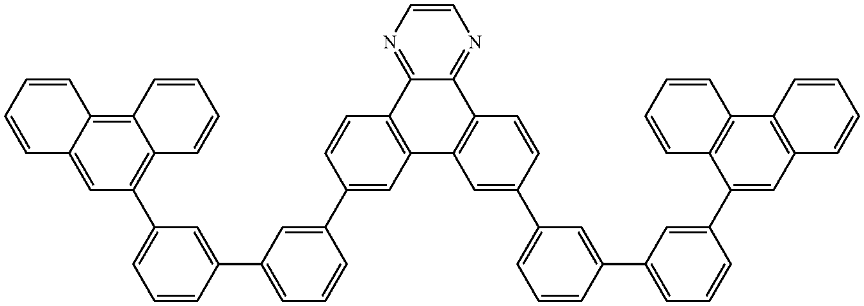
B8
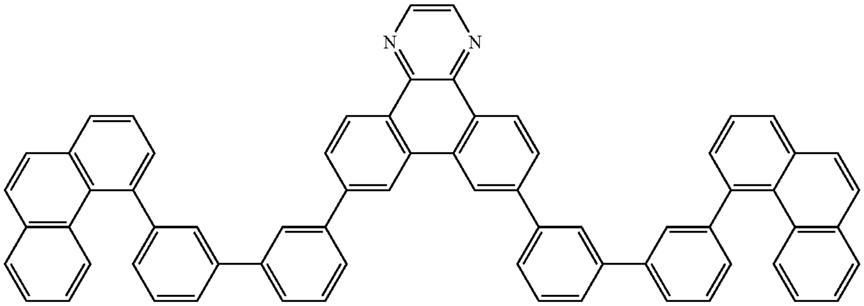

-continued
B9
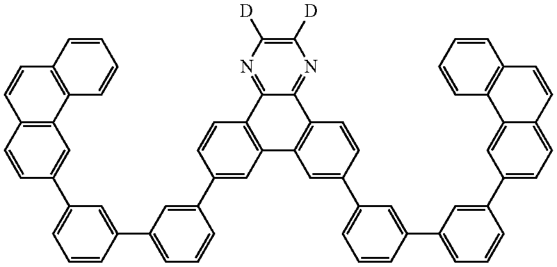
B10
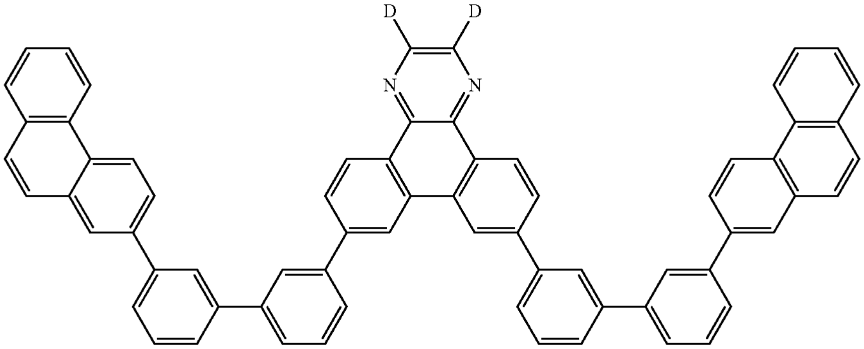
B11
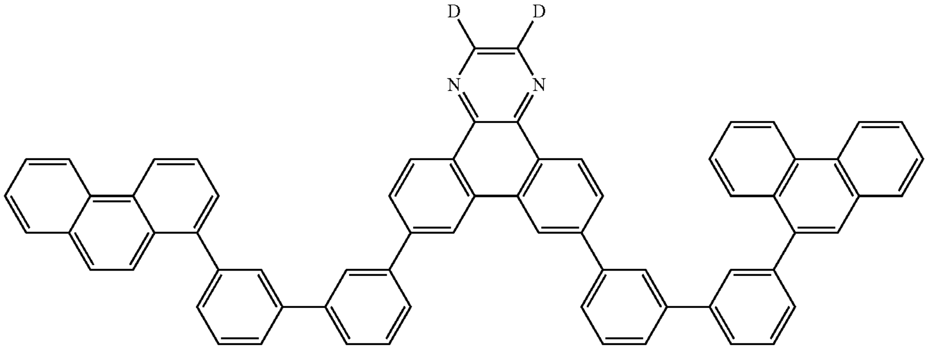
B12
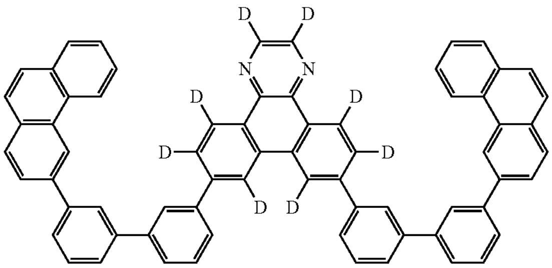
B13
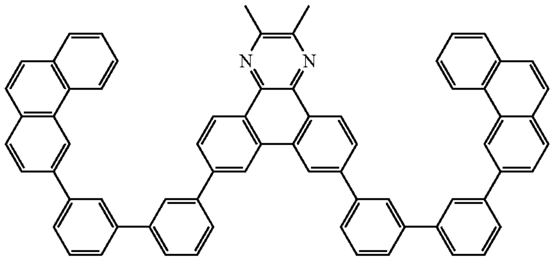
B14
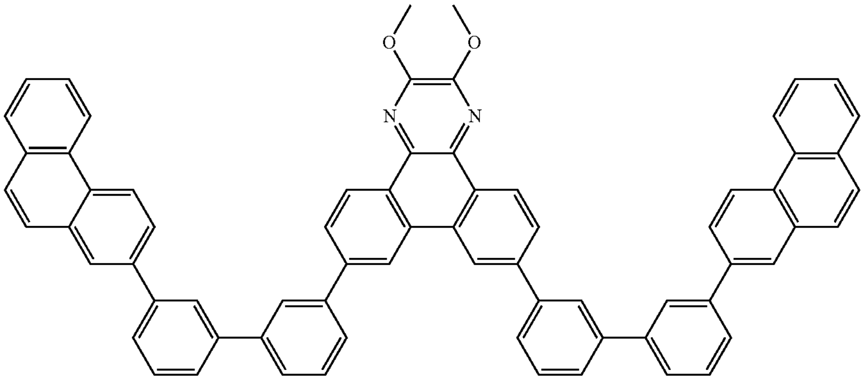

-continued
B15
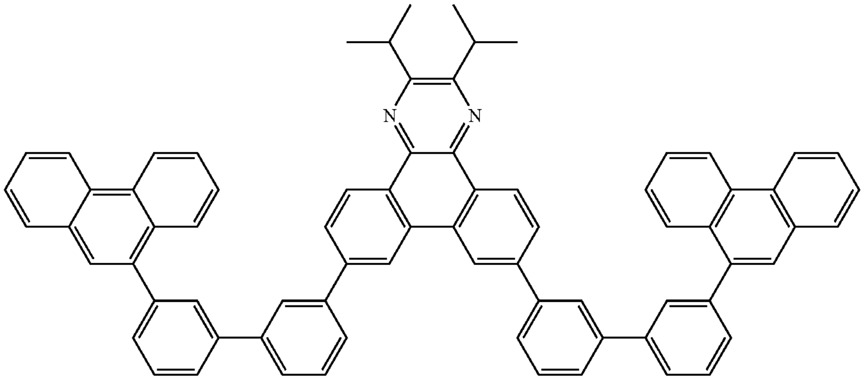
B16
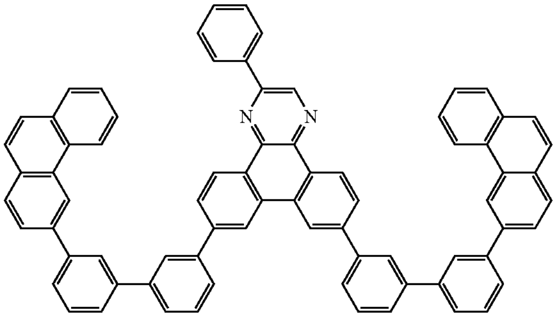
B17
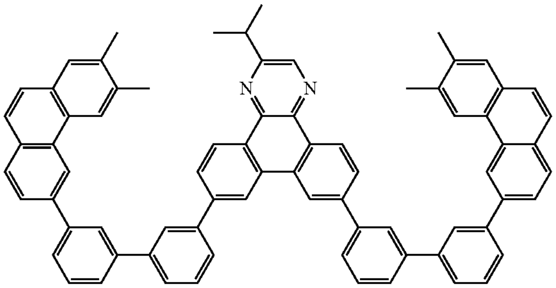
B18
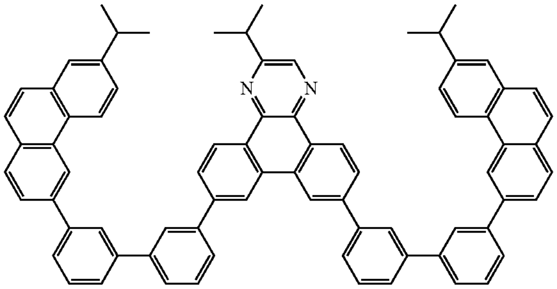
B19
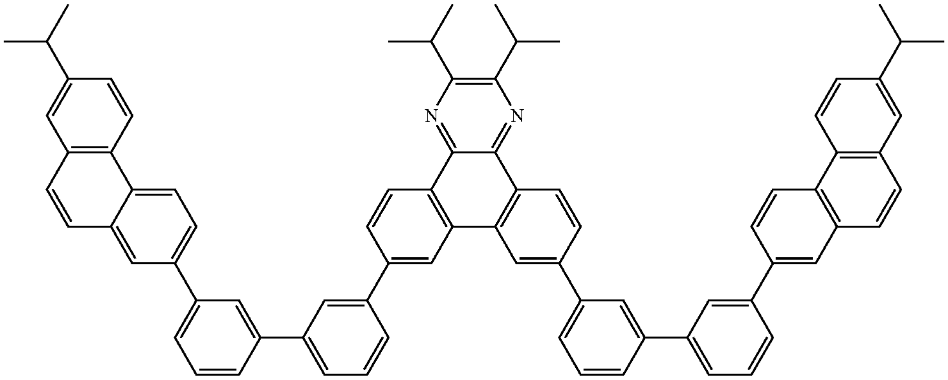

-continued
B20
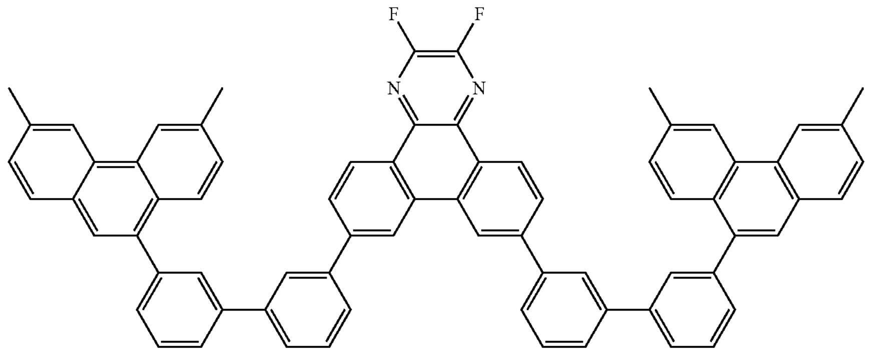
C1
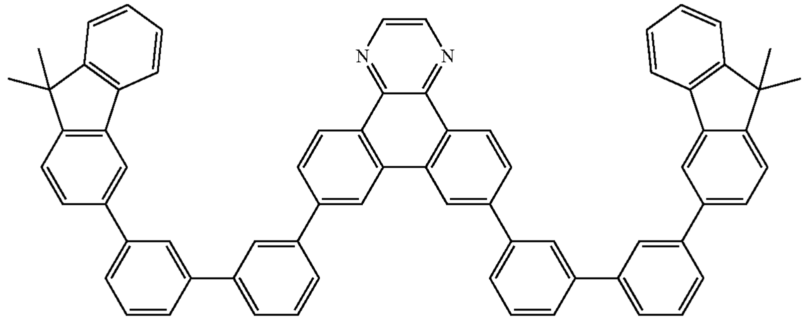
C2
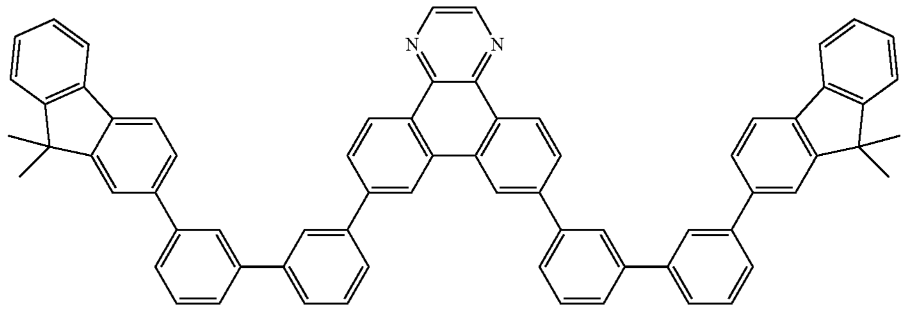
C3
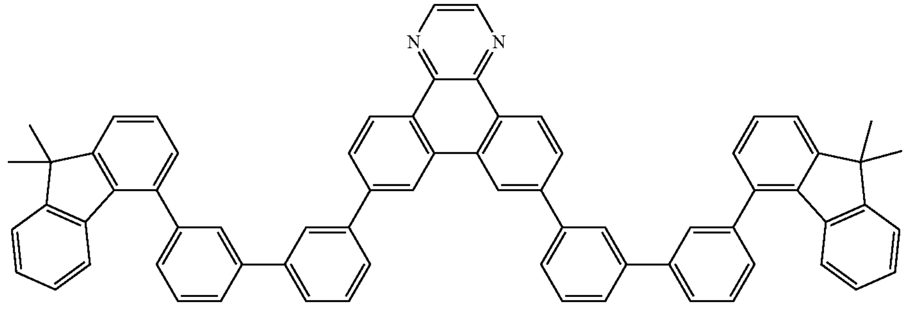
C4
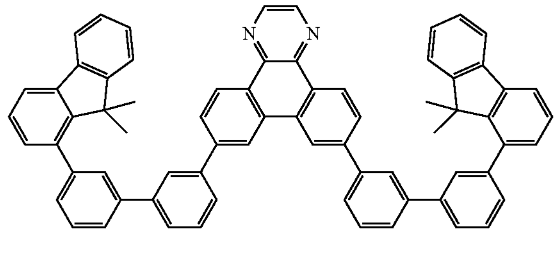

-continued
C5
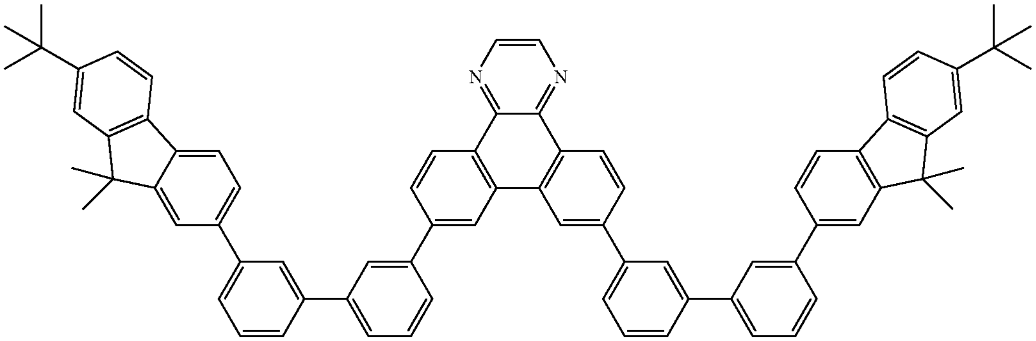
C6
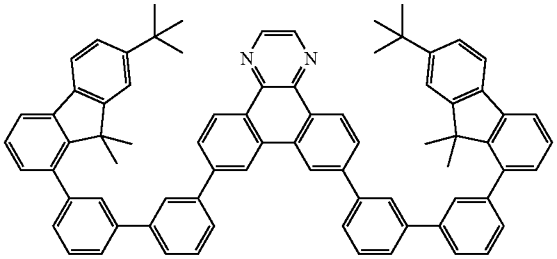
C7
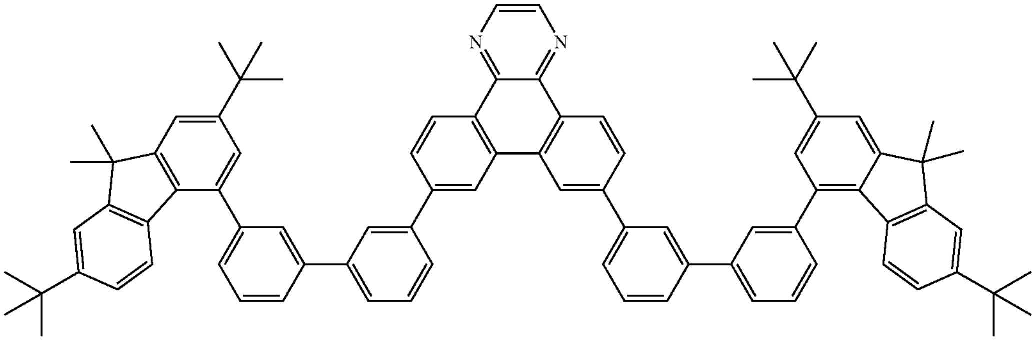
C8
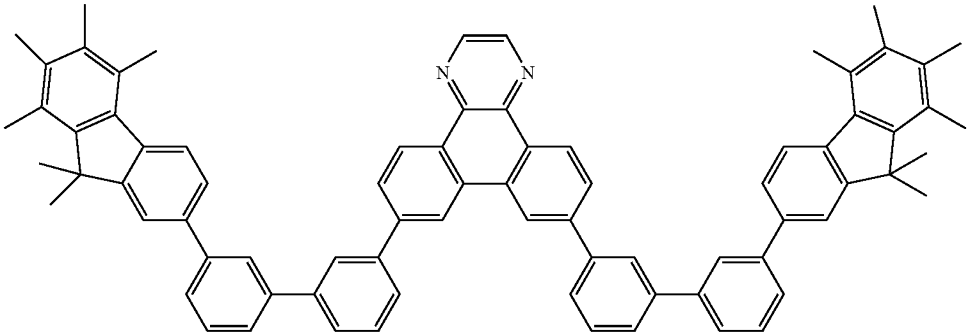
C9
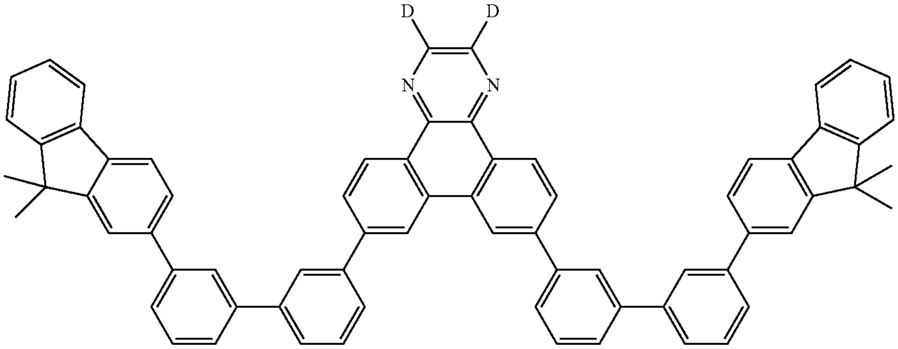

-continued
C10
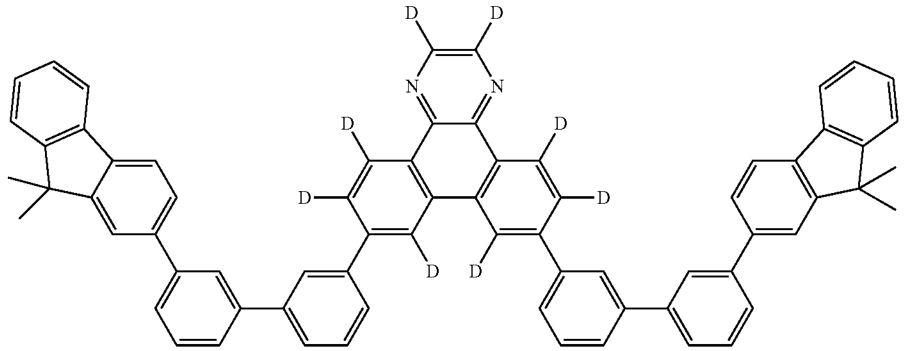
C11
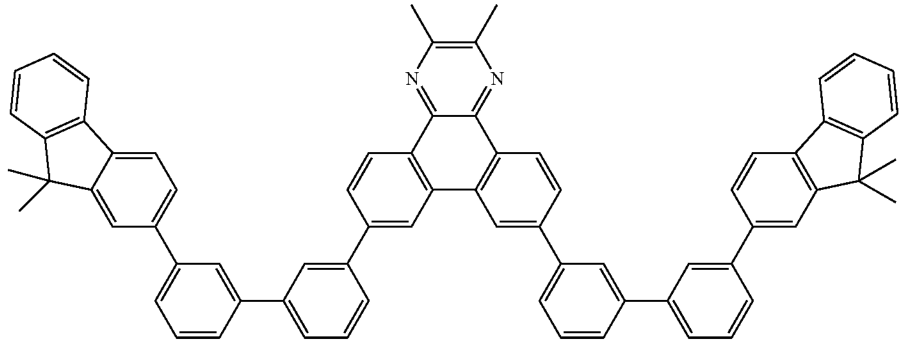
C12
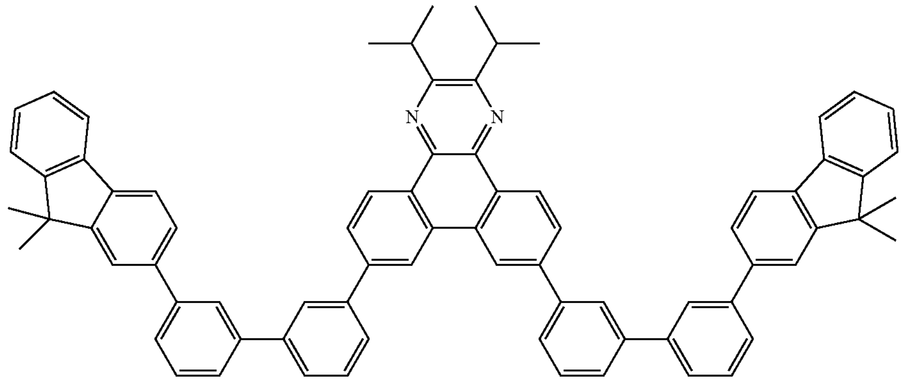
C13
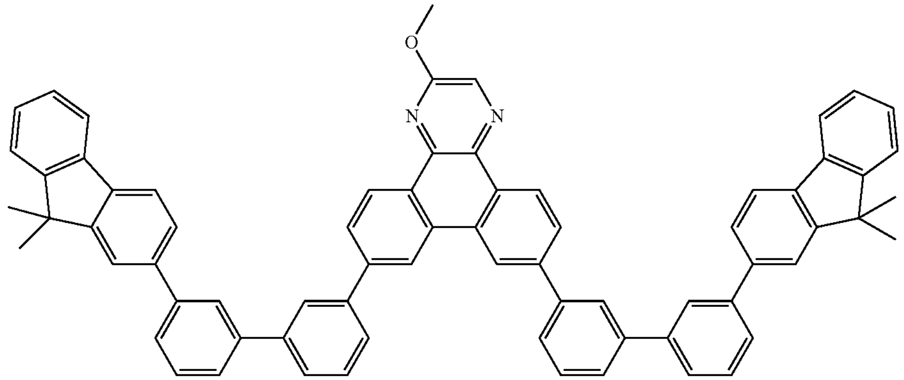

-continued

C14

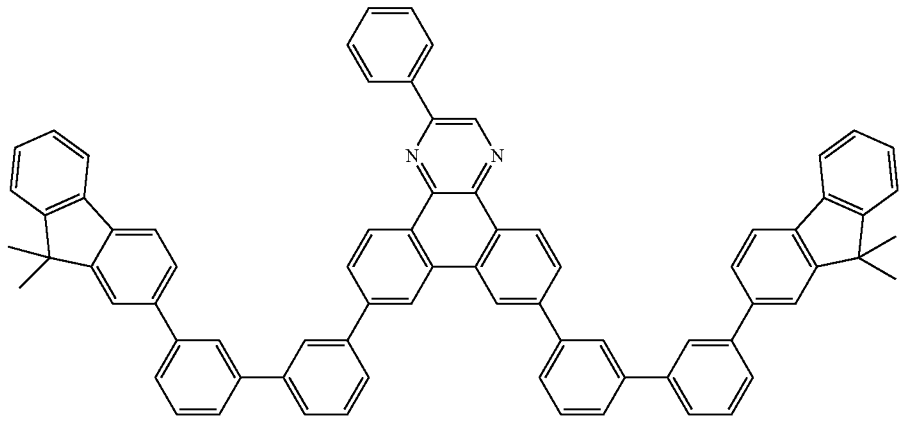

Exemplary compounds belonging to a group A are compounds in which B has a structure denoted by (B-1) to (B-6) and in which condensed rings B at both ends include a dibenzofuran ring, a dibenzothiophene ring, or a carbazole ring. These compounds are compounds in which, in particular, the carrier balance is readily adjusted since an oxygen atom, a sulfur atom, or a nitrogen atom is included in the condensed ring B, and the electric charge transportability is enhanced due to plentiful unshared electron pairs included in these atoms.

Exemplary compounds belonging to a group B are compounds in which B has a structure denoted by (B-7) to (B-11) and in which condensed rings B at both ends are composed of $SP^2$ carbon. These compounds are compounds having, in particular, excellent stability since the condensed ring is composed of an $SP^2$ hybrid orbital.

Exemplary compounds belonging to a group C are compounds in which B has a structure denoted by (B-12) to (B-15) and in which condensed rings B at both ends include a fluorene ring. These compounds including a methyl group at position 9 of the fluorene ring in a direction perpendicular to the in-plane direction of the fluorene ring enables condensed rings to be particularly suppressed from overlapping one another. Further, since including a tertiary alkyl group such as a t-Bu group as $R_9$ to $R_{15}$ enables intermolecular interaction to be suppressed from occurring, the compound has excellent sublimation properties regardless of a large molecular weight.

Properties of Organic Compound

Next, the properties of the organic compound according to the present embodiment will be described. The organic compound according to the present embodiment has the following characteristics and, therefore, is a compound having high $S_1$ (singlet energy) and $T_1$ (triplet energy) and having excellent film performance and sublimation properties. Further, the compound being used enables an organic light-emitting element having excellent light emission efficiency and element durability to be provided.

(1) high $S_1$ and $T_1$ due to a 1,1'-biphenylene group that has a condensed ring B of three or more rings at position 3' being bonded to positions 7 and 10 of dibenzo[f,h]quinoxaline (2) high compound stability due to two 1,1'-biphenylene groups being included in the molecule, a hydrogen atom being included at a substitution position other than positions 3 and 3' of the biphenylene group, and no substituent that increases a bonding distance being included (1) $S_1$ and $T_1$ are high due to a 1,1'-biphenylene group that has a condensed ring B of three or more rings at position 3' being bonded to positions 7 and 10 of dibenzo[f,h]quinoxaline.

Regarding the disclosure of the organic compound according to the present embodiment, the present inventors paid attention to the structure of a phenylene chain. Specifically, the organic compound according to the present embodiment has a structure in which a dibenzo[f,h]quinoxaline ring serves as a center and is bonded to each of two condensed rings B of three or more rings with a 1,1'-biphenylene group interposed therebetween. In the structure, since the dibenzo[f,h]quinoxaline ring and the condensed ring B of three or more rings are bonded to position 3 and position 3', respectively, of the 1,1'-biphenylene group serving as a coupling group, $S_1$ (singlet energy) and $T_1$ (triplet energy) are increased.

In this regard, the results of comparisons of each of $S_1$ (singlet energy) and $T_1$ (triplet energy) between Exemplary compound A4 that is the organic compound according to the present embodiment and Comparative compound 1-C are presented in Table 1. Herein, $S_1$ (singlet energy) and $T_1$ (triplet energy) were determined based on molecular orbital calculation.

TABLE 1

| | Structure | $S_1$(eV) | $T_1$(eV) |
|---|---|---|---|
| Exemplary compound A4 | 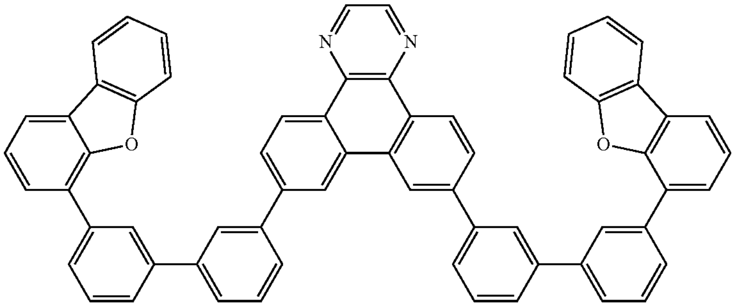 [SMILES: c1cc(-c2cccc(-c3cccc4c3oc3ccccc34)c2)cc(-c2ccc3c(c2)c2cc(-c4cccc(-c5cccc(-c6cccc7c6oc6ccccc67)c5)c4)ccc2c2nccnc32)c1] | 3.58 | 2.73 |
| Comparative compound 1-C | 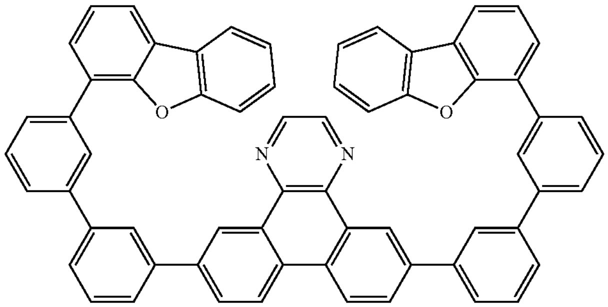 [SMILES: c1cc(-c2cccc(-c3cccc4c3oc3ccccc34)c2)cc(-c2ccc3c4ccc(-c5cccc(-c6cccc(-c7cccc8c7oc7ccccc78)c6)c5)cc4c4nccnc4c3c2)c1] | 3.28 | 2.63 |

As presented in Table 1, $S_1$ of Exemplary compound A4 is 3.58 eV, and $T_1$ is 2.73 eV. On the other hand, $S_1$ of Comparative compound 1-C is 3.28 eV, and $T_1$ is 2.63 eV. Consequently, it is clear that Exemplary compound A4 exhibits higher values with respect to both $S_1$ and $T_1$.

The reason for this is conjectured to be that the coupling group includes a 1,1'-biphenylene structure and that the coupling group is bonded to position 7 and position 10 of the dibenzo[f,h]quinoxaline ring.

Figure 1B:
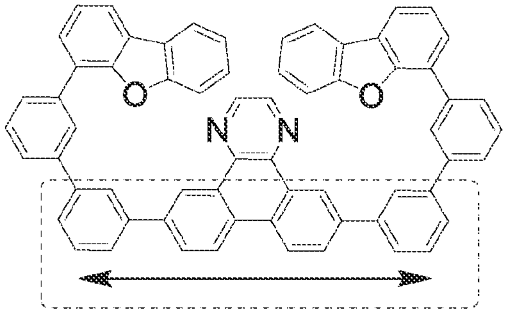

That is, when two 1,1'-biphenylene groups are bonded to position 6 and position 11, respectively, of the dibenzo[f,h]quinoxaline ring (positions-6,11-substituted product illustrated in FIG. 1B), in the structure, two benzene rings included in the dibenzo[f,h]quinoxaline ring, a benzene ring included in the biphenylene group bonded to position 6, and a benzene ring included in the biphenylene group bonded to position 11 are arranged on a straight line. That is, in the structure, four benzene rings are arranged on a straight line. Consequently, a conjugated system is elongated, and both $S_1$ and $T_1$ are reduced. On the other hand, when two 1,1'-biphenylene groups are bonded to position 7 and position 10, respectively, of the dibenzo[f,h]quinoxaline ring (positions-7,10-substituted product illustrated in FIG. 1A), in the structure, a pyrazine ring and one of benzene rings included in the dibenzo[f,h]quinoxaline ring and one of a benzene ring included in the biphenylene group bonded to position 7 and a benzene ring included in the biphenylene group bonded to position 10 are arranged on a straight line. That is, in the structure, three aromatic or benzene rings are arranged on a straight line. Consequently, a conjugated system being shortened compared with when two 1,1'-biphenylene groups are bonded to position 6 and position 11, respectively, of the dibenzo[f,h]quinoxaline ring enables $S_1$ and $T_1$ to be increased.

Herein, effects of the $S_1$ energy and the $T_1$ energy being high will be described. A phosphorescence light-emitting element is an organic light-emitting element which uses $T_1$ energy for emitting light. A light-emitting layer host material of the organic light-emitting element can have higher $T_1$ energy than the phosphorescence light-emitting material which emits phosphorescence. Regarding use as a carrier blocking layer around the light-emitting layer, $S_1$ can be high in addition to high $T_1$. In general, the $S_1$ energy increases with increased $T_1$ energy. On the other hand, high $S_1$ energy corresponds to a large band gap. Consequently, regarding use as the light-emitting layer host material or the carrier blocking layer around the light-emitting layer, the stability is high under excessive concentration of excitons or unnecessary electric charge accumulation, and advantages can be provided in element durability. Therefore, the organic compound can have sufficiently high $S_1$ energy and $T_1$ energy.

The organic compound according to the present embodiment has sufficiently high $S_1$ energy and $T_1$ energy since the coupling group such as a 1,1'-biphenylene group is included at position 7 and position 10 of the dibenzo[f,h]quinoxaline ring and the condensed ring B is included at position 3'. Consequently, the organic compound being used as the light-emitting layer host material or the carrier blocking layer of the organic light-emitting element enables an element having a high efficiency and a long life to be provided.

In this regard, the calculation technique of the molecular orbital calculation method used a currently widespread density functional theory (DFT). Regarding a functional, B3LYP was used, and regarding a basis function, 6-31G* was used. In this regard, the molecular orbital calculation method was performed based on a currently widespread Gaussian09 (Gaussian09, RevisionC. 01, M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T.

Vreven, J. A. Montgomery, Jr., J. E. Peralta, F. Ogliaro, M. Bearpark, J. J. Heyed, E. Brothers, K. N. Kudin, V. N. Staroverov, T. Keith, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Danneberg, S. Dapprich, A. D. Daniels, O. Farkas, J. B. Foresman, J. V. Ortiz, J. Cioslowski, and D. J. Fox, Gaussian, Inc., Wallingford CT, 2010.).

(2) The compound stability is high due to two 1,1'-biphenylene groups being included in the molecule, a hydrogen atom being included at a substitution position other than positions 3 and 3' of the 1,1'-biphenylene group, and no substituent that increases a bonding distance being included.

Regarding the disclosure of the organic compound according to the present embodiment, the present inventors paid attention to the degree of freedom of rotation of a bond included in the organic compound. Specifically, the organic compound according to the present embodiment has a structure in which condensed rings of three or more rings, including a dibenzo[f,h]quinoxaline ring, are bonded to position 3 and position 3' of two 1,1'-biphenylene group. Further, the organic compound according to the present embodiment has a structure in which a hydrogen atom is included at a substitution position other than positions 3 and 3' of the 1,1'-biphenylene group, and no substituent that increases a bonding distance is included. Consequently, the organic compound has a high degree of freedom of rotation.

In this regard, the results of comparisons of the thermal properties between Exemplary compound A4 that is the organic compound according to the present embodiment and Comparative compound 1-A are presented in Table 2. Herein, Comparative compound 1-A is Compound 1-A described in US 2014/0034925.

TABLE 2

| | Structure | Glass transition temperature (° C.) | Crystallization temperature (° C.) |
|---|---|---|---|
| Exemplary compound A4 | 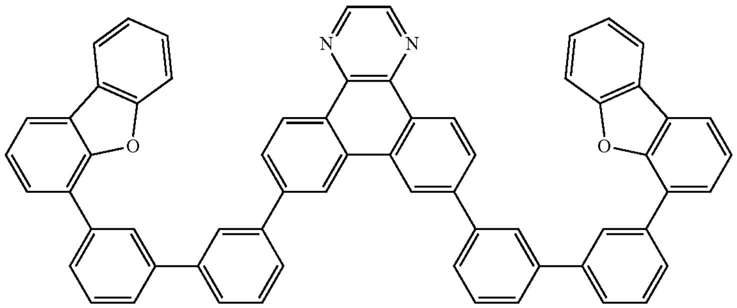 [SMILES: c1cc(-c2cccc(-c3cccc4c3oc3ccccc34)c2)cc(-c2ccc3c(c2)c2cc(-c4cccc(-c5cccc(-c6cccc7c6oc6ccccc67)c5)c4)ccc2c2nccnc32)c1] | 133 | not observed |
| Comparative example 1-A | 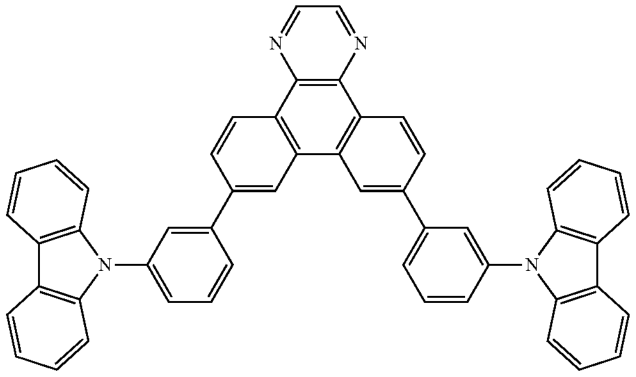 [SMILES: c1cc(-c2ccc3c(c2)c2cc(-c4cccc(-n5c6ccccc6c6ccccc65)c4)ccc2c2nccnc32)cc(-n2c3ccccc3c3ccccc32)c1] | 155 | 304 |

As presented in Table 2, the molecular weight increases and, further, the degree of freedom of rotation of the bond increases due to biphenylene groups that bond the condensed rings B at both ends of the molecular structure.

In Comparative compound 1-A, carbazole rings are present as condensed rings at both ends, and a phenylene group serving as a coupling group is included between the carbazole ring and the dibenzoquinoxaline ring at the center. On the other hand, regarding the Exemplary compound A4, it is clear that the degree of freedom of rotation is larger than the Comparative compound 1-A since dibenzofuran rings are present as condensed rings B at both ends, and a biphenylene group serving as a coupling group is included between the dibenzofuran ring and the dibenzoquinoxaline ring at the center.

Since the molecular weight increases and, further, the degree of freedom of rotation of the bond increases due to biphenylene groups serving as a coupling group being introduced, the following effects are exerted.

First, the molecular weight being increased enables molecular packing in which molecules overlap one another to be suppressed from occurring, crystallization does not readily occur, and amorphousness is enhanced. In this regard, high amorphousness, that is, good film performance, is favorable in use for an organic light-emitting element. The reason for this is that crystal grain boundaries in accordance with fine crystallization, a trap level, and quencher generation do not readily occur during operation of the element due to high amorphousness, and that favorable carrier transportability and highly efficient light emission characteristics are maintained. As a result, an organic light-emitting element having excellent durability and efficiency is provided.

Herein, Table 2 presents the results of evaluation of the glass transition temperature and the crystallization temperature of Exemplary compound A4 and Comparative compound 1-A based on the differential scanning calorimetry (DSC) measurement. It can be said that glass transition temperature being higher and the crystallization temperature being high or not observed correspond to high amorphousness and excellent thermal stability. Regarding the DSC measurement, the glass transition temperature and the crystallization temperature were measured by sealing about 2 mg of sample in an aluminum pan, performing rapid cooling from a high temperature higher than the melting temperature so as to make the sample to take on an amorphous state, and increasing the temperature at a temperature increasing rate of 10° C./min. Regarding a measurement apparatus, DSC 204 F1 produced by NETZSCH was used.

Comparative compound 1-A had a glass transition temperature of 155° C., and the crystallization temperature was observed at 304° C. during increasing of the temperature. On the other hand, Exemplary compound A4 had a glass transition temperature of 133° C. and the crystallization temperature was not observed during increasing of the temperature. That is, there is no risk of a thin film formed by heat vapor deposition in a vacuum being crystallized, and it can be said that the compound has high amorphousness and more excellent thermal stability. Therefore, it is possible to provide an organic light-emitting element that is capable of maintaining a stable amorphous film during operation of the element and that has a long life.

Second, the degree of freedom of rotation being increased enables the sublimation temperature to be lowered so as to enhance the sublimation properties. When the degree of freedom of rotation is low, the sublimation properties are deteriorated since organic compounds readily aggregate with each other. Regarding Exemplary compound A4, since the molecular weight is simply increased compared with Comparative compound 1-A, the sublimation properties tend to be readily deteriorated. However, since the 1,1'-biphenylene groups are used as the coupling groups of three condensed rings present in the molecule so that the condensed rings are bonded at positions 3 and 3' of the 1,1'-biphenylene groups, the degree of freedom of rotation is high so that intermolecular stacking is readily avoided. Therefore, a favorable film having no problem in sublimation properties is formed.

In this regard, the evaluation of the light emission characteristics and the thermal stability described in the features (1) and (2) of the organic compound according to the present embodiment will be described in the examples later in more detail.

In addition, when the organic compound according to the present embodiment further has the following features, the organic compound is particularly suitable for an organic light-emitting element.

(3) condensed rings B at both ends including no $SP^3$ carbon (4) condensed rings B at both ends being bonded to coupling groups at substitution positions without interference due to steric hindrance These features will be described below.

(3) The condensed rings B at both ends include no $SP^3$ carbon.

Regarding the organic compound according to the present embodiment, the dibenzoquinoxaline ring and the biphenylene group serving as the coupling group can include no $SP^3$ carbon, and, in addition, the condensed rings B at both ends can include no $SP^3$ carbon. The reason for this is that since a carbon-carbon bond of $SP^2$ carbon has a large bonding energy, cleavage of the bond is not readily occur during operation of the organic light-emitting element. Consequently, from the viewpoint of an improvement of element durability, the condensed rings B at both ends can have no $SP^3$ carbon. Specifically, B can have a structure denoted by (B-1) to (B-11), and the condensed ring B can be a phenanthrene ring, a dibenzofuran ring, a dibenzothiophene ring, or a carbazole ring.

(4) The condensed rings B at both ends are bonded to coupling groups at substitution positions without interference due to steric hindrance.

In the organic compound according to the present embodiment, the condensed rings B at both ends can be bonded to the coupling groups at substitution positions without interference due to steric hindrance. The reason for this is that when interfere between the condensed ring B and the coupling group due to steric hindrance does not occur, since the bonding distance between the condensed ring B and the coupling group is not readily increased, the bond is not readily cleaved.

Herein, the result of a comparison of the bonding distance between Exemplary compound B2 and Exemplary compound B3 is presented in Table 3.

TABLE 3

| | Structure | Dihedral angle of bond a |
|---|---|---|
| Exemplary compound B2 | 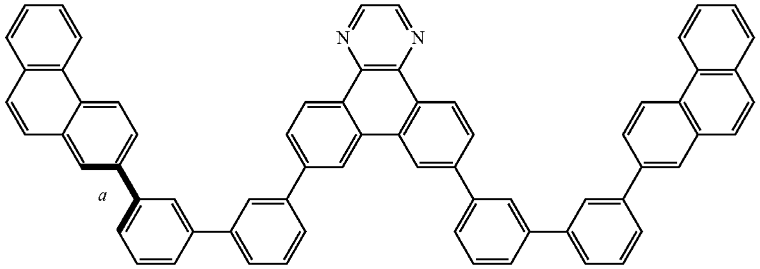 | 36.5° |

TABLE 3-continued

| | Structure | Dihedral angle of bond a |
|---|---|---|
| Exemplary compound B3 | 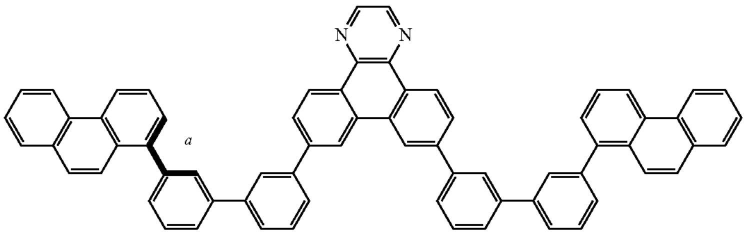 | 57.0° |

In Table 3, the bond between the condensed ring B and the coupling group is denoted as a, and the dihedral angle thereof is presented. The dihedral angle of Exemplary compound B2 is 36.5°, whereas the dihedral angle of Exemplary compound B3 is 57.0°. This means that Exemplary compound B2 has higher planarity under the influence of steric hindrance of a hydrogen atom at peri-position of the phenanthrene ring. A carrier mobility increases with increasing planarity. Regarding a structure having high planarity such as Exemplary compound B2, the heat resistance is improved and a bond is not readily cleaved.

Therefore, the condensed ring B can be bonded to the coupling group at a substitution position without interference due to steric hindrance.

In this regard, the bonding distance was visualized using the molecular orbital calculation.

Organic Light-Emitting Element

The organic light-emitting element according to the present embodiment includes at least a pair of electrodes composed of an anode and a cathode and an organic compound layer disposed between the electrodes. In the organic light-emitting element according to the present embodiment, the organic compound layer may be a single layer or a stacked body composed of a plurality of layers provided that a light-emitting layer is included. Herein, when the organic compound layer is a stacked body composed of a plurality of layers, the organic compound layer may include, in addition to a light-emitting layer, a hole injection layer, a hole transport layer, an electron blocking layer, a hole exciton blocking layer, an electron transport layer, an electron injection layer, and the like. In this regard, the light-emitting layer may be a single layer or a stacked body composed of a plurality of layers.

In the organic light-emitting element according to the present embodiment, the organic compound according to the present embodiment is contained in at least one layer of the organic compound layer. Specifically, the organic compound according to the present embodiment is contained in any one of the light-emitting layer, the hole injection layer, the hole transport layer, the electron blocking layer, the light-emitting layer, the hole exciton blocking layer, the electron transport layer, the electron injection layer, and the like. The organic compound according to the present embodiment can be contained in the light-emitting layer.

In the organic light-emitting element according to the present embodiment, when the organic compound according to the present embodiment is contained in the light-emitting layer, the light-emitting layer may be a layer composed of only the organic compound according to the present embodiment or a layer composed of the organic compound according to the present embodiment and other compounds. Herein, when the light-emitting layer is composed of the organic compound according to the present embodiment and other compounds, the organic compound according to the present embodiment may be used as a host of the light-emitting layer or may be used as a guest. Alternatively, the organic compound may be used as an assist material that may be contained in the light-emitting layer. In this regard, the host is a compound having the largest mass ratio in the compounds constituting the light-emitting layer. The guest is a compound that has a smaller mass ratio than the host in the compounds constituting the light-emitting layer and that has a responsibility for main light emission. The assist material is a compound that has a smaller mass ratio than the host in the compounds constituting the light-emitting layer and that assists the guest in emitting light. In this regard, the assist material is also called a second host.

The present inventors performed various research and found that the organic compound according to the present embodiment being used as the host or the assist of the light-emitting layer, in particular, as the host, enables an element which produces high-efficiency and high-luminance optical output and which has very high durability to be obtained. The light-emitting layer may be a single layer or a multilayer and, for example, color mixing may be performed by setting the emission color of the present embodiment to be green color emission and containing a light-emitting material having another emission color. The multilayer means a state in which the light-emitting layer and another light-emitting layer are stacked. In such an instance, the emission color of the organic light-emitting element is not limited to green. More specifically, the emission color may be a white color or may be an intermediate color. When the color is white, other light-emitting layers emit colors other than green, that is, blue and red. Regarding a film formation method, the film is formed by vapor deposition or coating film formation. The detail will be described later in the example.

The organic compound according to the present embodiment may be used as a constituent material of organic compound layers other than the light-emitting layer constituting the organic light-emitting element according to the present embodiment. Specifically, the organic compound may be used as a constituent material of the electron transport layer, the electron injection layer, the hole transport layer, the hole injection layer, the hole blocking layer, and the like. In such an instance, the emission color of the organic light-emitting element is not limited to green. More specifically, the emission color may be a white color or may be an intermediate color.

The compound according to the present embodiment can be used in the light-emitting layer in the organic light-emitting element under the following conditions.

(1) content of the compound according to the present embodiment used in the light-emitting layer being 30% by mass or more and 99% by mass or less (2) a light-emitting material mixed with the compound according to the present embodiment in the light-emitting layer being a phosphorescence light-emitting material, and the phosphorescence light-emitting material being an organometallic complex including a condensed ring of three or more rings as a ligand The above-described conditions will be described below.

(1) The content of the compound according to the present embodiment used in the light-emitting layer is 30% by mass or more and 99% by mass or less.

When the organic compound according to the present embodiment is used for the light-emitting layer, the content can be 30% by mass or more and 99% by mass or less relative to a total light-emitting layer. The organic compound according to the present embodiment has high amorphousness and, therefore, is a material suitable for the host material of the light-emitting layer. When the organic compound is used as the host material, the content is preferably 50% by mass or more and 99% by mass or less and more preferably 70% by mass or more and 99% by mass or less. The compound is a hard-to-crystallize material even when used at a content of 99% by mass and, therefore, realizes a function with excellent characteristics. From the viewpoint of an improvement in the film performance of the light-emitting layer, the organic compound may be used as the assist material. When the organic compound is used as the assist material, the content may be 30% by mass or more and less than 50% by mass. This is caused by the structural feature of the organic compound according to the present embodiment. Since the compound is not readily aggregated so that crystal boundaries due to aggregation of molecules do not readily occur even under operation of the organic light-emitting element, a light-emitting element having excellent characteristics is provided.

(2) A light-emitting material mixed with the compound according to the present embodiment in the light-emitting layer is a phosphorescence light-emitting material, and the phosphorescence light-emitting material is an organometallic complex including a condensed ring of three or more rings as a ligand.

The organic compound according to the present embodiment is a compound including a condensed ring B of three or more rings at both ends. Consequently, the phosphorescence light-emitting material used with the organic compound according to the present embodiment in the light-emitting layer can have a structure in which π conjugation of the ligand is extended. More specifically, an organometallic complex including a condensed ring of three or more rings in a structure of the ligand can be adopted. The reason for this is that, in a manner similar to the organic compound according to the present embodiment that serves as the host material, the organometallic complex that serves as the guest material having a high-planarity structure enables high-planarity sections to approach one another due to an interaction. More specifically, a planar portion of the host material and a ligand of the organometallic complex readily approach one another. Consequently, it is expected that the intermolecular distance between the host material and the organometallic complex be reduced.

Herein, regarding the triplet energy used for the phosphorescence light-emitting material, it is known that energy is transferred due to Dexter electron transfer. In the Dexter electron transfer, energy is transferred by contact of molecules with each other. That is, the intermolecular distance between the host material and the guest material being reduced makes energy transfer from the host material to the guest material to be performed efficiently. The high-planarity organometallic complex that includes a condensed ring of three or more rings in the structure of the ligand being used reduces the intermolecular distance between the host material that is an organic compound according to the present embodiment and the organometallic complex so that energy transfer from the host to the organometallic complex readily occurs. As a result, a high-efficiency organic light-emitting element is provided.

In this regard, the high-planarity condensed ring structure of three or more rings included in the ligand denotes, for example, a triphenylene ring, a phenanthrene ring, a fluorene ring, a benzofluorene ring, a dibenzofuran ring, a dibenzothiophene ring, a benzoisoquinoline ring, and a naphthoisoquinoline ring. That is, the organometallic complex in which at least any one of these structures is included in the ligand being used for the light-emitting material enables the organic compound according to the present embodiment to provide a higher-efficiency light-emitting element.

Specific Example of Organometallic Complex

Specific examples of the organometallic complex are described below, but the organometallic complex is not limited to these, as a matter of course. Specific examples of the organometallic complex include organometallic complexes having a partial structure denoted by formulae [Ir-1] to [Ir-16] below.

[Ir-1]

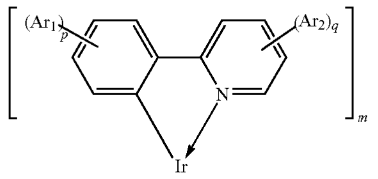

[Ir-2]

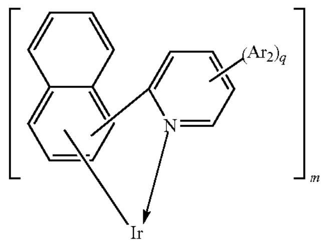

[Ir-3]

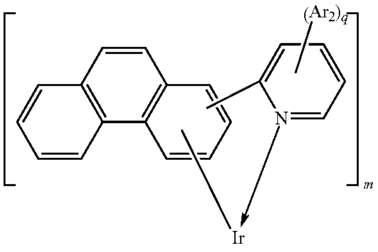

[Ir-4]
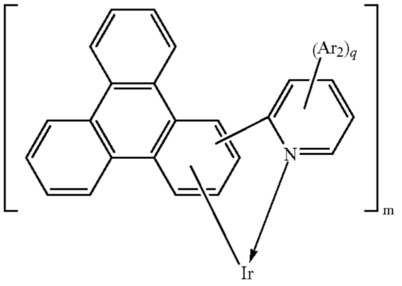
[Ir-5]
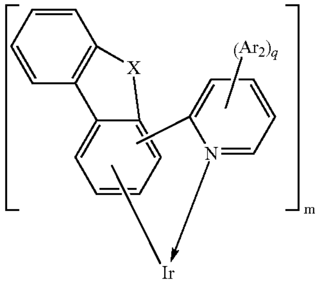
[Ir-6]
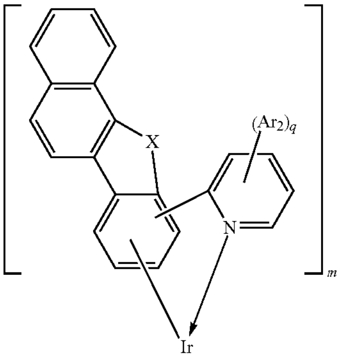
[Ir-7]
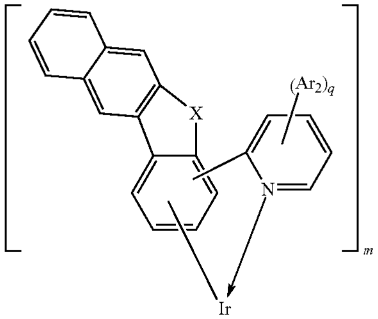
[Ir-8]
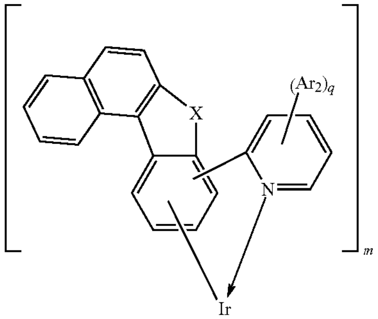
[Ir-9]
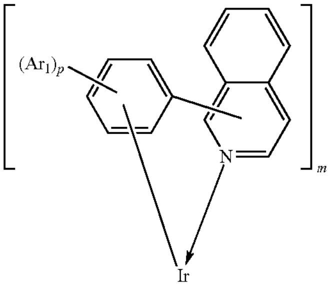
[Ir-10]
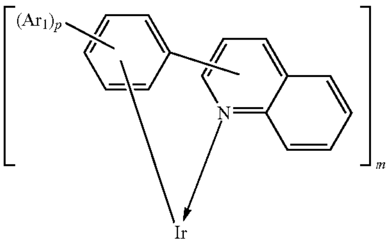
[Ir-11]
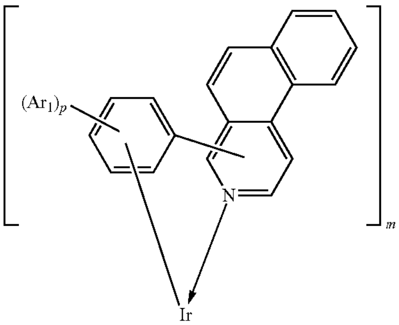
[Ir-12]
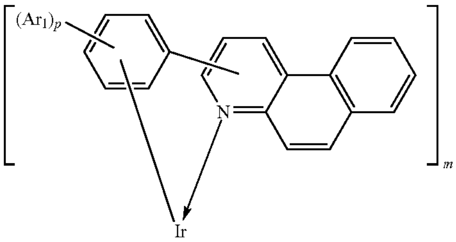
[Ir-13]
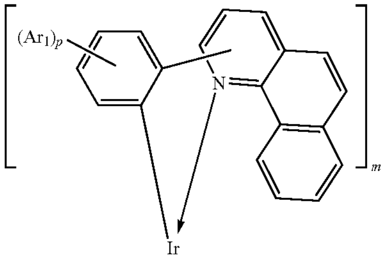

-continued

[Ir-14]

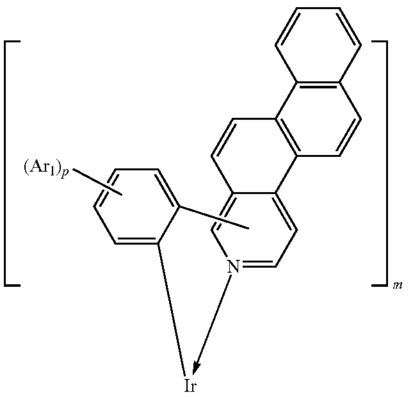

[Ir-15]

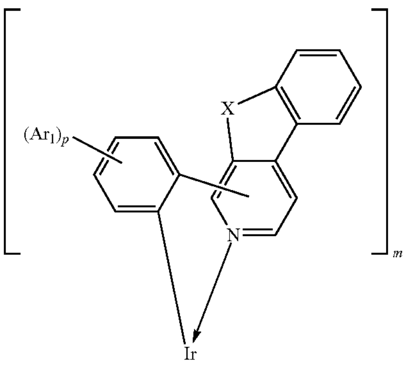

[Ir-16]

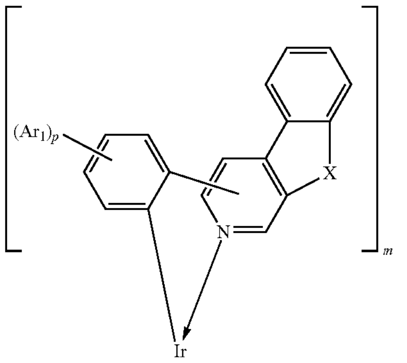

In formulae [Ir-1] to [Ir-16], each of $Ar_1$ and $Ar_2$ is selected from the group consisting of a deuterium atom, a substituted or unsubstituted alkyl group, a substituted or unsubstituted silyl group, a substituted or unsubstituted aromatic hydrocarbon group, a substituted or unsubstituted heterocyclic group, and a cyano group, p represents an integer of 0 or more and 4 or less, when p is 2 or more, a plurality of $Ar_1$s may be the same or differ from each other, q represents an integer of 0 or more and 4 or less, and when q is 2 or more, a plurality of $Ar_2$s may be the same or differ from each other.

X is selected from the group consisting of an oxygen atom, a sulfur atom, a substituted or unsubstituted carbon atom, and a substituted or unsubstituted nitrogen atom. Examples of the substituent of the carbon atom or the nitrogen atom include a substituted or unsubstituted alkyl group and a substituted or unsubstituted aromatic hydrocarbon group.

m represents an integer of 1 or more and 3 or less, and when m is 2 or more, a plurality of ligands may be the same or differ from each other.

A condensed ring bonded to a pyridine ring in formulae [Ir-1] to [Ir-8] and a condensed ring bonded to a benzene ring in formulae [Ir-9] to [Ir-16] may have a substituent such as a deuterium atom, a halogen atom, a substituted or unsubstituted alkyl group, a substituted or unsubstituted alkoxy group, and a cyano group.

Examples of the halogen atom, the alkyl group, the alkoxy group, the silyl group, the aromatic hydrocarbon group, and the heterocyclic group in formulae [Ir-1] to [Ir-16] include the materials akin to that described with respect to $R_1$ to $R_8$, but the above are not limited to these materials. The carbon number of the alkyl group is preferably 1 or more and 10 or less. In this regard, specific examples of the substituent that may be further included in the alkyl group, the silyl group, the aromatic hydrocarbon group, or the heterocyclic group include the materials akin to that described with respect to $R_1$ to $R_8$, but the substituent is not limited to these materials.

Of the organometallic complexes having a partial structure denoted by formulae [Ir-1] to [Ir-16] above, organometallic complexes including a condensed ring of three or more rings in the ligand are further favorable. Specifically, the favorable organometallic complex has a partial structure denoted by formulae [Ir-3] to [Ir-8] or [Ir-11] to [Ir-16] above. Specific examples of the organometallic complex are described below, but the organometallic complex is not limited to these, as a matter of course.

AA1

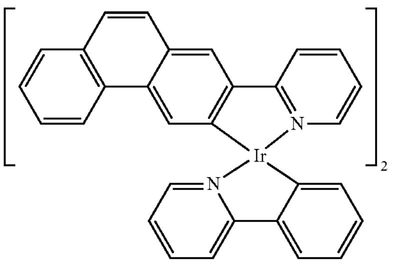

AA2

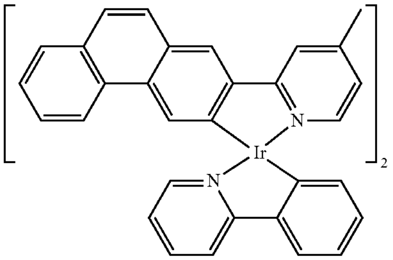

AA3

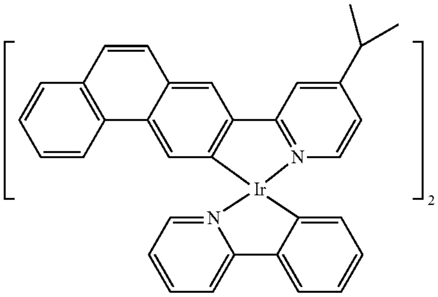

AA4
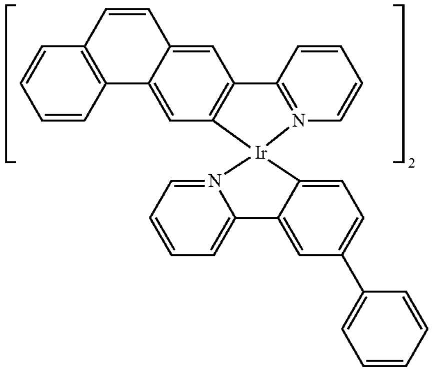
AA5
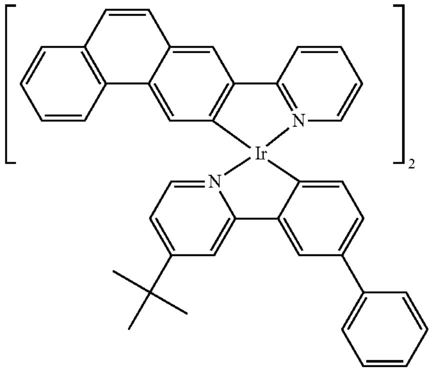
AA6
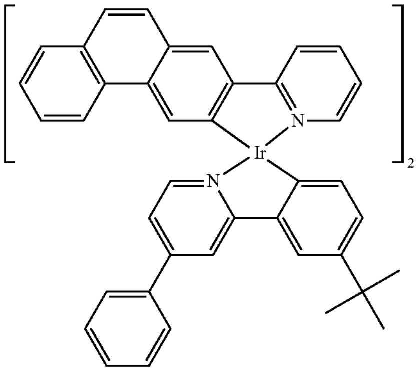
AA7
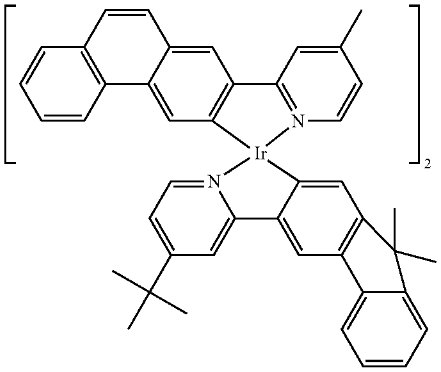
AA8
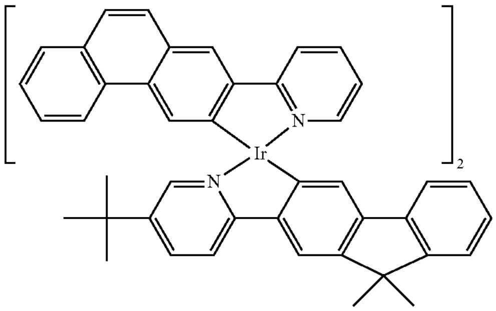
AA9
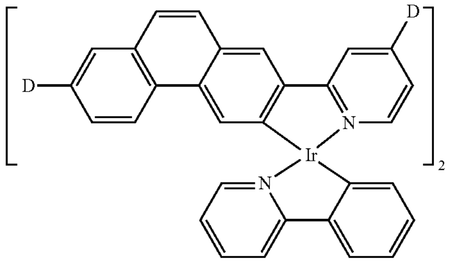
AA10
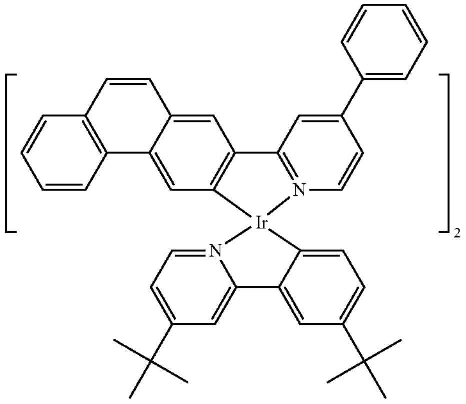
AA11
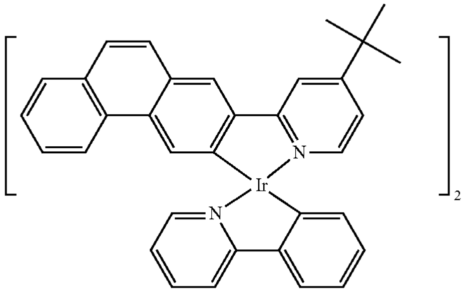

-continued
A12
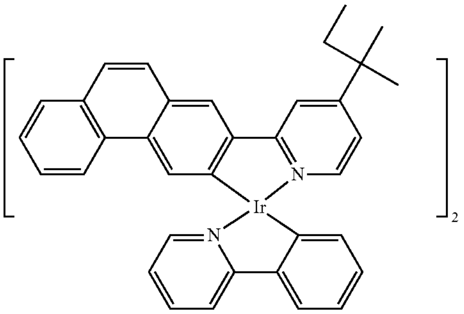
AA13
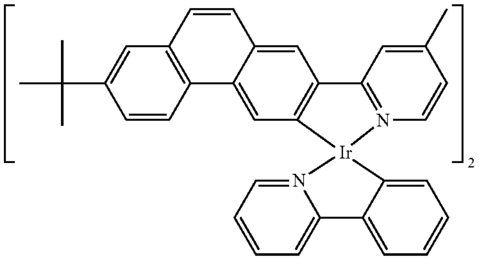
AA14
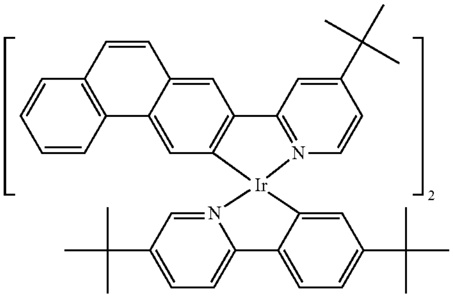
AA15
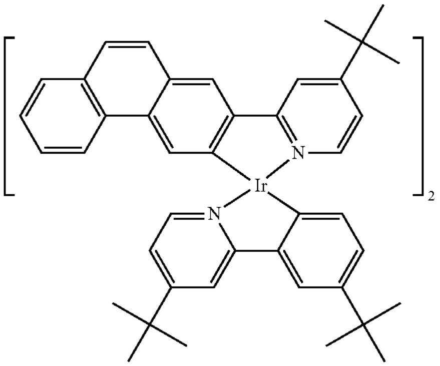
-continued
AA16
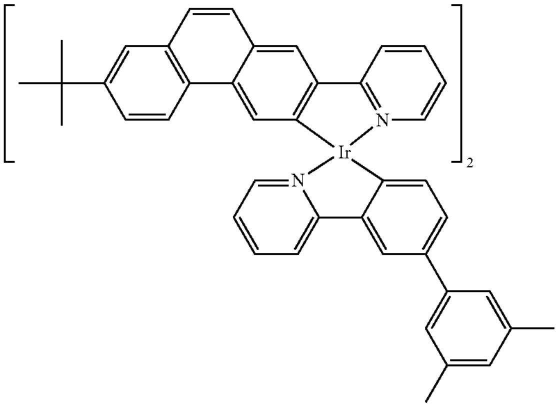
AA17
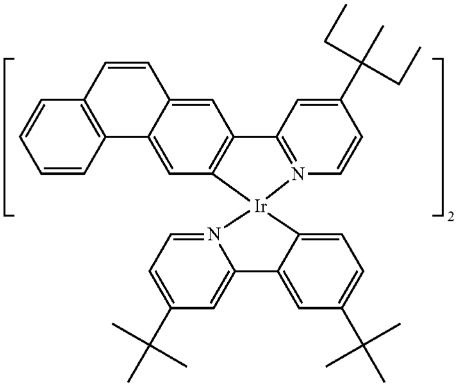
AA18
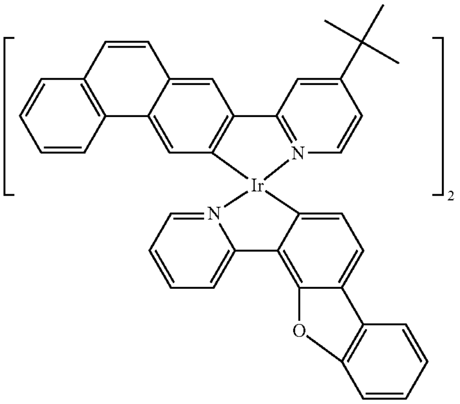
AA19
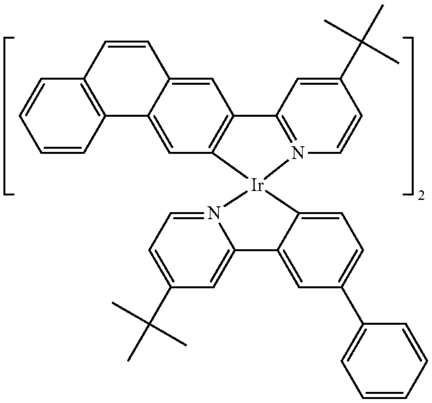

-continued
AA20
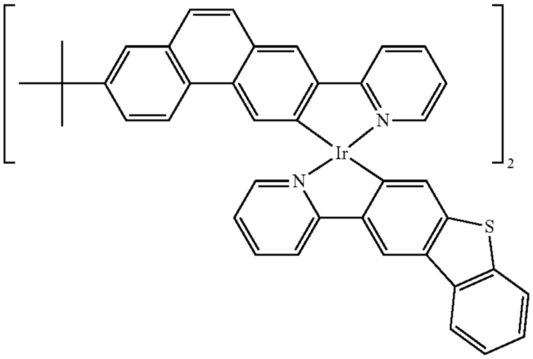
AA21
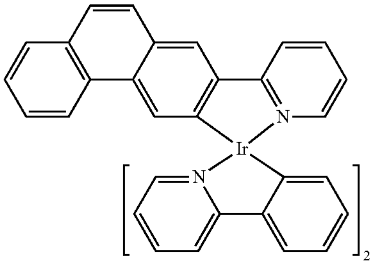
AA22
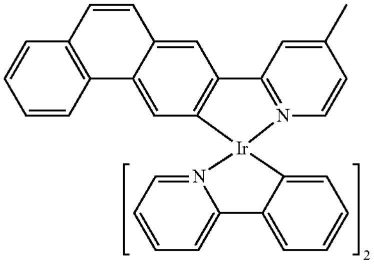
AA23
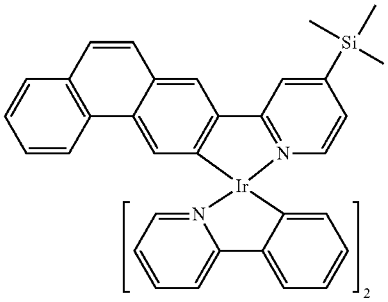
AA24
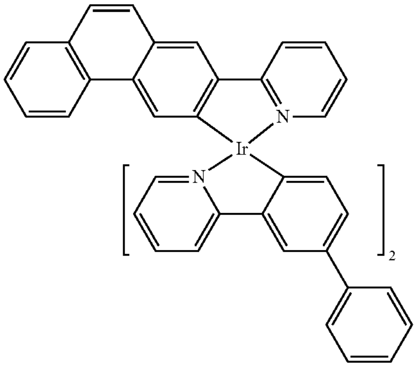
-continued
AA25
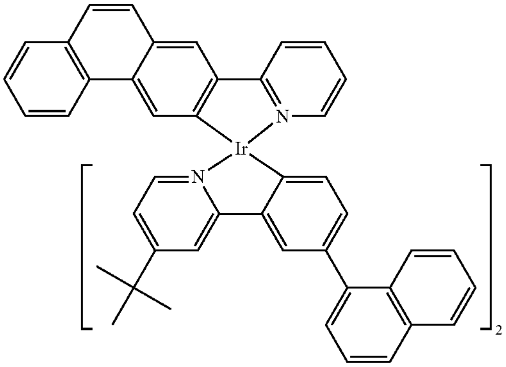
AA26
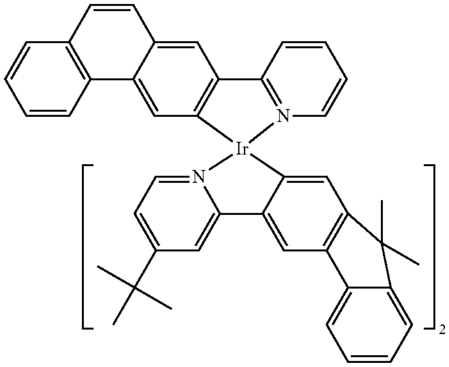
AA27
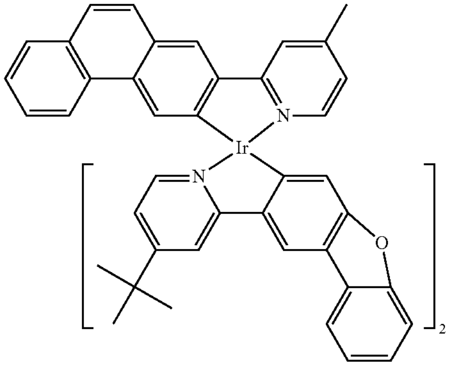
AA28
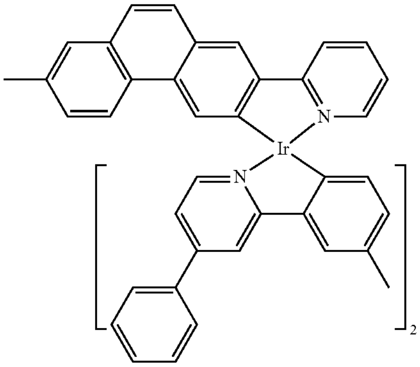

-continued
AA29
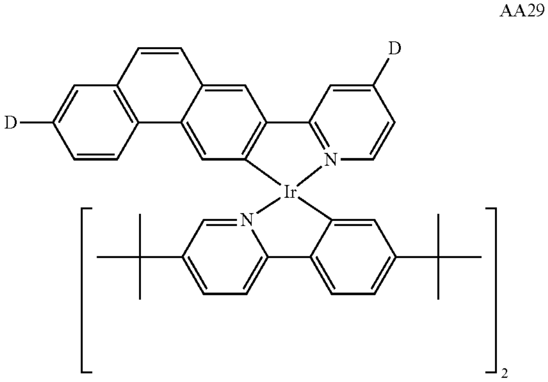
AA30
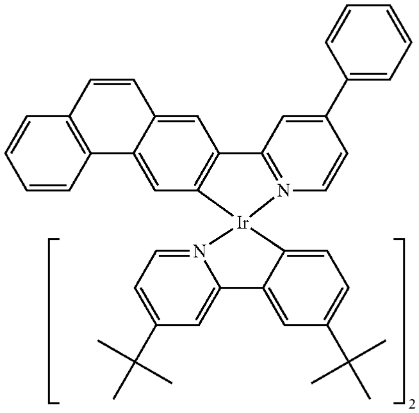
BB1
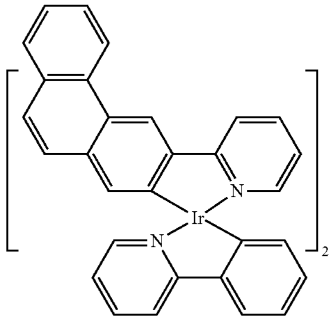
BB2
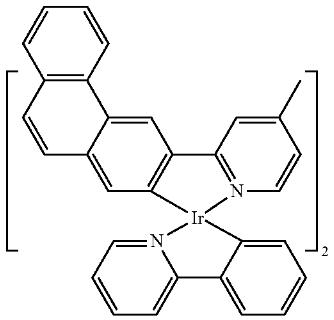
-continued
BB3
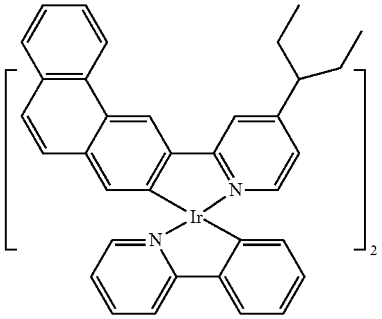
BB4
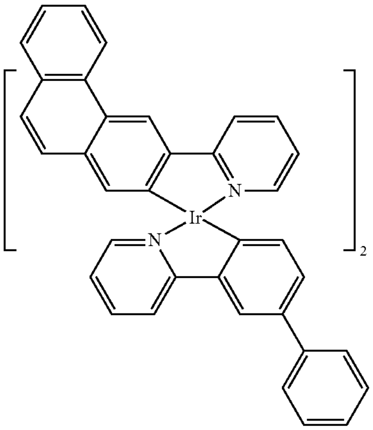
BB5
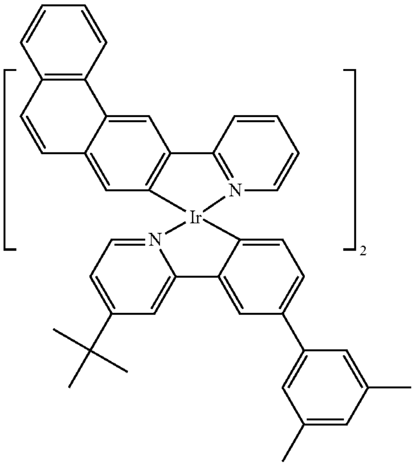
BB6
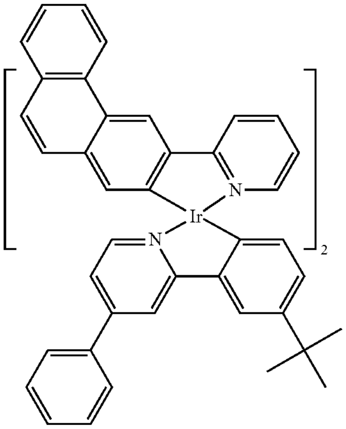

-continued
BB7
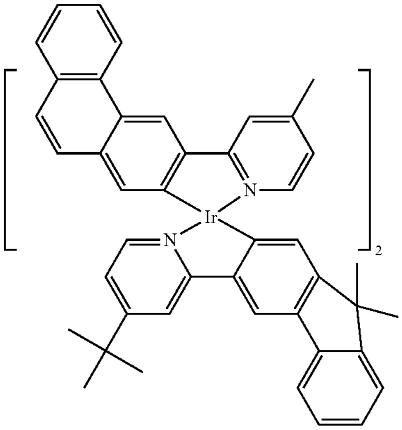
BB8
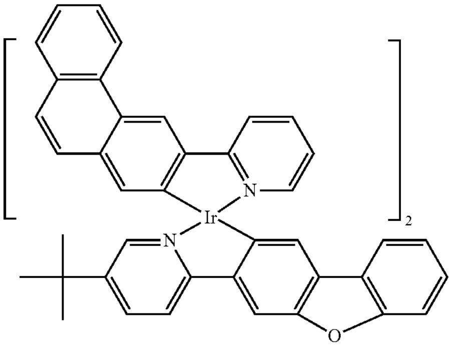
BB9
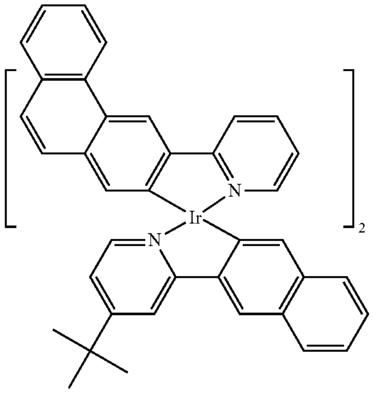
BB10
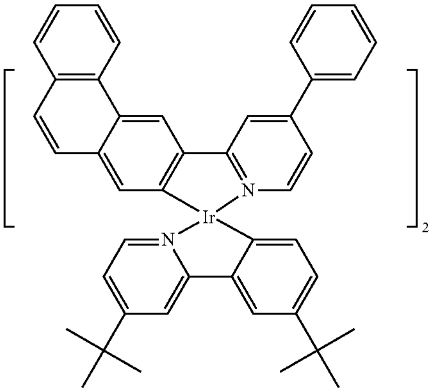
-continued
BB11
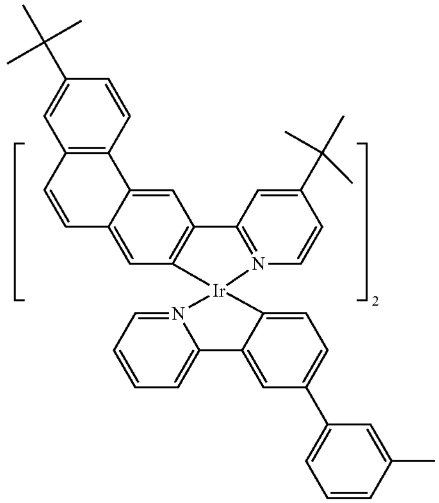
BB12
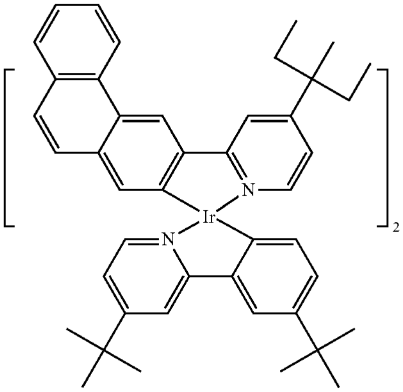
BB13
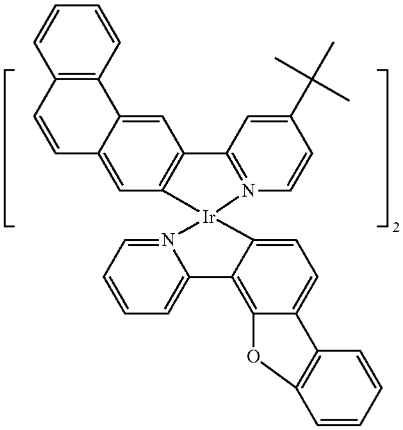

-continued
BB14
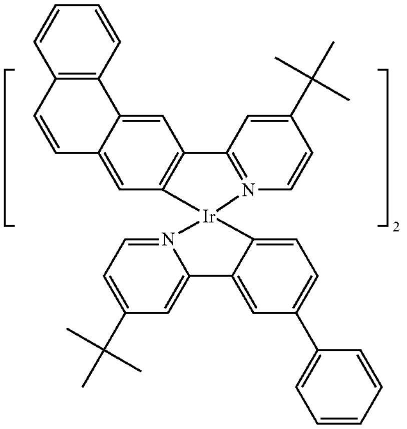
BB15
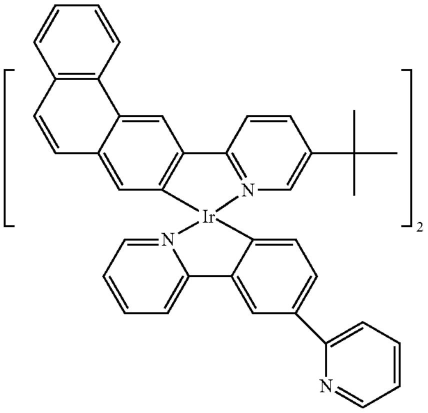
BB16
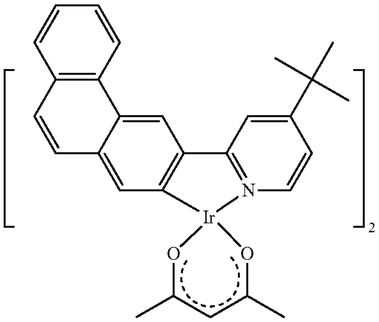
BB17
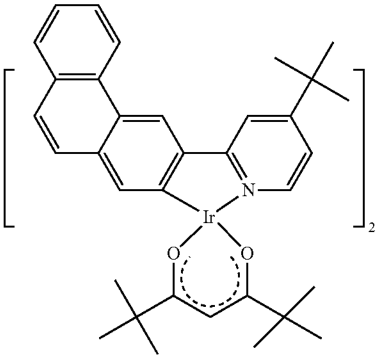
-continued
BB18
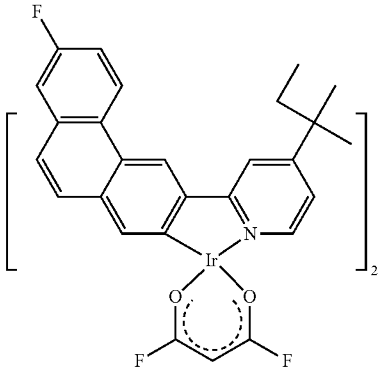
BB19
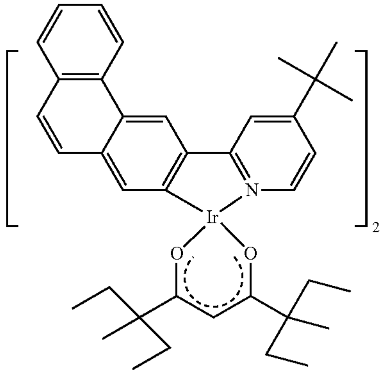
BB20
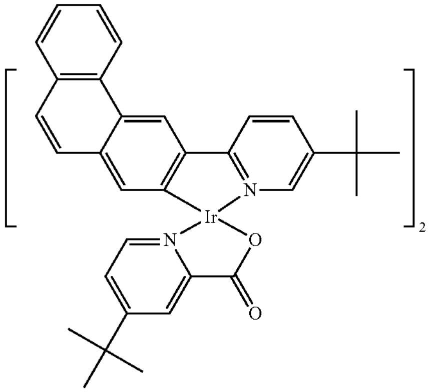
BB21
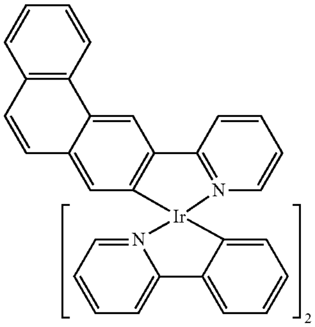

-continued
BB22
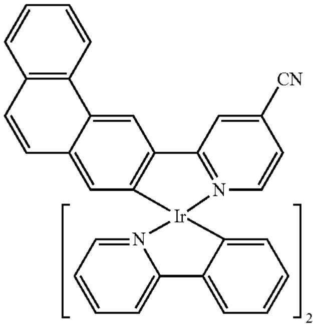
BB23
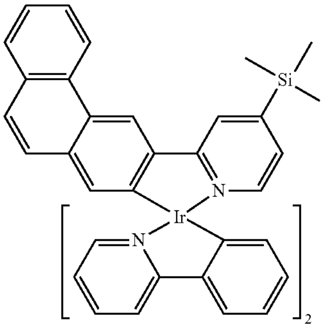
BB24
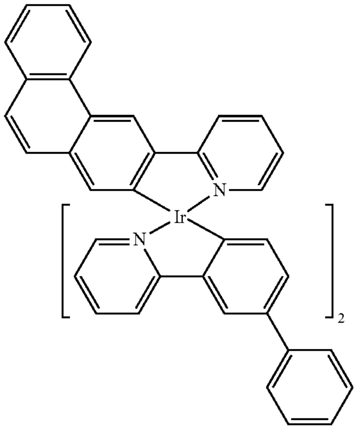
BB25
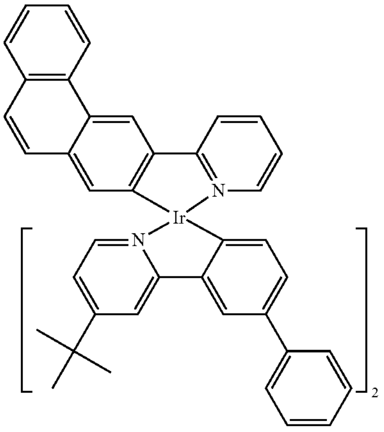
-continued
BB26
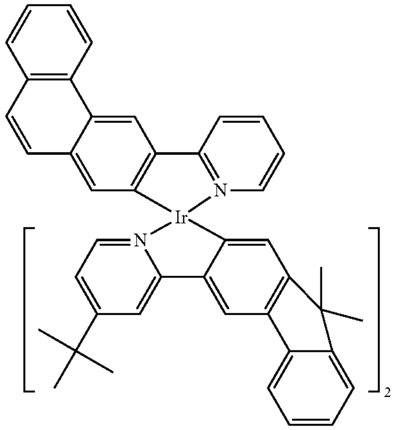
BB27
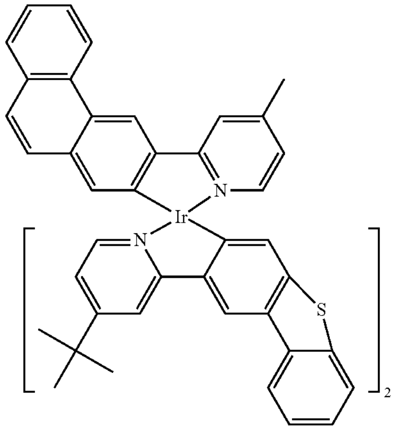
BB28
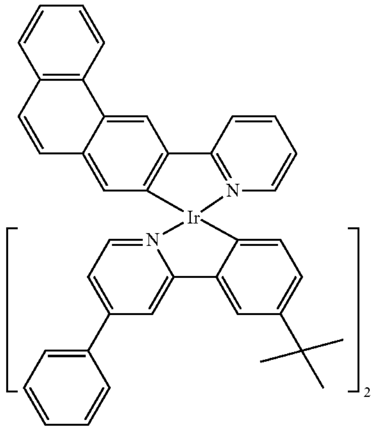
BB29
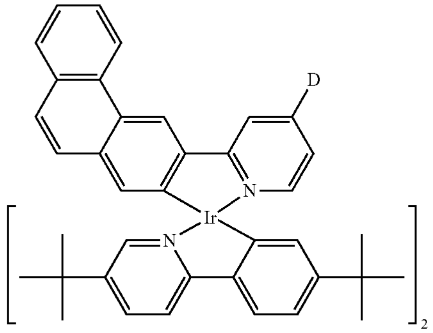

-continued
BB30
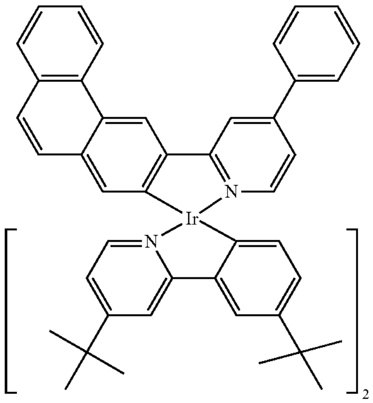
CC1
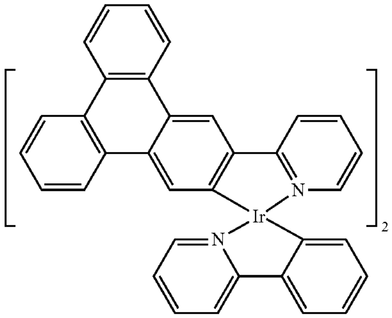
CC2
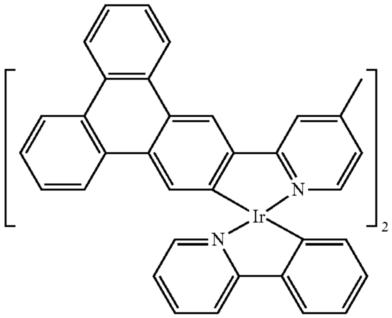
CC3
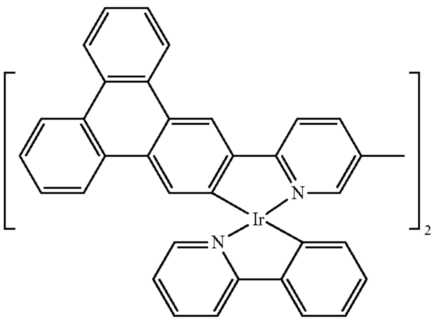
-continued
CC4
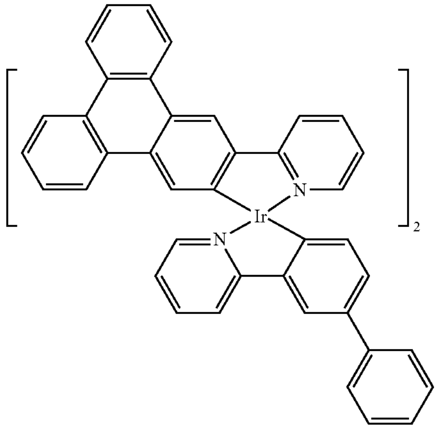
CC5
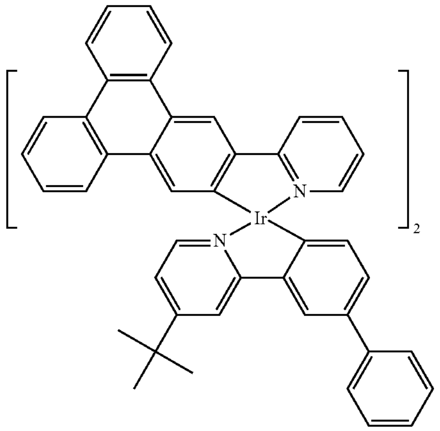
CC6
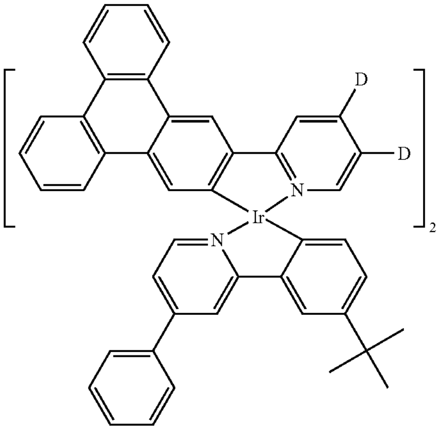

-continued
CC7
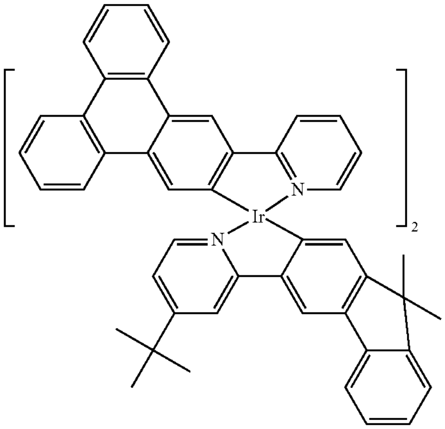
CC8
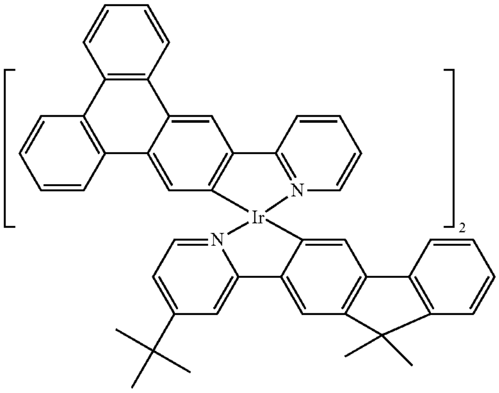
CC9
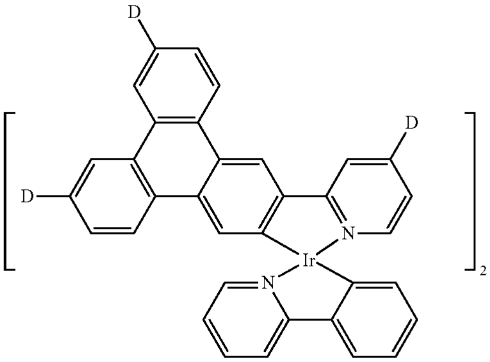
CC10
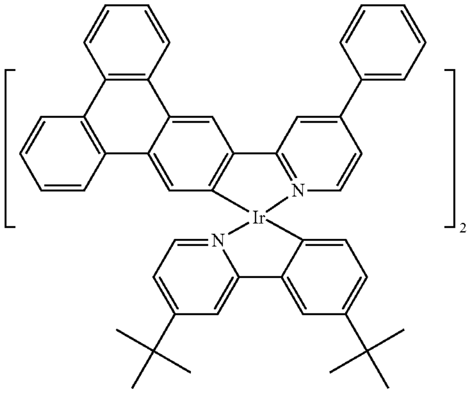
-continued
CC11
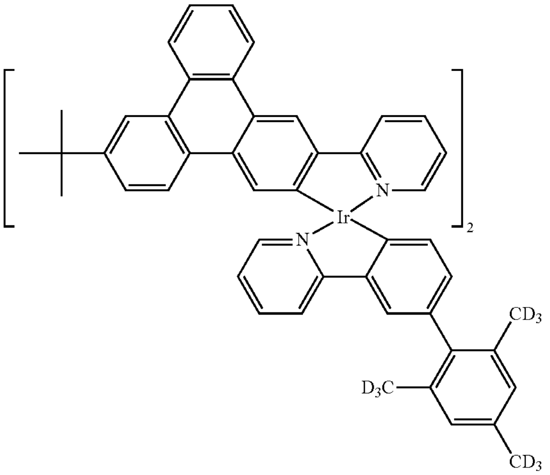
CC12
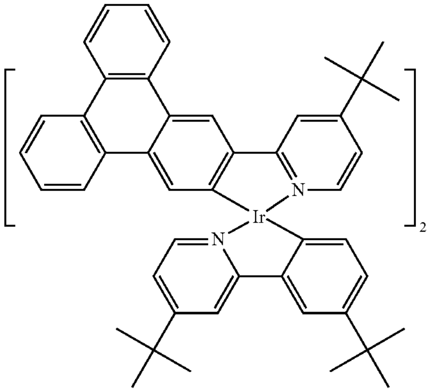
CC13
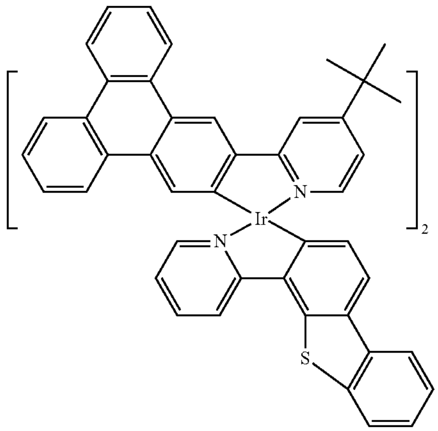

-continued
CC14
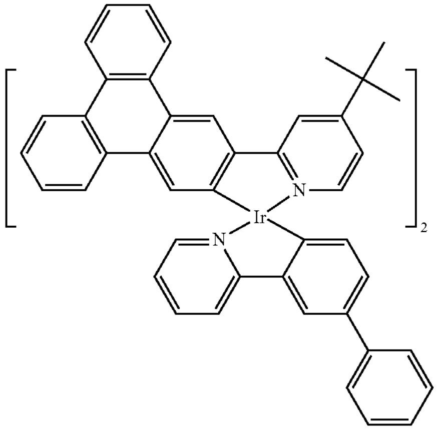
CC15
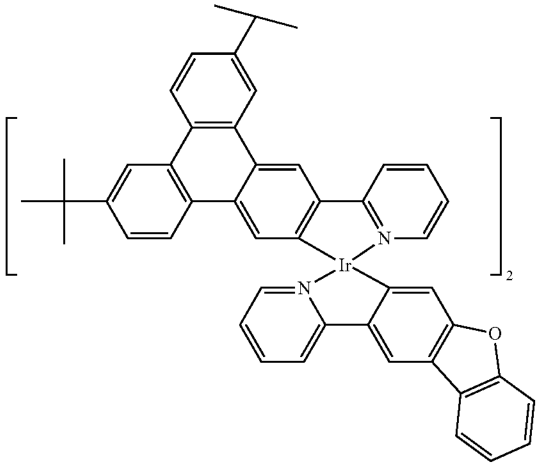
CC16
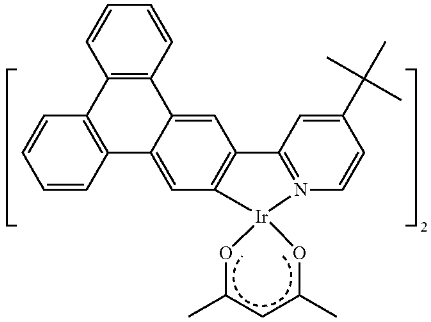
CC17
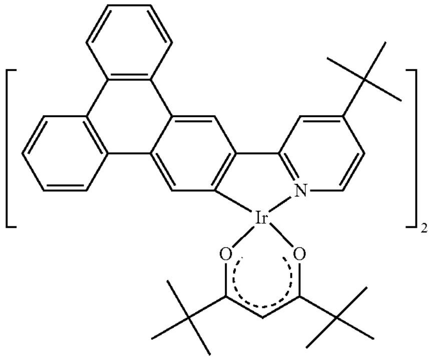
-continued
CC18
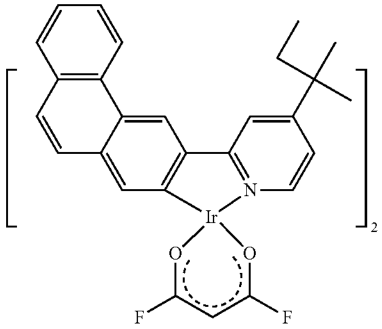
CC19
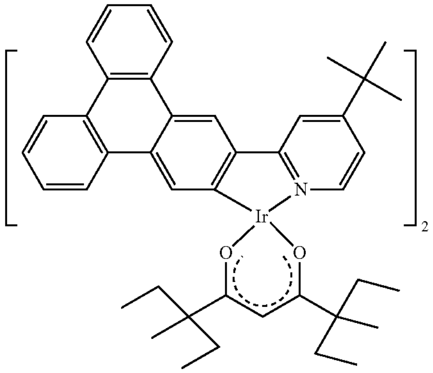
CC20
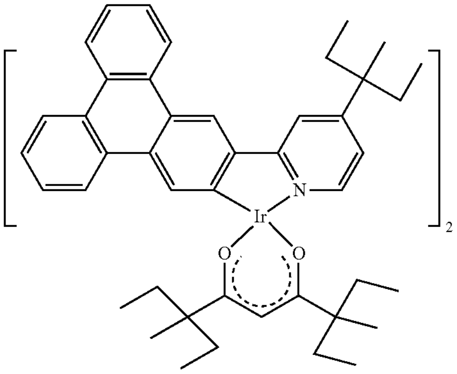
CC21
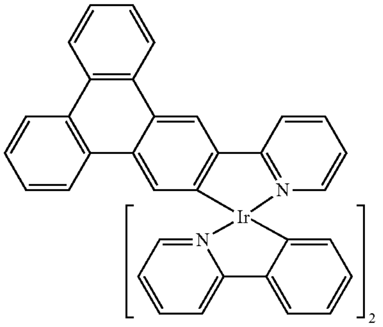

-continued
CC22
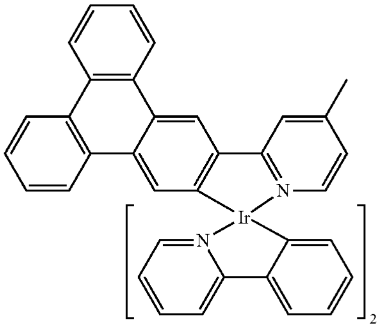
CC23
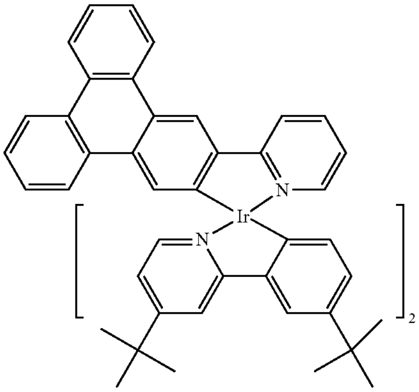
CC24
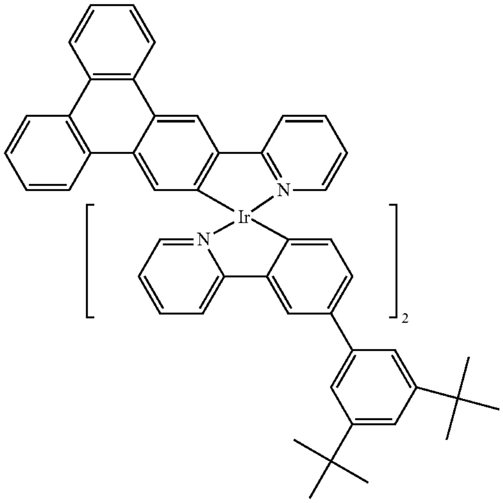
-continued
CC25
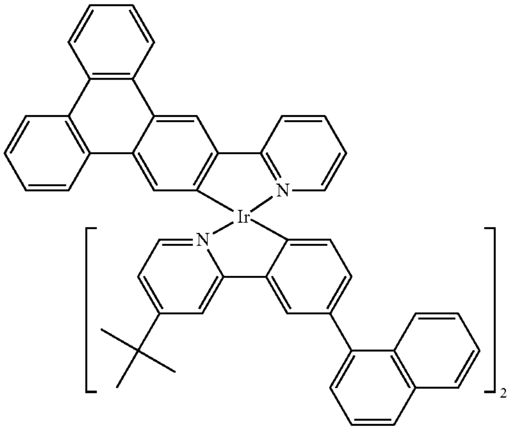
CC26
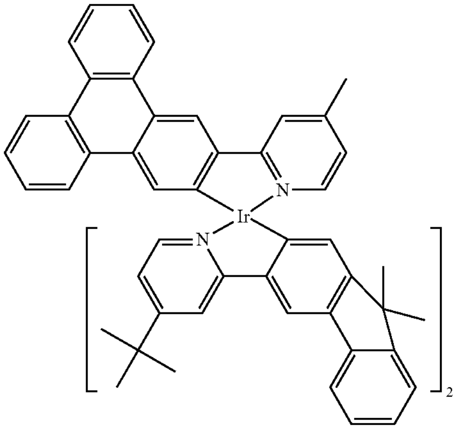
CC27
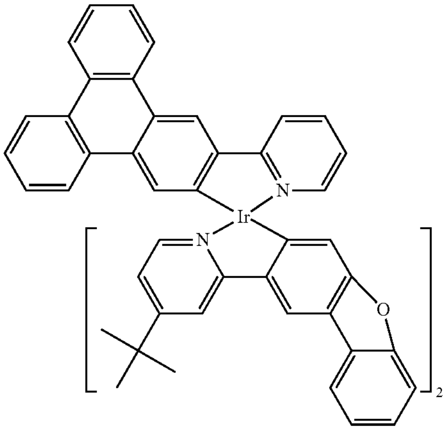

-continued
CC28
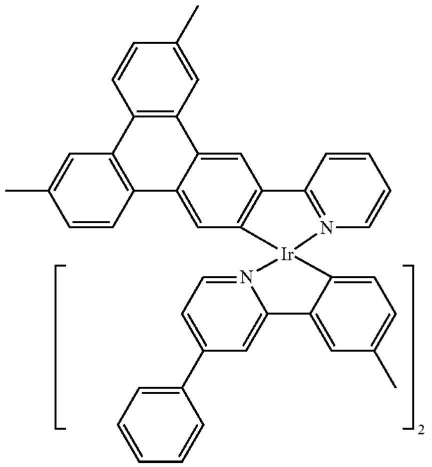
CC29
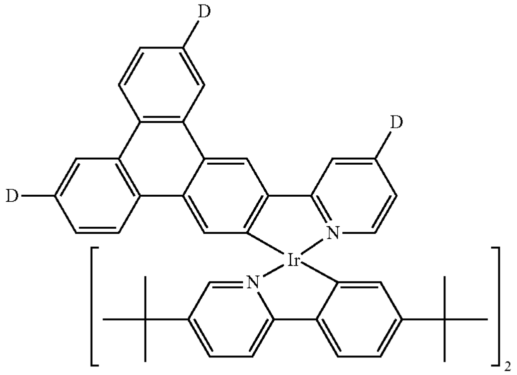
CC30
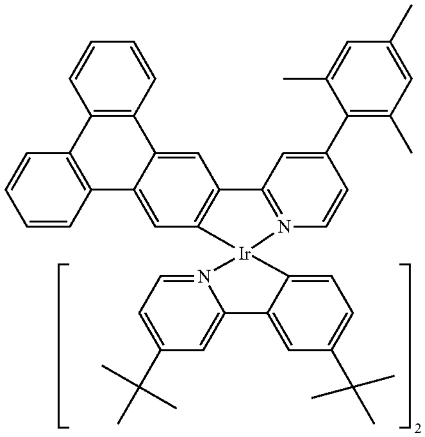
DD1
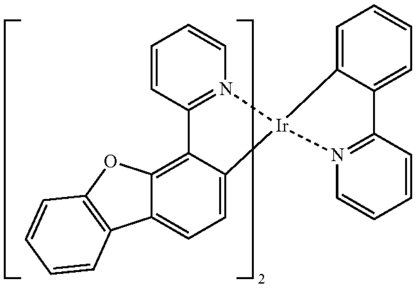
-continued
DD2
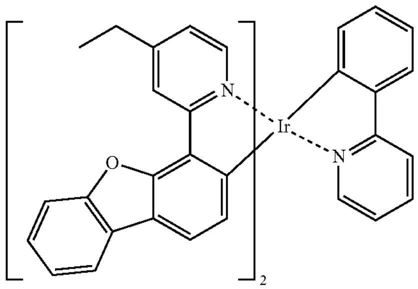
DD3
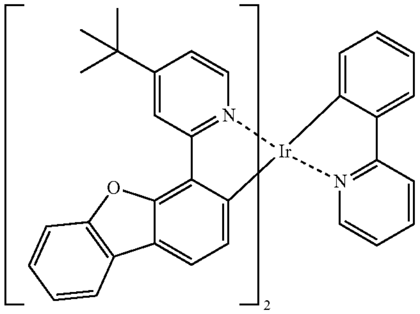
DD4
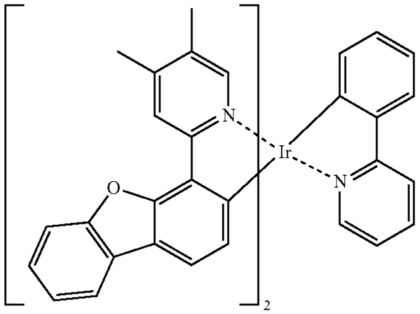
DD5
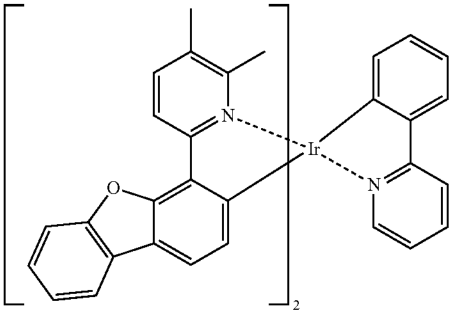
DD6
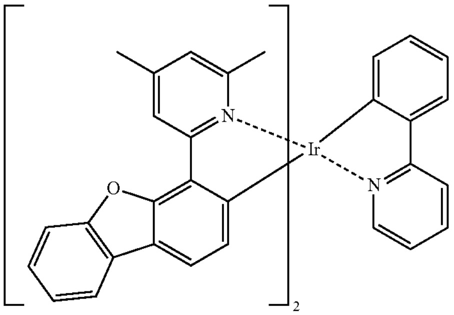

-continued
DD7
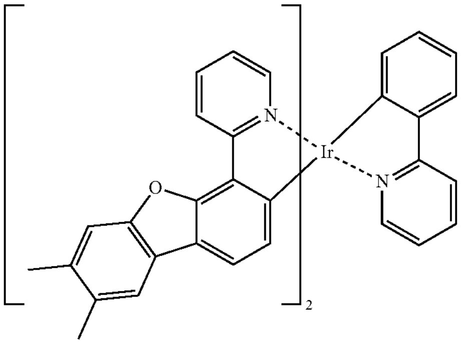
DD8
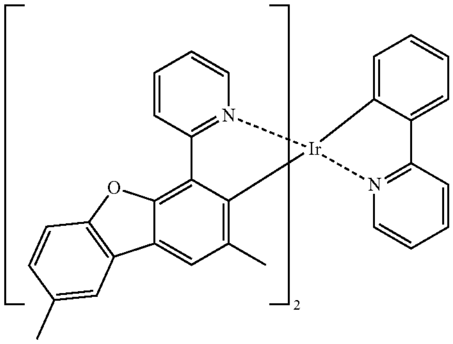
DD9
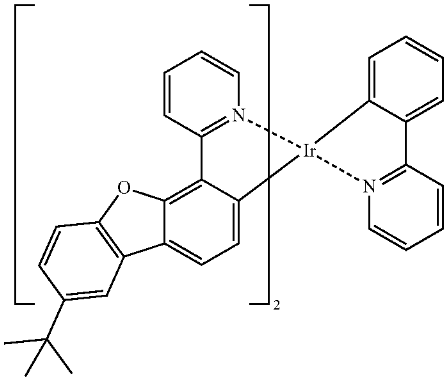
DD10
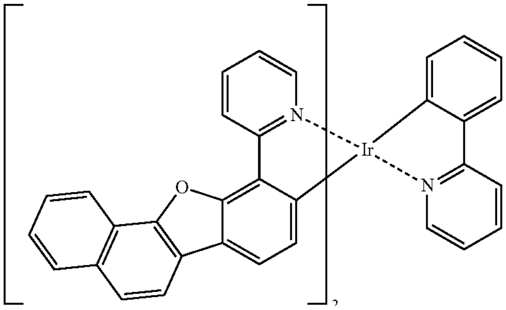
-continued
DD11
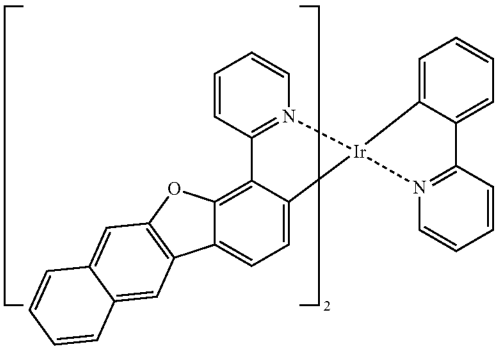
DD12
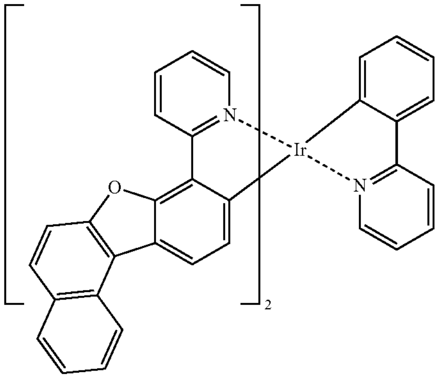
DD13
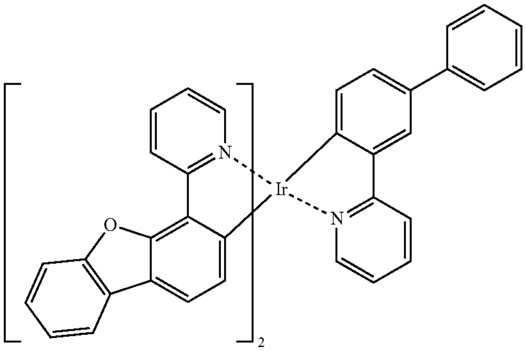
DD14
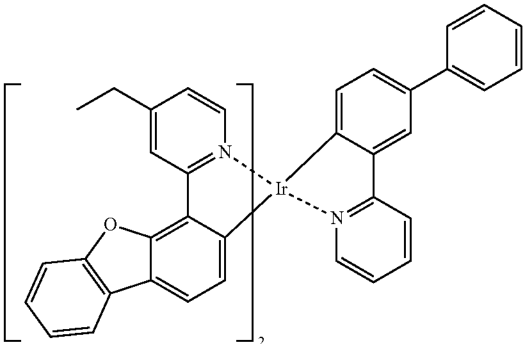

-continued
DD15
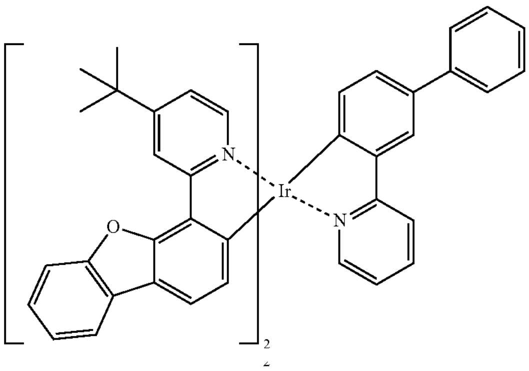
DD16
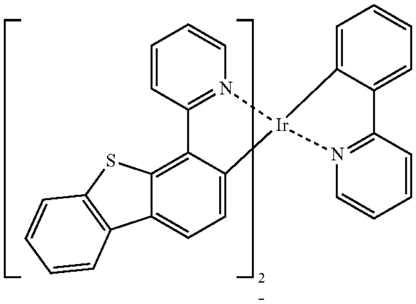
DD17
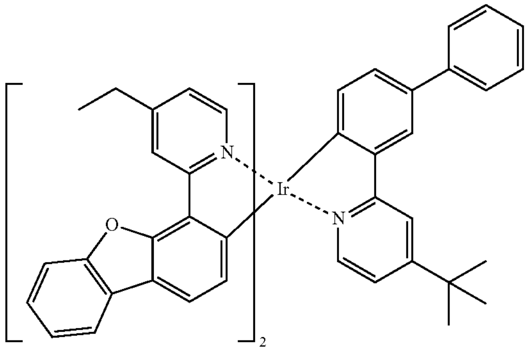
DD18
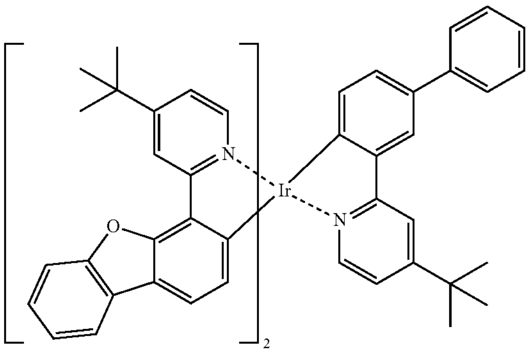
-continued
DD19
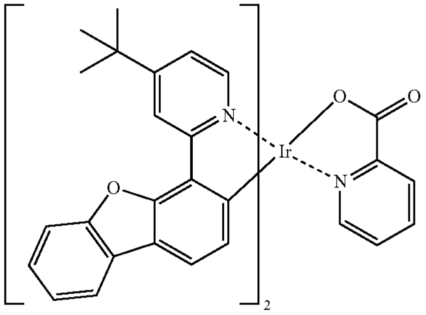
DD20
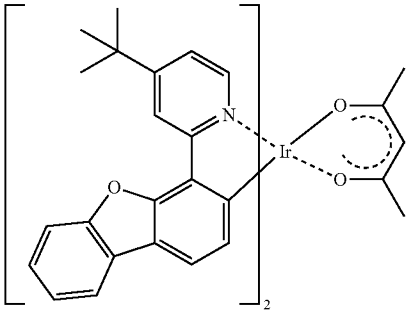
DD21
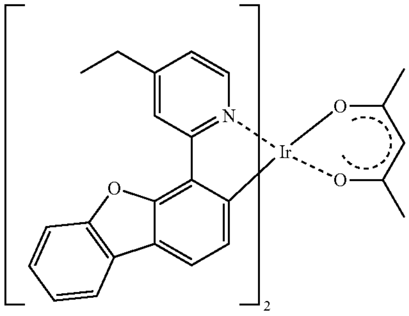
DD22
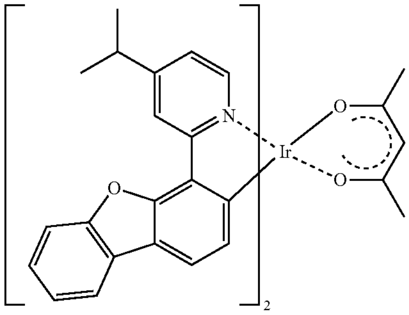
DD23
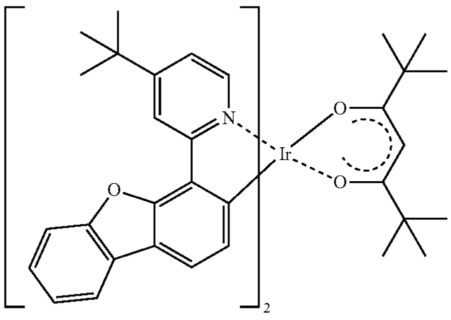

-continued
DD24
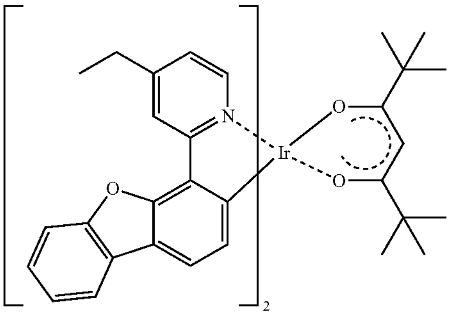
DD25
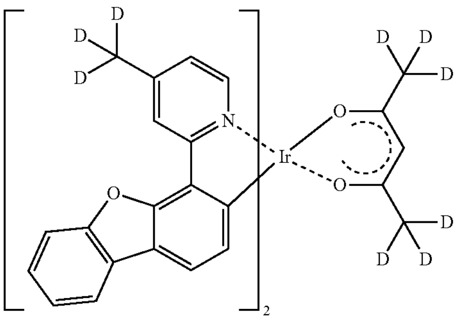
DD26
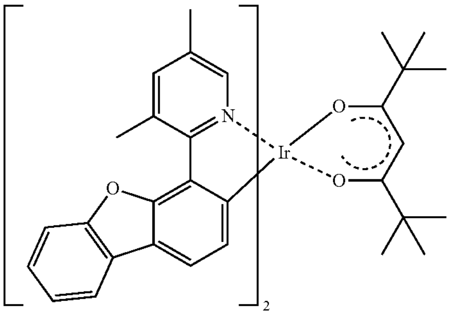
DD27
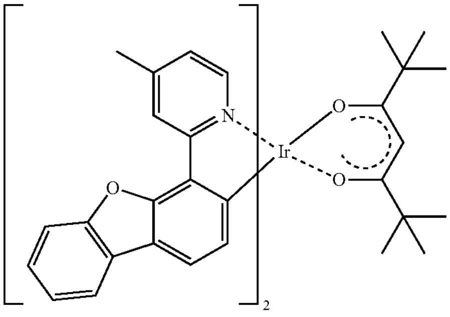
DD28
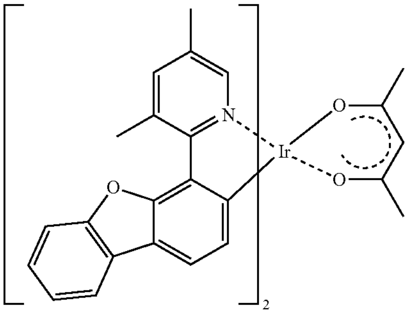
-continued
DD29
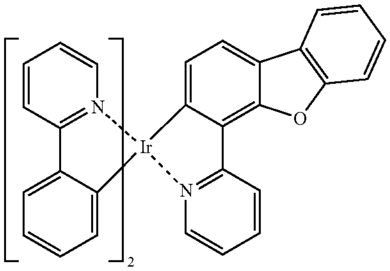
DD30
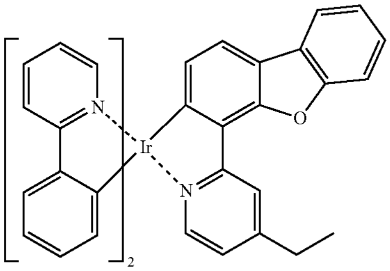
DD31
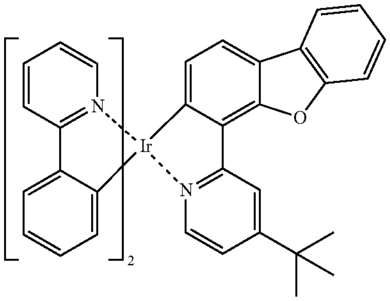
DD32
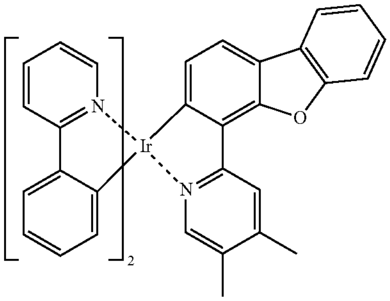
DD33
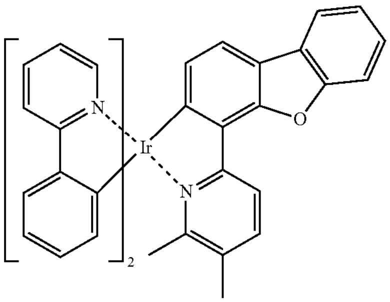

-continued
DD34
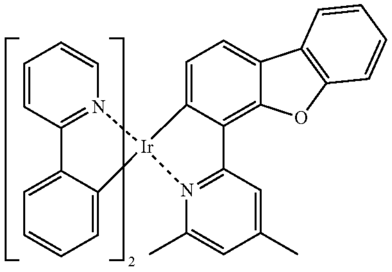
DD35
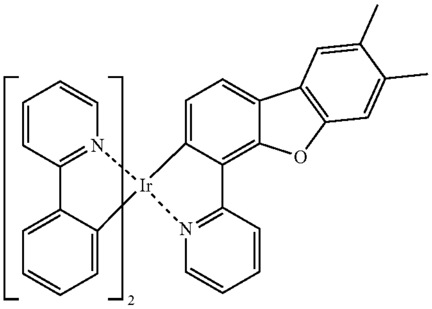
DD36
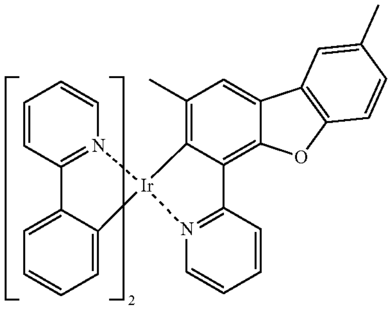
DD37
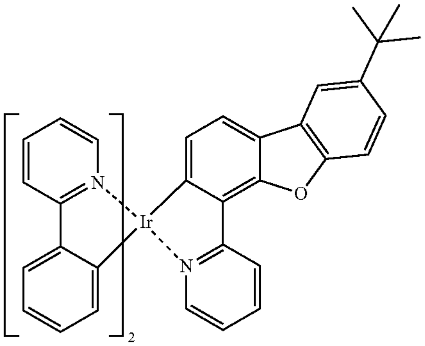
DD38
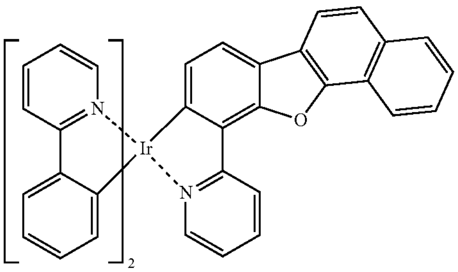
-continued
DD39
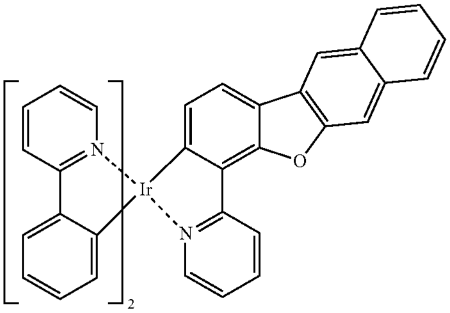
DD40
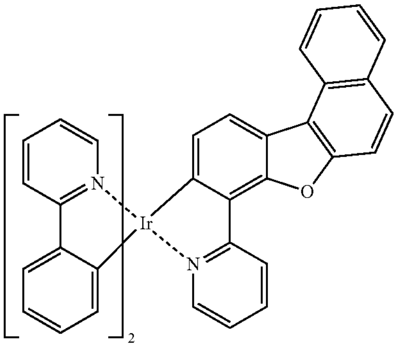
DD41
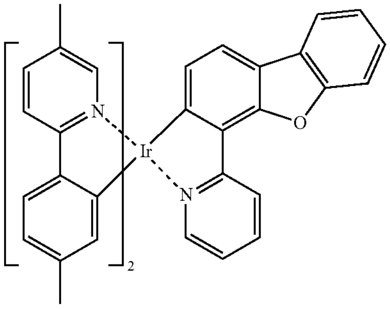
DD42
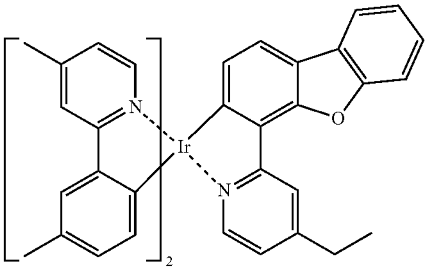
DD43
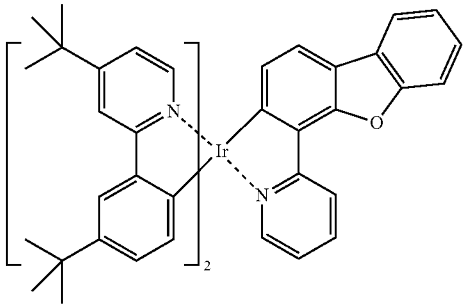

-continued
DD44
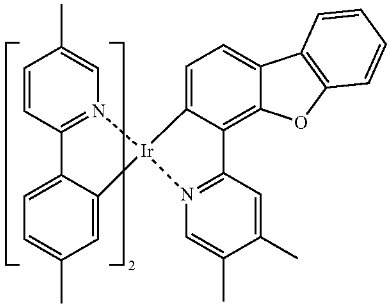
DD45
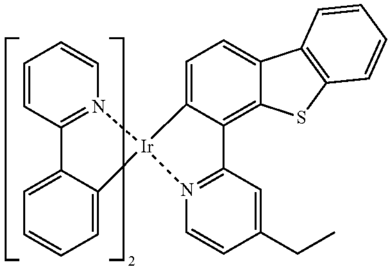
DD46
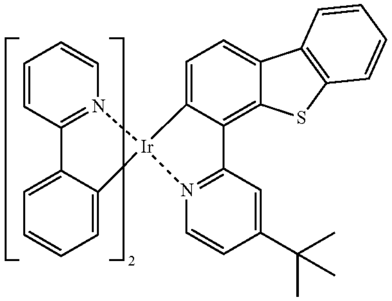
DD47
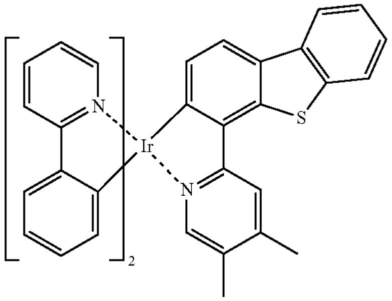
DD48
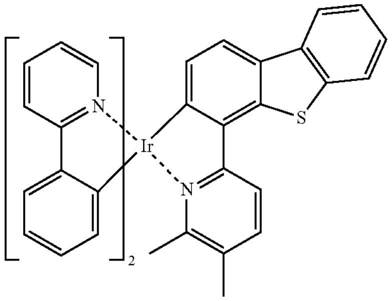
-continued
DD49
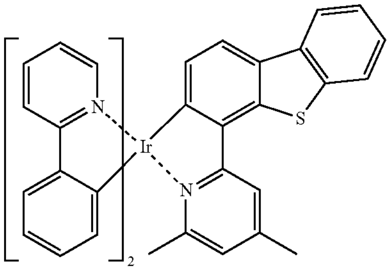
DD50
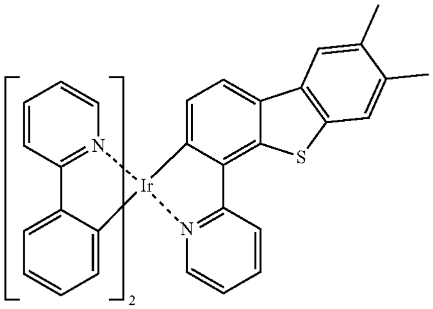
DD51
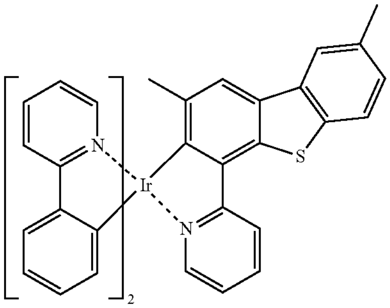
DD52
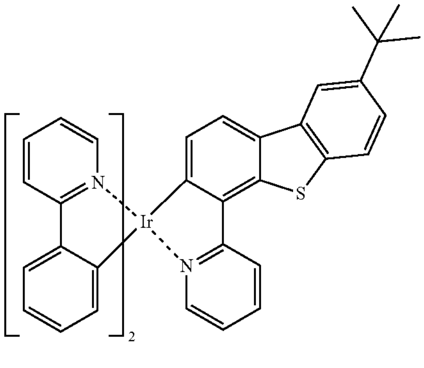
DD53
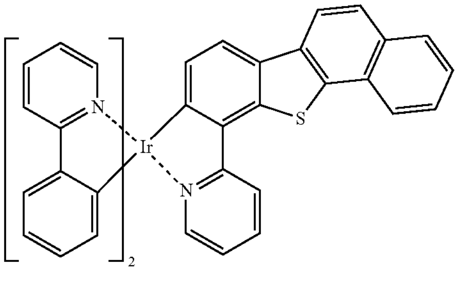

-continued
DD54
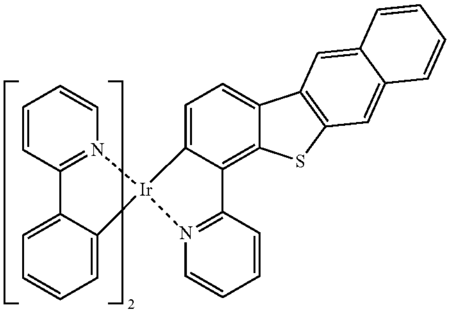
DD55
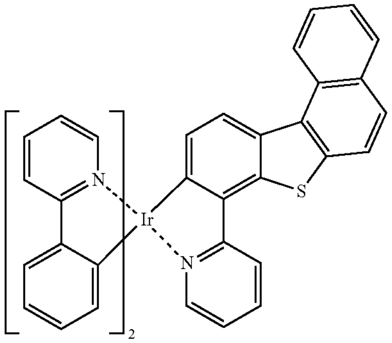
DD56
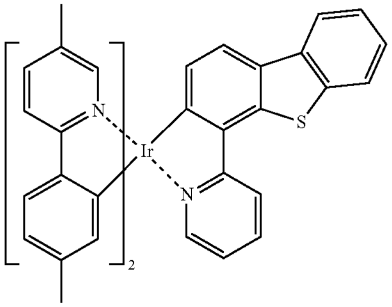
EE1
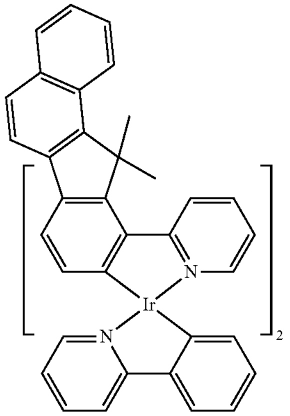
-continued
EE2
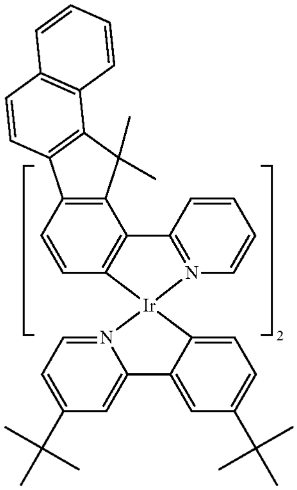
EE3
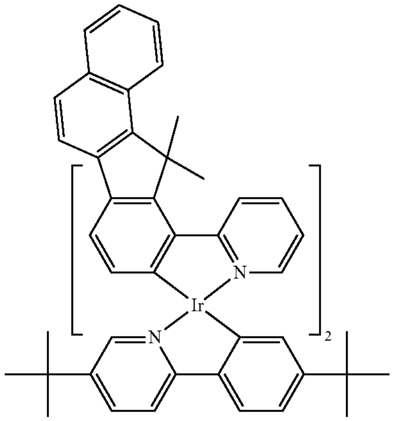
EE4
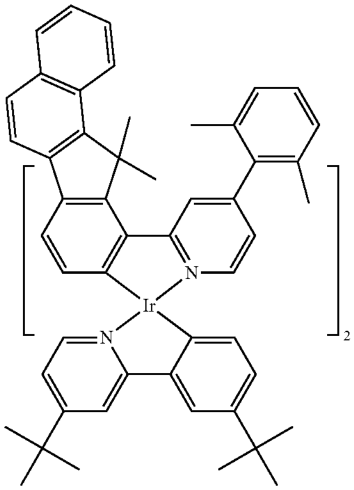

-continued
EE5
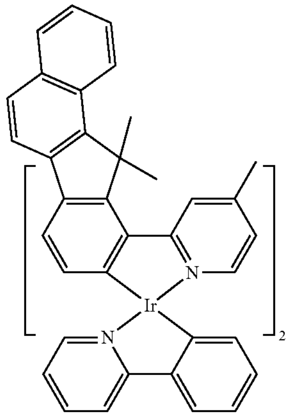
EE6
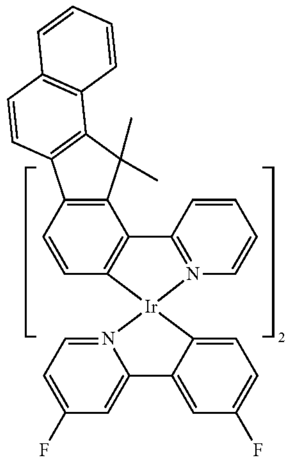
EE7
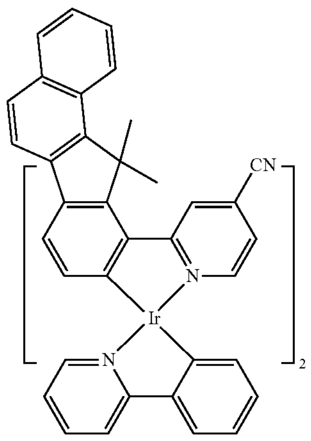
-continued
EE8
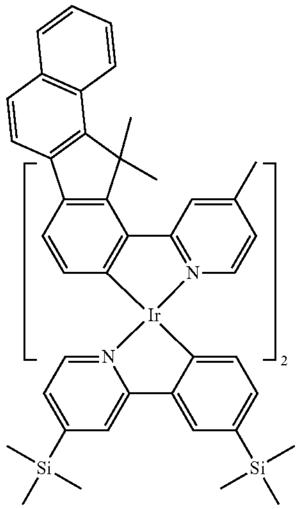
EE9
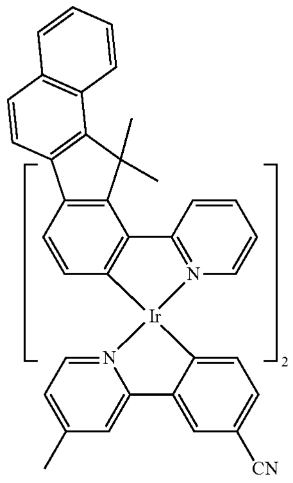
EE10
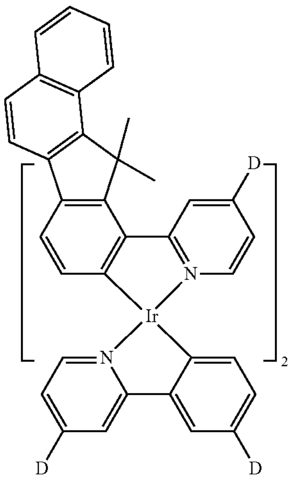

-continued
EE11
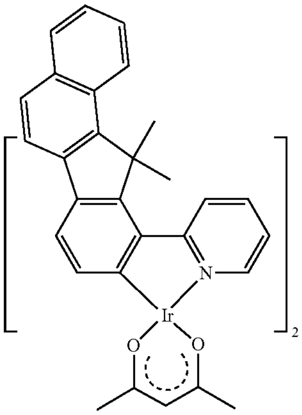
EE12
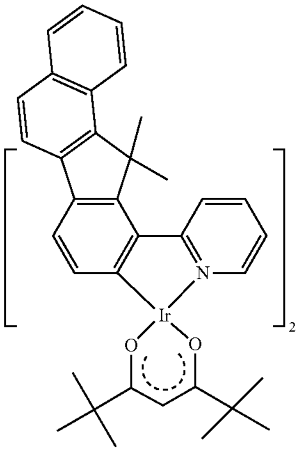
EE13
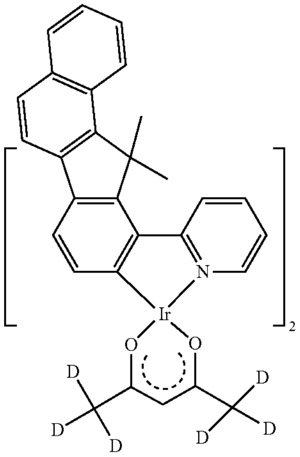
-continued
EE14
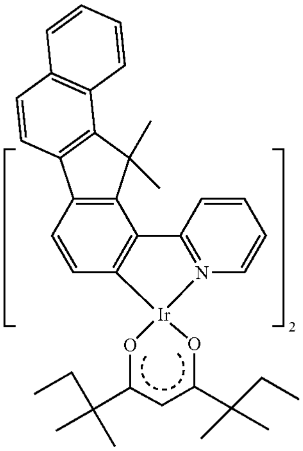
EE15
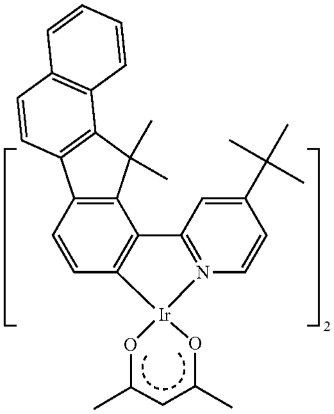
EE16
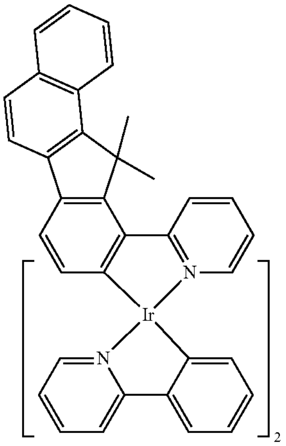

EE17
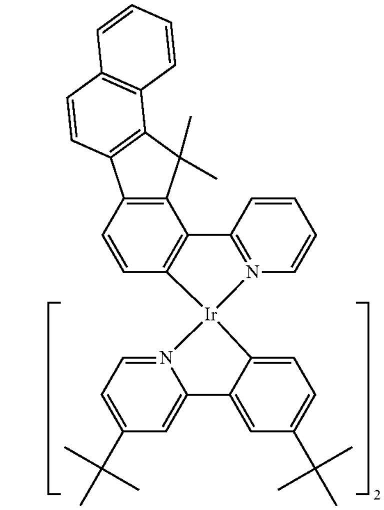
EE18
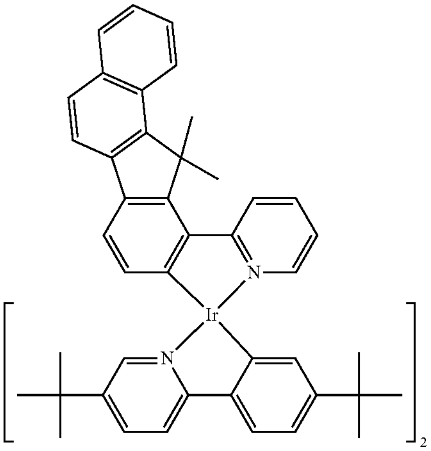
EE19
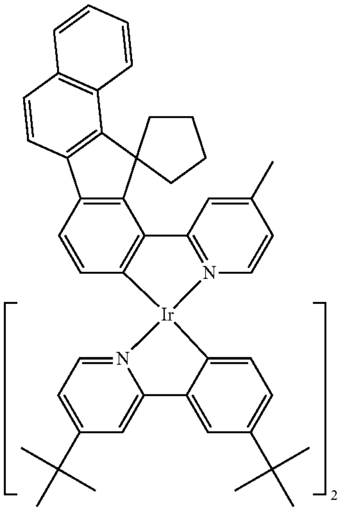
EE20
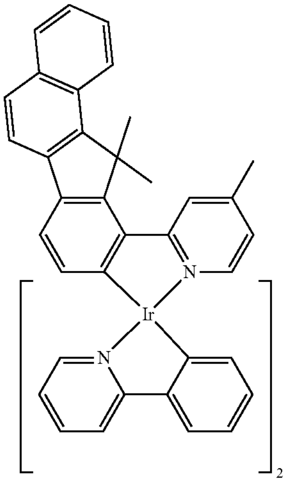
EE21
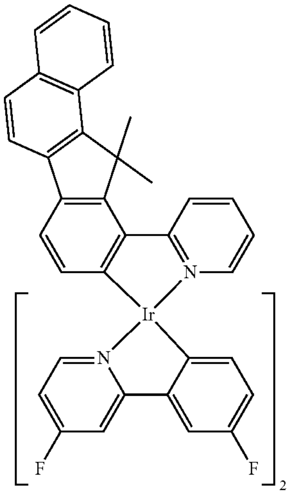
EE22
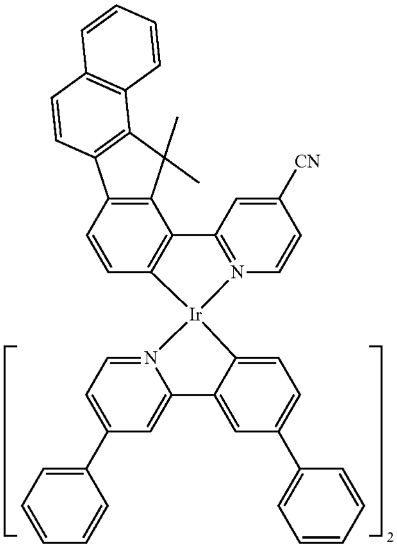

-continued
EE23
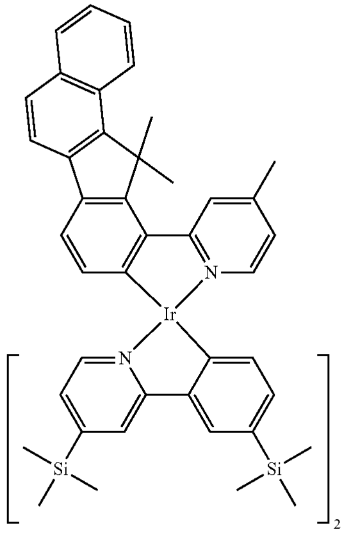
EE24
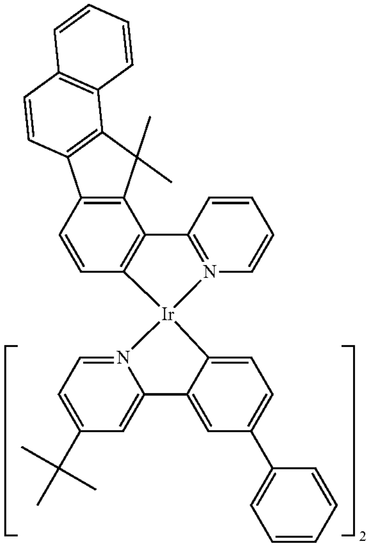
EE25
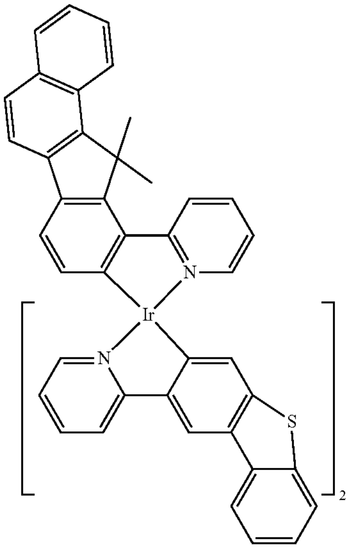
-continued
EE21
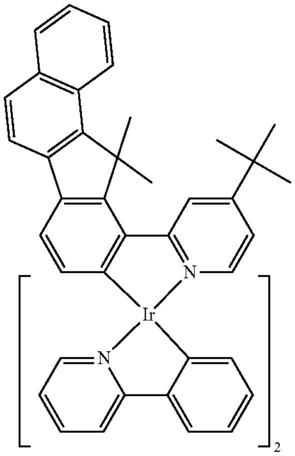
EE22
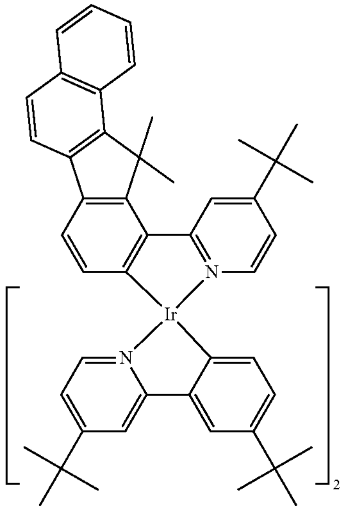
EE23
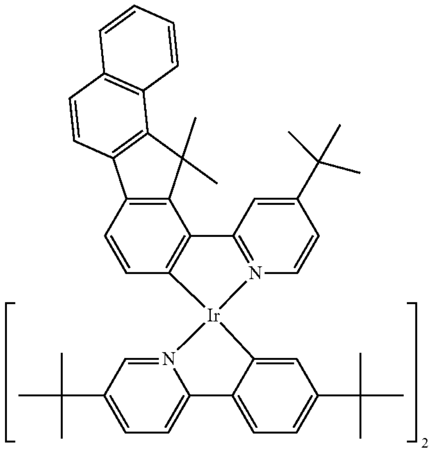

-continued
EE24
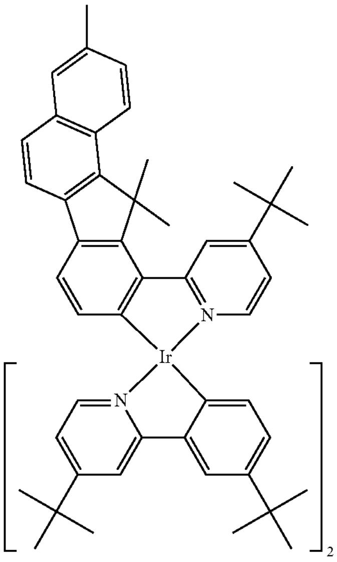
EE25
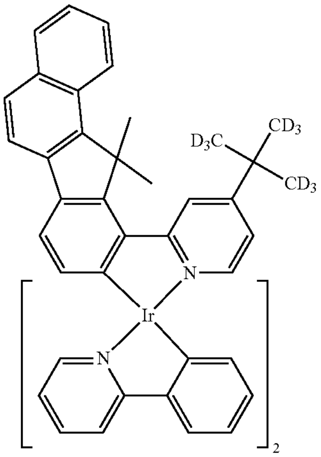
FF1
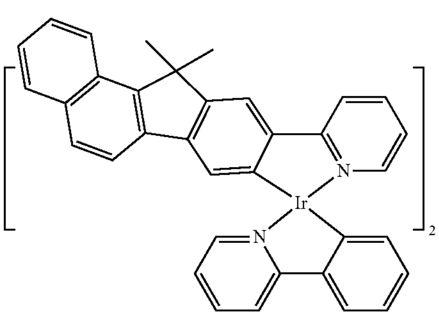
-continued
FF2
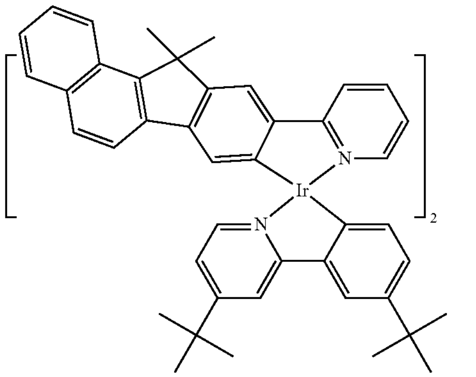
FF3
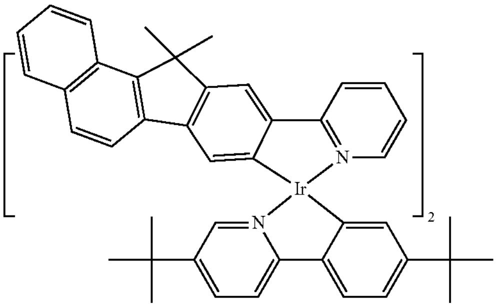
FF4
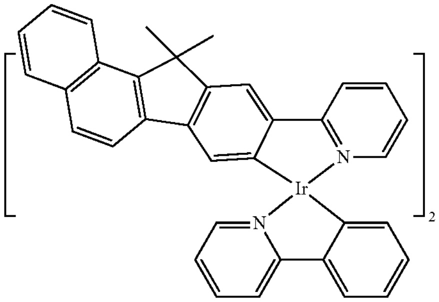
FF5
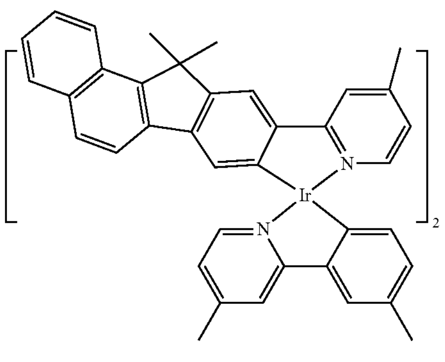

FF6
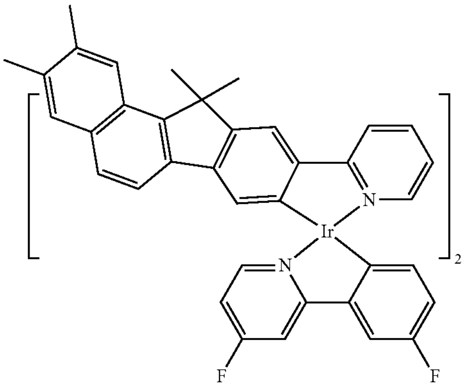
FF7
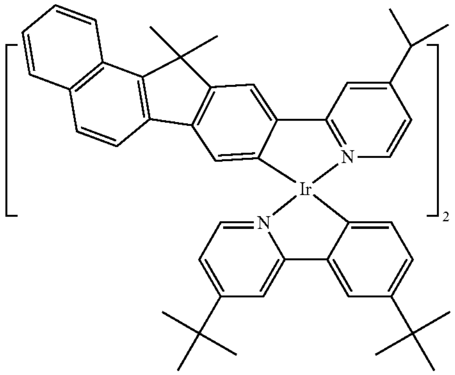
FF8
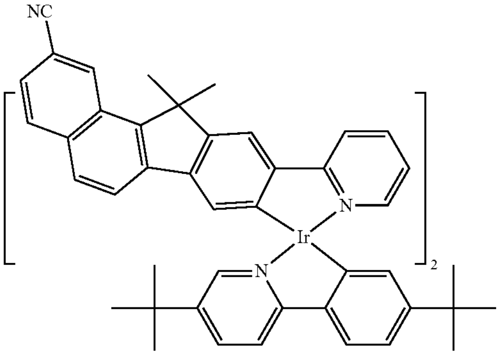
FF9
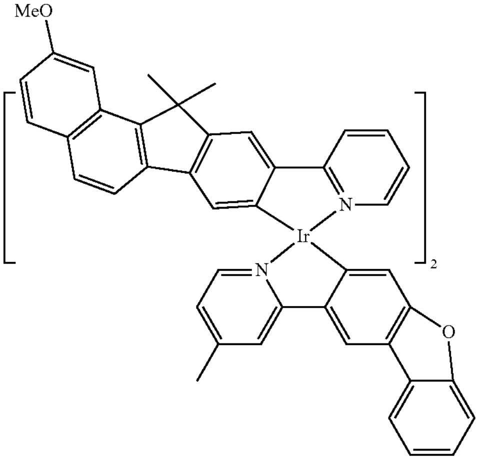
FF10
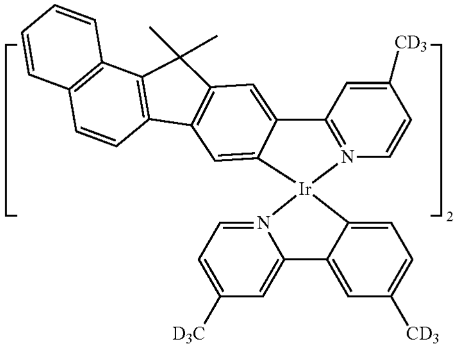
FF11
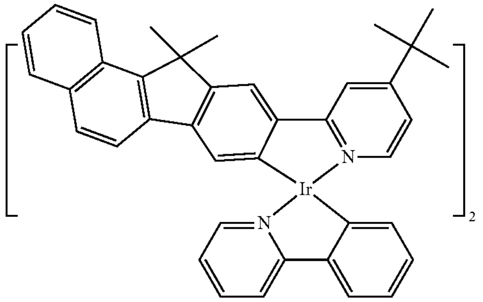
FF12
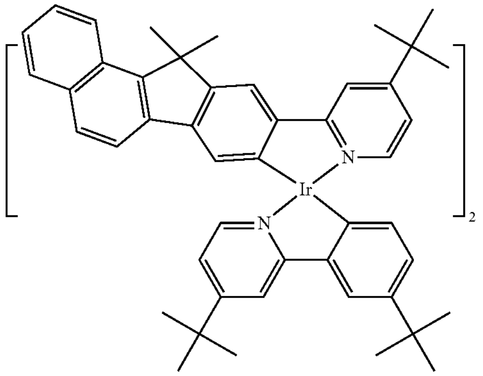
FF13
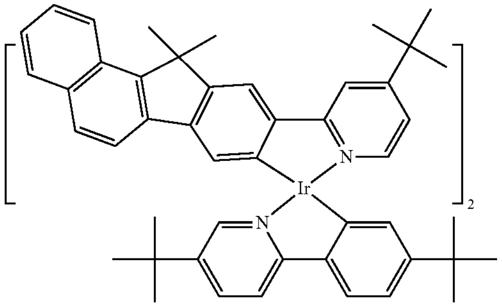

-continued
FF14
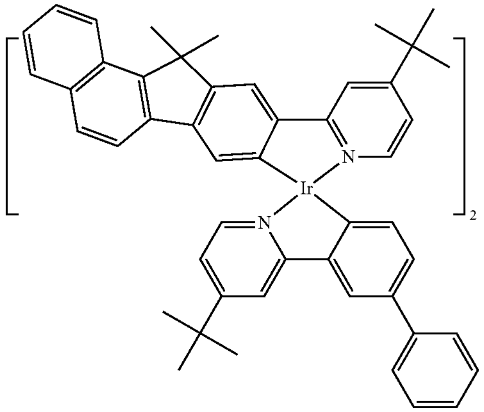
FF15
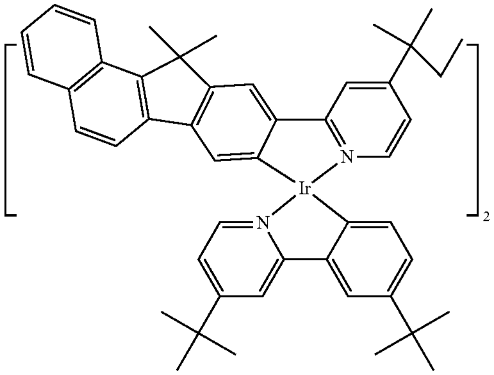
FF16
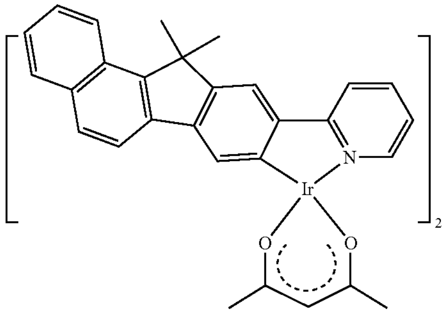
FF17
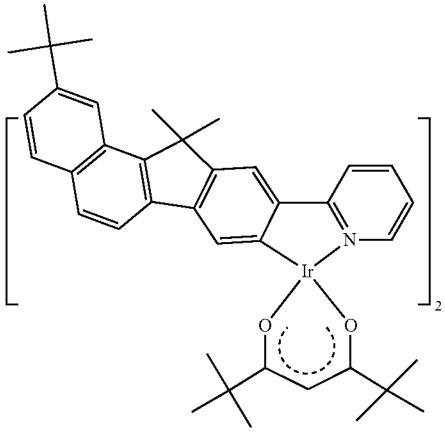
-continued
FF18
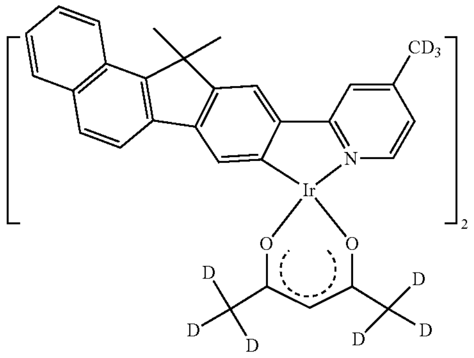
FF19
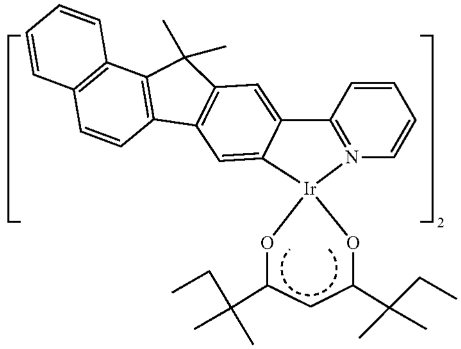
FF20
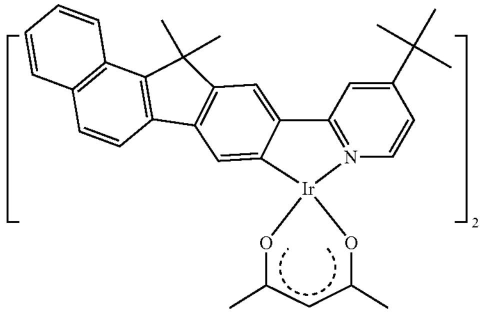
FF21
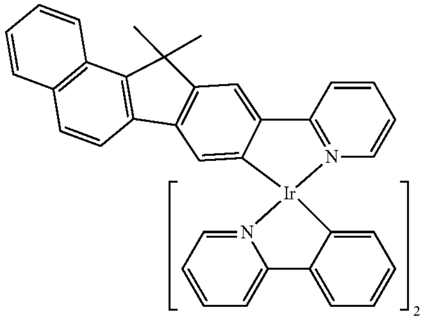

-continued
FF22
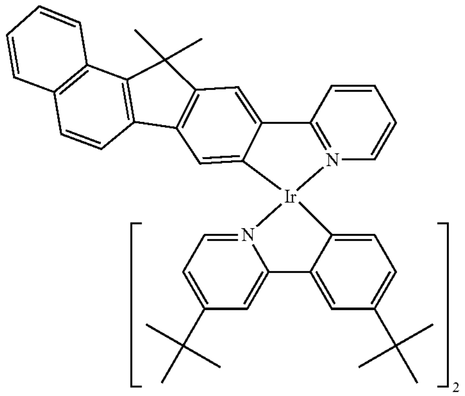
FF23
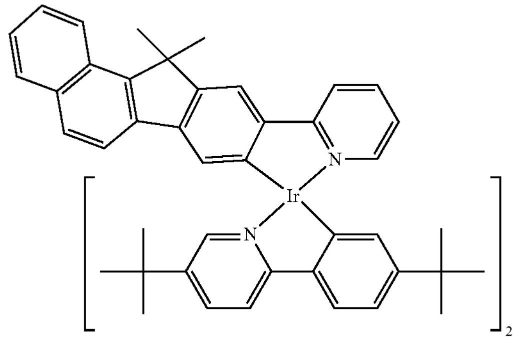
FF24
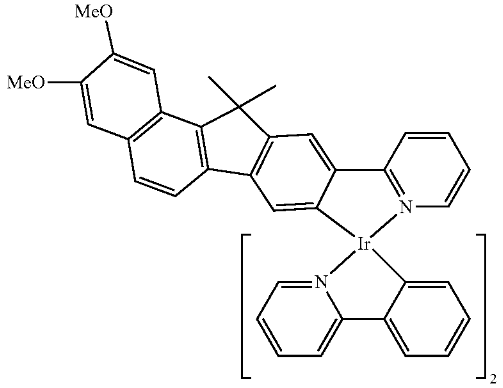
FF25
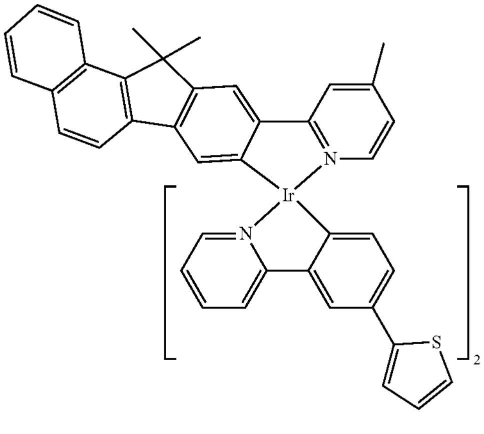
-continued
FF26
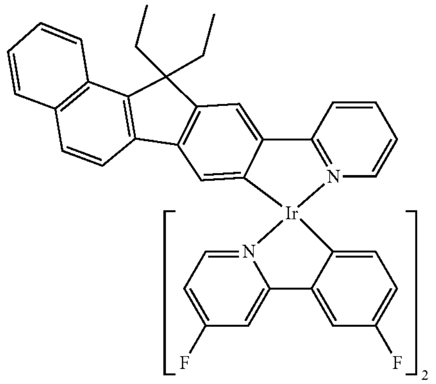
FF27
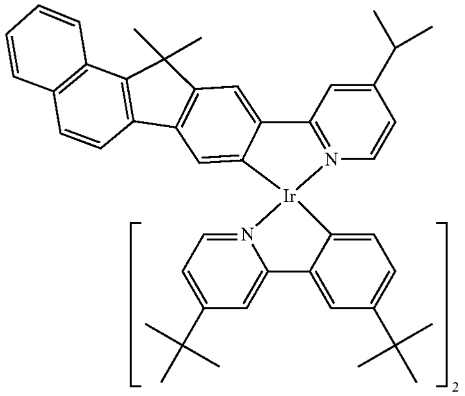
FF28
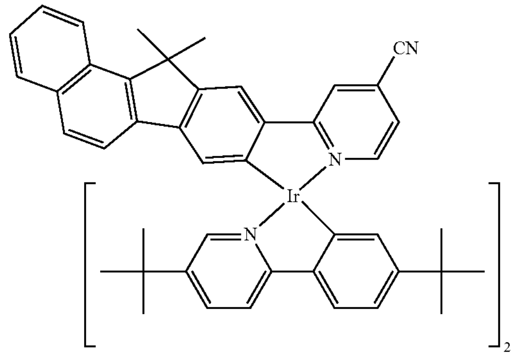
FF29
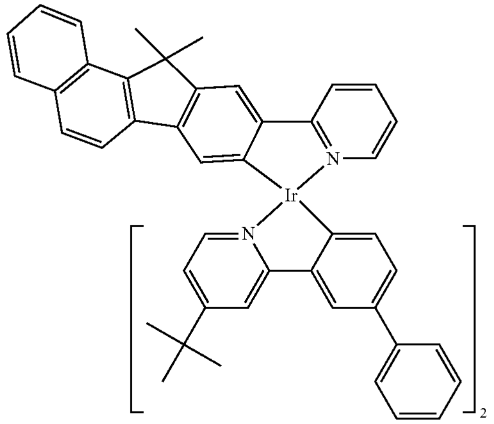

-continued
FF30
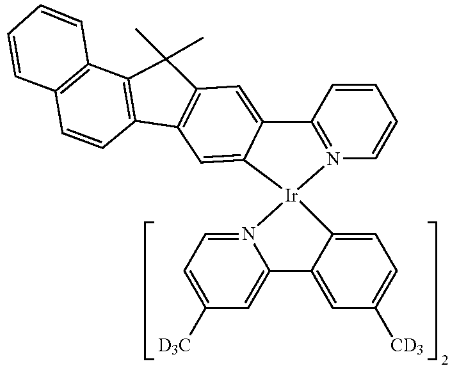
FF31
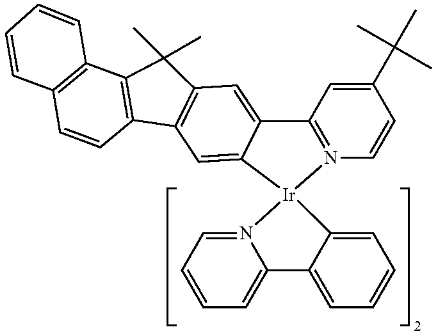
FF32
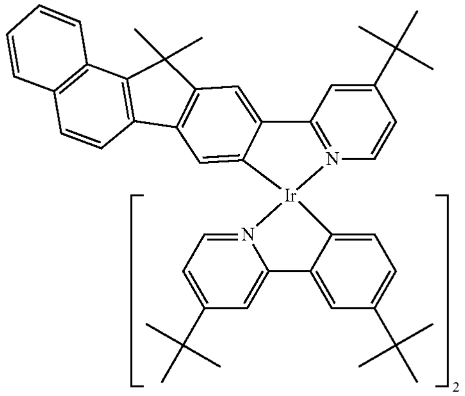
FF33
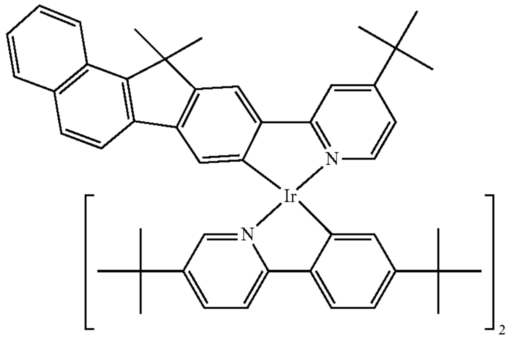
-continued
FF34
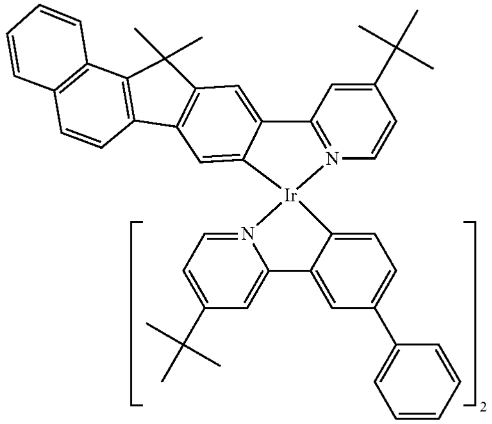
FF35
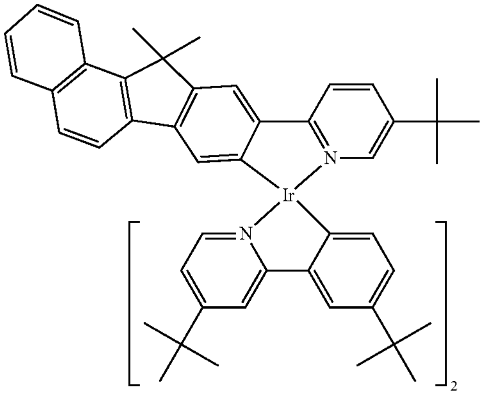
GG1
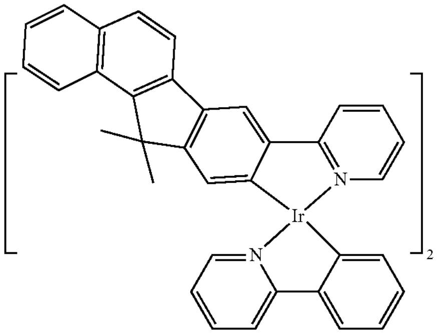
GG2
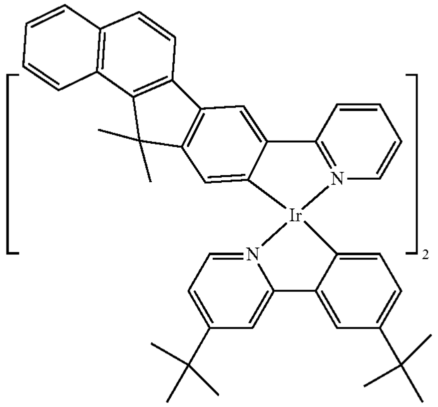

-continued
GG3
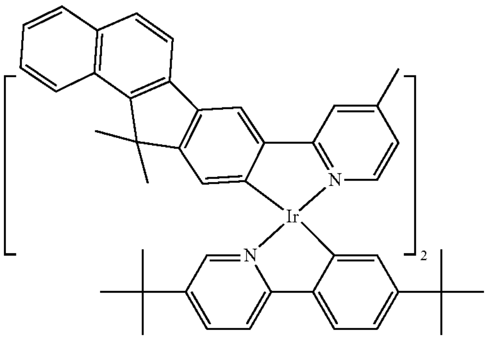
GG4
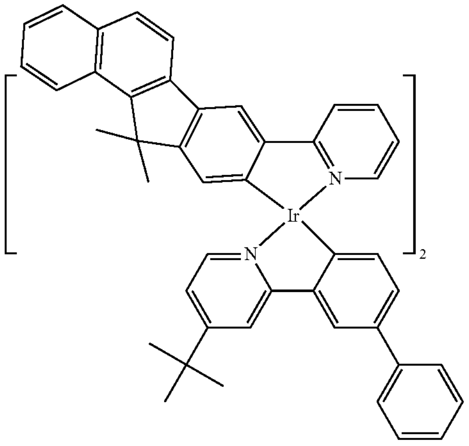
GG5
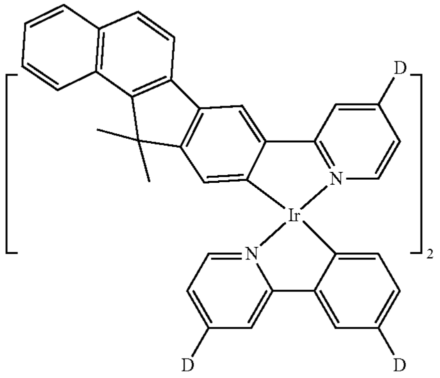
-continued
GG6
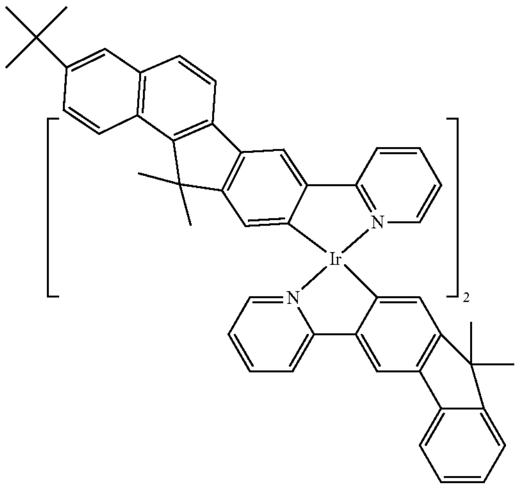
GG7
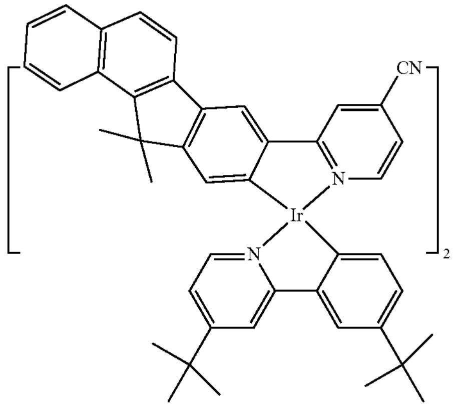
GG8
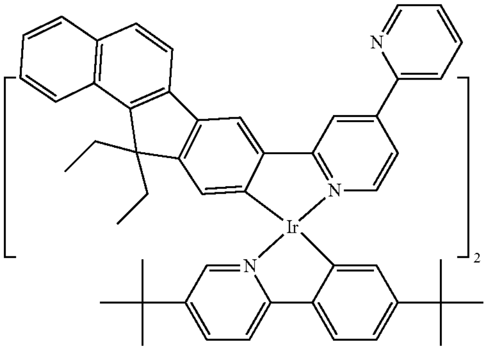

-continued
GG9
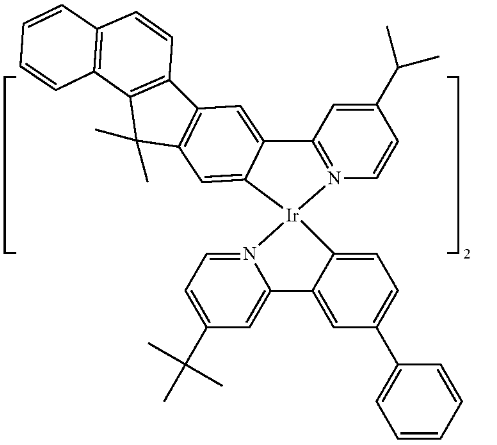
GG10
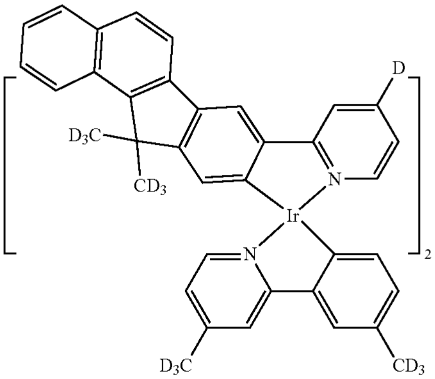
GG11
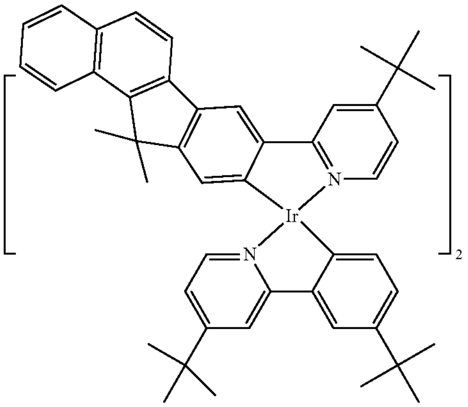
GG12
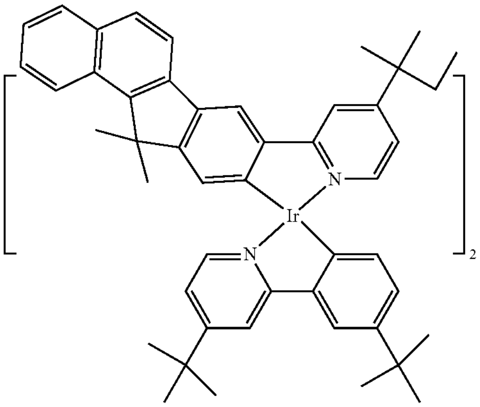
-continued
GG13
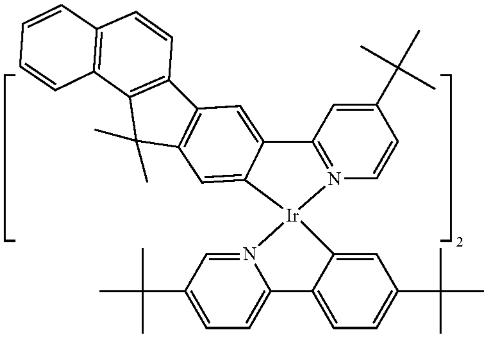
GG14
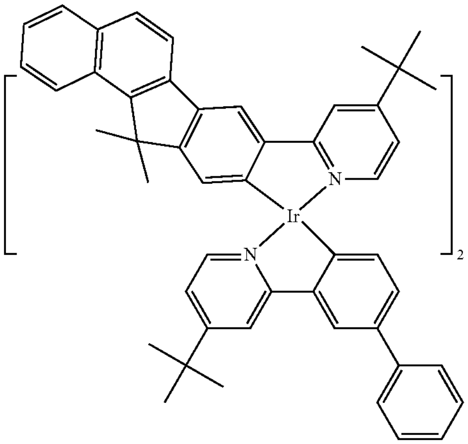
GG15
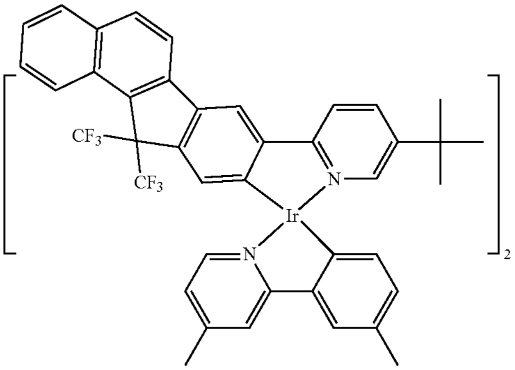
GG16
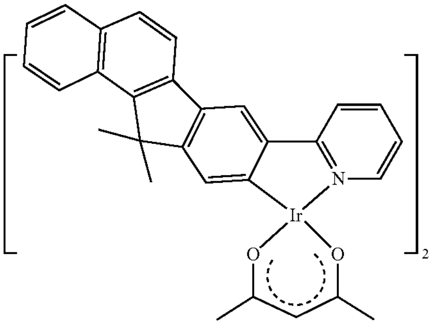

-continued
GG17
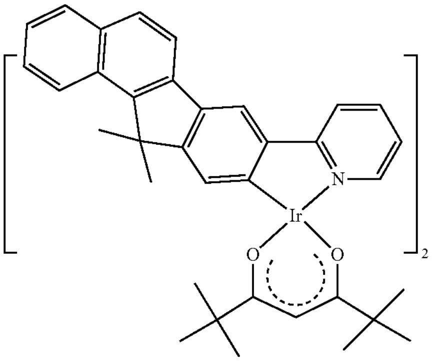
GG18
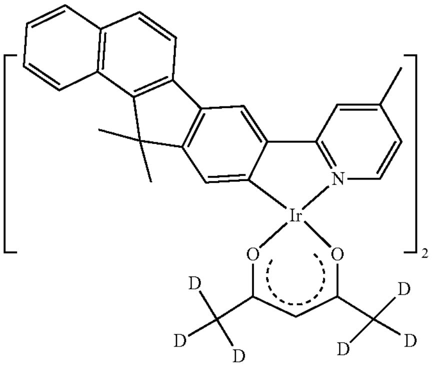
GG19
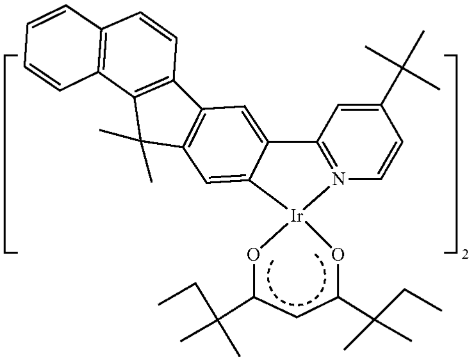
GG20
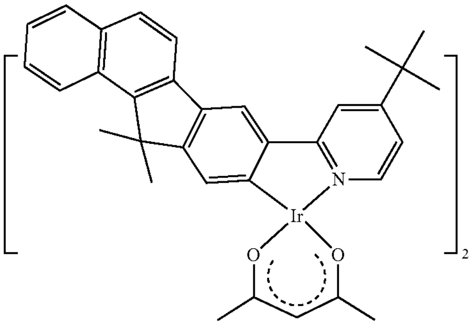
-continued
GG21
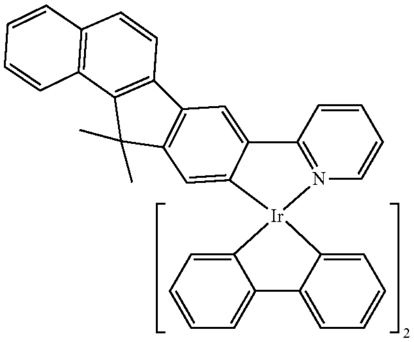
GG22
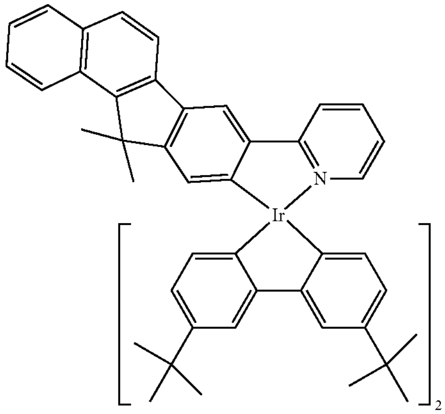
GG23
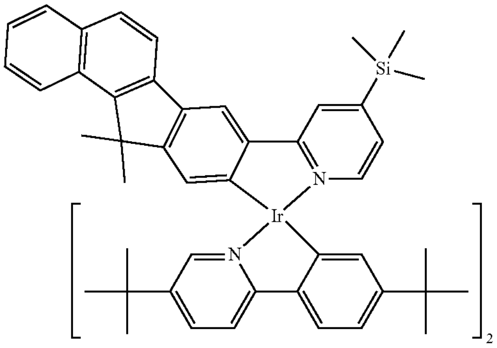
GG24
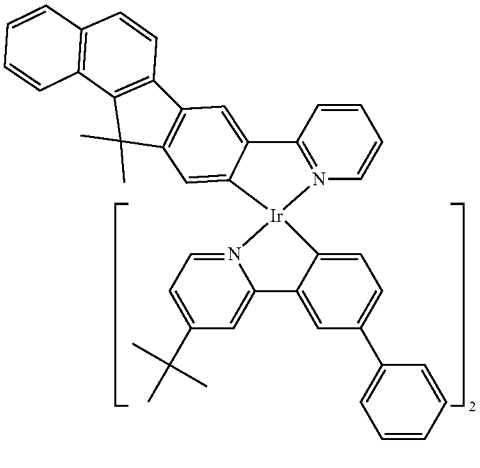

-continued
GG25
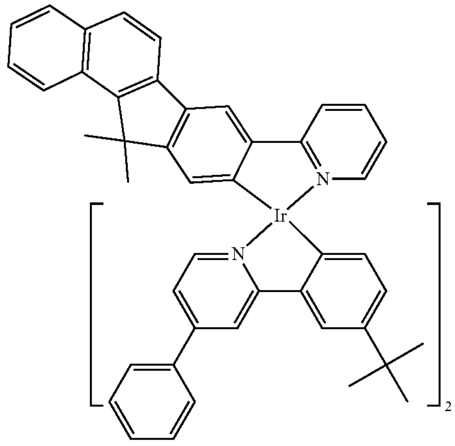
GG26
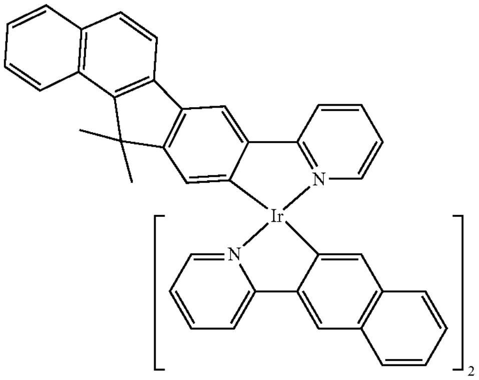
GG27
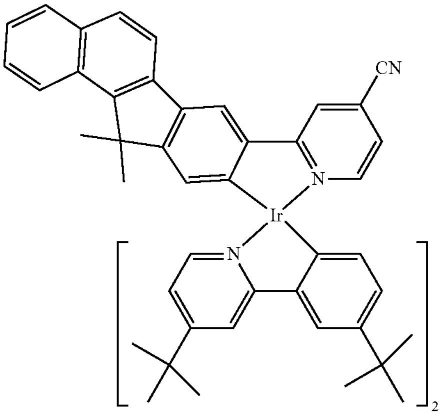
-continued
GG28
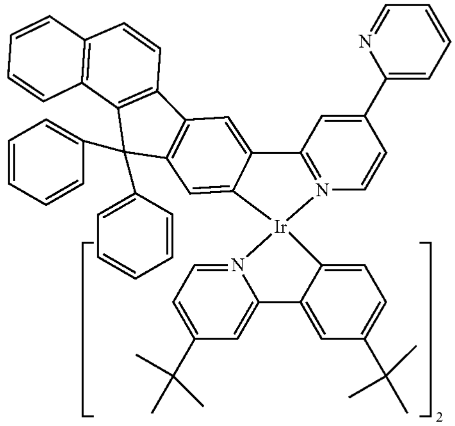
GG29
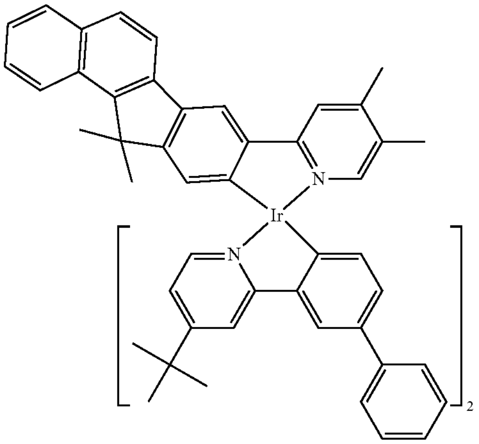
GG30
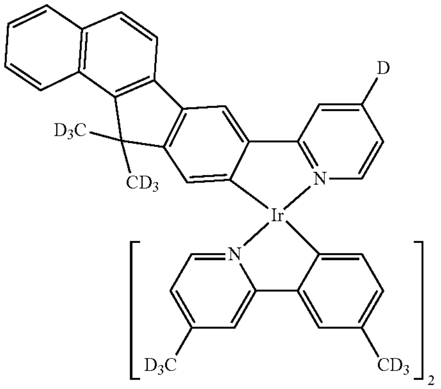

-continued
GG31
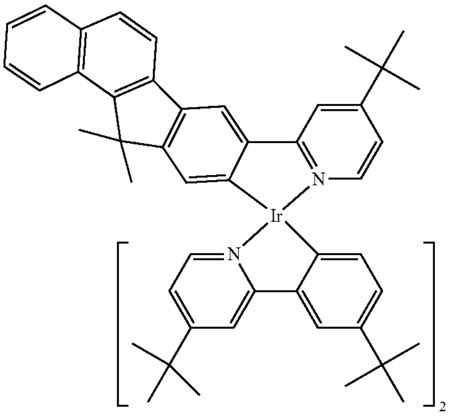
GG32
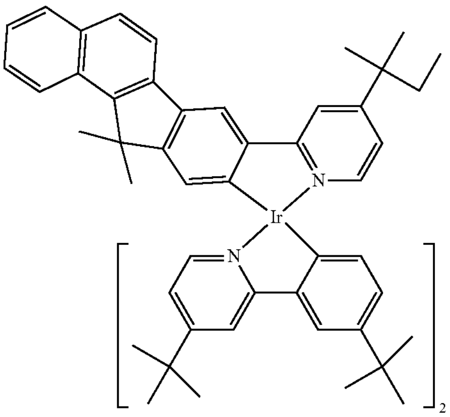
GG33
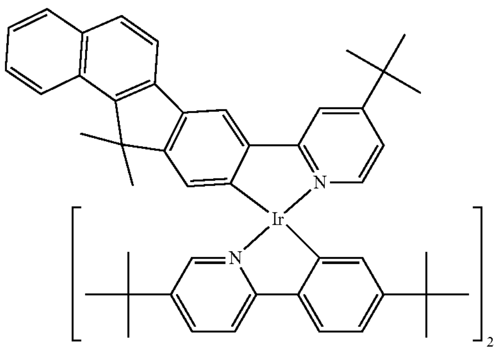
GG34
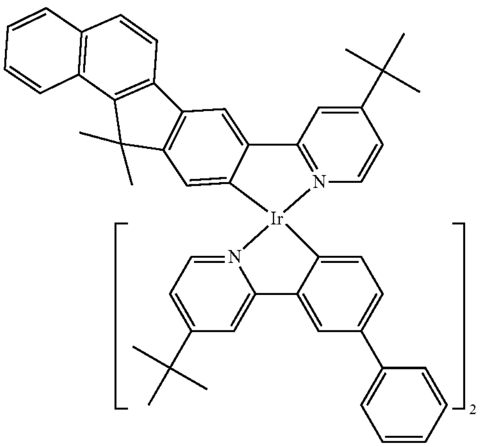
-continued
GG35
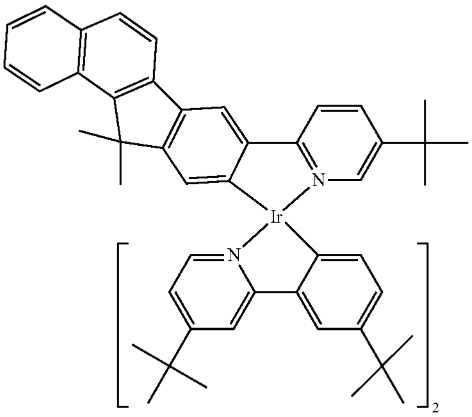
HH1
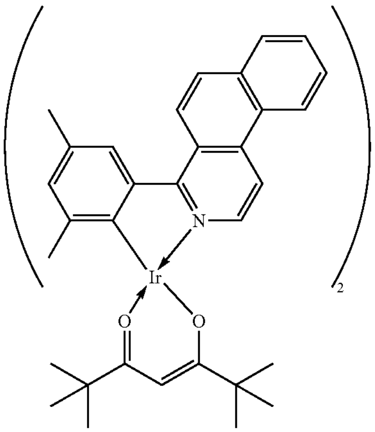
HH2
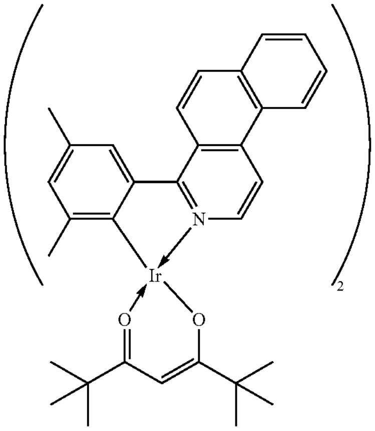

-continued
HH3
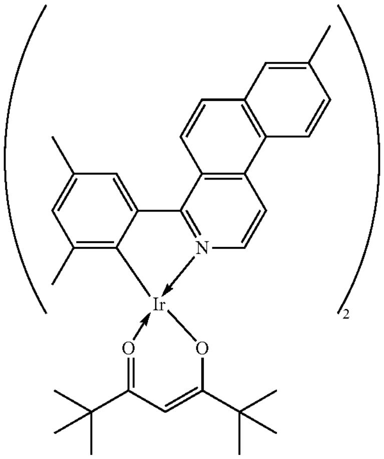
HH4
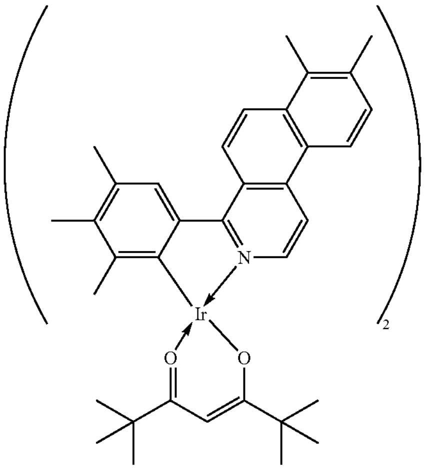
HH5
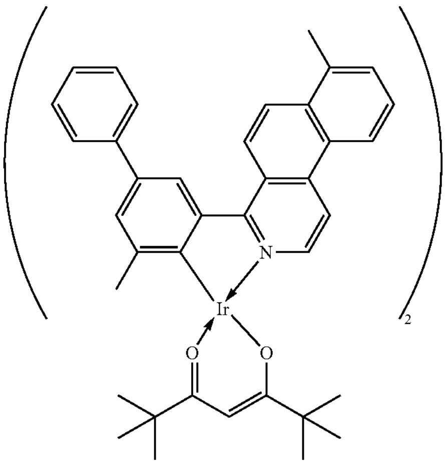
-continued
HH6
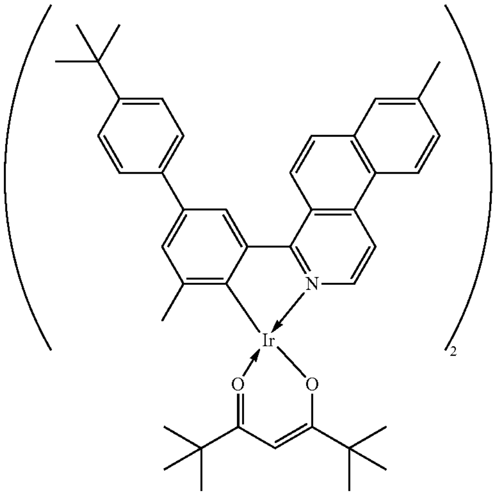
HH7
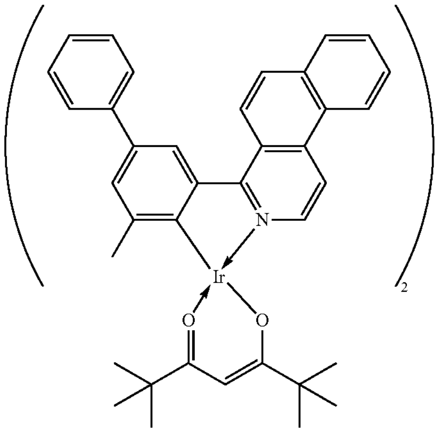
HH8
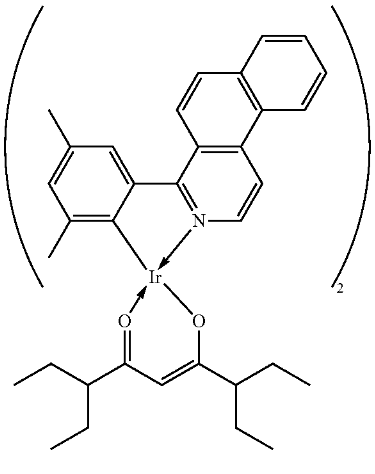

-continued
HH9
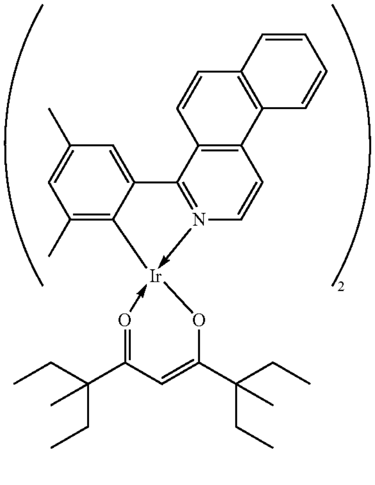
HH10
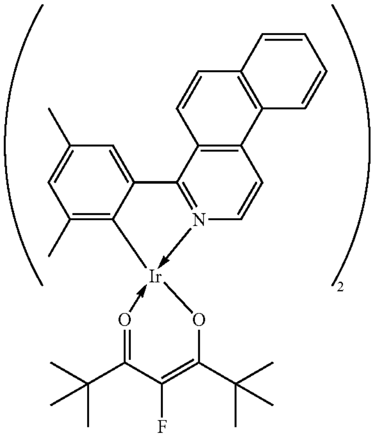
HH11
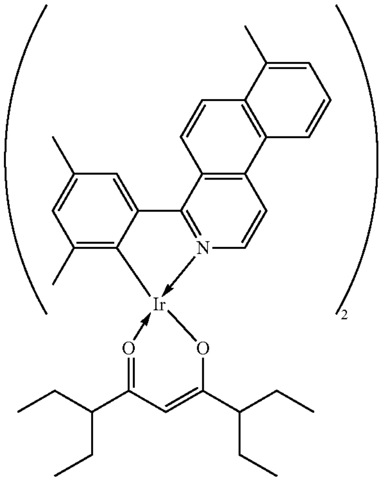
-continued
HH12
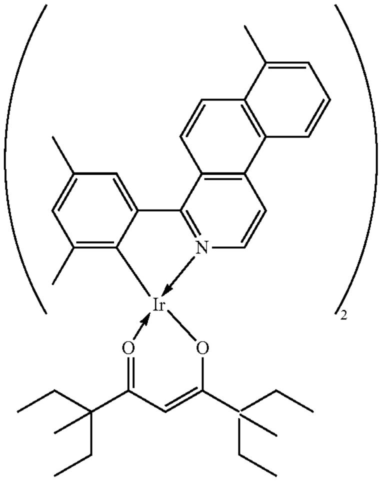
HH13
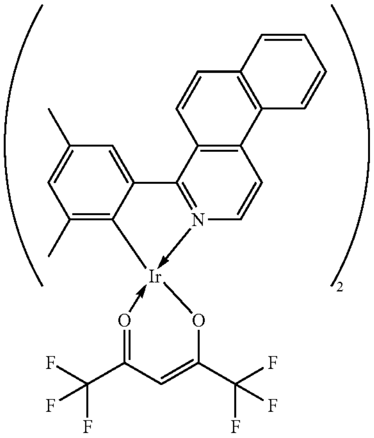
HH14
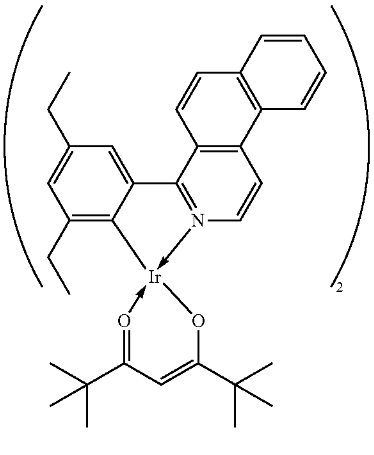

-continued
HH15
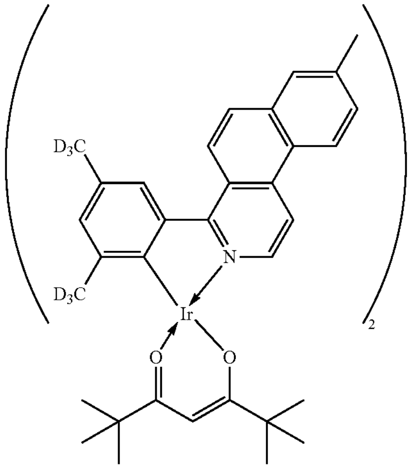
HH16
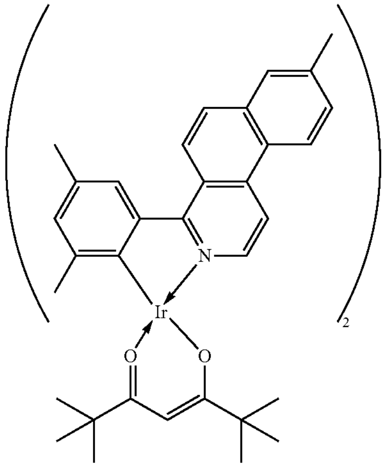
HH17
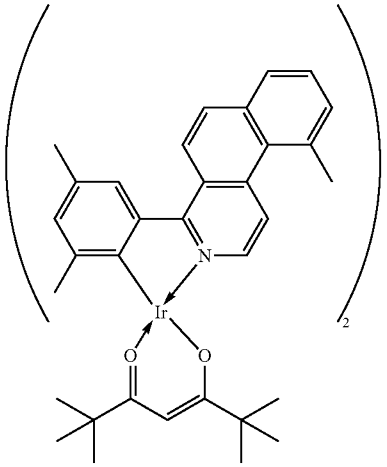
-continued
HH18
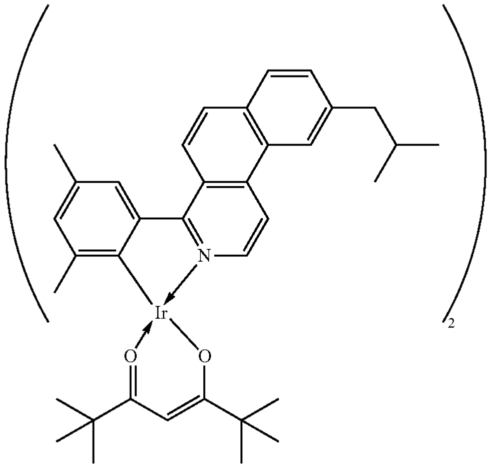
HH19
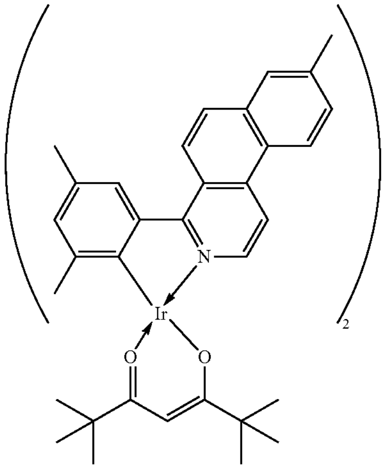
HH20
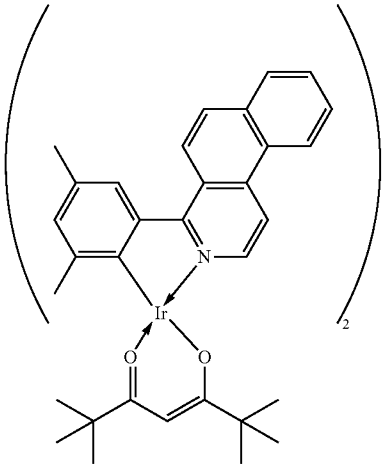

-continued
HH21
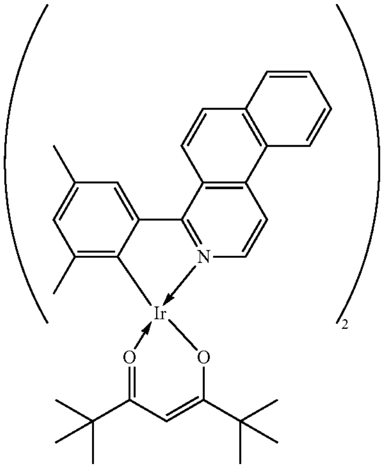
HH22
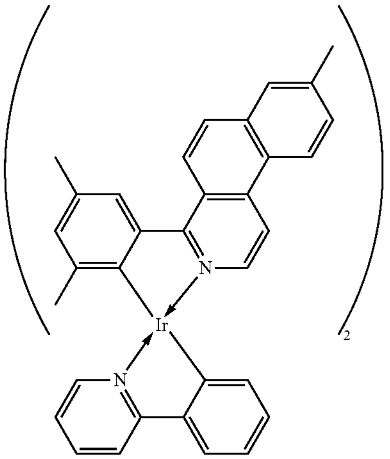
HH23
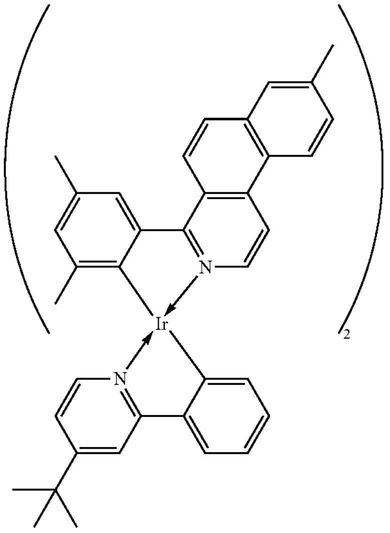
-continued
HH24
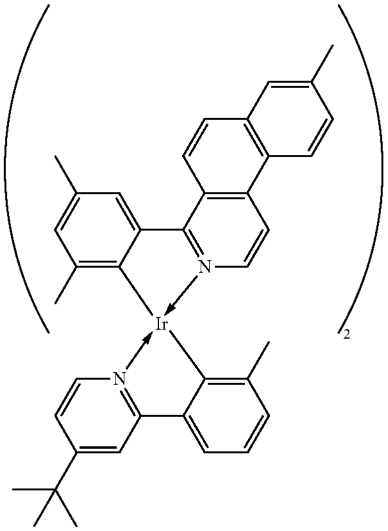
HH25
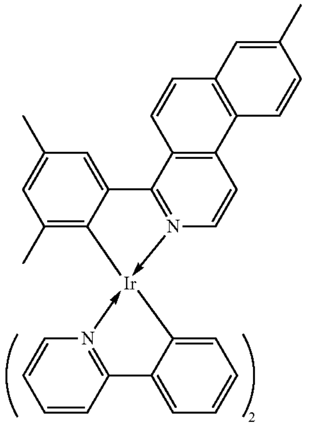
HH26
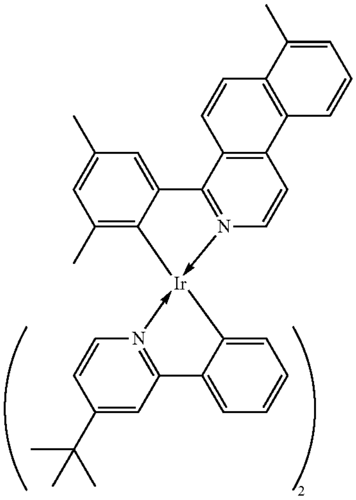

-continued
HH27
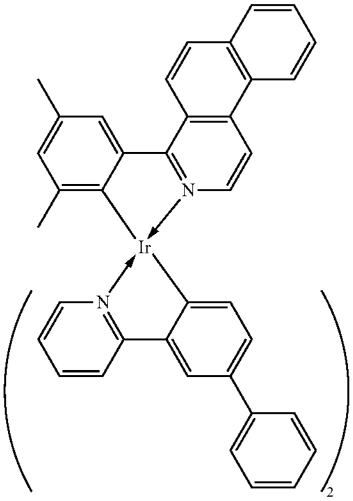
HH28
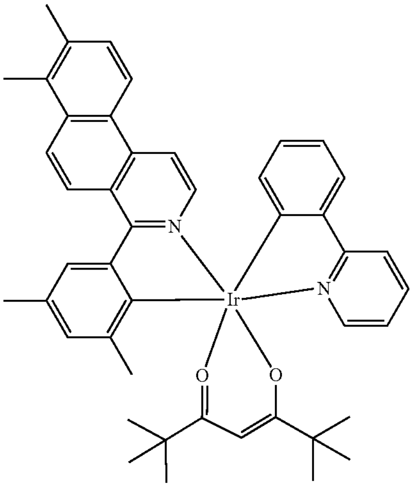
HH29
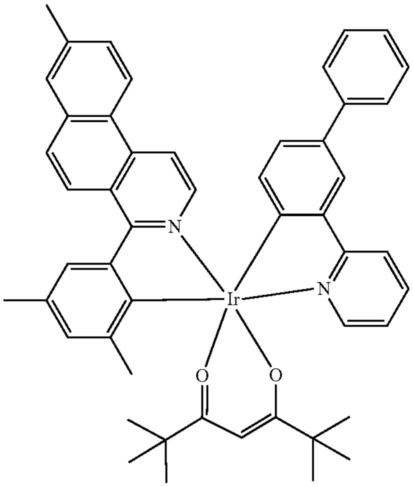
-continued
HH30
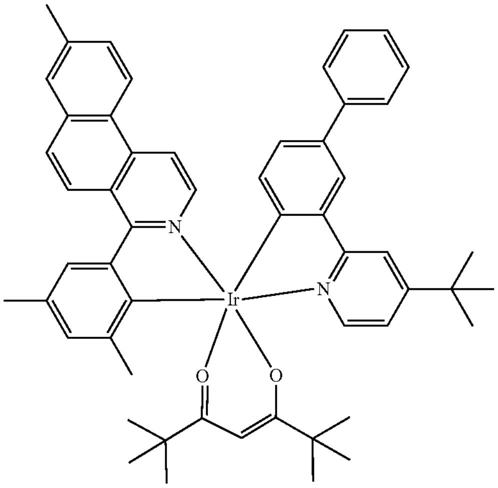
HH31
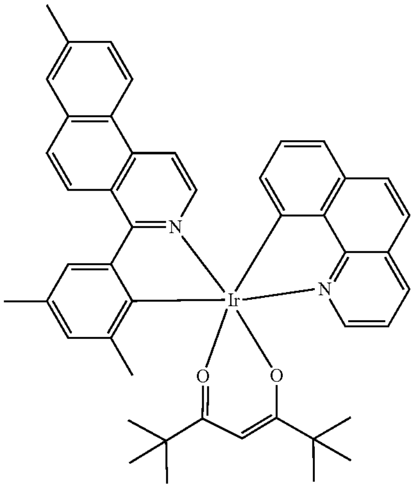
HH32
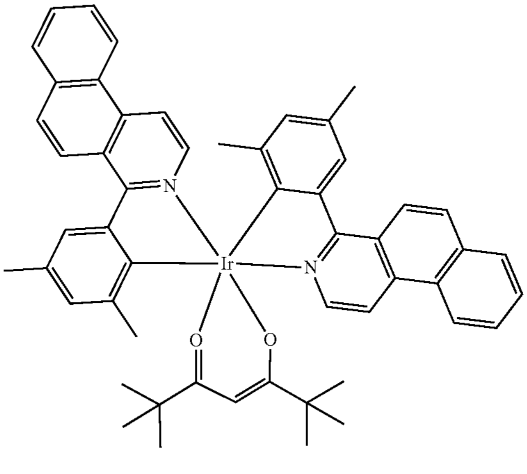

-continued
HH33
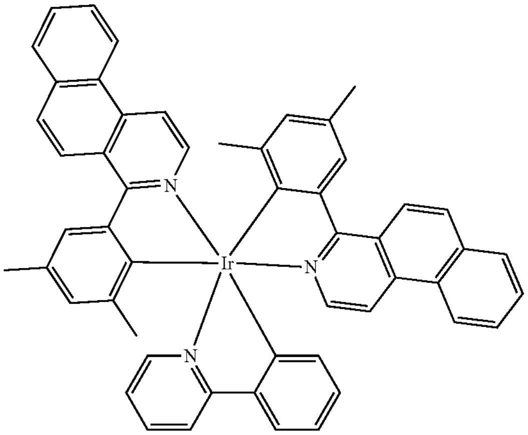
HH34
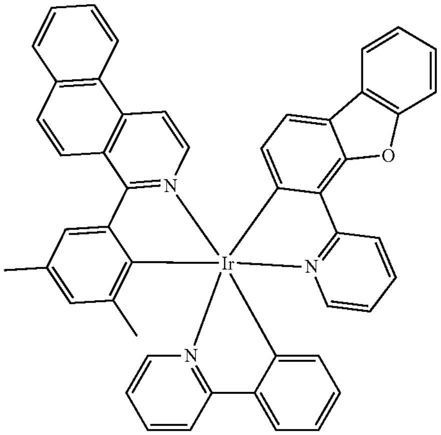
HH35
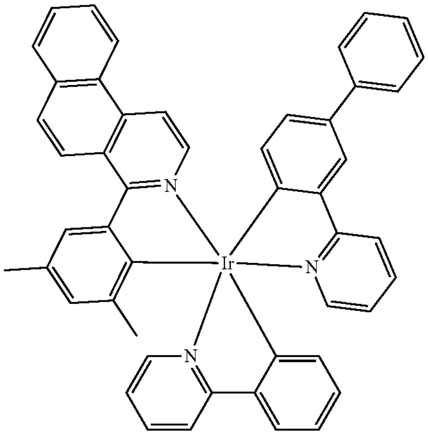
II1
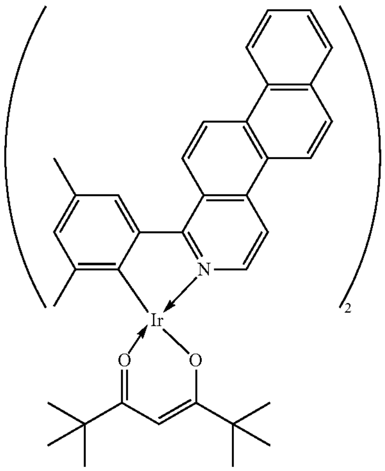
II2
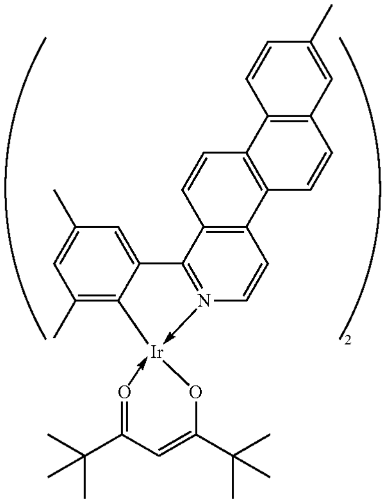
II3
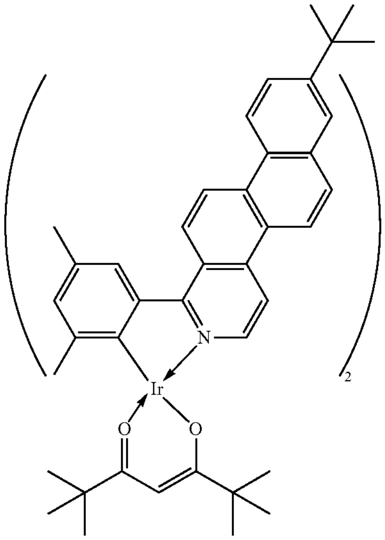

-continued
II4
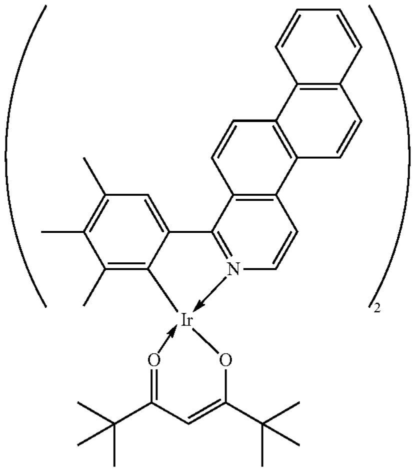
II5
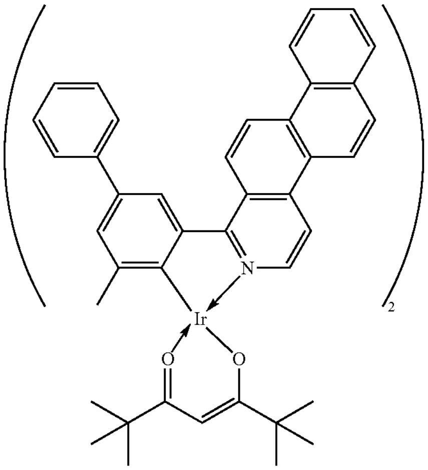
II6
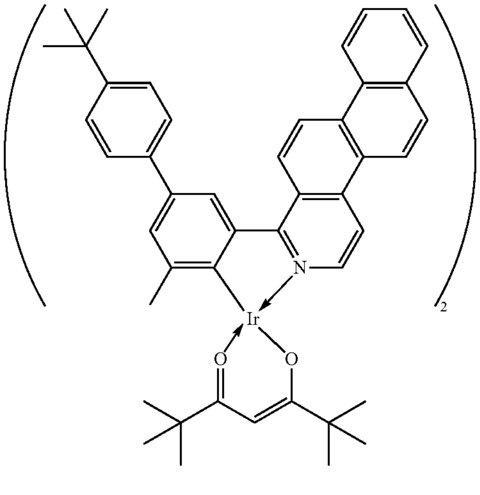
-continued
II7
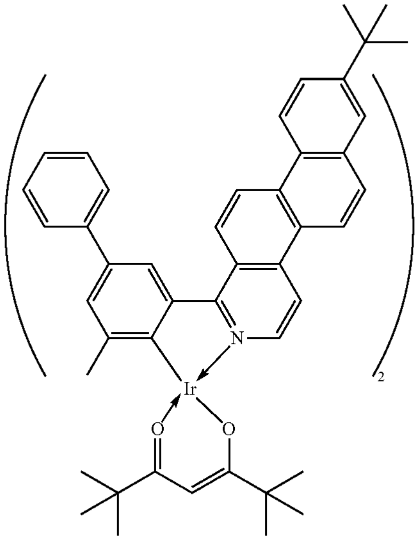
II8
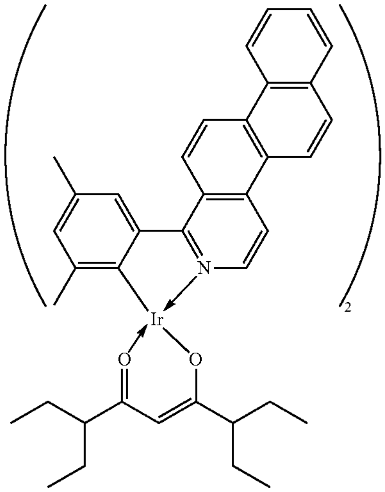
II9
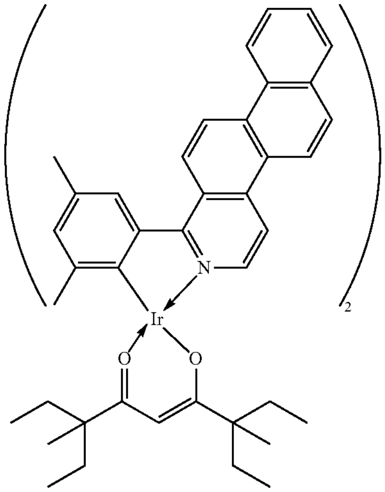

-continued
II10
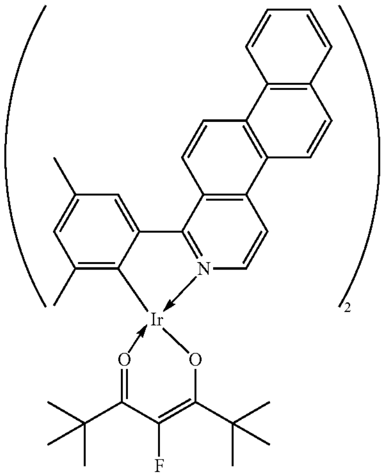
II11
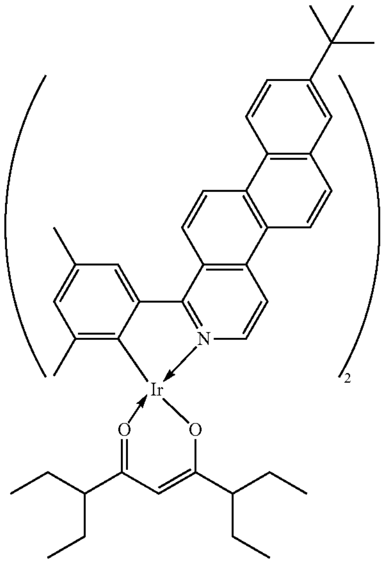
II12
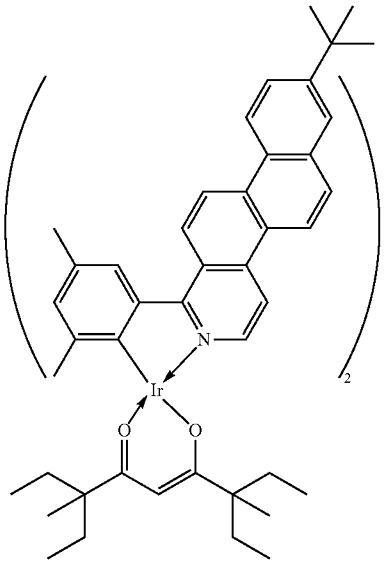
-continued
II13
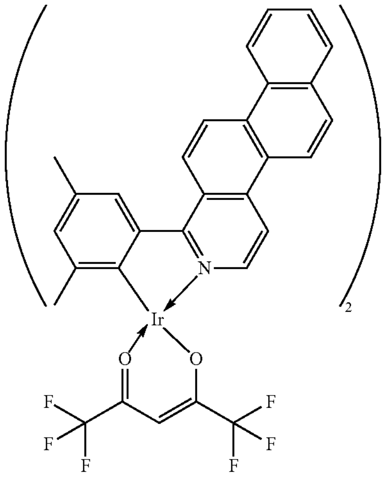
II14
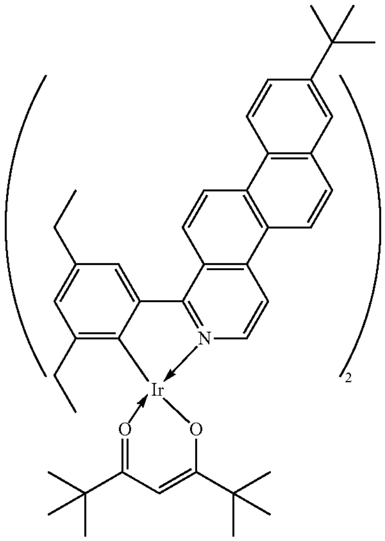
II15
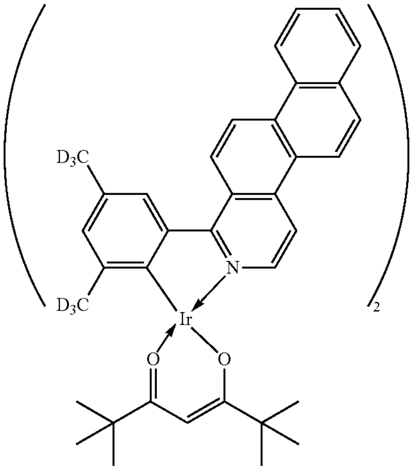

-continued
II16
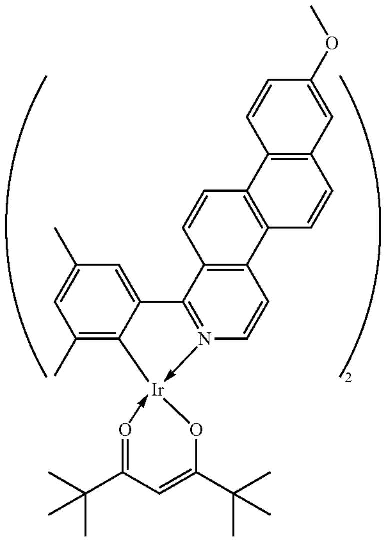
II17
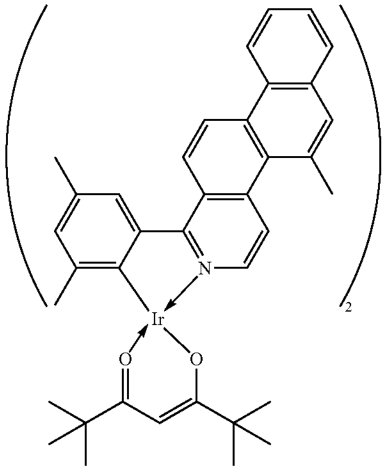
II18
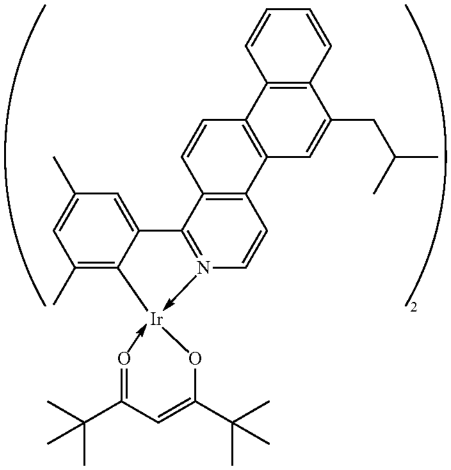
-continued
II19
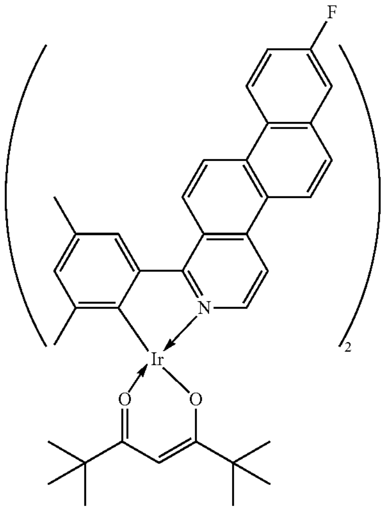
II20
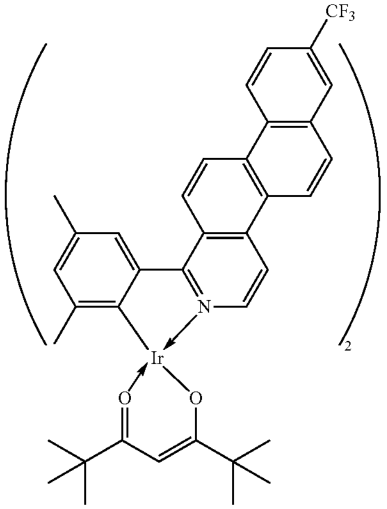
II21
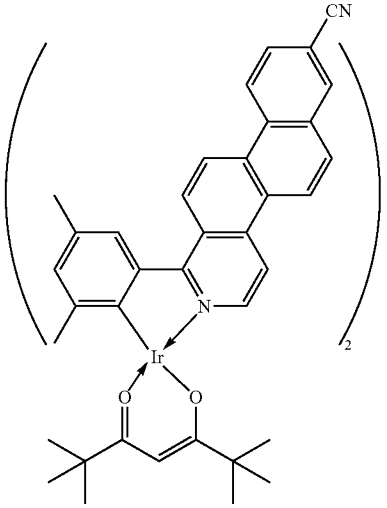

-continued
II22
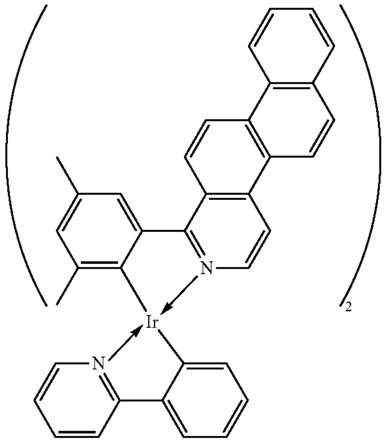
II23
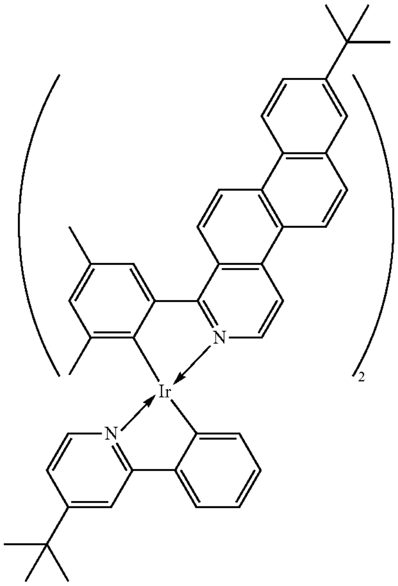
II24
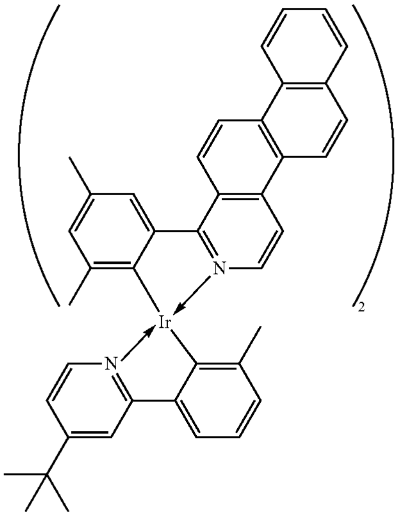
-continued
II25
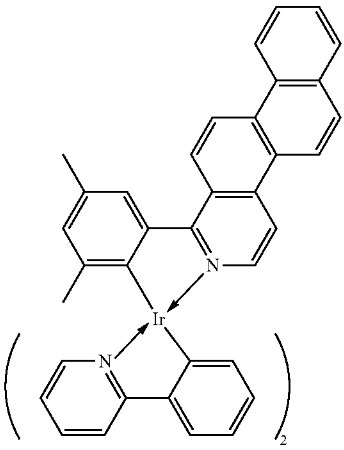
II26
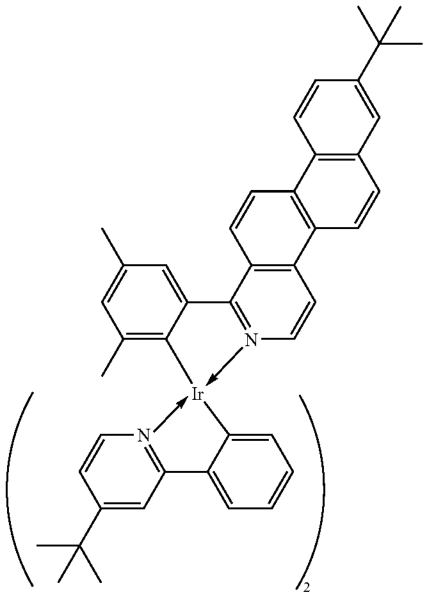
II27
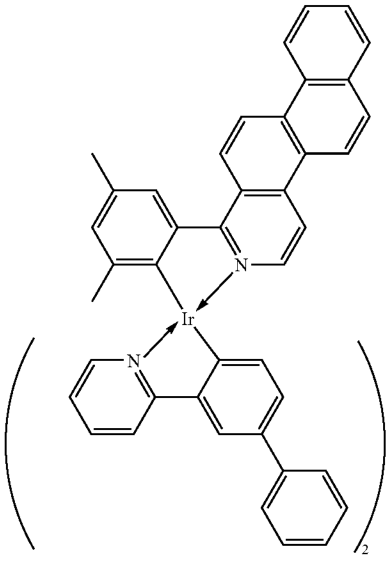

-continued
II28
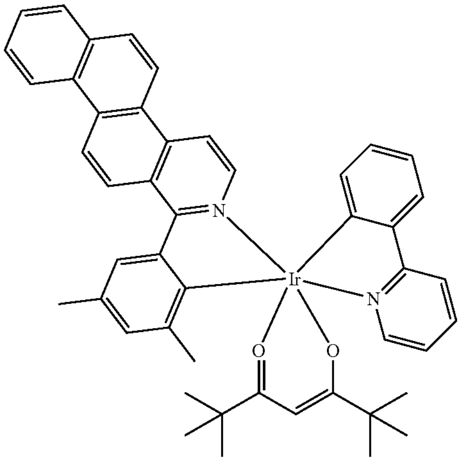
II29
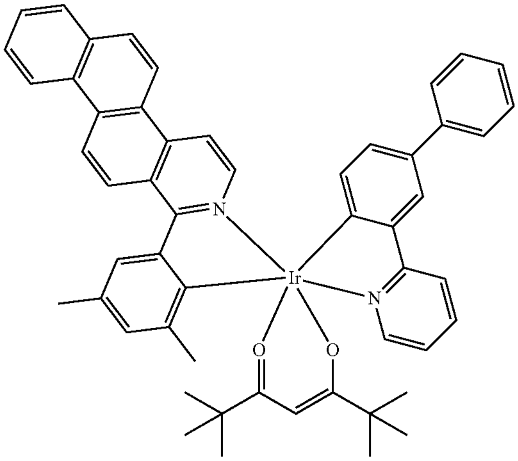
II30
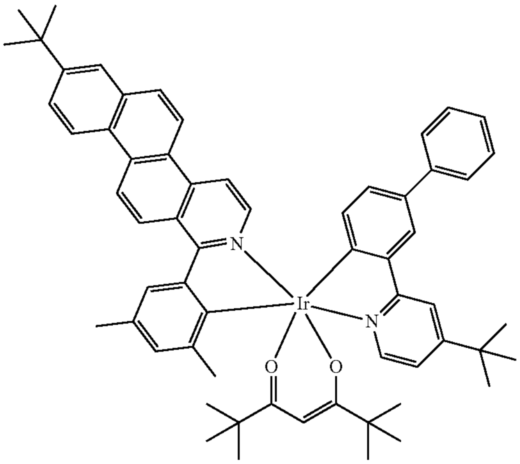
-continued
II31
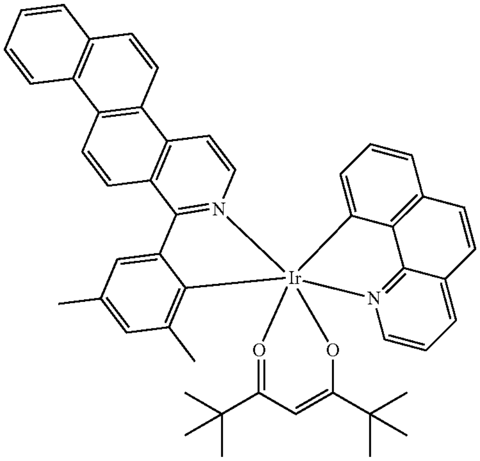
II32
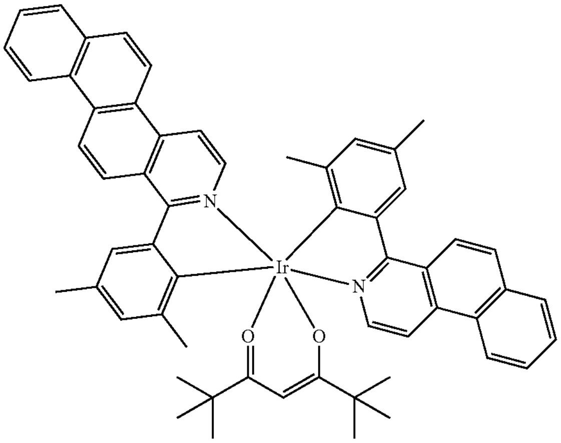
II33
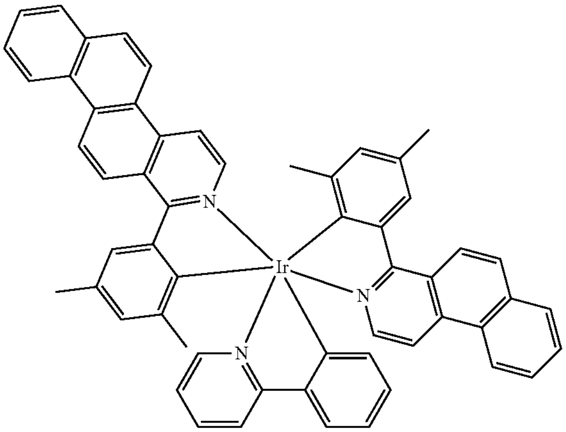

-continued

II34

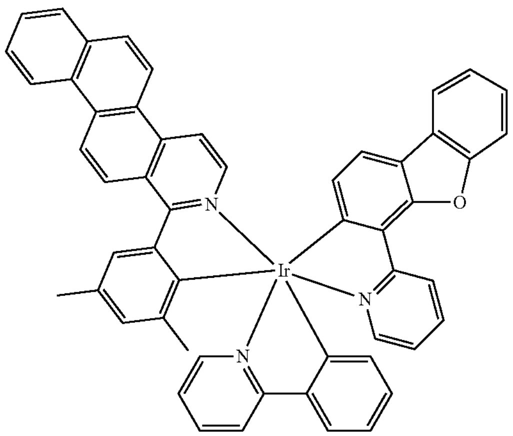

II35

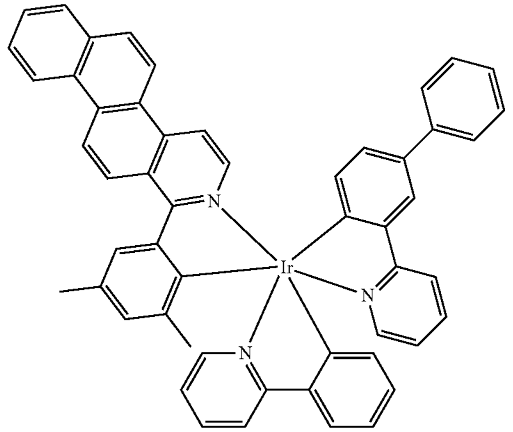

Exemplary compounds belonging to an AA group or a BB group are metal complexes having a partial structure denoted by formula [Ir-3] and are compounds including at least a phenanthrene ring in the ligand. These compounds are compounds having, in particular, excellent stability since the condensed ring is composed of an $SP^2$ hybrid orbital.

Exemplary compounds belonging to a CC group are metal complexes having a partial structure denoted by formula [Ir-4] and are compounds including at least a triphenylene ring in the ligand. These compounds are compounds having, in particular, excellent stability since the condensed ring is composed of an SP' hybrid orbital.

Exemplary compounds belonging to a DD group are metal complexes having a partial structure denoted by formulae [Ir-5] to [Ir-8] and are compounds including at least a dibenzofuran ring, a dibenzothiophene ring, a benzonaphthofuran ring, or a benzonaphthothiophene ring in the ligand. These compounds are compounds which are, in particular, easy-to-adjust a carrier balance since the condensed ring includes an oxygen atom or a sulfur atom so that the electric charge transportability is enhanced due to plentiful unshared electron pairs included in these atoms.

Exemplary compounds belonging to an EE group to a GG group are metal complexes having a partial structure denoted by formulae [Ir-6] to [Ir-8] and are compounds including at least a benzofluorene ring in the ligand. These compounds including a substituent at position 9 of the fluorene ring in a direction perpendicular to the in-plane direction of the fluorene ring enables condensed rings to be particularly suppressed from overlapping one another. Consequently, these compounds have, in particular, excellent sublimation properties.

Exemplary compounds belonging to an HH group are metal complexes having a partial structure denoted by formulae [Ir-11] to [Ir-13] and are compounds including at least a benzoisoquinoline ring in the ligand. These compounds are compounds which are, in particular, easy-to-adjust a carrier balance since the condensed ring includes a nitrogen atom so that the electric charge transportability is enhanced due to an unshared electron pair included in the atom and high electronegativity.

Exemplary compounds belonging to an II group are metal complexes having a partial structure denoted by formula [Ir-14] and are compounds including at least a naphthoisoquinoline ring in the ligand. These compounds are compounds which are, in particular, easy-to-adjust a carrier balance since the condensed ring includes a nitrogen atom so that the electric charge transportability is enhanced due to an unshared electron pair included in the atom and high electronegativity.

Compounds Other than Organic Compound According to Present Embodiment

As the situation demands, a known low-molecular-weight-based or polymer-based hole injection compound or hole transport compound, compound serving as the host, light-emitting compound, electron injection compound, electron transport compound, or the like may be used in combination in addition to the organic compound according to the present embodiment. Examples of these compounds will be described below.

The hole transport compound is favorably a material having high hole mobility to facilitate injection of a hole from an anode and to enable the injected hole to be transported to the light-emitting layer. In addition, a material having a high glass transition temperature is favorable to suppress the film quality such as crystallization from deteriorating in the organic light-emitting element. Examples of the low-molecular-weight-based or polymer-based material having hole injection-transport performance include triarylamine derivatives, arylcarbazole derivatives, phenylenediamine derivatives, stilbene derivatives, phthalocyanine derivatives, porphyrin derivatives, poly(vinylcarbazole)s, poly(thiophen)s, and other conductive polymers. Further, the above-described hole injection-transport materials are also favorably used for the electron blocking layer. Specific examples of the compound used as the hole injection-transport material will be described below, but the compound is not limited to these, as a matter of course.

HT1
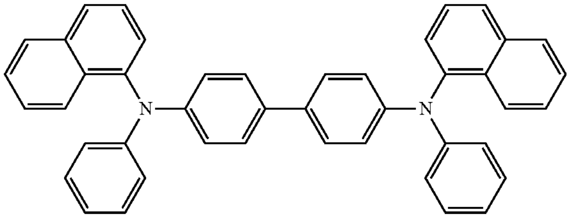
HT2
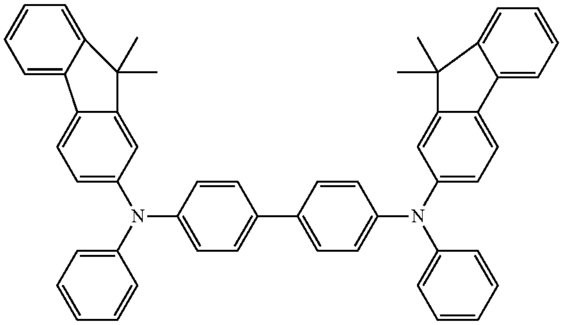
HT3
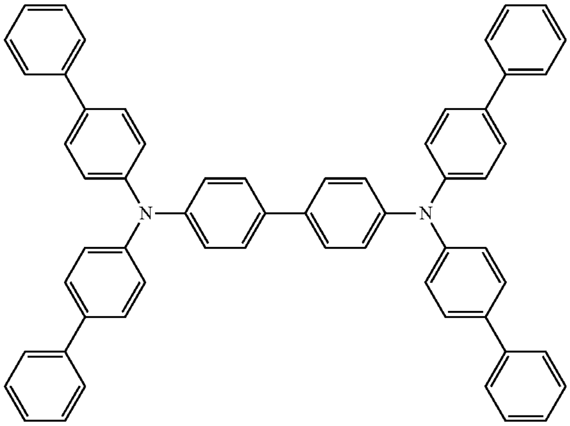
HT4
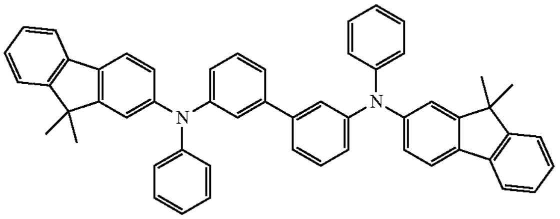
HT5
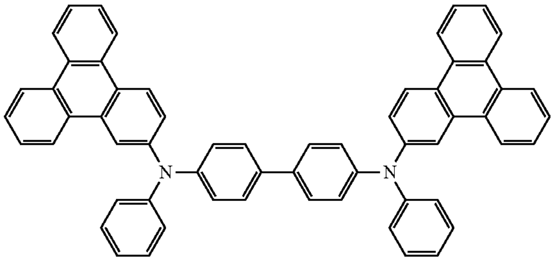
HT6
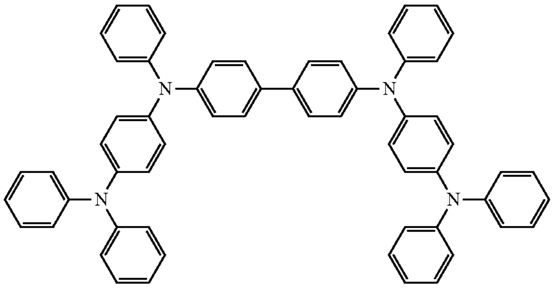
HT7
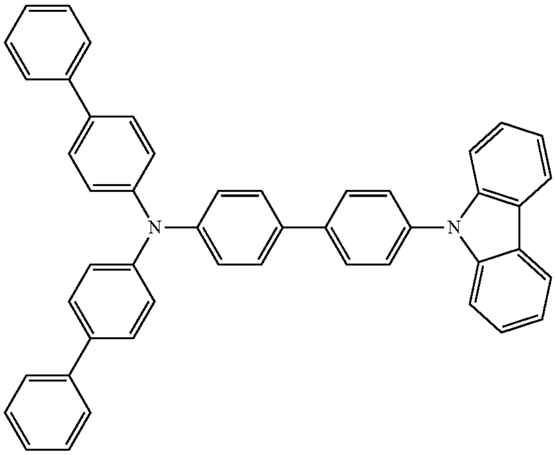
HT8
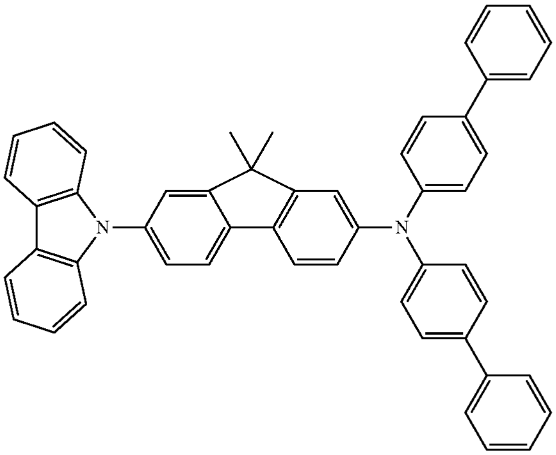

-continued
HT9
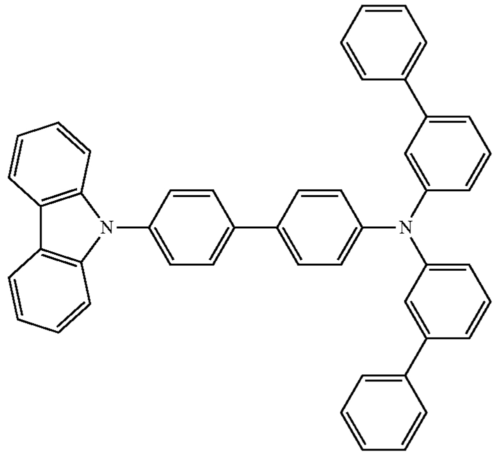
HT10
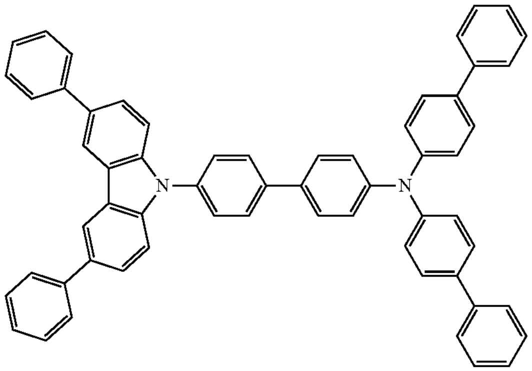
HT11
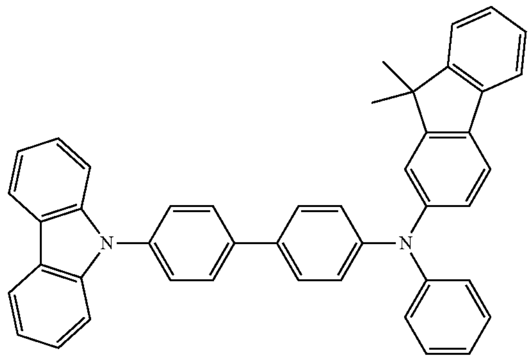
HT12
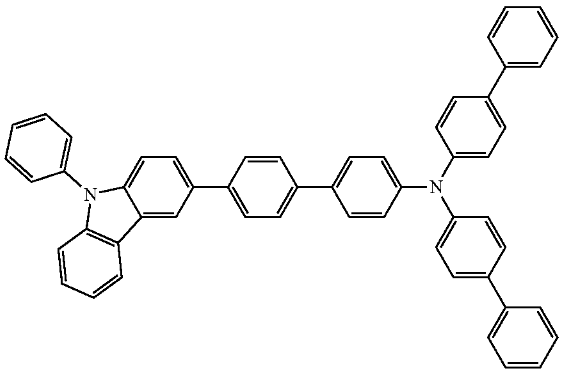
HT13
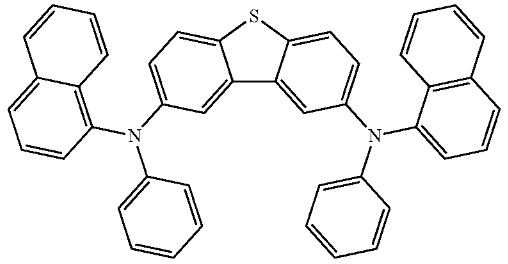
HT14
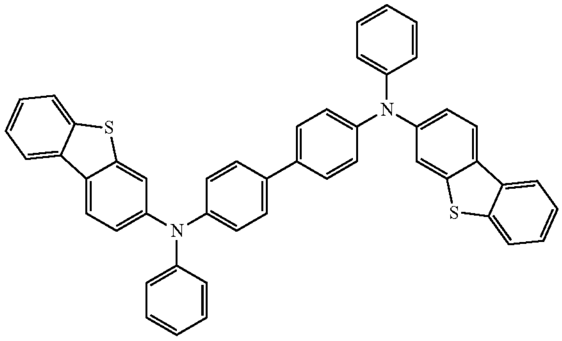
HT15
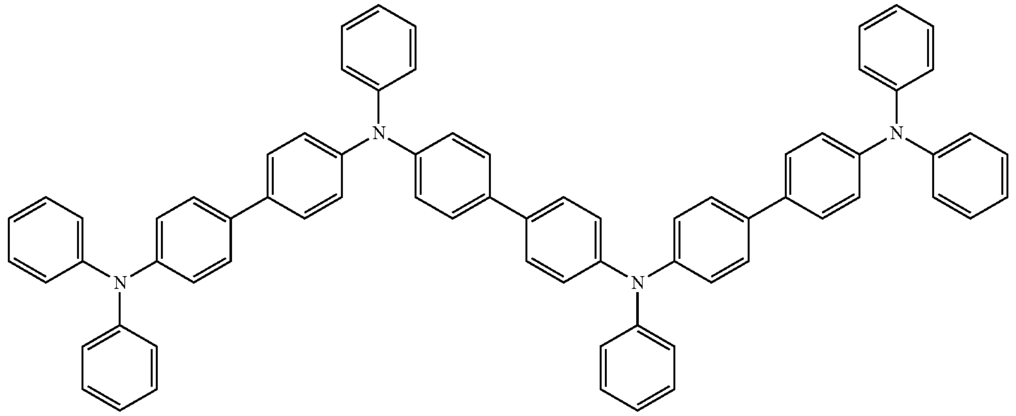

-continued

HT16

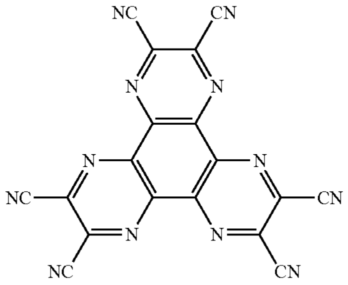

HT18

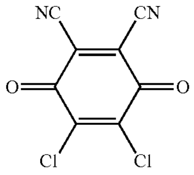

HT17

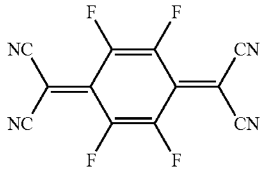

HT19

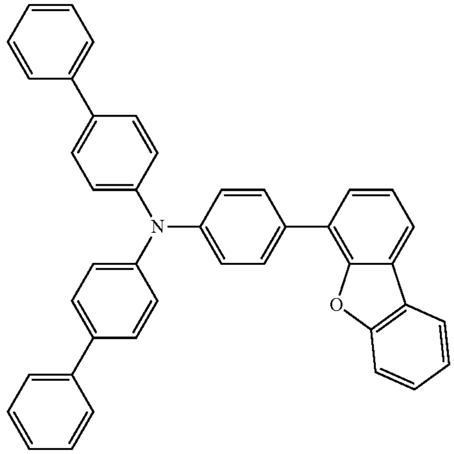

Examples of the light-emitting material mainly involved in the light-emitting function include condensed ring compounds (for example, fluorene derivatives, naphthalene derivatives, pyrene derivatives, perylene derivatives, tetracene derivatives, anthracene derivatives, and rubrene), quinacridone derivatives, coumarin derivatives, stilbene derivatives, organic aluminum complexes such as tris(8-quinolinolato)aluminum, iridium complexes, platinum complexes, rhenium complexes, copper complexes, europium complexes, ruthenium complexes, and polymer derivatives such as poly(phenylenevinylene) derivatives, poly(fluorene) derivatives, and poly(phenylene) derivatives. Specific examples of the compound used as the light-emitting material will be described below, but the compound is not limited to these, as a matter of course.

BD1

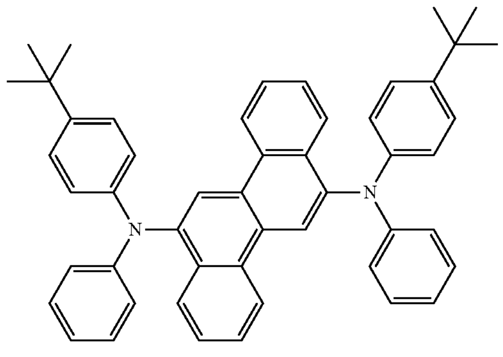

-continued

BD2

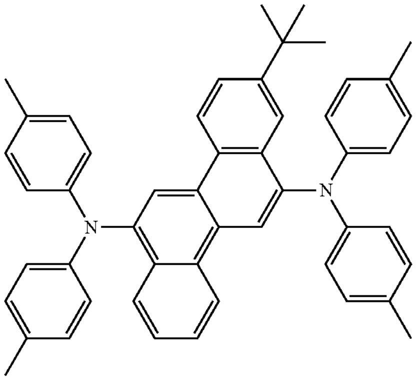

BD3

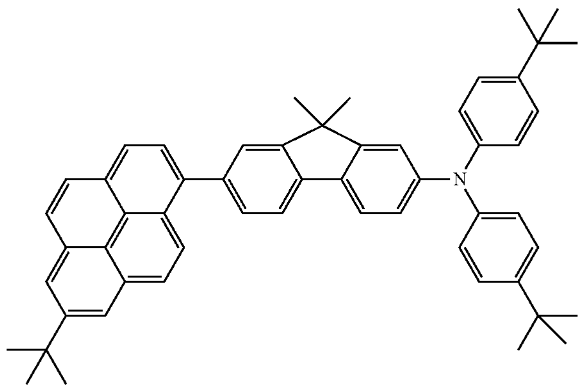

-continued
BD4
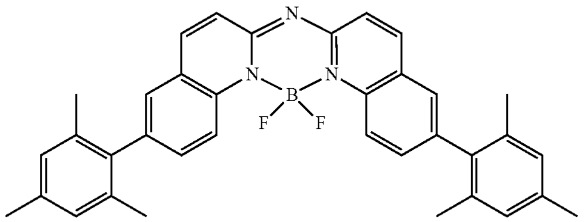
BD5
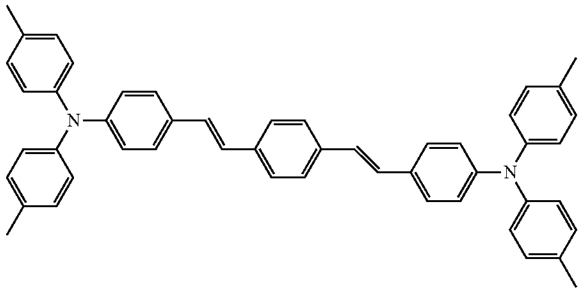
BD6
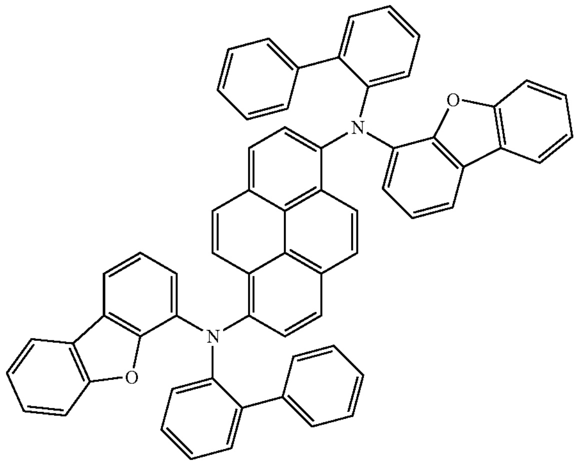
BD7
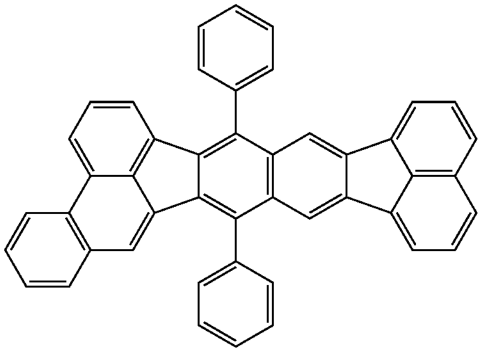
-continued
BD8
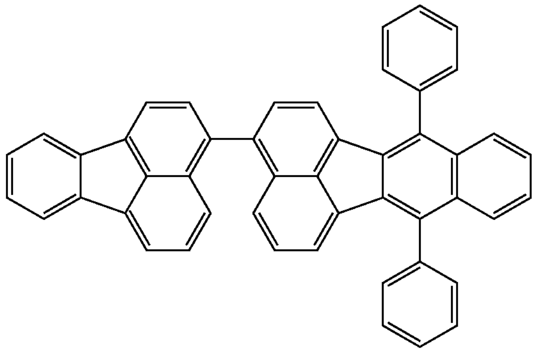
BD9
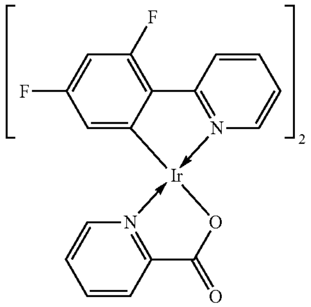
BD10
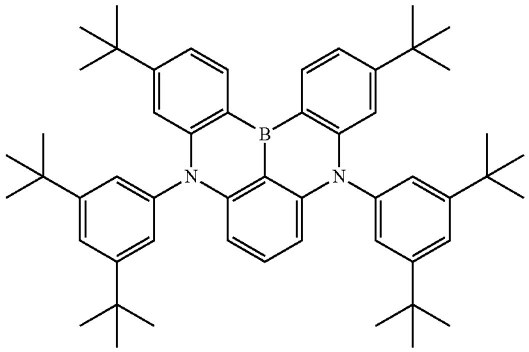
GD1
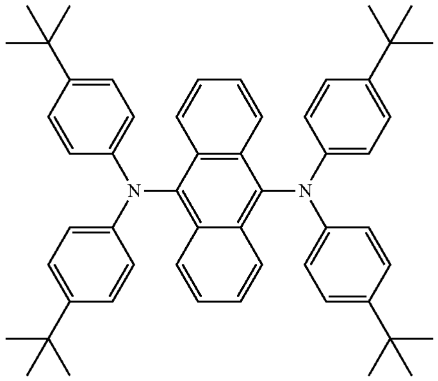

-continued
GD2
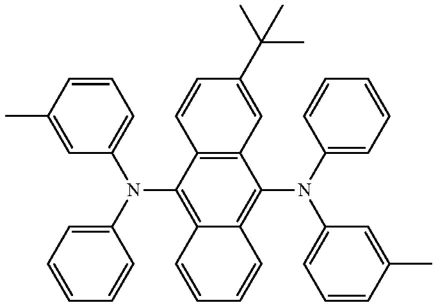
GD3
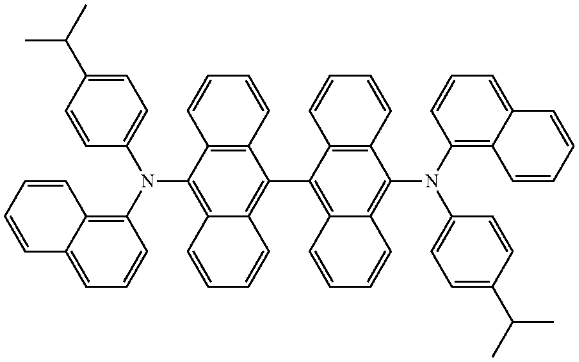
GD4
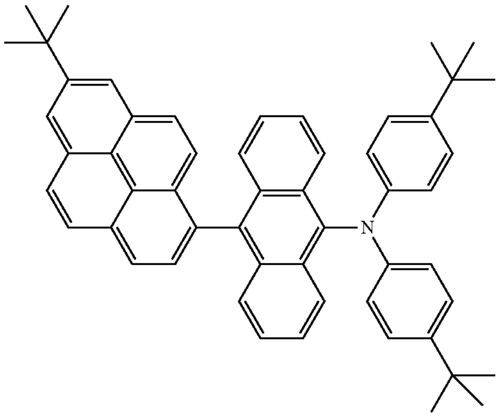
GD5
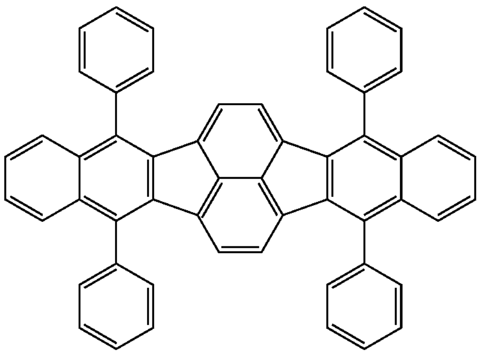
-continued
GD6
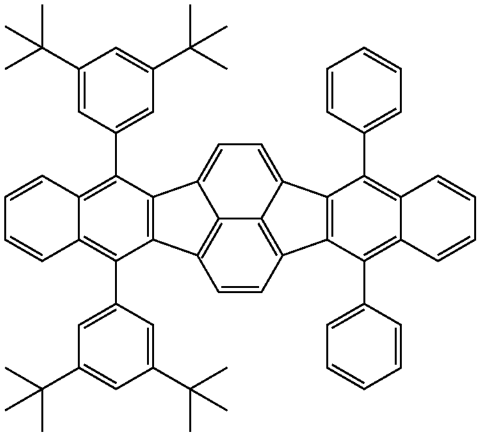
GD7
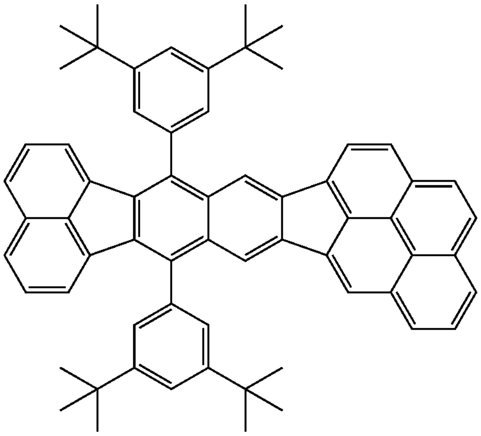
GD8
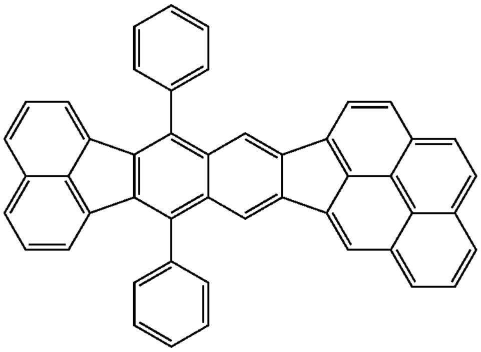

-continued
GD9
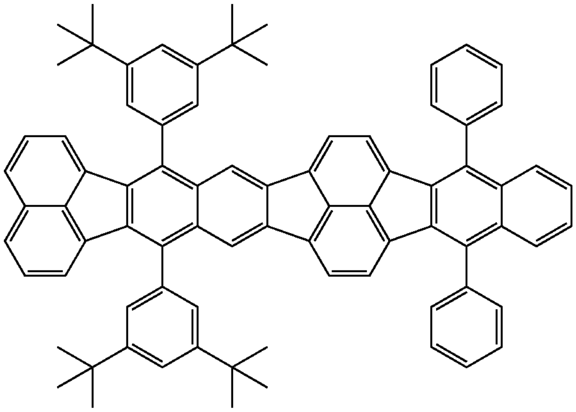
GD10
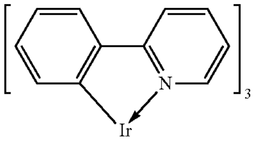
GD11
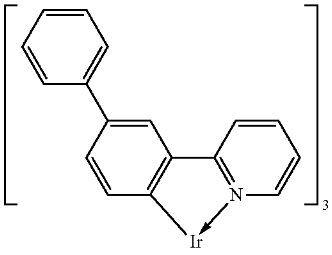
GD12
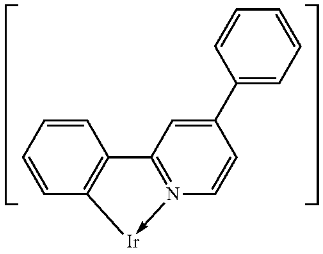
GD13
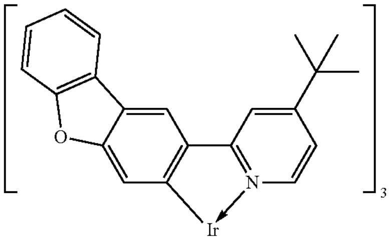
-continued
GD14
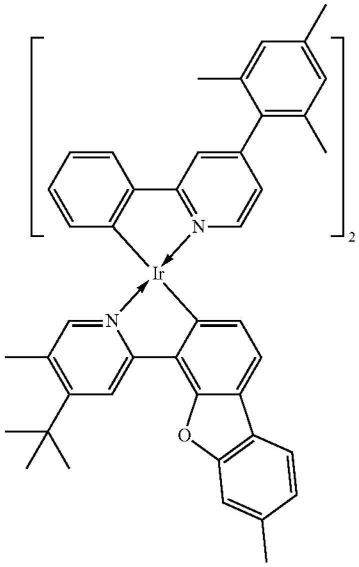
GD15
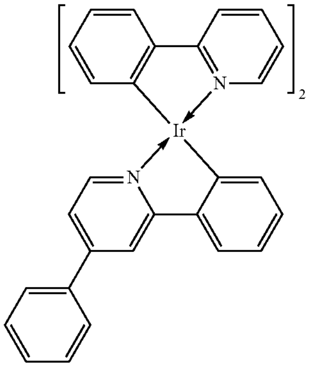
RD1
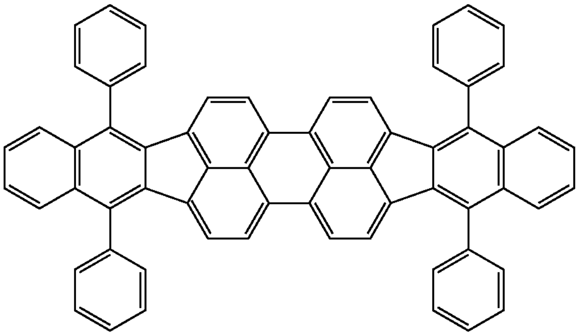
RD2
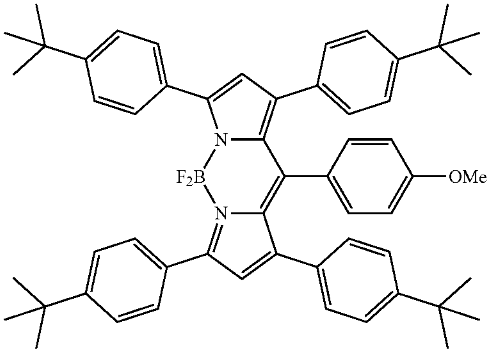

-continued

RD3

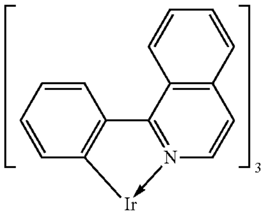

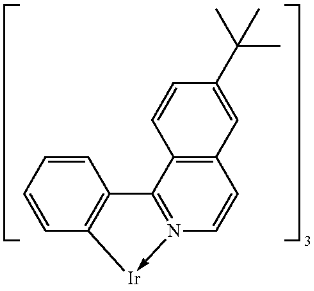

RD5

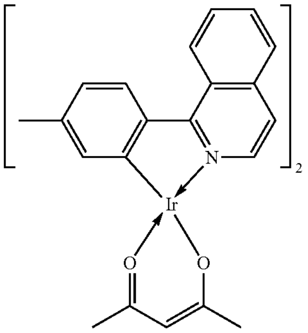

RD6

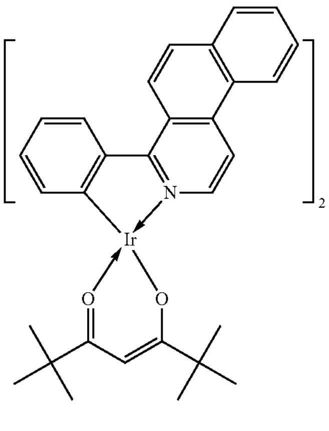

RD7

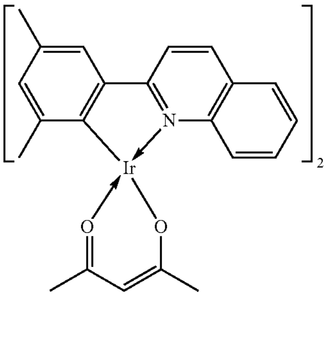

-continued

RD8

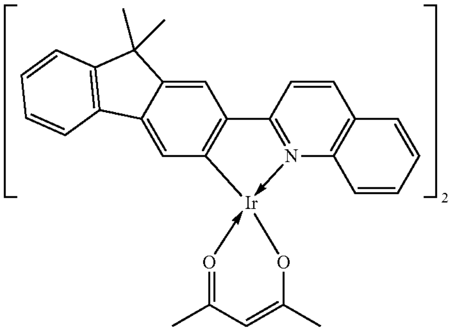

RD9

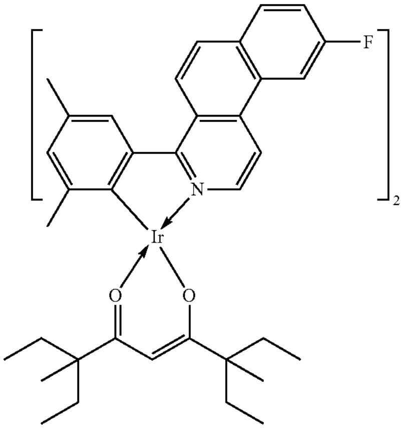

RD10

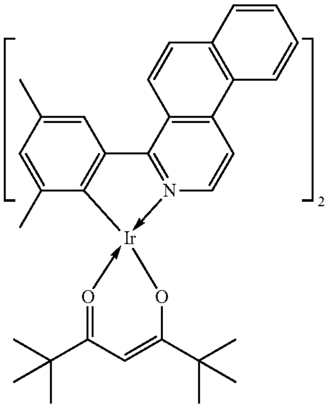

A compound other than the organic compound according to the present embodiment may be contained as a third component serving as the light-emitting layer host or the light-emission assist material included in the light-emitting layer. Examples of the third component include aromatic hydrocarbon compounds or derivatives thereof, carbazole derivatives, azine derivatives, xanthone derivatives, dibenzofuran derivatives, dibenzothiophene derivatives, organic aluminum complexes such as tris(8-quinolinolato)aluminum, and organic beryllium complexes.

In particular, the assist material can be a material having a carbazole skeleton, a material including an azine ring such as a diazine ring or a triazine ring in the skeleton, and a material including xanthone in the skeleton. The reason for this is that these materials are easy-to-adjust the HOMO level and the LUMO level due to a high electron donating property or a high electron attracting property. Since the organic compound according to the present embodiment has a structure in which the condensed rings B of three or more rings are bonded to both ends of a biphenylene chain, the band gap is increased to some extent. Therefore, a material having the above-described skeleton capable of adjusting the HOMO level and the LUMO level is particularly favorable as the assist material. When these assist materials and the organic compound according to the present embodiment are combined, a favorable carrier balance is realized.

Specific examples of the compound used as the light-emitting layer host or the light-emission assist material included in the light-emitting layer will be described below, but the compound is not limited to these, as a matter of course. Of the specific examples below, the materials which have a carbazole skeleton and which are favorable as the assist material are EM32 to EM38. The materials which include an azine ring in the skeleton and which are favorable as the assist material are EM35, EM36, EM37, EM38, EM39, and EM40. The materials which include xanthone in the skeleton and which are favorable as the assist material are EM28 and EM30.

EM1

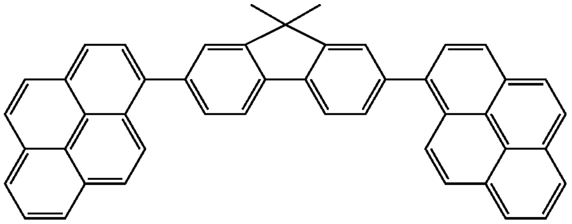

EM2

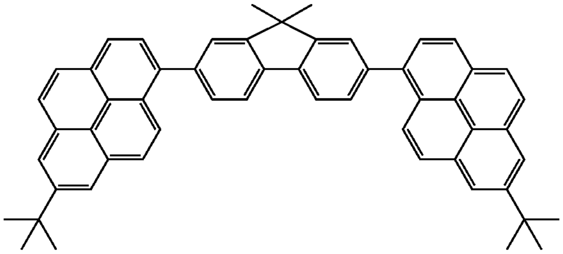

EM3

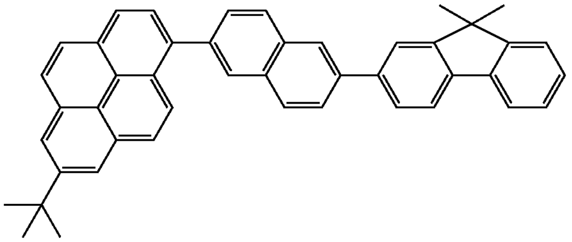

EM4

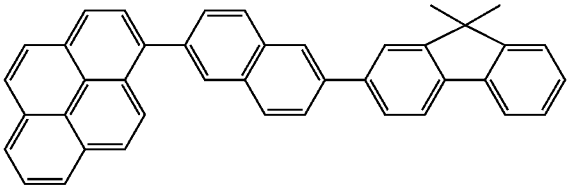

EM5

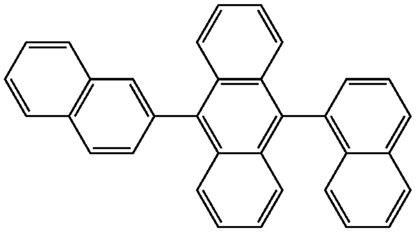

EM6

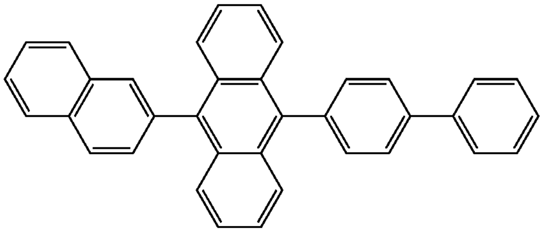

EM7

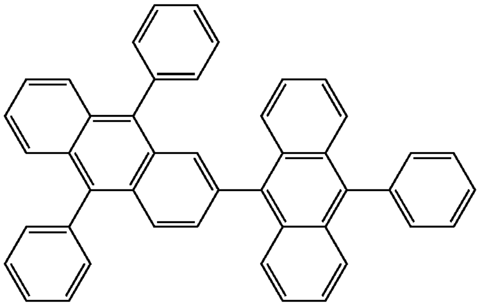

EM8

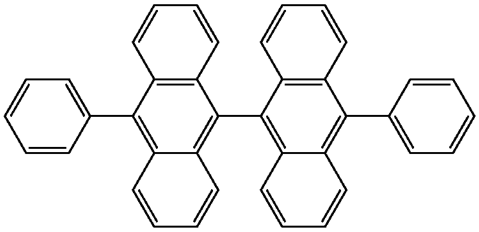

-continued
EM9
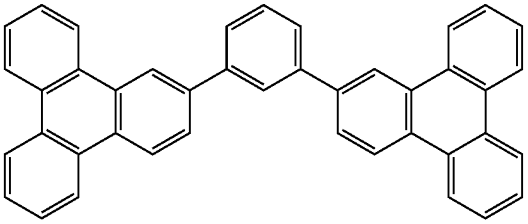
EM10
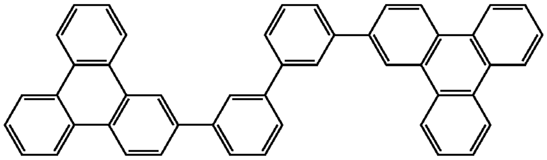
EM11
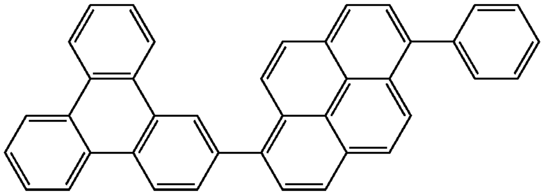
EM12
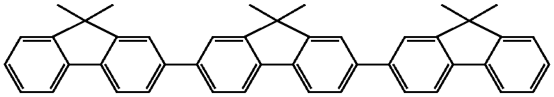
EM13
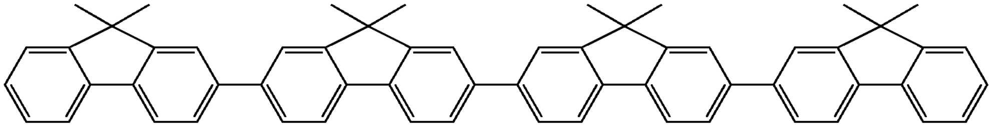
EM14
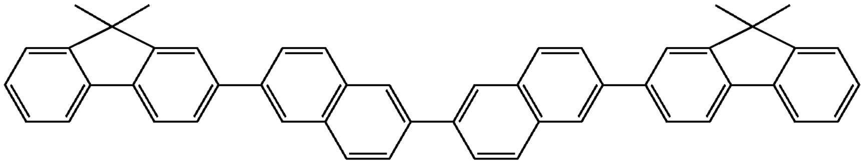
EM15
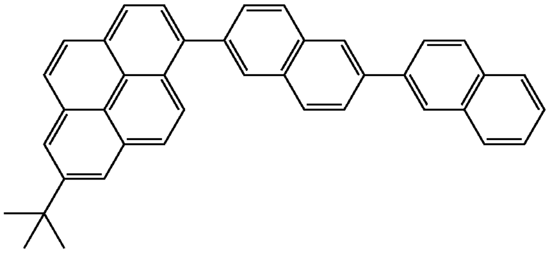
EM16
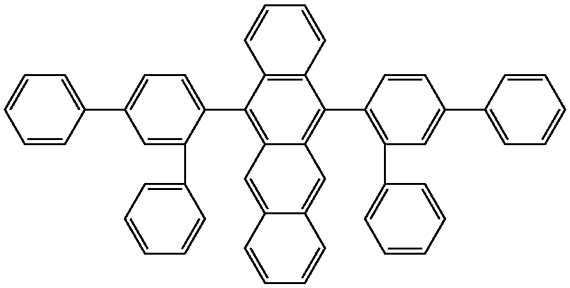
EM17
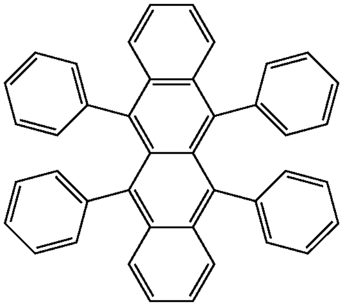
EM18
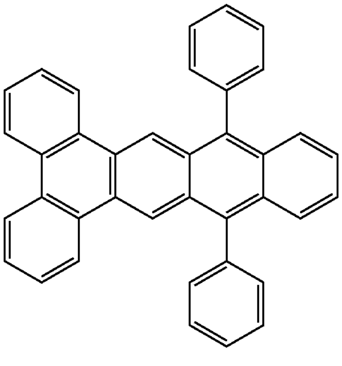

-continued
EM19
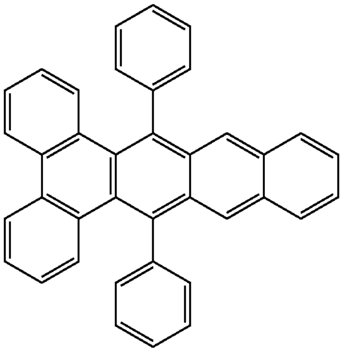
EM20
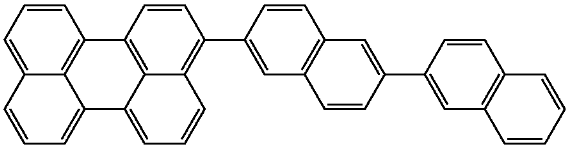
EM21
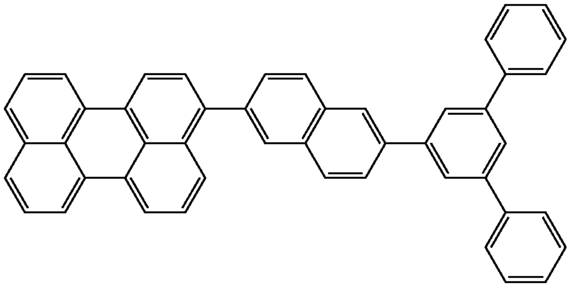
EM22
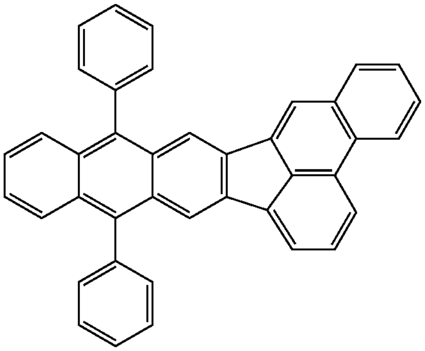
EM23
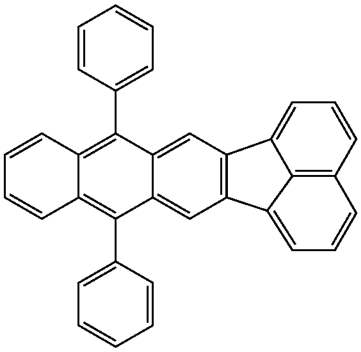
EM24
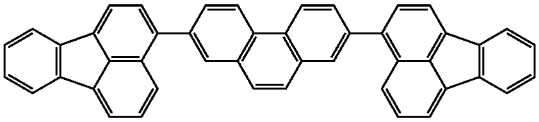
EM25
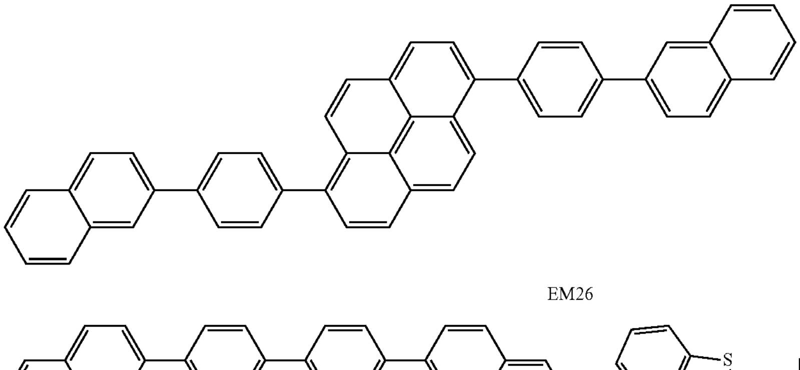
EM26
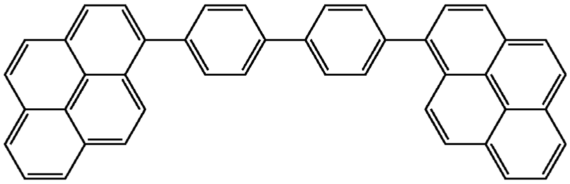
EM27
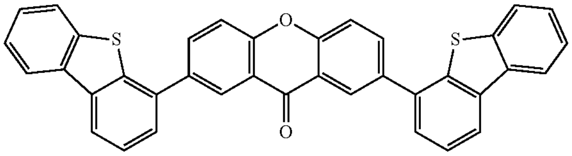

-continued

EM28

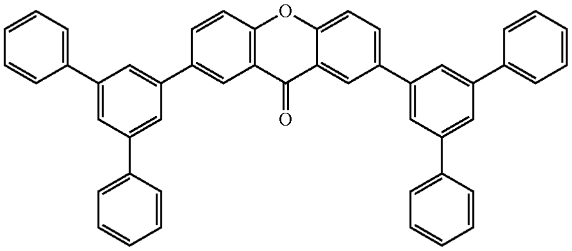

EM29

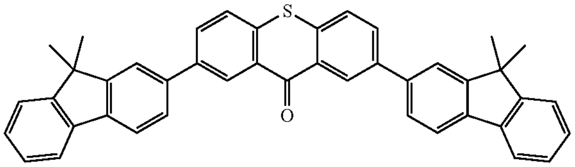

EM30

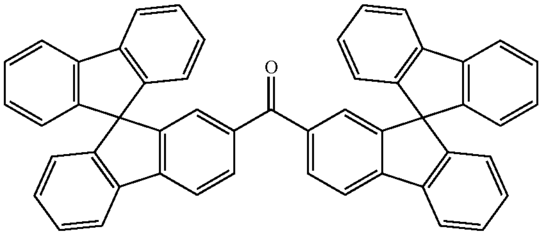

EM31

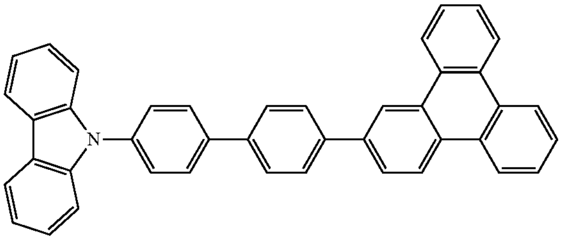

EM32

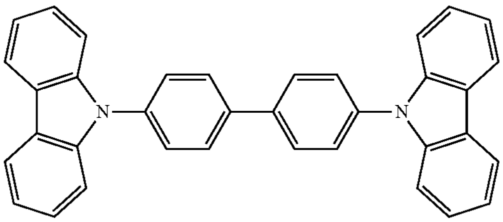

The electron transport material may be arbitrarily selected from materials capable of transporting an electron injected from the cathode to the light-emitting layer and is selected in consideration of, for example, a balance with the hole mobility of the hole transport material. Examples of the material having an electron transporting capability include oxadiazole derivatives, oxazole derivatives, pyrazine derivatives, triazole derivatives, triazine derivatives, quinoline derivatives, quinoxaline derivatives, phenanthroline derivatives, organic aluminum complexes, and condensed ring compounds (for example, fluorene derivatives, naphthalene derivatives, chrysene derivatives, and anthracene derivatives). Further, the above-described electron transport material is favorably used for the hole blocking layer. Specific examples of the compound used as the electron transport material will be described below, but the compound is not limited to these, as a matter of course.

ET1

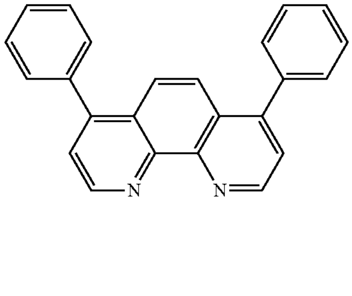

-continued

ET2

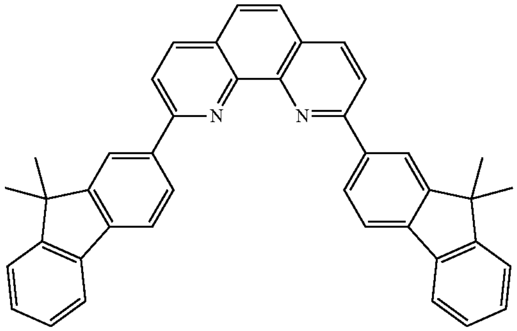

ET3

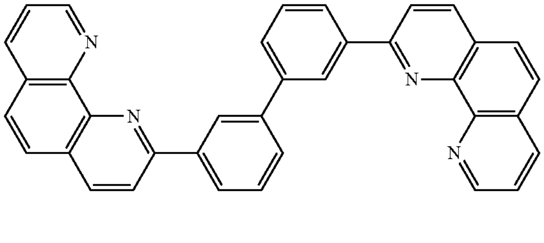

-continued
ET4
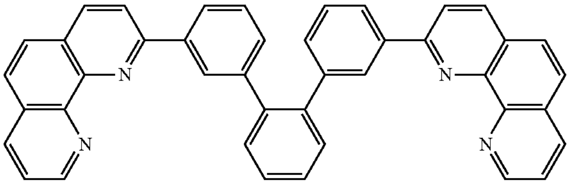
ET5
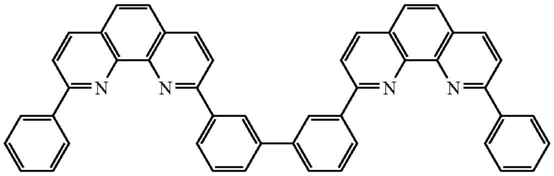
ET6
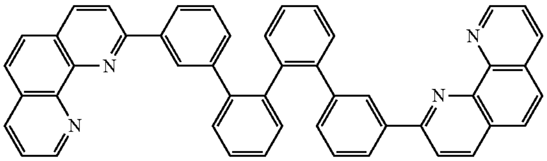
ET7
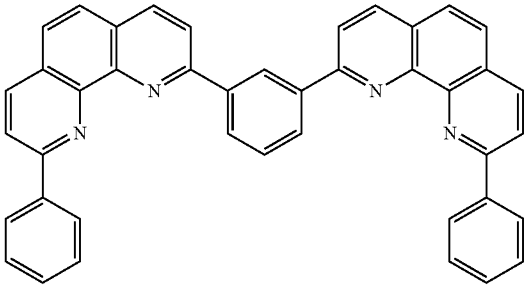
ET8
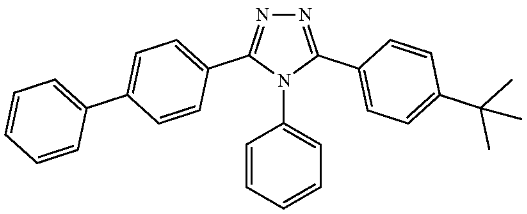
ET9
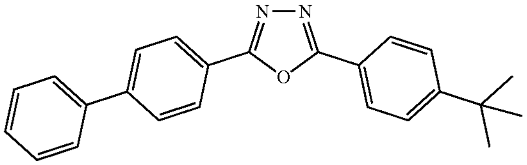
ET10
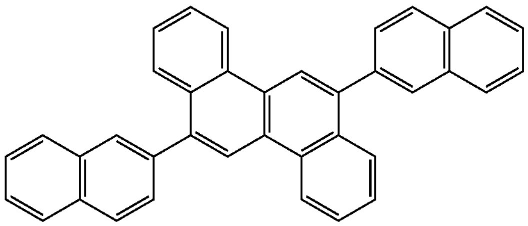
-continued
ET11
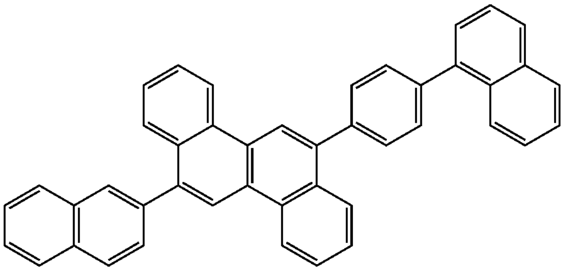
ET12
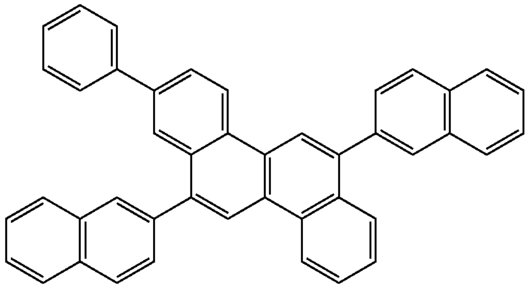
ET13
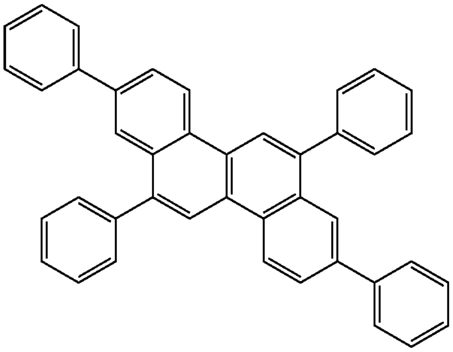
ET14
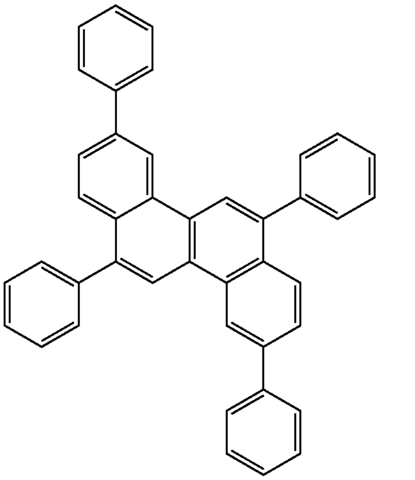

-continued

ET15

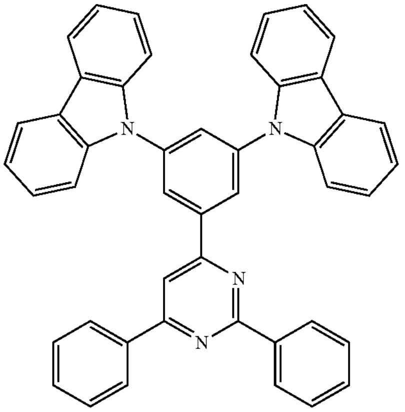

ET16

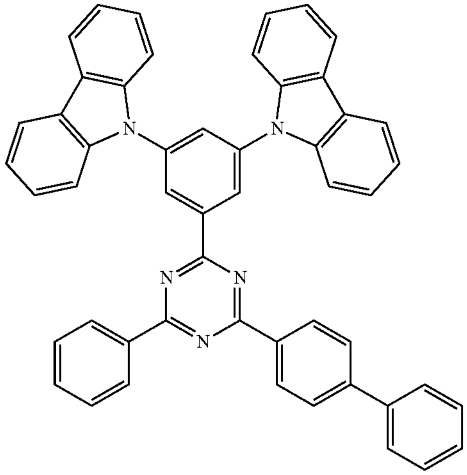

ET17

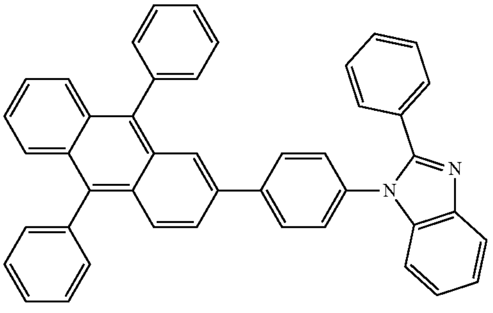

ET18

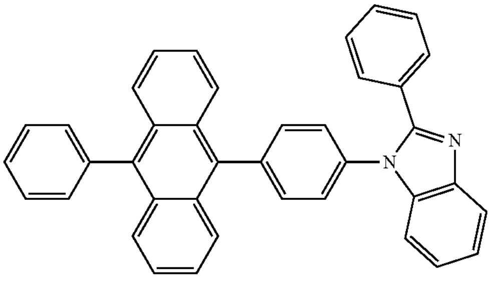

-continued

ET19

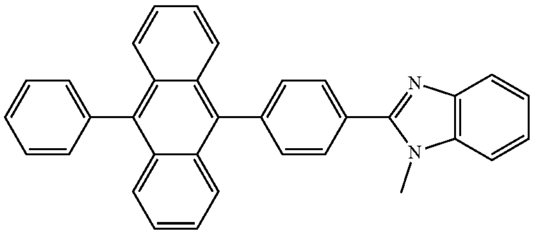

ET20

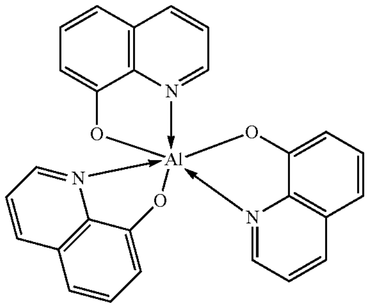

ET21

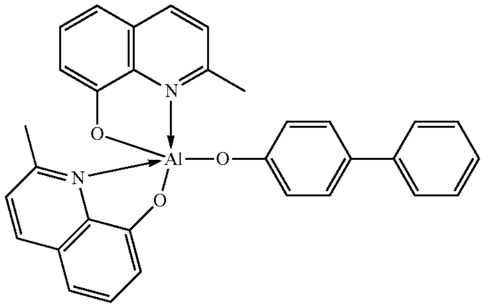

ET22

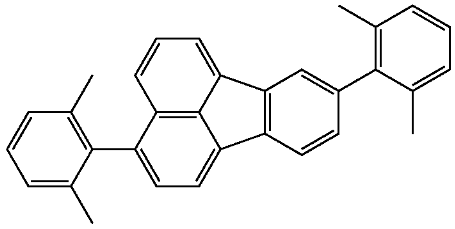

ET23

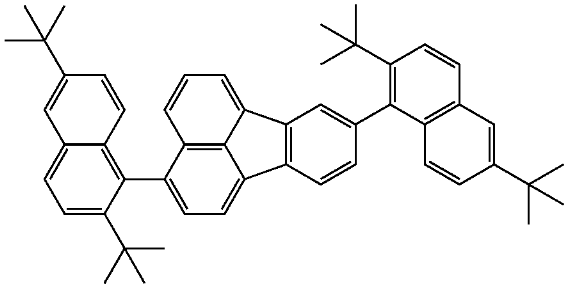

Configuration of Organic Light-Emitting Element

The organic light-emitting element is disposed by forming an insulating layer, a first electrode, an organic compound layer, and a second electrode on a substrate. A protective layer, a color filter, a microlens, and the like may be disposed on the second electrode. When the color filter is disposed, a planarization layer may be disposed between the protective layer and the color filter. The planarization layer may be composed of an acrylic resin or the like. The same applies when the planarization layer is disposed between the color filter and the microlens.

Substrate

Examples of the substrate include quartz, glass, silicon wafers, resins, and metals. A wiring line and a switching element such as a transistor are provided on the substrate, and an insulating layer may be provided thereon. There is no particular limitation regarding the material for forming the insulating layer provided that it is possible to form a contact hole for forming a wiring line connected to the first electrode and to ensure insulation from a wiring line which is not connected. For example, a resin such as a polyimide, silicon oxide, or silicon nitride may be used.

Electrode

A pair of electrodes may be used as the electrodes. The pair of electrodes may be an anode and a cathode.

When an electric field is applied in the direction of light emission from the organic light-emitting element, an electrode at a higher potential is the anode, and the other is the cathode. It can also be said that an electrode which supplies a hole to the light-emitting layer is the anode, and an electrode which supplies an electron is the cathode.

The material constituting the anode can have as large a work function as possible. For example, simple metals, such as gold, platinum, silver, copper, nickel, palladium, cobalt, selenium, vanadium, and tungsten, mixtures containing these, alloys of combination of these, and metal oxides, such as tin oxide, zinc oxide, indium oxide, indium tin oxide (ITO), and indium zinc oxide are usable. In addition, conductive polymers, such as polyanilines, polypyrroles, and polythiophenes, are also usable.

One type of these electrode substances may be used alone, or at least two types may be used in combination. In this regard, the anode may be composed of a single layer or a plurality of layers.

For example, chromium, aluminum, silver, titanium, tungsten, or molybdenum or an alloy or a stacked body of these may be used as a reflection electrode. The above-described materials are capable of functioning as a reflection film having no role as an electrode. For example, an oxide transparent conductive layer of indium tin oxide (ITO), indium zinc oxide, or the like may be used as a transparent electrode, but the material is not limited to these.

A photolithography technology may be used for forming the electrode.

On the other hand, favorably, the material constituting the cathode has a small work function. Examples include simple metals, such as lithium or other alkali metals, calcium or other alkaline-earth metals, aluminum, titanium, manganese, silver, lead, and chromium, and mixtures containing these. Alternatively, alloys of combinations of these simple metals may also be used. For example, magnesium-silver, aluminum-lithium, aluminum-magnesium, silver-copper, and zinc-silver may be used. Metal oxides such as indium tin oxide (ITO) may also be used. One type of these electrode materials may be used alone, or at least two types may be used in combination. The cathode may have a single layer configuration or a multilayer configuration. Of these, silver is favorably used, and a silver alloy is more favorable so as to reduce aggregation of silver. There is no particular limitation regarding the ratio of the alloy provided that aggregation of silver is reduced. For example, silver:other metal may be 1:1, 3:1, or the like.

There is no particular limitation regarding the cathode, and the cathode may be a top emission element by using an oxide conductive layer such as ITO or a bottom emission element by using a reflection electrode such as aluminum (Al). There is no particular limitation regarding the method for forming the cathode, and, more favorably, a direct current sputtering method, an alternating current sputtering method, or the like is used since coverage of the film is favorable so that the resistance of the film is readily reduced.

Organic Compound Layer

The organic compound layer may be formed from a single layer or a plurality of layers. When a plurality of layers are included, the layers may be referred to as a hole injection layer, a hole transport layer, an electron blocking layer, a light-emitting layer, a hole blocking layer, an electron transport layer, or an electron injection layer in accordance with the function of the layer. The organic compound layer is mainly composed of an organic compound but may contain an inorganic atom and an inorganic compound. For example, copper, lithium, magnesium, aluminum, iridium, platinum, molybdenum, or zinc may be contained. The organic compound layer may be disposed between a first electrode and a second electrode or be disposed in contact with the first electrode and the second electrode.

The organic compound layer (a hole injection layer, a hole transport layer, an electron blocking layer, a light-emitting layer, a hole blocking layer, an electron transport layer, an electron injection layer, and the like) constituting the organic light-emitting element according to an embodiment of the present disclosure is formed by a method described below.

Regarding the organic compound layer constituting the organic light-emitting element according to an embodiment of the present disclosure, a dry process, such as a vacuum vapor deposition method, an ionization vapor deposition method, sputtering, or plasma, may be used. In place of the dry process, a wet process in which dissolution into an appropriate solvent is performed, and a layer is formed by a known coating method (for example, spin coating, dipping, a casting method, an LB method, or an ink jet method) may be used.

In this regard, when a layer is formed by a vacuum vapor deposition method, a solution coating method, or the like, crystallization and the like does not readily occur, and the stability over time is excellent. In addition, when a film is formed by a coating method, a film may be formed in combination with an appropriate binder resin.

Examples of the binder resin include polyvinylcarbazole resins, polycarbonate resins, polyester resins, ABS resins, acrylic resins, polyimide resins, phenol resins, epoxy resins, silicon resins, and urea resins, but the binder resin is not limited to these.

One type of the binder resins may be used alone as a homopolymer or a copolymer, or at least two types may be used in combination. Further, as the situation demands, known plasticizers, antioxidants, ultraviolet absorbents, and the like may be used in combination.

Protective Layer

The protective layer may be disposed on the second electrode. For example, glass provided with a moisture absorbent being bonded to the second electrode enables water and the like to be suppressed from entering the organic compound layer and enables defective display to be suppressed from occurring. In another embodiment, a passivation film of silicon nitride or the like may be disposed on the second electrode so as to suppress water and the like from entering the organic compound layer. For example, the second electrode may be formed and, thereafter, transported to another chamber without breaking a vacuum, and a silicon nitride film having a thickness of 2 μm may be formed by a CVD method so as to serve as the protective layer. After film formation by the CVD method, a protective layer may be formed by using an atomic layer deposition (ALD) method. There is no particular limitation regarding the material for forming the film by the ALD method, and the material may be silicon nitride, silicon oxide, aluminum oxide, or the like. Further, a silicon nitride film may be formed by a CVD method on the film formed by the ALD method. The film formed by the ALD method may have smaller film thickness than the film formed by the CVD method. Specifically, the film thickness may be 50% or less and, further, 10% or less.

Color Filter

A color filter may be disposed on the protective layer. For example, a color filter in consideration of the size of the organic light-emitting element may be disposed on another substrate, and the resulting substrate may be bonded to the substrate provided with the organic light-emitting element, or a color filter may be patterned on the protective layer by using a photolithography technology. The color filter may be composed of a polymer.

Planarization Layer

The planarization layer may be included between the color filter and the protective layer. The planarization layer is disposed to reduce unevenness of an underlying layer. The layer may also called a resin material layer without limiting the purpose. The planarization layer may be composed of an organic compound and may be a low-molecular-weight compound or a polymer. The planarization layer can be a polymer.

The planarization layer may be disposed on and under the color filter, and the constituent materials thereof may be the same or may differ from each other. Specific examples include polyvinylcarbazole resins, polycarbonate resins, polyester resins, ABS resins, acrylic resins, polyimide resins, phenol resins, epoxy resins, silicon resins, and urea resins.

Microlens

The organic light-emitting element or the organic light emitting apparatus may include an optical member such as a microlens on the light-emitting side thereof. The microlens may be composed of an acrylic resin, an epoxy resin, or the like. The microlens may have purposes of increasing the amount of light extracted from the organic light-emitting element or the organic light-emitting apparatus and controlling the direction of the extracted light. The microlens may have a hemispherical shape. In the instance of a hemispherical shape, among tangents in contact with the hemisphere, there is a tangent parallel to the insulating layer, and the contact point between the tangent and the hemisphere is the vertex of the microlens. The vertex of the microlens is determined in the same manner in any sectional view. That is, among the tangents in contact with the semicircle of the microlens in the sectional view, there is a tangent parallel to the insulating layer, and the contact point between the tangent and the semicircle is the vertex of the microlens.

The midpoint of the microlens may also be defined. In a section of the microlens, a line segment from a point where an arc shape ends to another point where the arch shape ends is assumed, and the midpoint of the line segment may be referred to as the midpoint of the microlens. The section in which the vertex and the midpoint are determined may be a section perpendicular to the insulating layer.

Opposite Substrate

An opposite substrate may be disposed on the planarization layer. The opposite substrate is disposed at a position corresponding to the above-described substrate and thus is referred to as an opposite substrate. The opposite substrate may be composed of the same material as the above-described substrate. When the above-described substrate is defined as a first substrate, the opposite substrate may be defined as a second substrate.

Pixel Circuit

A light-emitting apparatus including the organic light-emitting element may include a pixel circuit connected to the organic light-emitting element. The pixel circuit may be an active matrix-type circuit that independently controls light emission of a first light-emitting element and a second light-emitting element. The active matrix-type circuit may be a voltage programming or current programming circuit. A driving circuit has a pixel circuit for each pixel. The pixel circuit may have a light-emitting element, a transistor that controls the emission luminance of the light-emitting element, a transistor that controls the timing of light emission, a capacitor that holds the gate voltage of the transistor for controlling the emission luminance, and a transistor for connecting to GND without through the light-emitting element.

The light-emitting apparatus has a display region and a peripheral region disposed around the display region. The display region includes a pixel circuit, and the peripheral region includes a display control circuit. The mobility of transistors constituting the pixel circuit may be smaller than the mobility of transistors constituting the display control circuit.

The slope of the current-voltage characteristics of the transistors constituting the pixel circuit may be smaller than the slope of the current-voltage characteristics of the transistors constituting the display control circuit. The slope of the current-voltage characteristics can be measured based on the so-called Vg-Ig characteristics. The transistors constituting the pixel circuit are transistors connected to light-emitting elements such as a first light-emitting element.

Pixel

The organic light-emitting apparatus including the organic light-emitting element may include a plurality of pixels. The pixel includes subpixels each emitting light of a color that differ from colors of other subpixels. For example, the subpixels may have emission colors of RGB, respectively.

The pixel emits light from a region that is also called a pixel aperture. This region is the same as a first region. The pixel aperture may have a size of 15 μm or less and 5 μm or more. More specifically, the pixel aperture may be, for example, 11 μm, 9.5 μm, 7.4 μm, or 6.4 μm. The distance between the subpixels may be 10 μm or less and may be specifically 8 μm, 7.4 μm, or 6.4 μm.

The pixels may have a publicly known arrangement form in plan view. For example, the arrangement form may be the stripe arrangement, the delta arrangement, the PenTile arrangement, or the Bayer arrangement. The subpixels may have any publicly known shape in plan view. For example, the shape may be a hexagon or a quadrangle such as a rectangle or a rhombus. Of course, figures that are not exactly rectangles but are close to rectangles are also regarded as rectangles. The shape of the subpixels and the pixel arrangement may be used in combination.

Application of Organic Light-Emitting Element

The organic light-emitting element according to the present embodiment may be used as a constituent member of a display apparatus or an illumination apparatus. In addition, the organic light-emitting element is used in, for example, an exposure light source of an electrophotographic image forming apparatus, a backlight of a liquid crystal display apparatus, and a light-emitting apparatus including a color filter as a white light source.

The display apparatus may be an image information processing apparatus that includes an image input unit to which image information is input from an area CCD, a linear CCD, a memory card, or the like and an information processing unit configured to process the input information and that displays an input image on a display unit. The display apparatus may have a plurality of pixels, and at least one of the plurality of pixels may include the organic light-emitting element according to the present embodiment and a transistor connected to the organic light-emitting element.

The display unit included in an imaging apparatus or an ink jet printer may have a touch panel function. There is no particular limitation regarding the driving system of the touch panel function, and the system may be an infrared system, an electrostatic capacitance system, a resistive film system, or an electromagnetic induction system. The display apparatus may be used in a display unit of a multifunctional printer.

Figure 2A:
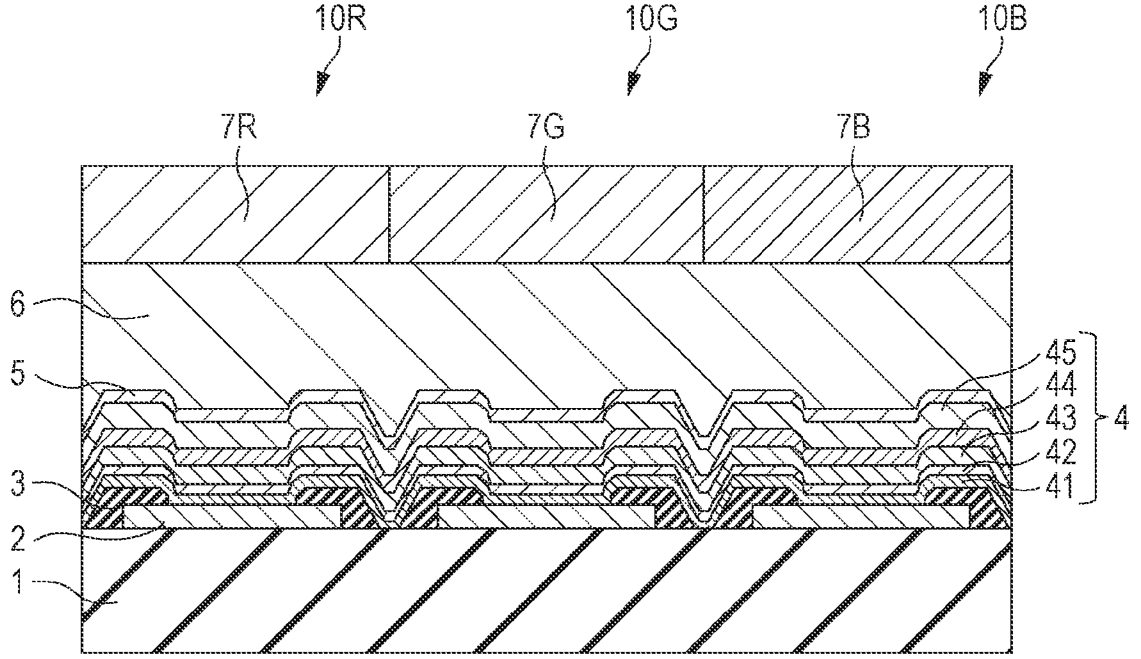
FIG. 2A is a schematic sectional view illustrating an example of a pixel of a display apparatus according to an embodiment of the present disclosure.
Figure 2B:
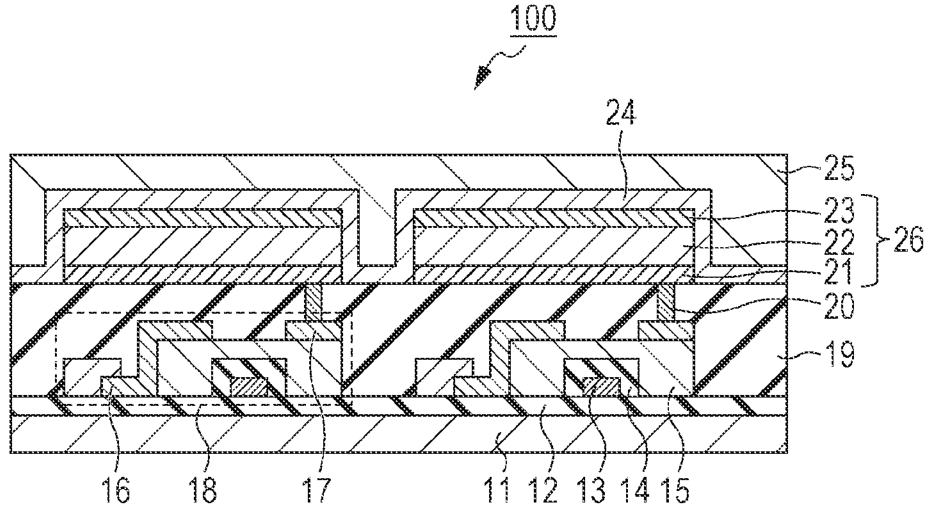
FIG. 2B is a schematic sectional view illustrating an example of a display apparatus including an organic light-emitting element according to an embodiment of the present disclosure.

Next, a display apparatus according to the present embodiment will be described with reference to the drawings. FIGS. 2A and 2B are schematic sectional views illustrating an example of a display apparatus including an organic light-emitting element and a transistor connected to the organic light-emitting element. The transistor is an example of an active element. The transistor may be a thin film transistor (TFT).

FIG. 2A illustrates an example of a pixel that is a constituent element of a display apparatus according to the present embodiment. The pixel has subpixels 10. The subpixels are divided into 10R, 10G, and 10B in accordance with the light emission thereof. The emission color may be distinguished based on the wavelength of the light emitted from the light-emitting layer, or the light emitted from the subpixel may be selectively passed through or subjected to color conversion by a color filter or the like. Each subpixel 10 includes a reflection electrode that is a first electrode 2 on an interlayer insulating layer 1, an insulating layer 3 covering the end of the first electrode 2, an organic compound layer 4 covering the first electrode 2 and the insulating layer 3, a transparent electrode that is a second electrode 5, a protective layer 6, and a color filter 7.

A transistor and a capacitative element may be disposed in a layer under or in the interior of the interlayer insulating layer 1.

The transistor may be electrically connected to the first electrode 2 through a contact hole or the like not illustrated in the drawing.

The insulating layer 3 is also referred to as a bank or a pixel isolation film. The insulating layer 3 is disposed covering the end of the first electrode 2 and surrounding the first electrode 2. A portion not provided with the insulating layer 3 is in contact with the organic compound layer 4 and serves as a light-emitting region.

The organic compound layer 4 includes a hole injection layer 41, a hole transport layer 42, a first light-emitting layer 43, a second light-emitting layer 44, and an electron transport layer 45.

The second electrode 5 may be a transparent electrode, a reflection electrode, or a semitransparent electrode.

The protective layer 6 reduces permeation of moisture into the organic compound layer 4. The protective layer 6 is a single layer in the drawing but may be a plurality of layers. An inorganic compound layer and an organic compound layer may be included on a layer basis.

The color filter 7 is divided into 7R, 7G, and 7B in accordance with the respective color. The color filter 7 may be formed on the planarization layer not illustrated in the drawing. A resin protective layer may be included on the color filter 7. Alternatively, the color filter 7 may be formed on the protective layer 6. Alternatively, the color filter 7 may be formed on the opposite substrate such as a glass substrate and, thereafter, may be bonded.

A display apparatus 100 illustrated in FIG. 2B includes an organic light-emitting element 26 and a TFT 18 as an example of the transistor. An insulating layer 12 is disposed over a substrate 11 composed of glass, silicon, or the like. An active element such as the TFT 18 is disposed on the insulating layer 12 so that a gate electrode 13, a gate insulating film 14, and a semiconductor layer 15 of the active element are disposed. The TFT 18 is composed of a drain electrode 16 and a source electrode 17 in addition to these. An insulating film 19 is disposed over the TFT 18. An anode 21 constituting an organic light-emitting element 26 is connected to the source electrode 17 through a contact hole 20 formed in the insulating layer 19.

An electrical connection system between the electrodes (anode 21 and cathode 23) included in the organic light-emitting element 26 and the electrodes (source electrode 17 and drain electrode 16) included in the TFT 18 is not limited to the form illustrated in FIG. 2B. That is, any one of the anode 21 and the cathode 23 has to be connected to any one of the source electrode 17 and the drain electrode 16 of the TFT 18. "TFT" represents a thin film transistor.

Regarding the display apparatus 100 illustrated in FIG. 2B, the organic compound layer 22 is a single layer in the drawing, but the organic compound layer 22 may be a plurality of layers. A first protective layer 24 and a second protective layer 25 for suppressing the organic light-emitting element 26 from deteriorating are disposed on the cathode 23.

In the display apparatus 100 illustrated in FIG. 2B, a transistor is used as a switching element but may be used as another switching element in place of this.

The transistor used in the display apparatus 100 illustrated in FIG. 2B is not limited to being a transistor including a single-crystal silicon wafer and may be a thin film transistor including an active layer on the insulating surface of the substrate. Examples of the active layer include single-crystal silicon, non-single-crystal silicon such as amorphous silicon and microcrystalline silicon, and non-single-crystal oxide semiconductors such as indium zinc oxide and indium gallium zinc oxide. The thin film transistor is also referred to as a TFT element.

The transistor included in the display apparatus 100 illustrated in FIG. 2B may be formed in a substrate such as a Si substrate. Herein, "be formed in a substrate" means that the transistor is produced by working just the substrate such as a Si substrate. That is, the transistor being included in the substrate may be conjectured that the substrate and the transistor are integrally formed.

The emission luminance of the organic light-emitting element according to the present embodiment is controlled by the TFT that is an example of the switching element, and a plurality of organic light-emitting elements being disposed in a plane enables an image to be displayed with the respective emission luminance. In this regard, the switching element according to the present embodiment is not limited to the TFT and may be a transistor formed of a low-temperature polysilicon or an active matrix driver formed on a substrate such as a Si substrate. “On the substrate” may translate into “in the substrate”. Whether the transistor is disposed in the substrate or the TFT is used is selected in accordance with the size of the display unit. For example, when the size is about 0.5 inches, it is favorable that the organic light-emitting element be disposed on the Si substrate.

Figure 3:
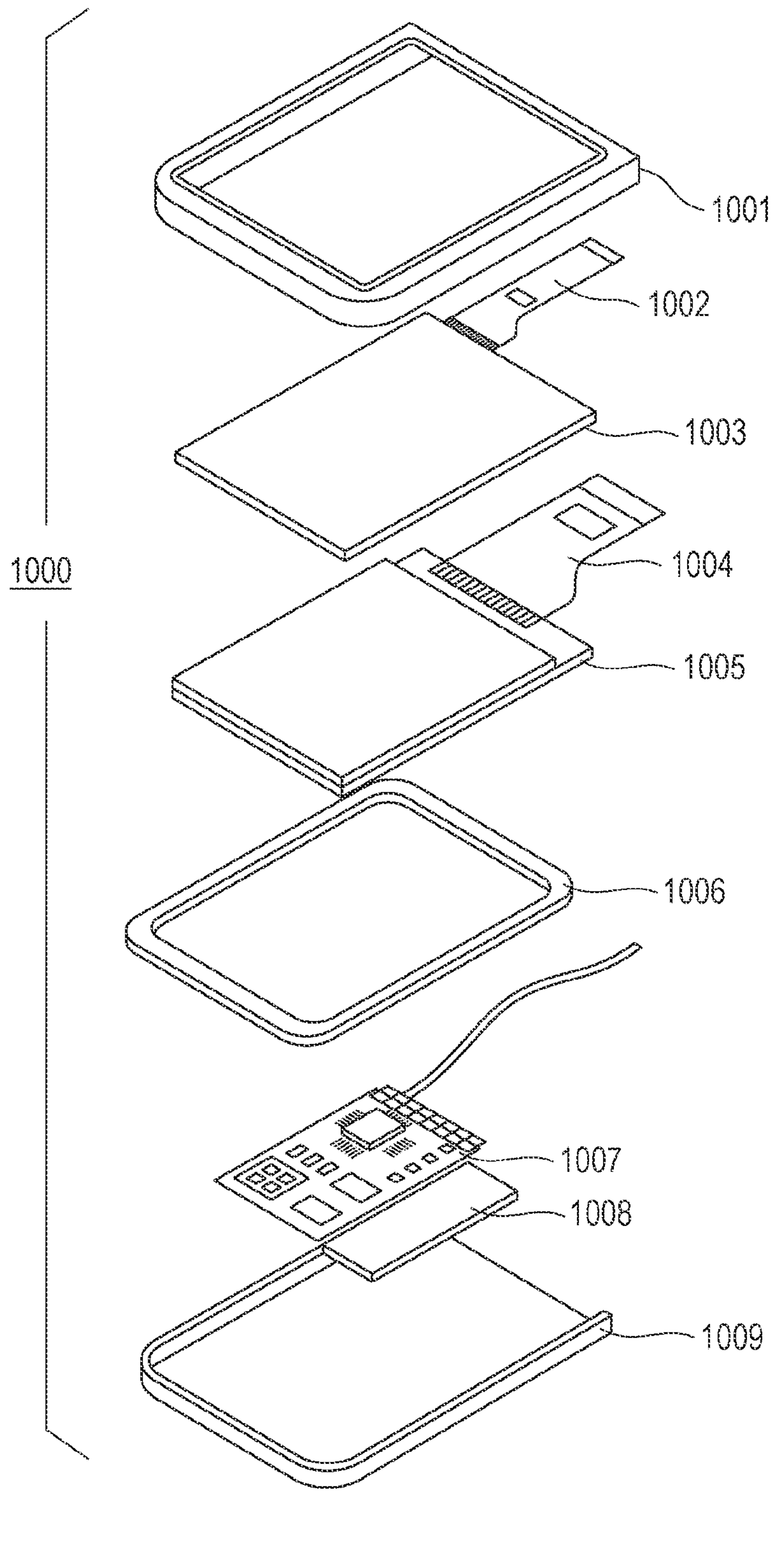
FIG. 3 is a schematic diagram illustrating an example of a display apparatus according to an embodiment of the present disclosure.

FIG. 3 is a schematic diagram illustrating an example of a display apparatus according to the present embodiment. A display apparatus 1000 may include a touch panel 1003, a display panel 1005, a frame 1006, a circuit substrate 1007, and a battery 1008 between an upper cover 1001 and a lower cover 1009. The touch panel 1003 and the display panel 1005 are connected to flexible printed circuits FPC 1002 and 1004, respectively. Transistors are printed onto the circuit substrate 1007. The battery 1008 is not necessarily installed unless the display apparatus is a portable apparatus or may be installed in a different position even if the display apparatus is a portable apparatus.

The display apparatus according to the present embodiment may include a color filter having red, green, and blue colors. The red, green, and blue colors of the color filter may be arranged in the delta arrangement.

The display apparatus according to the present embodiment may be used in a display unit of a portable terminal. In such an instance, the display apparatus may have both a display function and an operation function. Examples of the portable terminal include mobile phones such as smart phones, tablets, and head mount displays.

The display apparatus according to the present embodiment may be used in a display unit of an imaging apparatus including an optical unit that includes a plurality of lenses and an imaging element that receives light passed through the optical unit. The imaging apparatus may include a display unit that displays information acquired by the imaging element. The display unit may be a display unit exposed to the outside of the imaging apparatus or a display unit disposed in a viewfinder. The imaging apparatus may be a digital camera or a digital camcorder.

Figure 4A:
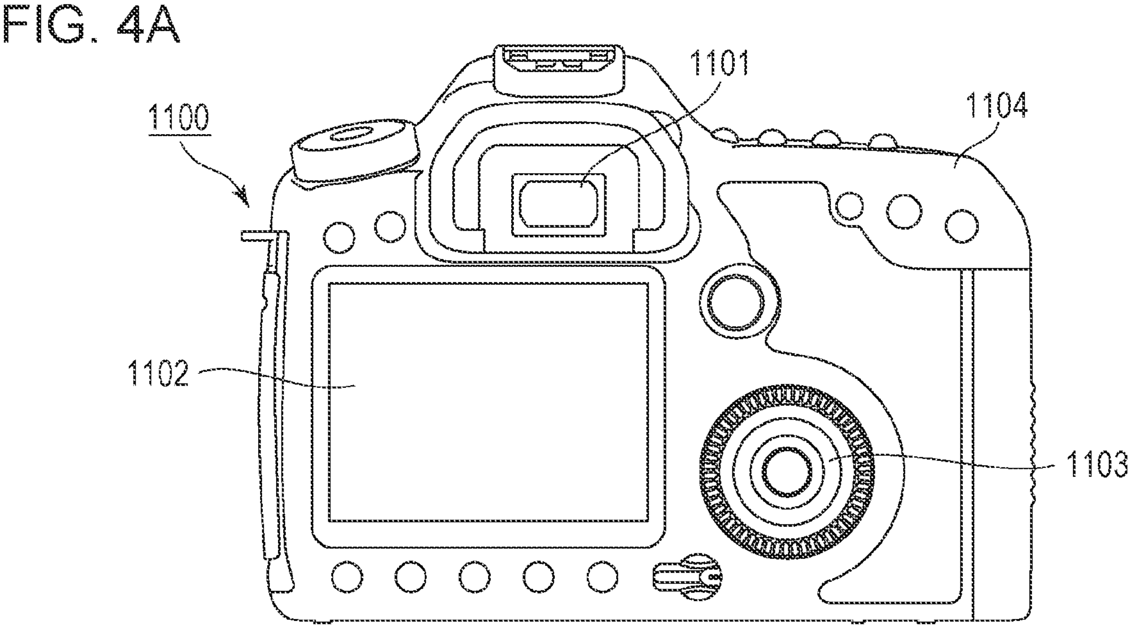
FIG. 4A is a schematic diagram illustrating an example of an imaging apparatus according to an embodiment of the present disclosure.

FIG. 4A is a schematic diagram illustrating an example of an imaging apparatus according to the present embodiment. An imaging apparatus 1100 may include a viewfinder 1101, a rear surface display 1102, an operation unit 1103, and a housing 1104. The viewfinder 1101 may include a display apparatus according to the present embodiment. In such an instance, the display apparatus may display not only an image to be imaged but also environmental information, imaging instructions, and the like. The environmental information may include, for example, the intensity of external light, the direction of external light, the moving speed of the subject, and the possibility that the subject may hide behind an obstacle.

Since the suitable timing for imaging is a very short period of time, it is desirable to display information as quickly as possible. Accordingly, a display apparatus that includes the organic light-emitting element according to the present embodiment can be used. This is because the organic light-emitting element has a high response speed. The display apparatus that includes an organic light-emitting element is more suitable than liquid crystal display apparatuses for use in these apparatuses for which a high display speed is required.

The imaging apparatus 1100 includes an optical unit not illustrated in the drawing. The optical unit includes a plurality of lenses and forms an image on an imaging element contained in the housing 1104. The plurality of lenses may adjust the focal point by adjusting their relative positions. This operation may be automatically performed. The imaging apparatus may also be referred to as a photoelectric conversion apparatus. The photoelectric conversion apparatus may employ, instead of a method in which images are successively imaged, imaging methods such as a method in which a difference from the previous image is detected and a method in which images are extracted from continuously recorded images.

Figure 4B:
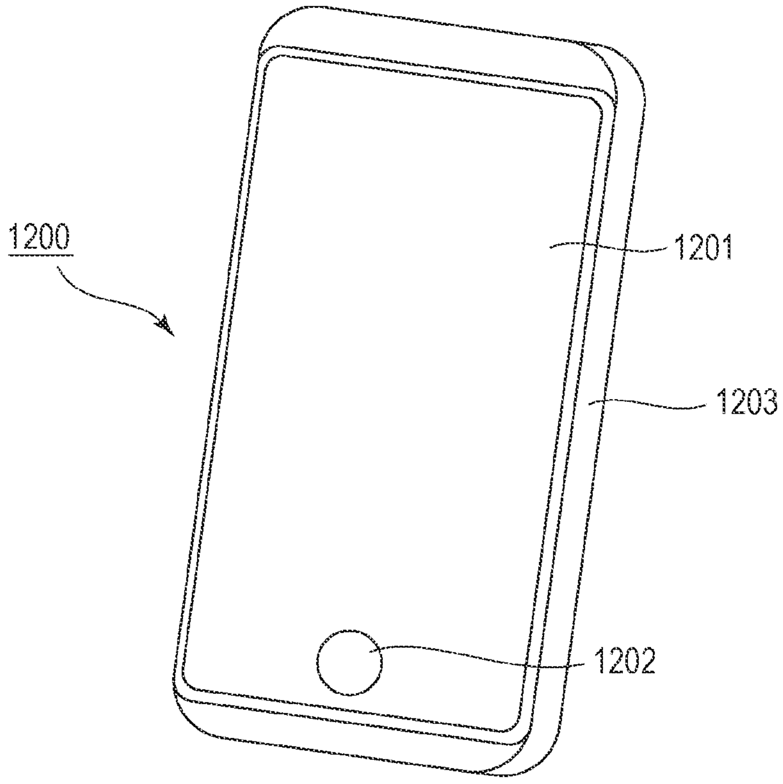
FIG. 4B is a schematic diagram illustrating an example of an electronic apparatus according to an embodiment of the present disclosure.

FIG. 4B is a schematic diagram illustrating an example of an electronic apparatus according to the present embodiment. An electronic apparatus 1200 includes a display unit 1201, an operation unit 1202, and a housing 1203. The housing 1203 may include circuits, a print substrate having the circuits, a battery, and a communication unit. The operation unit 1202 may be a button or a touch panel-type responsive unit. The operation unit may be a biometric authentication unit configured to, for example, recognize the fingerprints and release the lock. The electronic apparatus that includes a communication unit may also be referred to as a communication apparatus. The electronic apparatus 1200 may include a lens and an imaging element so as to further have a camera function. An image imaged by the camera function is displayed on the display unit 1201. Examples of the electronic apparatus 1200 include smart phones and notebook personal computers.

Figure 5A:
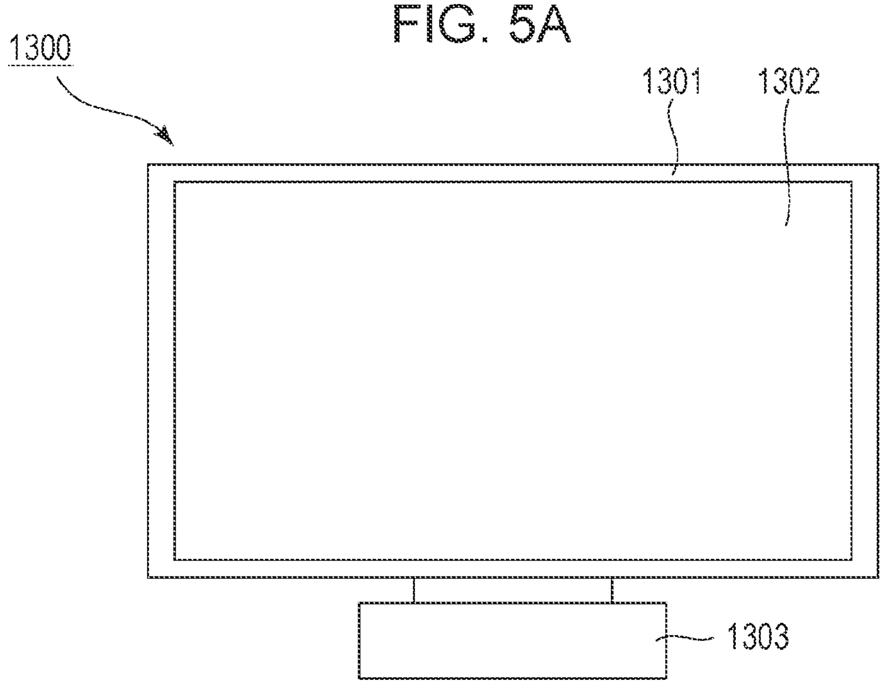
FIG. 5A is a schematic diagram illustrating an example of a display apparatus according to an embodiment of the present disclosure.
Figure 5B:
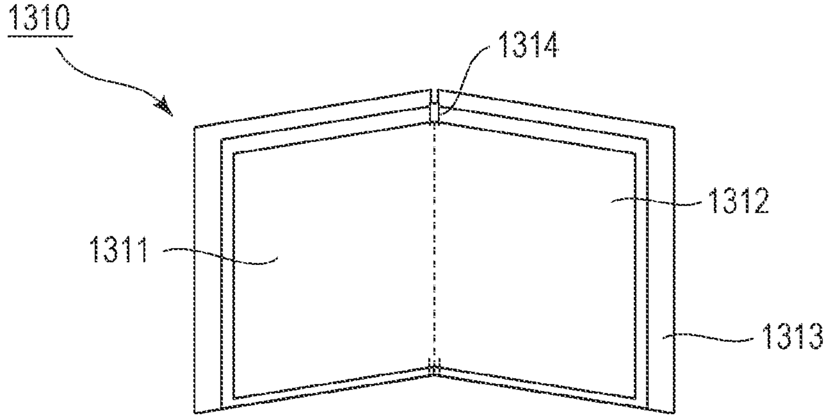
FIG. 5B is a schematic diagram illustrating an example of a foldable display apparatus according to an embodiment of the present disclosure.

FIGS. 5A and 5B are schematic diagrams each illustrating an example of a display apparatus according to the present embodiment. FIG. 5A illustrates a display apparatus such as a television monitor or a PC monitor. A display apparatus 1300 includes a frame 1301 and a display unit 1302. The light-emitting element according to the present embodiment may be used in the display unit 1302. A base 1303 that supports the frame 1301 and the display unit 1302 are included. The base 1303 is not limited to the form illustrated in FIG. 5A. The lower side of the frame 1301 may also function as the base. The frame 1301 and the display unit 1302 may be curved. The radius of curvature thereof may be 5,000 mm or more and 6,000 mm or less.

FIG. 5B is a schematic diagram illustrating another example of the display apparatus according to the present embodiment. A display apparatus 1310 illustrated in FIG. 5B is configured to be foldable and is a so-called foldable display apparatus. The display apparatus 1310 has a first display unit 1311, a second display unit 1312, a housing 1313, and an inflexion point 1314. Each of the first display unit 1311 and the second display unit 1312 may include the light-emitting element according to the present embodiment. The first display unit 1311 and the second display unit 1312 may be a single display apparatus without a joint. The first display unit 1311 and the second display unit 1312 is separated at the inflexion point. The first display unit 1311 and the second display unit 1312 may display images that differ from each other. Alternatively, an image may be displayed on a set of the first display unit and the second display unit.

Figure 6A:
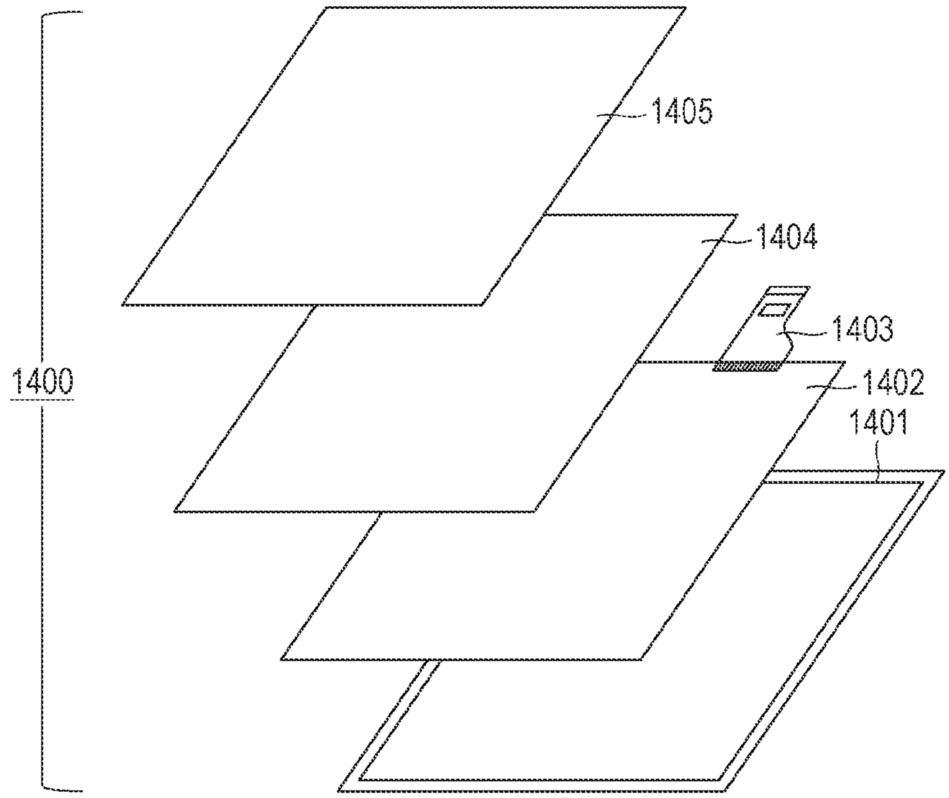
FIG. 6A is a schematic diagram illustrating an example of an illumination apparatus according to an embodiment of the present disclosure.

FIG. 6A is a schematic diagram illustrating an example of an illumination apparatus according to the present embodiment. An illumination apparatus 1400 may include a housing 1401, a light source 1402, a circuit substrate 1403, an optical filter 1404 for passing the light emitted from the light source 1402, and a light diffusion unit 1405. The light source 1402 may include the organic light-emitting element according to the present embodiment. The optical filter 1404 may be a filter that improves the color rendering properties of the light source. The light diffusion unit 1405 effectively diffuses light emitted from the light source and allows the light to reach a wide range, for example, for lighting up. The optical filter 1404 and the light diffusion unit 1405 may be disposed on the light emission side of the illumination. A cover may be optionally disposed on the outermost portion as the situation demands.

The illumination apparatus is, for example, an apparatus that illuminates a room. The illumination apparatus may emit light of a color such as white, natural white, or any other color from blue to red. The illumination apparatus may include a light modulating circuit configured to modulate the light.

The illumination apparatus may include the organic light-emitting element according to the present disclosure and a power supply circuit connected to the organic light-emitting element. The power supply circuit is a circuit configured to convert alternating current voltage to direct current voltage. The white is a color having a color temperature of 4,200 K, and the natural white is a color having a color temperature of 5,000 K. The illumination apparatus may include a color filter.

The illumination apparatus according to the present embodiment may include a heat dissipation unit. The heat dissipation unit dissipates heat in the apparatus to the outside of the apparatus. The heat dissipation unit may be formed of, for example, a metal having a high specific heat or liquid silicon.

Figure 6B:
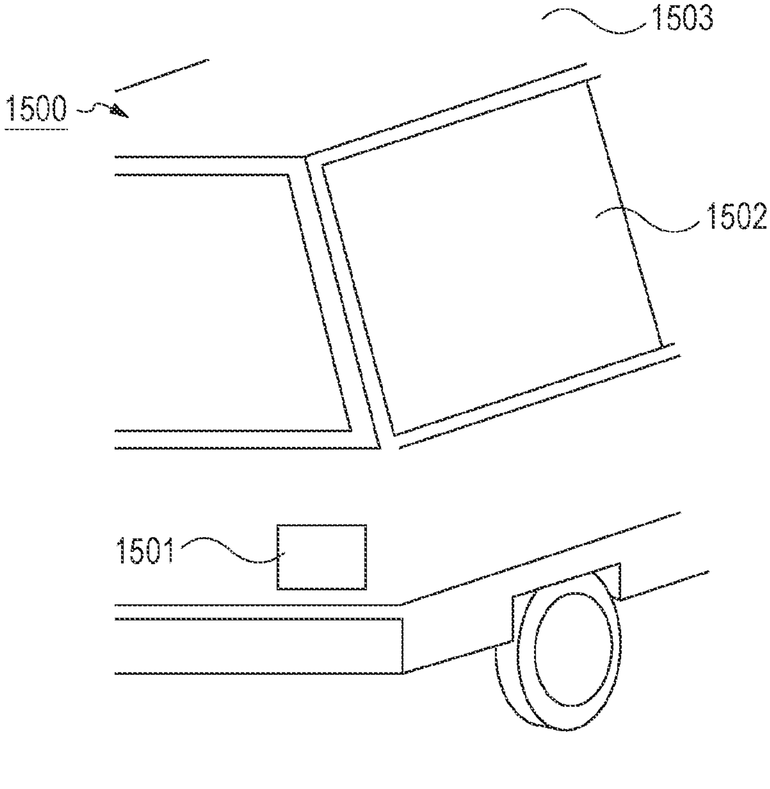
FIG. 6B is a schematic diagram illustrating an example of a moving object including a vehicle lighting fixture according to an embodiment of the present disclosure.

FIG. 6B is a schematic diagram illustrating an automobile which is an example of a moving object according to the present embodiment. The automobile has a tail lamp which is an example of a lighting fixture. An automobile 1500 has a tail lamp 1501, and the tail lamp 1501 may be lit up when, for example, the brakes are applied.

The tail lamp 1501 may include the organic light-emitting element according to the present embodiment. The tail lamp may include a protective member that protects the organic light-emitting element. There is no particular limitation regarding the material for forming the protective member provided that the material has high strength to a certain extent and is transparent, and the protective member can be composed of a polycarbonate or the like. The polycarbonate may be mixed with a furandicarboxylic acid derivative, an acrylonitrile derivative, or the like.

The automobile 1500 may include a car body 1503 and a window 1502 installed to the car body 1503. The window 1502 may be a transparent display unless it is a window for checking the front and the rear of the automobile. The transparent display may include the organic light-emitting element according to the present embodiment.

In such an instance, the constituent materials, such as the electrodes, included in the organic light-emitting element are formed of transparent members.

The moving object according to the present embodiment may be, for example, a ship, an aircraft, or a drone. The moving object may include a bodywork and a lighting fixture installed to the bodywork. The lighting fixture may emit light to indicate the position of the bodywork. The lighting fixture includes the organic light-emitting element according to the present embodiment.

Examples of applications of the display apparatuses according to the embodiments above will be described with reference to FIGS. 7A and 7B. The display apparatuses are applicable to systems that are worn as wearable devices, such as smart glasses, HMDs, and smart contact lenses. An imaging and display apparatus used in such an application example includes an imaging apparatus capable of photoelectrically converting visible light and a display apparatus capable of emitting visible light.

Figure 7A:
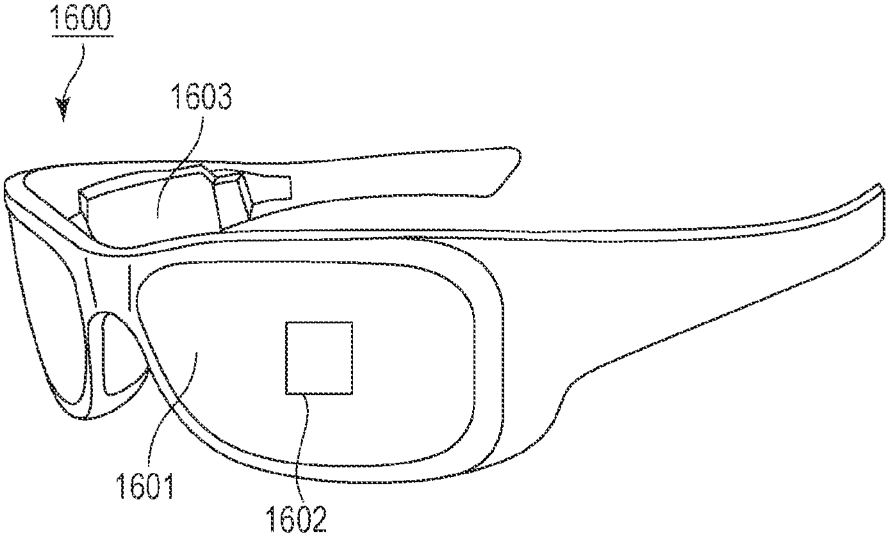
FIG. 7A is a schematic diagram illustrating an example of a wearable device according to an embodiment of the present disclosure.

FIG. 7A is a schematic diagram illustrating an example of a wearable device according to an embodiment of the present disclosure. Glasses 1600 (smart glasses) according to an application example will be described with reference to FIG. 7A. An imaging apparatus 1602 such as a CMOS sensor or a SPAD is disposed on the front side of a lens 1601 of the glasses 1600. The display apparatus according to any of the above-described embodiments is disposed on the back side of the lens 1601.

The glasses 1600 further include a control unit 1603. The control unit 1603 functions as a power supply that supplies electric power to the imaging apparatus 1602 and the display apparatus. The control unit 1603 controls the operation of the imaging apparatus 1602 and the display apparatus. An optical system for focusing light on the imaging apparatus 1602 is formed on the lens 1601.

Figure 7B:
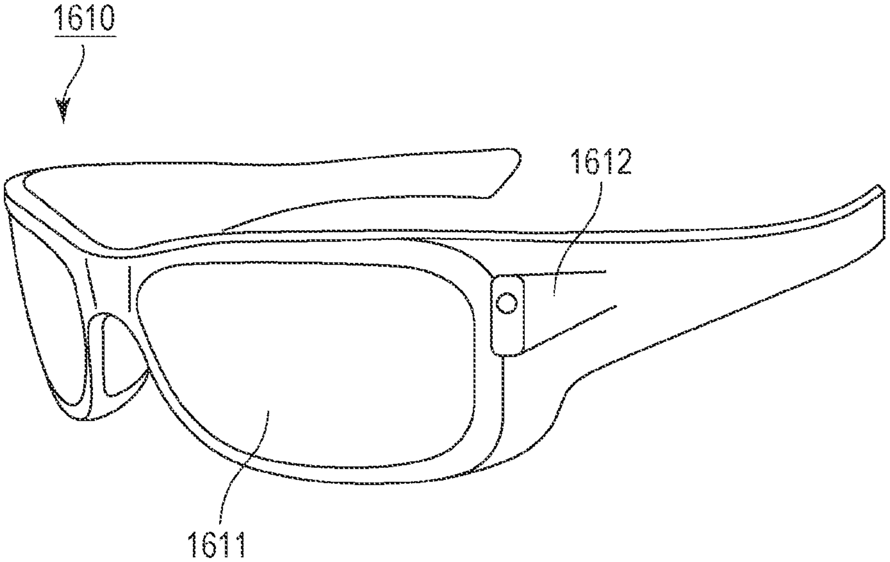
FIG. 7B is a schematic diagram illustrating another example of the wearable device according to an embodiment of the present disclosure.

FIG. 7B is a schematic diagram illustrating another example of the wearable device according to an embodiment of the present disclosure. Glasses 1610 (smart glasses) according to an application example will be described with reference to FIG. 7B. The glasses 1610 have a control unit 1612. The control unit 1612 includes an imaging apparatus corresponding to the imaging apparatus 1602 illustrated in FIG. 7A and a display apparatus. An optical system for projecting light emitted from the imaging apparatus and the display apparatus in the control unit 1612 is formed on a lens 1611, and an image is projected on the lens 1611. The control unit 1612 functions as a power supply that supplies electric power to the imaging apparatus and the display apparatus and controls the operation of the imaging apparatus and the display apparatus.

The control unit 1612 may have a gaze detection unit that detects the gaze of the wearer. Infrared rays may be used to detect the gaze. An infrared light-emitting unit emits infrared light to an eyeball of the user who is gazing at a displayed image. The emitted infrared light is reflected by the eyeball, and the reflected light is detected by an imaging unit including a light-receiving element so as to provide an imaged image of the eyeball. The deterioration of the image quality is reduced by providing a reducing unit that reduces light from the infrared light-emitting unit to a display unit in plan view. The gaze of the user to the displayed image is detected from the imaged image of the eyeball imaged with the infrared light. Any publicly known method is applicable to the gaze detection using the imaged image of the eyeball. As an example, a gaze detection method based on the Purkinje image formed by the reflection of irradiation light on the cornea is employed. More specifically, a gaze detection process based on a pupil-corneal reflection method is performed. The pupil-corneal reflection method is used, on the basis of the image of the pupil and the Purkinje image included in the imaged image of the eyeball, to calculate a gaze vector representing the direction (rotation angle) of the eyeball, thereby detecting the gaze of the user.

A display apparatus according to an embodiment of the present disclosure may include an imaging apparatus having a light-receiving element and may control a displayed image of the display apparatus on the basis of the gaze information of the user from the imaging apparatus. Specifically, in the display apparatus, a first field-of-view region at which the user gazes and a second field-of-view region other than the first field-of-view region are determined on the basis of the gaze information. The first field-of-view region and the second field-of-view region may be determined by the control unit of the display apparatus or may be determined by receiving those determined by an external control unit. In the display region of the display apparatus, the display resolution of the first field-of-view region may be controlled to be higher than the display resolution of the second field-of-view region. That is, the resolution of the second field-of-view region may be controlled to be lower than that of the first field-of-view region.

The display region includes a first display region and a second display region different from the first display region. A region of higher priority is determined from the first display region and the second display region on the basis of the gaze information. The first display region and the second display region may be determined by the control unit of the display apparatus or may be determined by receiving those determined by an external control unit. The resolution of a region of higher priority may be controlled to be higher than the resolution of a region other than the region of higher priority. That is, the resolution of a region of a relatively low priority may be controlled to be low.

The first field-of-view region or the region of higher priority may be determined using AI. The AI may be a model configured to estimate the angle of the gaze and the distance to a target object located in the gaze direction from images of the eyeball by using, as teaching data, images of the eyeball and the actual gaze direction of the eyeball in the images. The AI program may be stored in the display apparatus, the imaging apparatus, or an external apparatus. When the AI program is stored in the external apparatus, the AI program is transmitted through communication to the display apparatus.

In the instance of controlling the display on the basis of visual recognition detection, smart glasses further including an imaging apparatus that images an external image can be applied. The smart glasses are capable of displaying the imaged external information in real time.

Figure 8A:
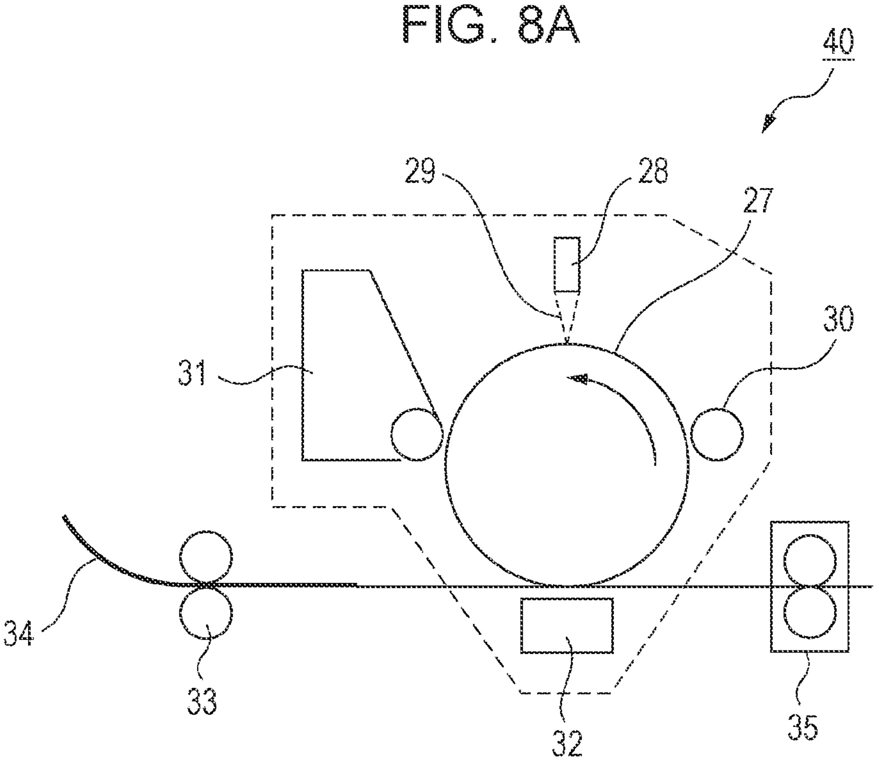
FIG. 8A is a schematic diagram illustrating an example of an image forming apparatus according to an embodiment of the present disclosure.

FIG. 8A is a schematic diagram illustrating an example of an image forming apparatus according to an embodiment of the present disclosure. An image forming apparatus 40 is an electrophotographic image forming apparatus including a photosensitive member 27, an exposure light source 28, a charge portion 30, a developing portion 31, a transfer unit 32, a transporting roller 33, and a fixing unit 35. Light 29 is applied from the exposure light source 28, and an electrostatic latent image is formed on the surface of the photosensitive member 27. The exposure light source 28 includes the organic light-emitting element according to the present embodiment. The developing portion 31 includes a toner and the like. The charge portion 30 charges the photosensitive member 27. The transfer unit 32 transfers the developed image to a recording medium 34. The transporting roller 33 transports the recording medium 34. The recording medium 34 is, for example, paper. The fixing unit 35 fixes the image formed on the recording medium 34.

Figure 8B:
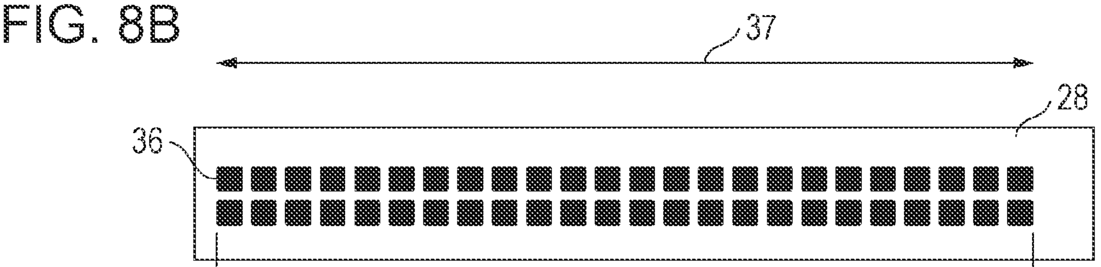
FIG. 8C is a schematic diagram illustrating an example of an exposure light source of an image forming apparatus according to an embodiment of the present disclosure.
Figure 8C:
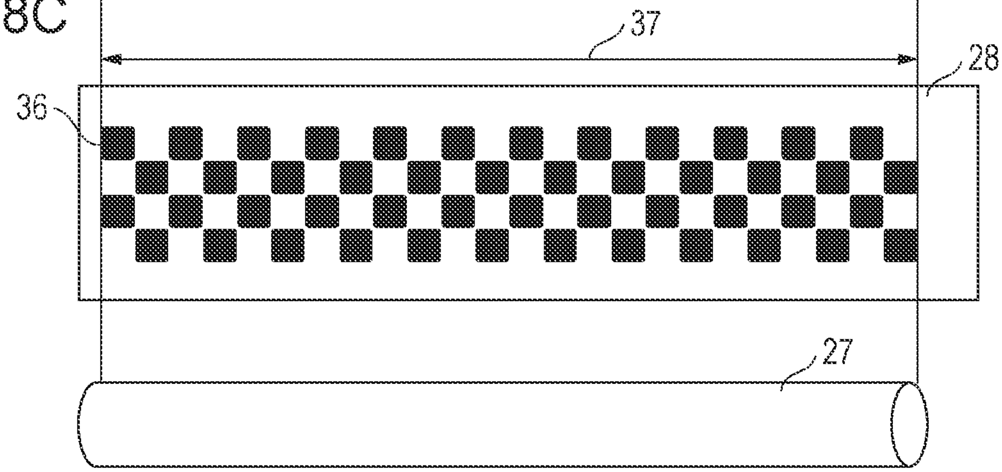

FIG. 8B and FIG. 8C are diagrams illustrating the exposure light sources 28 and are schematic diagrams illustrating the manner in which a plurality of light-emitting portions 36 are arranged on an elongated substrate. An arrow 37 indicates the direction parallel to the shaft of the photosensitive member and the line direction of the arranged organic light-emitting elements. The line direction is the same as the direction of the rotating shaft of the photosensitive member 27. This direction may be also referred to as the major axis direction. FIG. 8B illustrates a form in which light-emitting portions 36 are arranged in the major axis direction of the photosensitive member 27. FIG. 8C illustrates a form different from FIG. 8B and illustrates a form in which the light-emitting portions 36 in the first line and the second line are in a staggered arrangement in the line direction. The positions of the light-emitting portions 36 in the first line differ, in the row direction, from the positions of the light-emitting portions 36 in the second line. In the first line, the plurality of light-emitting portions 36 are arranged at a predetermined spacing. In the second line, the light-emitting portions 36 are located at the positions corresponding to the space between the light-emitting portions 36 in the first line. That is, the plurality of light-emitting portions 36 are also arranged at a predetermined spacing in the row direction. The arrangement illustrated in FIG. 8C may translate into, for example, a state in which the light-emitting portions 36 are arranged in a lattice pattern, a state in which the light-emitting portions 36 are arranged in a hound's-tooth check pattern, or a checkered pattern.

As described above, using an apparatus that uses the organic light-emitting element according to the present embodiment enables stable display with good image quality even for a long time to be realized.

EXAMPLES

The present disclosure will be described below with reference to the examples. However, the present disclosure is not limited to these.

Example 1 (Synthesis of Exemplary Compound A4)

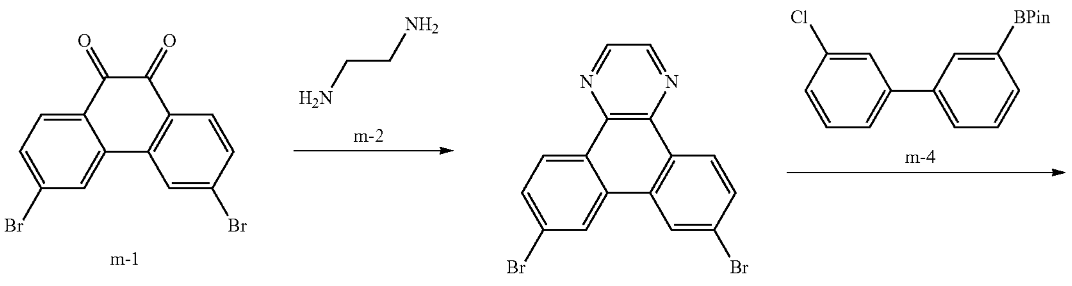

m-1 m-2 m-3 m-4

-continued

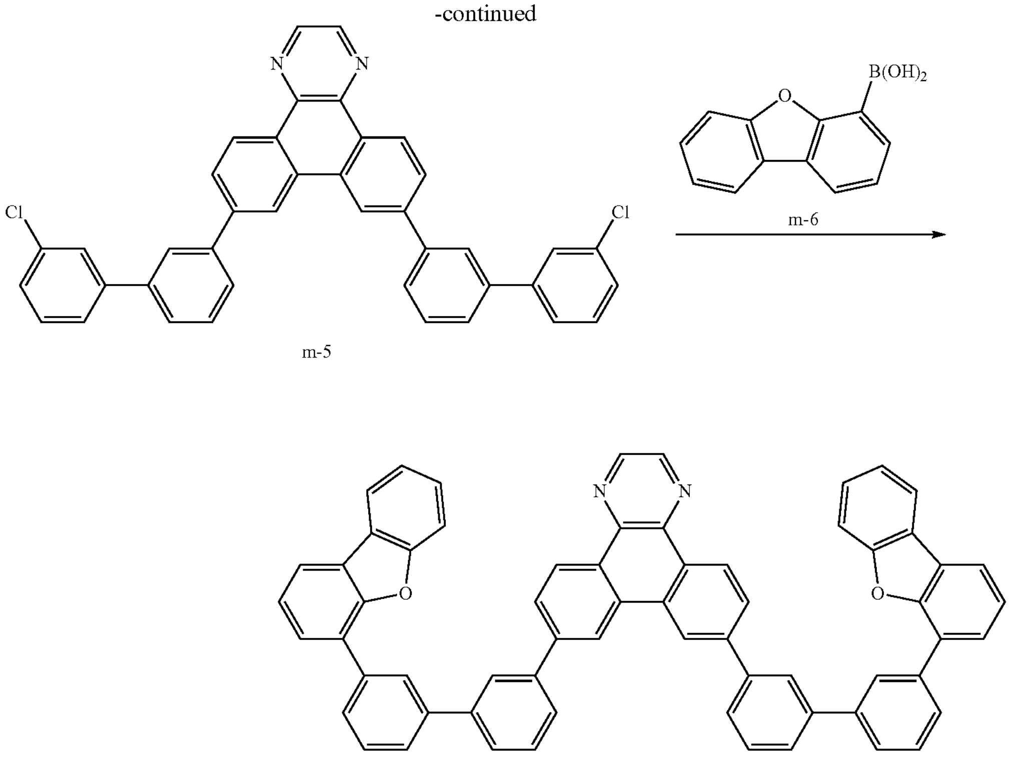

m-5

A4

(1) Synthesis of Compound m-3

A 100-ml eggplant flask was charged with reagents and solvents described below.

Compound m-1: 1.0 g (2.7 mmol)

Compound m-2: 0.2 g (3.3 mmol)

Ethanol: 20 ml

Acetic acid: 20 ml

The reaction solution was subjected to heat-reflux-agitation in a nitrogen gas stream and agitation was performed for 6 hours. Subsequently, acetic acid was added, and reflux-agitation was performed for 6 hours in a nitrogen gas stream. After the reaction was completed, water and toluene were added and liquid separation was performed. Thereafter, a toluene solution was concentrated and slurry washing with methanol was performed so as to obtain 0.69 g (yield: 65%) of yellow solid Compound m-3.

(2) Synthesis of Compound m-5

A 100-ml eggplant flask was charged with reagents and solvents described below.

Compound m-3: 0.5 g (1.3 mmol)

Compound m-4: 0.9 g (2.8 mmol)

$Pd(PPh_3)_4$: 0.05 g

Toluene: 15 ml

Ethanol: 8 ml

2M-Sodium carbonate aqueous solution: 8 ml

The reaction solution was subjected to heat-reflux-agitation in a nitrogen gas stream and agitation was performed for 6 hours. After the reaction was completed, water and toluene were added and liquid separation was performed. This was refined through column chromatography (toluene:heptane) and recrystallized with toluene so as to obtain 0.6 g (yield: 80%) of light-yellow solid Compound m-5.

(3) Synthesis of Exemplary compound A4

A 200-ml eggplant flask was charged with reagents and solvents described below.

Compound m-5: 0.4 g (0.65 mmol)

Compound m-6: 0.3 g (1.4 mmol)

$Pd(dba)_2$: 0.011 g

Sphos: 0.024 g

Potassium phosphate: 0.34 g

Toluene: 12 ml

Ethanol: 6 ml

Water: 6 ml

The reaction solution was subjected to heat-reflux-agitation in a nitrogen gas stream and agitation was performed for 6 hours. After the reaction was completed, filtration was performed, and dissolution into xylene and silica gel adsorption washing were performed. Thereafter, the solvent was concentrated, slurry washing with methanol was performed, and filtration was performed so as to obtain 0.45 g (yield: 81%) of white solid Exemplary compound A4.

Exemplary compound A4 was subjected to mass analysis by using MALDI-TOF-MS (Autoflex LRF produced by Bruker).

MALDI-TOF-MS measured value: m/z=867, calculated value: $C_{64}H_{38}N_2O_2$=867

Examples 2 to 20 (Synthesis of Exemplary Compound)

As presented in Table 4 and Table 5, exemplary compounds in Examples 2 to 20 were synthesized in the manner akin to that in Example 1 except that the raw materials m-2 and m-6 in Example 1 were changed. In this regard, the measured values of m/z measured in the manner akin to that in Example 1 are presented.

TABLE 4
| Example | Exemplary compound | Raw material m-2 | Raw material m-6 | m/z |
|---|---|---|---|---|
| 2 | A1 | 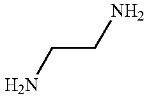 | 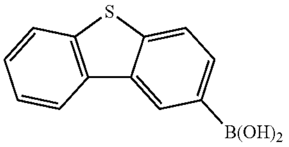 | 899 |
| 3 | A2 | 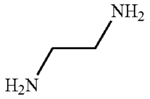 | 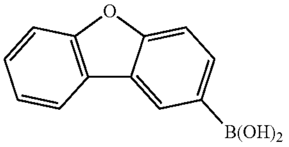 [SMILES: OB(O)c1ccc2oc3ccccc3c2c1] | 867 |
| 4 | A3 | 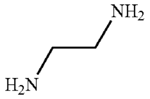 | 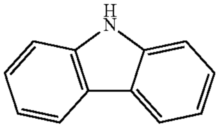 | 865 |
| 5 | A8 | 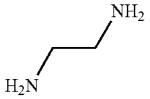 | 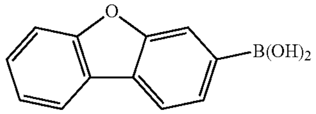 [SMILES: OB(O)c1ccc2c(c1)oc1ccccc12] | 867 |
| 6 | A16 | 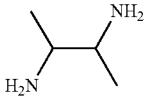 | 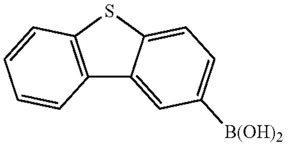 [SMILES: OB(O)c1ccc2oc3ccccc3c2c1] | 927 |
| 7 | A17 | 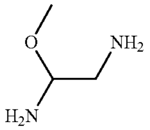 | 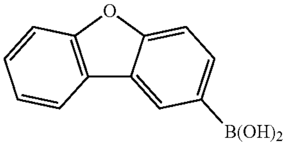 | 897 |
| 8 | A19 | 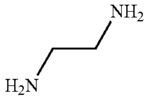 | 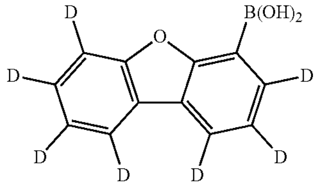 [SMILES: [2H]c1c([2H])c([2H])c2c(oc3c(B(O)O)c([2H])c([2H])c([2H])c32)c1[2H]] | 881 |
| 9 | A21 | 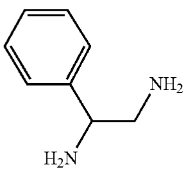 | 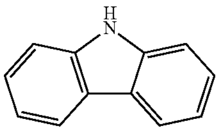 [SMILES: c1ccc2c(c1)[nH]c1ccccc12] | 941 |
| 10 | A24 | 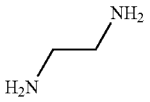 | 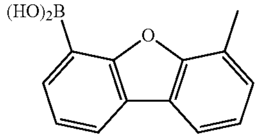 [SMILES: Cc1cccc2c1oc1c(B(O)O)cccc12] | 895 |

TABLE 4-continued
| Example | Exemplary compound | Raw material m-2 | Raw material m-6 | m/z |
|---|---|---|---|---|
| 11 | A31 | 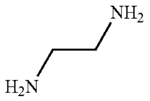 | 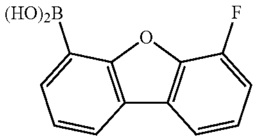 [SMILES: OB(O)c1cccc2c1oc1c(F)cccc12] | 903 |
TABLE 5
| Example | Exemplary compound | Raw material m-2 | Raw material m-6 | m/z |
|---|---|---|---|---|
| 12 | B1 | 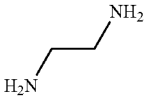 | 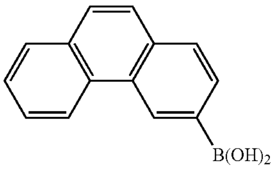 [SMILES: OB(O)c1ccc2ccc3ccccc3c2c1] | 887 |
| 13 | B2 | 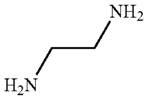 | 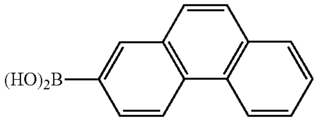 [SMILES: OB(O)c1ccc2c(ccc3ccccc32)c1] | 887 |
| 14 | B7 | 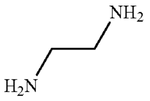 | 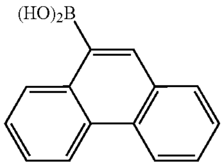 [SMILES: OB(O)c1cc2ccccc2c2ccccc12] | 887 |
| 15 | B13 | 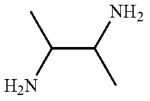 | 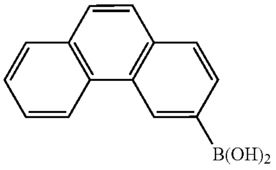 [SMILES: OB(O)c1ccc2ccc3ccccc3c2c1] | 915 |
| 16 | B18 | 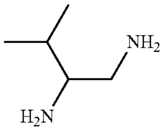 | 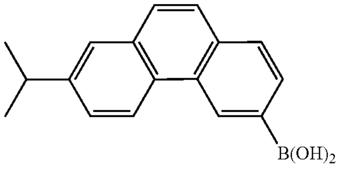 [SMILES: CC(C)c1ccc2c(ccc3ccc(B(O)O)cc32)c1] | 1013 |
| 17 | C1 | 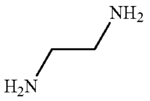 | 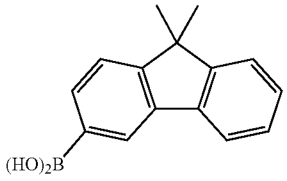 [SMILES: CC1(C)c2ccccc2-c2cc(B(O)O)ccc21] | 919 |

TABLE 5-continued

| Example | Exemplary compound | Raw material m-2 | Raw material m-6 | m/z |
|---|---|---|---|---|
| 18 | C2 | 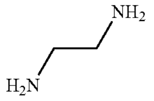 | 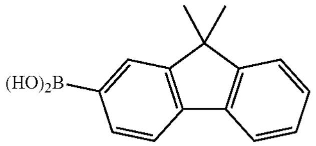 [SMILES: CC1(C)c2ccccc2-c2ccc(B(O)O)cc21] | 919 |
| 19 | C7 | 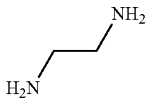 | 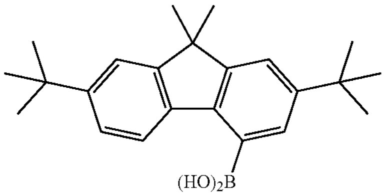 [SMILES: CC(C)(C)c1ccc2c(c1)C(C)(C)c1cc(C(C)(C)C)cc(B(O)O)c1-2] | 1143 |
| 20 | C11 | 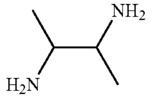 | 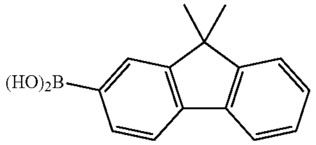 [SMILES: CC1(C)c2ccccc2-c2ccc(B(O)O)cc21] | 947 |

Example 21

An organic light-emitting element having a bottom emission type structure in which an anode, a hole injection layer, a hole transport layer, an electron blocking layer, a light-emitting layer, a hole blocking layer, an electron transport layer, an electron injection layer, and a cathode were successively formed was produced.

An ITO film was formed on a glass substrate, and a predetermined patterning was performed so as to form an ITO electrode (anode). At this time, the film thickness of the ITO electrode was set to be 100 nm. The substrate provided with the thus formed ITO electrode was used as an ITO substrate in the steps below. Subsequently, an organic compound layer and an electrode layer presented in Table 6 were continuously formed on the above-described ITO substrate by performing vacuum vapor deposition due to resistance heating in a vacuum chamber at $1.33\times10^{-4}$ Pa. In this regard, the electrode area of the opposite electrode (metal electrode layer, cathode) was set to be 3 $mm^2$.

TABLE 6

| | | Material | Film thickness (nm) |
|---|---|---|---|
| Cathode | | Al | 100 |
| Electron injection layer (EIL) | | LiF | 1 |
| Electron transport layer (ETL) | | ET2 | 20 |
| Hole blocking layer (HBL) | | ET11 | 20 |
| Light-emitting layer (EML) | Host A4<br>Guest AA2 | Mass ratio<br>A4:AA2 = 90:10 | 20 |
| Electron blocking layer (EBL) | | HT19 | 15 |
| Hole transport layer (HTL) | | HT3 | 30 |
| Hole injection layer (HIL) | | HT16 | 5 |

Regarding the resulting element, the characteristics of the element were measured and evaluated. The maximum emission wavelength of the light-emitting element was 522 nm, and the maximum external quantum efficiency (E.Q.E.) was 1.3 where that of Comparative example 1 was assumed to be 1.0. Further, a continuous driving test at a current density of 100 mA/$cm^2$ was performed, and a time when the luminance deterioration rate reached 5% (LT95) was measured. As a result, the ratio of luminance deterioration rate was 1.4 where that of Comparative example 1 was assumed to be 1.0. In the present example, regarding the specific measuring apparatus, the current-voltage characteristics were measured using a microammeter 4140B produced by Hewlett-Packard Company, and the emission luminance was measured using BM7 produced by TOPCON CORPORATION.

Examples 22 to 41 and Comparative Example 1

Organic light-emitting elements were produced in the manner akin to that in Example 21 except that compounds were appropriately changed to the compounds presented in Table 7. Regarding the resulting elements, the characteristics of the elements were measured and evaluated in the manner akin to that in Example 21. The measurement results are presented in Table 7. In this regard, Comparative compound 1-A used as the host material in Comparative example 1 is Compound 1-A described in US 2014/0034925.

TABLE 7

| | HIL | HTL | EBL | EML Host | Guest | HBL | ETL | Ratio of external quantum efficiency | Ratio of illumination deterioration rate |
|---|---|---|---|---|---|---|---|---|---|
| Example 22 | HT16 | HT2 | HT15 | A1 | BB26 | ET11 | ET2 | 1.2 | 1.5 |
| Example 23 | HT16 | HT2 | HT15 | A4 | AA27 | ET12 | ET2 | 1.3 | 1.4 |
| Example 24 | HT16 | HT2 | HT15 | A4 | AA30 | ET11 | ET15 | 1.1 | 1.4 |
| Example 25 | HT16 | HT3 | HT19 | A3 | GD10 | ET11 | ET2 | 1.1 | 1.1 |
| Example 26 | HT16 | HT2 | HT19 | A2 | GD10 | ET12 | ET2 | 1.3 | 1.1 |
| Example 27 | HT16 | HT3 | HT15 | A1 | AA26 | ET11 | ET15 | 1.4 | 1.4 |
| Example 28 | HT16 | HT2 | HT19 | B1 | BB24 | ET12 | ET2 | 1.3 | 1.5 |
| Example 29 | HT16 | HT3 | HT15 | B1 | CC17 | ET12 | ET2 | 1.4 | 1.4 |
| Example 30 | HT16 | HT3 | HT19 | B3 | CC17 | ET11 | ET15 | 1.5 | 1.3 |
| Example 31 | HT16 | HT2 | HT15 | B2 | DD5 | ET11 | ET2 | 1.6 | 1.1 |
| Example 32 | HT16 | HT3 | HT19 | B13 | DD31 | ET12 | ET15 | 1.2 | 1.3 |
| Example 33 | HT16 | HT2 | HT15 | C2 | EE1 | ET11 | ET2 | 1.2 | 1.2 |
| Example 34 | HT16 | HT2 | HT19 | C2 | EE2 | ET11 | ET2 | 1.6 | 1.4 |
| Example 35 | HT16 | HT3 | HT19 | C11 | EE29 | ET12 | ET15 | 1.7 | 1.3 |
| Example 36 | HT16 | HT3 | HT19 | C11 | DD27 | ET12 | ET15 | 1.5 | 1.2 |
| Example 37 | HT16 | HT3 | HT19 | C1 | DD27 | ET11 | ET15 | 1.2 | 1.2 |
| Example 38 | HT16 | HT2 | HT15 | EM13 | HH27 | A1 | ET2 | 1.3 | 1.4 |
| Example 39 | HT16 | HT2 | HT15 | EM14 | GG7 | A4 | ET15 | 1.2 | 1.4 |
| Example 40 | HT16 | HT3 | HT19 | EM13 | FF1 | A3 | ET2 | 1.2 | 1.2 |
| Example 41 | HT16 | HT2 | HT15 | EM14 | II2 | B1 | ET15 | 1.3 | 1.4 |
| Comparative example 1 | HT16 | HT3 | HT15 | Comparative compound 1-A | GD10 | ET11 | ET2 | 1.0 | 1.0 |

As presented in Table 7, the maximum external quantum efficiency (E.Q.E.) of each example was more than 1.0 relative to that of Comparative example 1, and, therefore, the light-emitting elements of the examples have higher light emission efficiency. The cause of this is due to the compounds according to the present embodiment having larger $S_1$ and $T_1$. In addition, the light-emitting elements according to the examples had longer life. The cause of this is due to the compounds according to the present embodiment having more excellent film performance and sublimation properties. Consequently, using the compounds according to the present embodiment enables the element having higher efficiency and excellent durability characteristics to be provided.

Example 42

An organic light-emitting element was produced in the manner akin to that in Example 21 except that the organic compound layer and the electrode layer presented in Table 8 were continuously produced.

TABLE 8

| | | | Material | Film thickness (nm) |
|---|---|---|---|---|
| Cathode | | | Al | 100 |
| Electron injection layer (EIL) | | | LiF | 1 |
| Electron transport layer (ETL) | | | ET2 | 20 |
| Hole blocking layer (HBL) | | | ET11 | 20 |
| Light-emitting layer (EML) | Host | A4 | Mass ratio | 20 |
| | Guest | AA2 | A4:AA2:EM30 = | |
| | Assist | EM30 | 60:10:30 | |

TABLE 8-continued

| | Material | Film thickness (nm) |
|---|---|---|
| Electron blocking layer (EBL) | HT19 | 15 |
| Hole transport layer (HTL) | HT3 | 30 |
| Hole injection layer (HIL) | HT16 | 5 |

Regarding the resulting element, the characteristics of the element were measured and evaluated. The emission color of the light-emitting element was green. In addition, a time when the luminance deterioration rate reached 5% (LT95) was measured in the manner akin to that in Example 21. As a result, the ratio of luminance deterioration rate was 1.8 where that of Comparative example 2 was assumed to be 1.0.

Examples 43 to 50 and Comparative Example 2

Organic light-emitting elements were produced in the manner akin to that in Example 42 except that compounds were appropriately changed to the compounds presented in Table 9. Regarding the resulting elements, the characteristics of the elements were measured and evaluated in the manner akin to that in Example 42. The measurement results are presented in Table 9.

TABLE 9

| | | | | EML | | | | | Ratio of deterioration rate |
|---|---|---|---|---|---|---|---|---|---|
| | HIL | HTL | EBL | Host | Guest | Assist | HBL | ETL | luminance |
| Example 43 | HT16 | HT2 | HT15 | A1 | DD31 | ET17 | ET26 | ET3 | 1.8 |
| Example 44 | HT16 | HT3 | HT19 | A4 | DD27 | EM29 | ET13 | ET2 | 1.6 |
| Example 45 | HT16 | HT2 | HT15 | A4 | GD12 | EM30 | ET13 | ET2 | 1.7 |
| Example 46 | HT16 | HT3 | HT19 | A3 | EE2 | EM31 | ET16 | ET15 | 1.5 |
| Example 47 | HT16 | HT2 | HT15 | B1 | EE29 | EM39 | ET13 | ET2 | 1.8 |
| Example 48 | HT16 | HT2 | HT15 | B3 | RD9 | EM37 | ET13 | ET2 | 1.7 |
| Example 49 | HT16 | HT3 | HT19 | B2 | RD7 | AA16 | ET16 | ET15 | 1.5 |
| Example 50 | HT16 | HT3 | HT19 | C2 | GG7 | EM30 | ET16 | ET15 | 1.5 |
| Comparative example 2 | HT16 | HT3 | HT19 | Comparative compound 1-A | DD27 | EM29 | ET13 | ET2 | 1.0 |

The organic compound according to the present disclosure has large $S_1$ and $T_1$, has excellent film performance and sublimation properties, and is a compound suitable for the organic light-emitting element. Consequently, using the organic compound according to the present disclosure as a constituent material of an organic light-emitting element enables the organic light-emitting element having favorable light emission characteristics and durability characteristics to be obtained.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2021-187046, filed Nov. 17, 2021, which is hereby incorporated by reference herein in its entirety.

What is claimed is:

1. An organic light-emitting element comprising:

an anode;

a cathode; and a light-emitting layer disposed between the anode and the cathode, wherein at least one layer of the light-emitting layer contains an organic compound denoted by formula (1)

(1)

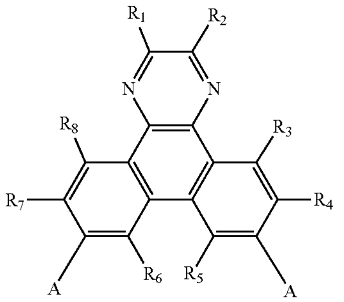

in formula (1), each of $R_1$ to $R_8$ is selected from the group consisting of a hydrogen atom, a deuterium atom, a halogen atom, a substituted or unsubstituted alkyl group, a substituted or unsubstituted alkoxy group, a substituted or unsubstituted amino group, a substituted or unsubstituted aryloxy group, a substituted or unsubstituted heteroaryloxy group, a substituted or unsubstituted silyl group, a substituted or unsubstituted aromatic hydrocarbon group, a substituted or unsubstituted heterocyclic group, and a cyano group, and A represents

A:

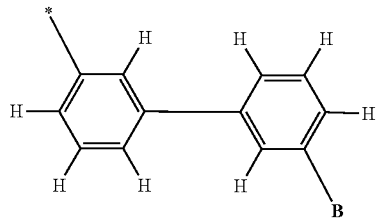

in A above, * represents a position where bonding is performed, and B is selected from the group consisting of structures denotes by (B-12) to (B-15)

(B-12)

B:

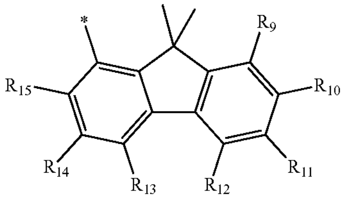

(B-13)

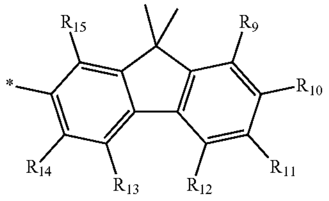

(B-14)

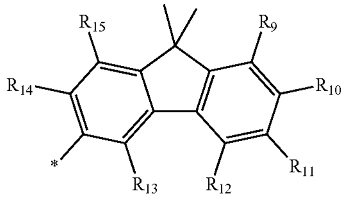

-continued (B-15)

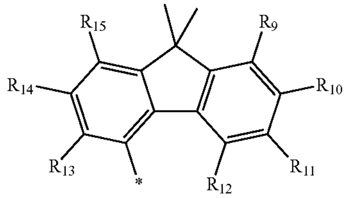

in (B-12) to (B-15) above, * represents a position where bonding is performed, and each of $R_9$ to $R_{17}$ is selected from the group consisting of a hydrogen atom, a deuterium atom, a halogen atom, a substituted or unsubstituted alkyl group, a substituted or unsubstituted alkyoxy group, a substituted or unsubstituted amino group, a substituted or unsubstituted aryloxy group, a substituted or unsubstituted heteroaryloxy group, a substituted or unsubstituted silyl group, a substituted or unsubstituted aromatic hydrocarbon group, a substituted or unsubstituted heterocyclic group, and a cyano group, wherein the light-emitting layer further contains a phosphorescence light-emitting material, the content of the organic compound is 30% by mass or more and 99% by mass or less, and wherein the light-emitting layer further contains a third component.

2. The organic light-emitting element according to claim 1, wherein the phosphorescence light-emitting material is an organometallic complex and has a ligand including a condensed ring of three or more rings.

3. The organic light-emitting element according to claim 2, wherein the condensed ring of three or more rings is a ring selected from the group consisting of a triphenylene ring, a phenanthrene ring, a benzofluorene ring, a dibenzofuran ring, a dibenzothiophene ring, a benzoisoquinoline ring, and a naphthoisoquinoline ring.

4. The organic light-emitting element according to claim 1, wherein the third component has at least a carbazole skeleton.

5. The organic light-emitting element according to claim 1, wherein the third component has at least an azine ring in the skeleton.

6. The organic light-emitting element according to claim 1, wherein the third component has at least xanthone in the skeleton.

7. The organic light-emitting element according to claim 1, wherein another light-emitting layer that is stacked on the light-emitting layer and that emits light with a color different from the emission color emitted from the light-emitting layer is further included.

8. The organic light-emitting element according to claim 7, wherein white light is emitted.

9. A display apparatus comprising a plurality of pixels, wherein at least one of the plurality of pixels includes the organic light-emitting element according to claim 1 and a transistor connected to the organic light-emitting element.

10. A photoelectric conversion apparatus comprising:

an optical portion having a plurality of lenses;

an imaging element for receiving light passed through the optical portion; and a display portion for displaying an image imaged by the imaging element, wherein the display portion includes the organic light-emitting element according to claim 1.

11. An electronic apparatus comprising:

a display portion including the organic light-emitting element according to claim 1;

a housing provided with the display portion; and a communications portion that is disposed in the housing and that communicates with an outside.

12. An illumination apparatus comprising:

a light source including the organic light-emitting element according to claim 1; and a light diffusion portion or an optical filter for passing through light emitted from the light source.

13. A moving object comprising:

a lighting fixture including the organic light-emitting element according to claim 1; and a bodywork provided with the lighting fixture.

14. An exposure light source of electrophotographic image forming apparatus comprising the organic light-emitting element according to claim 1.

* * * * *